United States Patent
Shaheen et al.

(10) Patent No.: US 12,358,979 B2
(45) Date of Patent: Jul. 15, 2025

(54) ANTIBODIES THAT BIND INTERLEUKIN 13 AND METHODS OF USE

(71) Applicant: Apogee Therapeutics, Inc., Waltham, MA (US)

(72) Inventors: Hussam H. Shaheen, Waltham, MA (US); Kenneth Evan Thompson, Waltham, MA (US); Peter Harwin, Waltham, MA (US); Tomas Kiselak, Waltham, MA (US)

(73) Assignee: Apogee Therapeutics, Inc., Waltham, MA (US)

( * ) Notice: Subject to any disclaimer, the term of this patent is extended or adjusted under 35 U.S.C. 154(b) by 0 days.

(21) Appl. No.: 18/979,795

(22) Filed: Dec. 13, 2024

(65) Prior Publication Data

US 2025/0129150 A1    Apr. 24, 2025

Related U.S. Application Data

(63) Continuation of application No. PCT/US2023/068621, filed on Jun. 16, 2023.

(60) Provisional application No. 63/469,167, filed on May 26, 2023, provisional application No. 63/462,822, filed on Apr. 28, 2023, provisional application No. 63/353,367, filed on Jun. 17, 2022.

(51) Int. Cl.
C07K 16/24    (2006.01)
A61K 39/00    (2006.01)

(52) U.S. Cl.
CPC ...... C07K 16/244 (2013.01); *A61K 2039/505* (2013.01); *C07K 2317/24* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 7,615,213 B2 | 11/2009 | Kasaian et al. | |
| 7,674,459 B2 | 3/2010 | Fung et al. | |
| 7,863,426 B2 | 1/2011 | Wan et al. | |
| 8,067,199 B2 | 11/2011 | Fung et al. | |
| 8,088,618 B2 | 1/2012 | Fung et al. | |
| 8,221,752 B2 | 7/2012 | Kasaian et al. | |
| 8,318,160 B2 | 11/2012 | Fung et al. | |
| 8,734,797 B2 | 5/2014 | Fung et al. | |
| 8,734,801 B2 | 5/2014 | Fung et al. | |
| 9,067,994 B2 | 6/2015 | Fung et al. | |
| 9,605,065 B2 | 3/2017 | Fung et al. | |
| 9,920,120 B2 | 3/2018 | Yu et al. | |
| 10,000,562 B2 | 6/2018 | Deshmukh et al. | |
| 10,093,730 B2 | 10/2018 | Hass et al. | |
| 10,112,994 B2 | 10/2018 | Giulianotti et al. | |
| 10,597,446 B2 | 3/2020 | Yu et al. | |
| 10,597,447 B2 | 3/2020 | Yu et al. | |
| 10,683,348 B2 | 6/2020 | Fuh et al. | |
| 10,723,795 B2 | 7/2020 | Hass et al. | |
| 10,738,131 B2 | 8/2020 | Chen et al. | |
| 10,752,703 B2 | 8/2020 | Chen et al. | |
| 10,882,922 B2 | 1/2021 | Yang et al. | |
| 10,947,307 B2 | 3/2021 | Deshmukh et al. | |
| 11,192,960 B2 | 12/2021 | Yang et al. | |
| 11,226,341 B2 | 1/2022 | Arron et al. | |
| 11,299,539 B2 | 4/2022 | Giulianotti et al. | |
| 11,434,286 B2 | 9/2022 | Lin et al. | |
| 11,434,287 B2 | 9/2022 | Fung et al. | |
| 11,453,727 B2 | 9/2022 | Rao et al. | |
| 11,725,050 B2 | 8/2023 | Hass et al. | |
| 11,754,573 B2 | 9/2023 | Morgan et al. | |
| 11,827,671 B2 | 11/2023 | Soubrane et al. | |
| 11,840,566 B2 | 12/2023 | Rommelaere et al. | |
| 11,891,437 B2 | 2/2024 | Famili et al. | |
| 2003/0031666 A1 | 2/2003 | Debinski et al. | |
| 2006/0063228 A1 | 3/2006 | Kasaian et al. | |
| 2007/0292442 A1 | 12/2007 | Wan et al. | |
| 2009/0098142 A1 | 4/2009 | Kasaian et al. | |
| 2010/0129360 A1 | 5/2010 | Kasaian et al. | |
| 2014/0044645 A1* | 2/2014 | Arron | G01N 33/6887 530/387.9 |

(Continued)

FOREIGN PATENT DOCUMENTS

| | | | |
|---|---|---|---|
| EP | 1703893 B1 | 4/2012 | |
| EP | 1711528 B1 | 7/2012 | |
| EP | 2332575 B1 | 11/2014 | |
| EP | 3060685 B1 | 5/2019 | |
| EP | 2805728 B1 | 2/2020 | |
| EP | 3218403 B1 | 5/2020 | |
| EP | 3091029 B1 | 12/2022 | |
| EP | 3528838 B1 | 7/2023 | |
| EP | 3443006 B1 | 8/2023 | |
| EP | 3718564 B1 | 10/2023 | |
| EP | 3083682 B1 | 4/2024 | |

(Continued)

OTHER PUBLICATIONS

Dall'Acqua WF, et al., "Properties of human IgG1s engineered for enhanced binding to the neonatal Fc receptor (FcRn)," J Biol Chem., vol. 281(33):23514-23524 (2006).

(Continued)

*Primary Examiner* — Marianne P Allen

(74) *Attorney, Agent, or Firm* — Nelson Mullins Riley & Scarborough LLP; Jane E. Remillard, Esq.; Jill Gorny Sloper, Esq.

(57) ABSTRACT

Described herein are novel and improved antibodies that bind Interleukin 13 (IL-13) and methods of use thereof. In certain aspects, described herein are methods of inhibiting IL-13 biological activity. In certain aspects, described herein are pharmaceutical compositions comprising the anti-IL-13 antibodies. In certain aspects, the antibodies and methods described herein are used for treatment of an inflammatory disease or disorder associated with elevated levels of IL-13 and/or IgE.

21 Claims, 15 Drawing Sheets

Specification includes a Sequence Listing.

(56) References Cited

U.S. PATENT DOCUMENTS

| | | |
|---|---|---|
| 2015/0225479 A1 | 8/2015 | Huille et al. |
| 2016/0207995 A1 | 7/2016 | Yansura et al. |
| 2016/0230226 A1 | 8/2016 | Abbas et al. |
| 2016/0272706 A1* | 9/2016 | Carmen .............. C07K 16/2866 |
| 2016/0363591 A1 | 12/2016 | Streicher et al. |
| 2017/0067108 A1 | 3/2017 | Abbas et al. |
| 2017/0298119 A1* | 10/2017 | Wollacott ............... A61K 39/12 |
| 2017/0334985 A1 | 11/2017 | Wu et al. |
| 2018/0251538 A1 | 9/2018 | Fung et al. |
| 2018/0356429 A1 | 12/2018 | Morimoto et al. |
| 2019/0002552 A1* | 1/2019 | Deshmukh ............... A61P 37/08 |
| 2019/0024178 A1 | 1/2019 | Abbas et al. |
| 2019/0062836 A1 | 2/2019 | Abbas et al. |
| 2020/0165679 A1 | 5/2020 | Abbas et al. |
| 2021/0115124 A1 | 4/2021 | Koenig et al. |
| 2021/0155684 A1 | 5/2021 | Deshmukh et al. |
| 2021/0188965 A1 | 6/2021 | Rommelaere et al. |
| 2021/0261649 A1 | 8/2021 | Parry et al. |
| 2022/0033520 A1 | 2/2022 | Lazar et al. |
| 2022/0089728 A1 | 3/2022 | Degenhardt et al. |
| 2022/0153854 A1 | 5/2022 | Rommelaere et al. |
| 2022/0177564 A1 | 6/2022 | Rommelaere et al. |
| 2022/0177566 A1 | 6/2022 | Rommelaere et al. |
| 2022/0228107 A1 | 7/2022 | Smith et al. |
| 2022/0275102 A1 | 9/2022 | Cameron et al. |
| 2022/0372131 A1 | 11/2022 | Lin et al. |
| 2022/0389449 A1 | 12/2022 | Paul et al. |
| 2023/0235088 A1 | 7/2023 | Rao et al. |
| 2023/0250165 A1 | 8/2023 | Yu et al. |
| 2023/0357381 A1 | 11/2023 | Bardroff et al. |
| 2024/0101675 A1 | 3/2024 | Demishtein et al. |
| 2024/0117030 A1 | 4/2024 | Agostinelli et al. |

FOREIGN PATENT DOCUMENTS

| | | |
|---|---|---|
| WO | 2005062967 A2 | 7/2005 |
| WO | 2008140455 A1 | 11/2008 |
| WO | 2015038888 A1 | 3/2015 |
| WO | 2017011773 A2 | 1/2017 |
| WO | 2018/220216 A1 | 12/2018 |
| WO | 2021021676 A1 | 2/2021 |
| WO | 2022097060 A1 | 5/2022 |
| WO | 2023287590 A1 | 1/2023 |
| WO | 2023019260 A1 | 2/2023 |
| WO | 2023044313 A1 | 3/2023 |
| WO | 2023215769 A1 | 11/2023 |
| WO | 2023245187 A2 | 12/2023 |
| WO | 2024227141 A1 | 10/2024 |

OTHER PUBLICATIONS

Deuschl, F. et al., "Molecular characterization of the hypothetical 66.3-kDa protein in mouse: Lyso-somal targeting, glycosylation, processing and tissue distribution," FEBS Letters, vol. 580: 5747-5752 (2006).

Dumet, C. et al., "Insights into the IgG heavy chain engineering patent landscape as applied to IgG4 antibody development," Mabs, vol. 11(8):1341-1350 (2019) doi: 10.1080/19420862.2019.1664365.

Gutierrez, A. et al., "Of 'hamsters and men: A new perspective on host cell proteins," Human Vac-cines, vol. 8 (9): 1172-1174 (2012).

Hammitt LL, et al. "Nirsevimab for prevention of RSV in healthy late-preterm and term infants," N Engl J Med., vol. 386(9):837-846 (2022).

Hezareh M, et al., "Effector function activities of a panel of mutants of a broadly neutralizing anti-body against human immunodeficiency virus type 1," J Virol., vol. 75(24):12161-12168 (2001) doi:10.1128/JVI.75.24.12161-12168.2001.

International Preliminary Report on Patentability, PCT/US2023/068621, dated Dec. 10, 2024, 9 pages.

International Search Report and Written Opinion, PCT/US2023/068621, dated Jun. 11, 2024, 13 pages.

Kato Y, et al., "Hydrophobic interaction chromatography at low salt concentration for the capture of monoclonal antibodies," J Chromatogr., vol. 1036:45-50 (2004).

Liu et al., "Recovery and purification process development for monoclonal antibody production," mAbs, vol. 2 (5): 480-499 (2010).

Lytvyn, Y. et al., "Targeting Interleukin 13 for the Treatment of Atopic Dermatitis," Pharmaceutics, vol. 15(2):568 doi: 10.3390/pharmaceutics15020568 (2023).

NCT04718103, "A Study of GSK3511294 (Depemokimab) in Participants With Severe Asthma With an Eosinophilic Phenotype (SWIFT-2)" 2 pages.

Ortega H, et al., "Pharmacokinetics and absolute bioavailability of mepolizumab following administration at subcutaneous and intramuscular sites," Clin Pharmacol Drug Dev., vol. 3(1):57-62 (2014). doi:10.1002/cpdd.60.

Ridker PM, et al., "IL-6 inhibition with ziltivekimab in patients at high atherosclerotic risk (RES-CUE): a double-blind, randomised, placebo-controlled, phase 2 trial," Lancet, vol. 397(10289):2060-2069 (2021) doi:10.1016/S0140-6736(21)00520-1.

Robbie GJ, et al., "A novel investigational Fc-modified humanized monoclonal antibody, motavi-zumab-YTE, has an extended half-life in healthy adults," Antimicrob Agents Chemother., vol. 57(12):6147-6153 (2013) doi: 10.1128/AAC.01285-13.

Robbie GJ, et al., "Population pharmacokinetics of palivizumab, a humanized anti-respiratory syncyt-ial virus monoclonal antibody, in adults and children," Antimicrob Agents Chemother., vol. 56(9):4927-4936 (2012). doi:10.1128/AAC.06446-11.

Rocca A, et al. "Passive immunoprophylaxis against respiratory syncytial virus in children: where are we now?" Int J Mol Sci., vol. 22(7):3703 (2021) doi:10.3390/ijms22073703.

Saunders KO, "Conceptual approaches to modulating antibody effector functions and circulation half-life," Front Immunol., vol. 10:1296 (2019) doi:10.3389/fimmu.2019.01296.

Shukla, A. et al., "Downstream processing of monoclonal antibodies-application of platform approaches," J. Chromatogr., 28-39 (2007).

Singh D, et al., "A Phase 1 study of the long-acting anti-IL-5 monoclonal antibody GSK3511294 in pa-tients with asthma," Br J Clin Pharmacol., vol. 88(2):702-712 (2022).

Vanderlaan, Martin et al., "Hamster phospholipase B-like 2 (PLBL2): A host-cell protein impurity in therapeutic monoclonal antibodies derived from Chinese hamster ovary cells," BioProcess International, vol. 13. (2015).

Wines BD, et al., "The IgG Fc contains distinct Fc receptor (FcR) binding sites: the leukocyte recep-tors Fc gamma RI and Fc gamma RIIa bind to a region in the Fc distinct from that recognized by neo-natal FcR and protein A," J Immunol., vol. 164(10):5313-5318 (2000) doi:10.4049/jimmunol.164.10.5313.

* cited by examiner

SEQUENCE LISTING

```
Sequence total quantity: 609
SEQ ID NO: 1              moltype = AA  length = 118
FEATURE                   Location/Qualifiers
source                    1..118
                          mol_type = protein
                          organism = synthetic construct
SEQUENCE: 1
QVQLQESGPG LVAPSQSLSI TCTVSGFSLN AYSVNWVRQP PGKGLEWLGM IWGDGKIVYN    60
SALKSRLNIS KDSSKSQVFL KMSSLQSDDT ARYYCAGDGY YPYAMDNWGH GTSVTVSS     118

SEQ ID NO: 2              moltype = AA  length = 118
FEATURE                   Location/Qualifiers
source                    1..118
                          mol_type = protein
                          organism = synthetic construct
SEQUENCE: 2
QVQLQESGPG LVAPSQSLSI TCTVSGFSLN AYSVNWVRQP PGKGLEWLGM IWGDGKIVYN    60
SALKSRLTIS KDSSKSQVFL KMSSLQSDDT ARYYCAGDGY YPYAMDNWGH GTSVTVSS     118

SEQ ID NO: 3              moltype = AA  length = 118
FEATURE                   Location/Qualifiers
source                    1..118
                          mol_type = protein
                          organism = synthetic construct
SEQUENCE: 3
EVQLQESGPG LVKPSETLSL TCTVSGFSLN AYSVNWIRQP PGKGLEWLGM IWGDGKIVYN    60
SALKSRLTIS KDSSKNQVSL KLSSVTAADT AVYYCAGDGY YPYAMDNWGQ GTTVTVSS     118

SEQ ID NO: 4              moltype = AA  length = 118
FEATURE                   Location/Qualifiers
source                    1..118
                          mol_type = protein
                          organism = synthetic construct
SEQUENCE: 4
EVQLVQSGAE VKKPGASVKV SCKASGFSLN AYSVNWVRQA PGQGLEWLGM IWGDGKIVYN    60
SALKSRLTIT KDSSTSTVYM ELSSLRSEDT AVYYCAGDGY YPYAMDNWGQ GTTVTVSS     118

SEQ ID NO: 5              moltype = AA  length = 118
FEATURE                   Location/Qualifiers
source                    1..118
                          mol_type = protein
                          organism = synthetic construct
SEQUENCE: 5
EVQLVQSGAE VKKPGSSVKV SCKASGFSLN AYSVNWVRQA PGQGLEWLGM IWGDGKIVYN    60
SALKSRLTIT KDSSTSTVYM ELSSLRSEDT AVYYCAGDGY YPYAMDNWGQ GTTVTVSS     118

SEQ ID NO: 6              moltype = AA  length = 118
FEATURE                   Location/Qualifiers
source                    1..118
                          mol_type = protein
                          organism = synthetic construct
SEQUENCE: 6
EVQLVESGGG LVKPGGSLRL SCAASGFSLN AYSVNWVRQA PGKGLEWLGM IWGDGKIVYN    60
SALKSRLTIS KDSSKNTVYL QMNSLKTEDT AVYYCAGDGY YPYAMDNWGQ GTTVTVSS     118

SEQ ID NO: 7              moltype = AA  length = 118
FEATURE                   Location/Qualifiers
source                    1..118
                          mol_type = protein
                          organism = synthetic construct
SEQUENCE: 7
EVQLLESGGG LVQPGGSLRL SCAASGFSLN AYSVNWVRQA PGKGLEWLGM IWGDGKIVYN    60
```

```
SALKSRLTIS KDSSKNTVYL QMNSLRAEDT AVYYCAGDGY YPYAMDNWGQ GTTVTVSS    118

SEQ ID NO: 8            moltype = AA   length = 118
FEATURE                 Location/Qualifiers
source                  1..118
                        mol_type = protein
                        organism = synthetic construct
SEQUENCE: 8
EVQLQESGPG LVKPSETLSL TCTVSGGSLN AYSVNWVRQP PGKGLEWLGM IWGDGKIVYN    60
SALKSRLTIS LDTSKSQVFL KMSSLTAADT AVYYCARDGY YPYAMDNWGQ GTTVTVSS    118

SEQ ID NO: 9            moltype = AA   length = 118
FEATURE                 Location/Qualifiers
source                  1..118
                        mol_type = protein
                        organism = synthetic construct
SEQUENCE: 9
QVQLQESGPG LVKPSETLSL TCTVSGGSLN AYSWNWVRQP PGKGLEWLGY IYGDGKTNYN    60
PALKSRLTIS LDTSKSQVFL KMSSLTAADT AVYYCARDGY YYYAMDVWGQ GTTVTVSS    118

SEQ ID NO: 10           moltype = AA   length = 118
FEATURE                 Location/Qualifiers
source                  1..118
                        mol_type = protein
                        organism = synthetic construct
SEQUENCE: 10
EVQLLESGGG LVQPGGSLRL SCAASGYSLN AYSVNWVRQA PGKGLEWLGM IWGDGKIVYN    60
SALKSRLTIS KDSSKNTVYL QMNSLRAEDT AVYYCAGDGY YPYAMDNWGQ GTTVTVSS    118

SEQ ID NO: 11           moltype = AA   length = 118
FEATURE                 Location/Qualifiers
source                  1..118
                        mol_type = protein
                        organism = synthetic construct
SEQUENCE: 11
EVQLLESGGG LVQPGGSLRL SCAASGFSLR AYSVNWVRQA PGKGLEWLGM IWGDGKIVYN    60
SALKSRLTIS KDSSKNTVYL QMNSLRAEDT AVYYCAGDGY YPYAMDNWGQ GTTVTVSS    118

SEQ ID NO: 12           moltype = AA   length = 118
FEATURE                 Location/Qualifiers
source                  1..118
                        mol_type = protein
                        organism = synthetic construct
SEQUENCE: 12
EVQLLESGGG LVQPGGSLRL SCAASGFSLH AYSVNWVRQA PGKGLEWLGM IWGDGKIVYN    60
SALKSRLTIS KDSSKNTVYL QMNSLRAEDT AVYYCAGDGY YPYAMDNWGQ GTTVTVSS    118

SEQ ID NO: 13           moltype = AA   length = 118
FEATURE                 Location/Qualifiers
source                  1..118
                        mol_type = protein
                        organism = synthetic construct
SEQUENCE: 13
EVQLLESGGG LVQPGGSLRL SCAASGFSLD AYSVNWVRQA PGKGLEWLGM IWGDGKIVYN    60
SALKSRLTIS KDSSKNTVYL QMNSLRAEDT AVYYCAGDGY YPYAMDNWGQ GTTVTVSS    118

SEQ ID NO: 14           moltype = AA   length = 118
FEATURE                 Location/Qualifiers
source                  1..118
                        mol_type = protein
                        organism = synthetic construct
SEQUENCE: 14
EVQLLESGGG LVQPGGSLRL SCAASGFSLY AYSVNWVRQA PGKGLEWLGM IWGDGKIVYN    60
SALKSRLTIS KDSSKNTVYL QMNSLRAEDT AVYYCAGDGY YPYAMDNWGQ GTTVTVSS    118

SEQ ID NO: 15           moltype = AA   length = 118
FEATURE                 Location/Qualifiers
source                  1..118
                        mol_type = protein
                        organism = synthetic construct
SEQUENCE: 15
EVQLLESGGG LVQPGGSLRL SCAASGFSLS AYSVNWVRQA PGKGLEWLGM IWGDGKIVYN    60
SALKSRLTIS KDSSKNTVYL QMNSLRAEDT AVYYCAGDGY YPYAMDNWGQ GTTVTVSS    118

SEQ ID NO: 16           moltype = AA   length = 118
FEATURE                 Location/Qualifiers
source                  1..118
                        mol_type = protein
                        organism = synthetic construct
```

```
SEQUENCE: 16
EVQLLESGGG LVQPGGSLRL SCAASGFSLN RYSVNWVRQA PGKGLEWLGM IWGDGKIVYN   60
SALKSRLTIS KDSSKNTVYL QMNSLRAEDT AVYYCAGDGY YPYAMDNWGQ GTTVTVSS    118

SEQ ID NO: 17             moltype = AA  length = 118
FEATURE                   Location/Qualifiers
source                    1..118
                          mol_type = protein
                          organism = synthetic construct
SEQUENCE: 17
EVQLLESGGG LVQPGGSLRL SCAASGFSLN KYSVNWVRQA PGKGLEWLGM IWGDGKIVYN   60
SALKSRLTIS KDSSKNTVYL QMNSLRAEDT AVYYCAGDGY YPYAMDNWGQ GTTVTVSS    118

SEQ ID NO: 18             moltype = AA  length = 118
FEATURE                   Location/Qualifiers
source                    1..118
                          mol_type = protein
                          organism = synthetic construct
SEQUENCE: 18
EVQLLESGGG LVQPGGSLRL SCAASGFSLN HYSVNWVRQA PGKGLEWLGM IWGDGKIVYN   60
SALKSRLTIS KDSSKNTVYL QMNSLRAEDT AVYYCAGDGY YPYAMDNWGQ GTTVTVSS    118

SEQ ID NO: 19             moltype = AA  length = 118
FEATURE                   Location/Qualifiers
source                    1..118
                          mol_type = protein
                          organism = synthetic construct
SEQUENCE: 19
EVQLLESGGG LVQPGGSLRL SCAASGFSLN QYSVNWVRQA PGKGLEWLGM IWGDGKIVYN   60
SALKSRLTIS KDSSKNTVYL QMNSLRAEDT AVYYCAGDGY YPYAMDNWGQ GTTVTVSS    118

SEQ ID NO: 20             moltype = AA  length = 118
FEATURE                   Location/Qualifiers
source                    1..118
                          mol_type = protein
                          organism = synthetic construct
SEQUENCE: 20
EVQLLESGGG LVQPGGSLRL SCAASGFSLN EYSVNWVRQA PGKGLEWLGM IWGDGKIVYN   60
SALKSRLTIS KDSSKNTVYL QMNSLRAEDT AVYYCAGDGY YPYAMDNWGQ GTTVTVSS    118

SEQ ID NO: 21             moltype = AA  length = 118
FEATURE                   Location/Qualifiers
source                    1..118
                          mol_type = protein
                          organism = synthetic construct
SEQUENCE: 21
EVQLLESGGG LVQPGGSLRL SCAASGFSLN SYSVNWVRQA PGKGLEWLGM IWGDGKIVYN   60
SALKSRLTIS KDSSKNTVYL QMNSLRAEDT AVYYCAGDGY YPYAMDNWGQ GTTVTVSS    118

SEQ ID NO: 22             moltype = AA  length = 118
FEATURE                   Location/Qualifiers
source                    1..118
                          mol_type = protein
                          organism = synthetic construct
SEQUENCE: 22
EVQLLESGGG LVQPGGSLRL SCAASGFSLN YYSVNWVRQA PGKGLEWLGM IWGDGKIVYN   60
SALKSRLTIS KDSSKNTVYL QMNSLRAEDT AVYYCAGDGY YPYAMDNWGQ GTTVTVSS    118

SEQ ID NO: 23             moltype = AA  length = 118
FEATURE                   Location/Qualifiers
source                    1..118
                          mol_type = protein
                          organism = synthetic construct
SEQUENCE: 23
EVQLLESGGG LVQPGGSLRL SCAASGFSLN AESVNWVRQA PGKGLEWLGM IWGDGKIVYN   60
SALKSRLTIS KDSSKNTVYL QMNSLRAEDT AVYYCAGDGY YPYAMDNWGQ GTTVTVSS    118

SEQ ID NO: 24             moltype = AA  length = 118
FEATURE                   Location/Qualifiers
source                    1..118
                          mol_type = protein
                          organism = synthetic construct
SEQUENCE: 24
EVQLLESGGG LVQPGGSLRL SCAASGFSLN AYSVNWVRQA PGKGLEWLGM IWSDGKIVYN   60
SALKSRLTIS KDSSKNTVYL QMNSLRAEDT AVYYCAGDGY YPYAMDNWGQ GTTVTVSS    118

SEQ ID NO: 25             moltype = AA  length = 118
FEATURE                   Location/Qualifiers
source                    1..118
```

```
                              mol_type = protein
                              organism = synthetic construct
SEQUENCE: 25
EVQLLESGGG LVQPGGSLRL SCAASGFSLN AYSVNWVRQA PGKGLEWLGM IWADGKIVYN   60
SALKSRLTIS KDSSKNTVYL QMNSLRAEDT AVYYCAGDGY YPYAMDNWGQ GTTVTVSS    118

SEQ ID NO: 26            moltype = AA   length = 118
FEATURE                  Location/Qualifiers
source                   1..118
                         mol_type = protein
                         organism = synthetic construct
SEQUENCE: 26
EVQLLESGGG LVQPGGSLRL SCAASGFSLN AYSVNWVRQA PGKGLEWLGM IWGDGKIVYN   60
SALKSRLTIS KDSSKNTVYL QMNSLRAEDT AVYYCAGHGY YPYAMDNWGQ GTTVTVSS    118

SEQ ID NO: 27            moltype = AA   length = 118
FEATURE                  Location/Qualifiers
source                   1..118
                         mol_type = protein
                         organism = synthetic construct
SEQUENCE: 27
EVQLLESGGG LVQPGGSLRL SCAASGFSLN AYSVNWVRQA PGKGLEWLGM IWGDGKIVYN   60
SALKSRLTIS KDSSKNTVYL QMNSLRAEDT AVYYCAGDLY YPYAMDNWGQ GTTVTVSS    118

SEQ ID NO: 28            moltype = AA   length = 118
FEATURE                  Location/Qualifiers
source                   1..118
                         mol_type = protein
                         organism = synthetic construct
SEQUENCE: 28
EVQLLESGGG LVQPGGSLRL SCAASGFSLN AYSVNWVRQA PGKGLEWLGM IWGDGKIVYN   60
SALKSRLTIS KDSSKNTVYL QMNSLRAEDT AVYYCAGDKY YPYAMDNWGQ GTTVTVSS    118

SEQ ID NO: 29            moltype = AA   length = 118
FEATURE                  Location/Qualifiers
source                   1..118
                         mol_type = protein
                         organism = synthetic construct
SEQUENCE: 29
EVQLLESGGG LVQPGGSLRL SCAASGFSLN AYSVNWVRQA PGKGLEWLGM IWGDGKIVYN   60
SALKSRLTIS KDSSKNTVYL QMNSLRAEDT AVYYCAGDGY YGYAMDNWGQ GTTVTVSS    118

SEQ ID NO: 30            moltype = AA   length = 118
FEATURE                  Location/Qualifiers
source                   1..118
                         mol_type = protein
                         organism = synthetic construct
SEQUENCE: 30
EVQLLESGGG LVQPGGSLRL SCAASGFSLN AYSVNWVRQA PGKGLEWLGM IWGDGKIVYN   60
SALKSRLTIS KDSSKNTVYL QMNSLRAEDT AVYYCAGDGY YAYAMDNWGQ GTTVTVSS    118

SEQ ID NO: 31            moltype = AA   length = 118
FEATURE                  Location/Qualifiers
source                   1..118
                         mol_type = protein
                         organism = synthetic construct
SEQUENCE: 31
EVQLLESGGG LVQPGGSLRL SCAASGFSLN AYSVNWVRQA PGKGLEWLGM IWGDGKIVYN   60
SALKSRLTIS KDSSKNTVYL QMNSLRAEDT AVYYCAGDGY YSYAMDNWGQ GTTVTVSS    118

SEQ ID NO: 32            moltype = AA   length = 118
FEATURE                  Location/Qualifiers
source                   1..118
                         mol_type = protein
                         organism = synthetic construct
SEQUENCE: 32
EVQLLESGGG LVQPGGSLRL SCAASGFSLN AYSVNWVRQA PGKGLEWLGM IWGDGKIVYN   60
SALKSRLTIS KDSSKNTVYL QMNSLRAEDT AVYYCAGDGY YTYAMDNWGQ GTTVTVSS    118

SEQ ID NO: 33            moltype = AA   length = 111
FEATURE                  Location/Qualifiers
source                   1..111
                         mol_type = protein
                         organism = synthetic construct
SEQUENCE: 33
NIVLTQSPAS LAVSLGQRAT ISCRASKSVD SYGNSFMHWY QQKPGQPPKL LIYLASNLES   60
GVPARFSGSG SRTDFTLTID PVEADDAASY YCQQNNEDPR TFGGGTKLEI K           111

SEQ ID NO: 34            moltype = AA   length = 111
```

```
FEATURE                 Location/Qualifiers
source                  1..111
                        mol_type = protein
                        organism = synthetic construct
SEQUENCE: 34
DIQLTQSPSS LSASVGDRVT ITCRASKSVD SYGNSFMHWY QQKPGKAPKL LIYLASNLES    60
GVPSRFSGSG SRTDFTLTIS SLQPEDFATY YCQQNNEDPR TFGGGTKVEI K            111

SEQ ID NO: 35           moltype = AA   length = 111
FEATURE                 Location/Qualifiers
source                  1..111
                        mol_type = protein
                        organism = synthetic construct
SEQUENCE: 35
DIQLTQSPSS LSASVGDRVT ITCRASKSVD SYGNSFMHWY QQKPGKAPKL LIYLASNLES    60
GVPSRFSGSG SRTDFTLTIS SLQPEDFATY YCQQNNEDPR TFGGGTKVEI K            111

SEQ ID NO: 36           moltype = AA   length = 111
FEATURE                 Location/Qualifiers
source                  1..111
                        mol_type = protein
                        organism = synthetic construct
SEQUENCE: 36
EIVLTQSPAT LSVSPGERAT LSCRASKSVD SYGNSFMHWY QQKPGQAPRL LIYLASNLES    60
GIPARFSGSG SRTEFTLTIS SLQSEDFAVY YCQQNNEDPR TFGGGTKVEI K            111

SEQ ID NO: 37           moltype = AA   length = 111
FEATURE                 Location/Qualifiers
source                  1..111
                        mol_type = protein
                        organism = synthetic construct
SEQUENCE: 37
DIVLTQSPLS LPVTPGEPAS ISCRASKSVD SYGNSFMHWY LQKPGQSPQL LIYLASNLES    60
GVPDRFSGSG SRTDFTLKIS RVEAEDVGVY YCQQNNEDPR TFGGGTKVEI K            111

SEQ ID NO: 38           moltype = AA   length = 111
FEATURE                 Location/Qualifiers
source                  1..111
                        mol_type = protein
                        organism = synthetic construct
SEQUENCE: 38
DIVLTQSPDS LAVSLGERAT INCRASKSVD SYGNSFMHWY QQKPGQPPKL LIYLASNLES    60
GVPDRFSGSG SGTDFTLTIS SLQAEDVAVY YCQQNNEDPR TFGGGTKVEI K            111

SEQ ID NO: 39           moltype = AA   length = 111
FEATURE                 Location/Qualifiers
source                  1..111
                        mol_type = protein
                        organism = synthetic construct
SEQUENCE: 39
DIQLTQSPSS LSASVGDRVT ITCRASKSVD SYGNSFMHWY QQKPGKAPKL LIYLASNLES    60
GVPSRFSGSG SGTDFTLTIS SLQPEDFATY YCQQNNEDPR TFGGGTKVEI K            111

SEQ ID NO: 40           moltype = AA   length = 111
FEATURE                 Location/Qualifiers
source                  1..111
                        mol_type = protein
                        organism = synthetic construct
SEQUENCE: 40
EIVLTQSPAT LSVSPGERAT LSCRASKSVD SYGNSFMHWY QQKPGQAPRL LIYLASNLES    60
GIPARFSGSG SGTEFTLTIS SLQSEDFAVY YCQQNNEDPR TFGGGTKVEI K            111

SEQ ID NO: 41           moltype = AA   length = 111
FEATURE                 Location/Qualifiers
source                  1..111
                        mol_type = protein
                        organism = synthetic construct
SEQUENCE: 41
DIVLTQSPLS LPVTPGEPAS ISCRASKSVD SYGNSFMHWY LQKPGQSPQL LIYLASNLES    60
GVPDRFSGSG SGTDFTLKIS RVEAEDVGVY YCQQNNEDPR TFGGGTKVEI K            111

SEQ ID NO: 42           moltype = AA   length = 111
FEATURE                 Location/Qualifiers
source                  1..111
                        mol_type = protein
                        organism = synthetic construct
SEQUENCE: 42
DIVLTQSPAS LAVSPGERAT ISCRASKSVD SYGNSFMHWY QQKPGQPPKL LIYLASNLES    60
GVPDRFSGSG SGTDFTLTIS RVEADDVAVY YCQQNNEDPR TFGGGTKLEI K            111
```

```
SEQ ID NO: 43            moltype = AA   length = 111
FEATURE                  Location/Qualifiers
source                   1..111
                         mol_type = protein
                         organism = synthetic construct
SEQUENCE: 43
DIVLTQSPAS LAVSPGERAT ISCRASQSVD SNGNNFLHWY QQKPGQPPKL LIYLASNRES    60
GVPDRFSGSG SGTDFTLTIS RVEADDVAVY YCQQNNHTPR TFGGGTKLEI K            111

SEQ ID NO: 44            moltype = AA   length = 111
FEATURE                  Location/Qualifiers
source                   1..111
                         mol_type = protein
                         organism = synthetic construct
SEQUENCE: 44
DIQLTQSPSS LSASVGDRVT ITCRASKSVD SYGNSRMHWY QQKPGKAPKL LIYLASNLES    60
GVPSRFSGSG SGTDFTLTIS SLQPEDFATY YCQQNNEDPR TFGGGTKVEI K            111

SEQ ID NO: 45            moltype = AA   length = 111
FEATURE                  Location/Qualifiers
source                   1..111
                         mol_type = protein
                         organism = synthetic construct
SEQUENCE: 45
DIQLTQSPSS LSASVGDRVT ITCRASKSVD SYGNSSMHWY QQKPGKAPKL LIYLASNLES    60
GVPSRFSGSG SGTDFTLTIS SLQPEDFATY YCQQNNEDPR TFGGGTKVEI K            111

SEQ ID NO: 46            moltype = AA   length = 111
FEATURE                  Location/Qualifiers
source                   1..111
                         mol_type = protein
                         organism = synthetic construct
SEQUENCE: 46
DIQLTQSPSS LSASVGDRVT ITCRASKSVD SYGNSFMHWY QQKPGKAPKL LIRLASNLES    60
GVPSRFSGSG SGTDFTLTIS SLQPEDFATY YCQQNNEDPR TFGGGTKVEI K            111

SEQ ID NO: 47            moltype = AA   length = 111
FEATURE                  Location/Qualifiers
source                   1..111
                         mol_type = protein
                         organism = synthetic construct
SEQUENCE: 47
DIQLTQSPSS LSASVGDRVT ITCRASKSVD SYGNSFMHWY QQKPGKAPKL LIFLASNLES    60
GVPSRFSGSG SGTDFTLTIS SLQPEDFATY YCQQNNEDPR TFGGGTKVEI K            111

SEQ ID NO: 48            moltype = AA   length = 111
FEATURE                  Location/Qualifiers
source                   1..111
                         mol_type = protein
                         organism = synthetic construct
SEQUENCE: 48
DIQLTQSPSS LSASVGDRVT ITCRASKSVD SYGNSFMHWY QQKPGKAPKL LIYLASHLES    60
GVPSRFSGSG SGTDFTLTIS SLQPEDFATY YCQQNNEDPR TFGGGTKVEI K            111

SEQ ID NO: 49            moltype = AA   length = 111
FEATURE                  Location/Qualifiers
source                   1..111
                         mol_type = protein
                         organism = synthetic construct
SEQUENCE: 49
DIQLTQSPSS LSASVGDRVT ITCRASKSVD SYGNSFMHWY QQKPGKAPKL LIYLASDLES    60
GVPSRFSGSG SGTDFTLTIS SLQPEDFATY YCQQNNEDPR TFGGGTKVEI K            111

SEQ ID NO: 50            moltype = AA   length = 111
FEATURE                  Location/Qualifiers
source                   1..111
                         mol_type = protein
                         organism = synthetic construct
SEQUENCE: 50
DIQLTQSPSS LSASVGDRVT ITCRASKSVD SYGNSFMHWY QQKPGKAPKL LIYLASQLES    60
GVPSRFSGSG SGTDFTLTIS SLQPEDFATY YCQQNNEDPR TFGGGTKVEI K            111

SEQ ID NO: 51            moltype = AA   length = 111
FEATURE                  Location/Qualifiers
source                   1..111
                         mol_type = protein
                         organism = synthetic construct
SEQUENCE: 51
```

```
DIQLTQSPSS LSASVGDRVT ITCRASKSVD SYGNSFMHWY QQKPGKAPKL LIYLASELES    60
GVPSRFSGSG SGTDFTLTIS SLQPEDFATY YCQQNNEDPR TFGGGTKVEI K            111

SEQ ID NO: 52           moltype = AA   length = 111
FEATURE                 Location/Qualifiers
source                  1..111
                        mol_type = protein
                        organism = synthetic construct
SEQUENCE: 52
DIQLTQSPSS LSASVGDRVT ITCRASKSVD SYGNSFMHWY QQKPGKAPKL LIYLASNLES    60
GVPSRFSGSG SGTDFTLTIS SLQPEDFATY YCQQNHEDPR TFGGGTKVEI K            111

SEQ ID NO: 53           moltype = AA   length = 111
FEATURE                 Location/Qualifiers
source                  1..111
                        mol_type = protein
                        organism = synthetic construct
SEQUENCE: 53
DIQLTQSPSS LSASVGDRVT ITCRASKSVD SYGNSFMHWY QQKPGKAPKL LIYLASNLES    60
GVPSRFSGSG SGTDFTLTIS SLQPEDFATY YCQQNYEDPR TFGGGTKVEI K            111

SEQ ID NO: 54           moltype = AA   length = 111
FEATURE                 Location/Qualifiers
source                  1..111
                        mol_type = protein
                        organism = synthetic construct
SEQUENCE: 54
DIQLTQSPSS LSASVGDRVT ITCRASKSVD SYGNSFMHWY QQKPGKAPKL LIYLASNLES    60
GVPSRFSGSG SGTDFTLTIS SLQPEDFATY YCQQNSEDPR TFGGGTKVEI K            111

SEQ ID NO: 55           moltype = AA   length = 111
FEATURE                 Location/Qualifiers
source                  1..111
                        mol_type = protein
                        organism = synthetic construct
SEQUENCE: 55
DIQLTQSPSS LSASVGDRVT ITCRASKSVD SYGNSFMHWY QQKPGKAPKL LIYLASNLES    60
GVPSRFSGSG SGTDFTLTIS SLQPEDFATY YCQQNNRDPR TFGGGTKVEI K            111

SEQ ID NO: 56           moltype = AA   length = 111
FEATURE                 Location/Qualifiers
source                  1..111
                        mol_type = protein
                        organism = synthetic construct
SEQUENCE: 56
DIQLTQSPSS LSASVGDRVT ITCRASKSVD SYGNSFMHWY QQKPGKAPKL LIYLASNLES    60
GVPSRFSGSG SGTDFTLTIS SLQPEDFATY YCQQNNDDPR TFGGGTKVEI K            111

SEQ ID NO: 57           moltype = AA   length = 111
FEATURE                 Location/Qualifiers
source                  1..111
                        mol_type = protein
                        organism = synthetic construct
SEQUENCE: 57
DIQLTQSPSS LSASVGDRVT ITCRASKSVD SYGNSFMHWY QQKPGKAPKL LIYLASNLES    60
GVPSRFSGSG SGTDFTLTIS SLQPEDFATY YCQQNNQDPR TFGGGTKVEI K            111

SEQ ID NO: 58           moltype = AA   length = 5
FEATURE                 Location/Qualifiers
source                  1..5
                        mol_type = protein
                        organism = synthetic construct
SEQUENCE: 58
AYSVN                                                                5

SEQ ID NO: 59           moltype = AA   length = 5
FEATURE                 Location/Qualifiers
source                  1..5
                        mol_type = protein
                        organism = synthetic construct
SEQUENCE: 59
RYSVN                                                                5

SEQ ID NO: 60           moltype = AA   length = 5
FEATURE                 Location/Qualifiers
source                  1..5
                        mol_type = protein
                        organism = synthetic construct
SEQUENCE: 60
```

```
KYSVN                                                                                  5

SEQ ID NO: 61           moltype = AA  length = 5
FEATURE                 Location/Qualifiers
source                  1..5
                        mol_type = protein
                        organism = synthetic construct
SEQUENCE: 61
HYSVN                                                                                  5

SEQ ID NO: 62           moltype = AA  length = 5
FEATURE                 Location/Qualifiers
source                  1..5
                        mol_type = protein
                        organism = synthetic construct
SEQUENCE: 62
QYSVN                                                                                  5

SEQ ID NO: 63           moltype = AA  length = 5
FEATURE                 Location/Qualifiers
source                  1..5
                        mol_type = protein
                        organism = synthetic construct
SEQUENCE: 63
EYSVN                                                                                  5

SEQ ID NO: 64           moltype = AA  length = 5
FEATURE                 Location/Qualifiers
source                  1..5
                        mol_type = protein
                        organism = synthetic construct
SEQUENCE: 64
SYSVN                                                                                  5

SEQ ID NO: 65           moltype = AA  length = 5
FEATURE                 Location/Qualifiers
source                  1..5
                        mol_type = protein
                        organism = synthetic construct
SEQUENCE: 65
YYSVN                                                                                  5

SEQ ID NO: 66           moltype = AA  length = 5
FEATURE                 Location/Qualifiers
source                  1..5
                        mol_type = protein
                        organism = synthetic construct
SEQUENCE: 66
AESVN                                                                                  5

SEQ ID NO: 67           moltype = AA  length = 7
FEATURE                 Location/Qualifiers
source                  1..7
                        mol_type = protein
                        organism = synthetic construct
SEQUENCE: 67
GFSLSAY                                                                                7

SEQ ID NO: 68           moltype = AA  length = 7
FEATURE                 Location/Qualifiers
source                  1..7
                        mol_type = protein
                        organism = synthetic construct
SEQUENCE: 68
GFSLNAY                                                                                7

SEQ ID NO: 69           moltype = AA  length = 7
FEATURE                 Location/Qualifiers
source                  1..7
                        mol_type = protein
                        organism = synthetic construct
SEQUENCE: 69
GGSLNAY                                                                                7

SEQ ID NO: 70           moltype = AA  length = 7
FEATURE                 Location/Qualifiers
source                  1..7
                        mol_type = protein
                        organism = synthetic construct
```

```
SEQUENCE: 70
GGSLNAY                                                                          7

SEQ ID NO: 71           moltype = AA  length = 7
FEATURE                 Location/Qualifiers
source                  1..7
                        mol_type = protein
                        organism = synthetic construct
SEQUENCE: 71
GYSLNAY                                                                          7

SEQ ID NO: 72           moltype = AA  length = 7
FEATURE                 Location/Qualifiers
source                  1..7
                        mol_type = protein
                        organism = synthetic construct
SEQUENCE: 72
GFSLRAY                                                                          7

SEQ ID NO: 73           moltype = AA  length = 7
FEATURE                 Location/Qualifiers
source                  1..7
                        mol_type = protein
                        organism = synthetic construct
SEQUENCE: 73
GFSLHAY                                                                          7

SEQ ID NO: 74           moltype = AA  length = 7
FEATURE                 Location/Qualifiers
source                  1..7
                        mol_type = protein
                        organism = synthetic construct
SEQUENCE: 74
GFSLDAY                                                                          7

SEQ ID NO: 75           moltype = AA  length = 7
FEATURE                 Location/Qualifiers
source                  1..7
                        mol_type = protein
                        organism = synthetic construct
SEQUENCE: 75
GFSLYAY                                                                          7

SEQ ID NO: 76           moltype = AA  length = 7
FEATURE                 Location/Qualifiers
source                  1..7
                        mol_type = protein
                        organism = synthetic construct
SEQUENCE: 76
GFSLNRY                                                                          7

SEQ ID NO: 77           moltype = AA  length = 7
FEATURE                 Location/Qualifiers
source                  1..7
                        mol_type = protein
                        organism = synthetic construct
SEQUENCE: 77
GFSLNKY                                                                          7

SEQ ID NO: 78           moltype = AA  length = 7
FEATURE                 Location/Qualifiers
source                  1..7
                        mol_type = protein
                        organism = synthetic construct
SEQUENCE: 78
GFSLNHY                                                                          7

SEQ ID NO: 79           moltype = AA  length = 7
FEATURE                 Location/Qualifiers
source                  1..7
                        mol_type = protein
                        organism = synthetic construct
SEQUENCE: 79
GFSLNQY                                                                          7

SEQ ID NO: 80           moltype = AA  length = 7
FEATURE                 Location/Qualifiers
source                  1..7
                        mol_type = protein
```

-continued

```
                              organism = synthetic construct
SEQUENCE: 80
GFSLNEY                                                              7

SEQ ID NO: 81                 moltype = AA   length = 7
FEATURE                       Location/Qualifiers
source                        1..7
                              mol_type = protein
                              organism = synthetic construct
SEQUENCE: 81
GFSLNSY                                                              7

SEQ ID NO: 82                 moltype = AA   length = 7
FEATURE                       Location/Qualifiers
source                        1..7
                              mol_type = protein
                              organism = synthetic construct
SEQUENCE: 82
GFSLNYY                                                              7

SEQ ID NO: 83                 moltype = AA   length = 7
FEATURE                       Location/Qualifiers
source                        1..7
                              mol_type = protein
                              organism = synthetic construct
SEQUENCE: 83
GFSLNAE                                                              7

SEQ ID NO: 84                 moltype = AA   length = 8
FEATURE                       Location/Qualifiers
source                        1..8
                              mol_type = protein
                              organism = synthetic construct
SEQUENCE: 84
GFSLSAYS                                                             8

SEQ ID NO: 85                 moltype = AA   length = 8
FEATURE                       Location/Qualifiers
source                        1..8
                              mol_type = protein
                              organism = synthetic construct
SEQUENCE: 85
GFSLNAYS                                                             8

SEQ ID NO: 86                 moltype = AA   length = 8
FEATURE                       Location/Qualifiers
source                        1..8
                              mol_type = protein
                              organism = synthetic construct
SEQUENCE: 86
GGSLNAYS                                                             8

SEQ ID NO: 87                 moltype = AA   length = 8
FEATURE                       Location/Qualifiers
source                        1..8
                              mol_type = protein
                              organism = synthetic construct
SEQUENCE: 87
GYSLNAYS                                                             8

SEQ ID NO: 88                 moltype = AA   length = 8
FEATURE                       Location/Qualifiers
source                        1..8
                              mol_type = protein
                              organism = synthetic construct
SEQUENCE: 88
GFSLRAYS                                                             8

SEQ ID NO: 89                 moltype = AA   length = 8
FEATURE                       Location/Qualifiers
source                        1..8
                              mol_type = protein
                              organism = synthetic construct
SEQUENCE: 89
GFSLHAYS                                                             8

SEQ ID NO: 90                 moltype = AA   length = 8
FEATURE                       Location/Qualifiers
source                        1..8
```

```
                        mol_type = protein
                        organism = synthetic construct
SEQUENCE: 90
GFSLDAYS                                                                        8

SEQ ID NO: 91           moltype = AA  length = 8
FEATURE                 Location/Qualifiers
source                  1..8
                        mol_type = protein
                        organism = synthetic construct
SEQUENCE: 91
GFSLYAYS                                                                        8

SEQ ID NO: 92           moltype = AA  length = 8
FEATURE                 Location/Qualifiers
source                  1..8
                        mol_type = protein
                        organism = synthetic construct
SEQUENCE: 92
GFSLSAYS                                                                        8

SEQ ID NO: 93           moltype = AA  length = 8
FEATURE                 Location/Qualifiers
source                  1..8
                        mol_type = protein
                        organism = synthetic construct
SEQUENCE: 93
GFSLNRYS                                                                        8

SEQ ID NO: 94           moltype = AA  length = 8
FEATURE                 Location/Qualifiers
source                  1..8
                        mol_type = protein
                        organism = synthetic construct
SEQUENCE: 94
GFSLNKYS                                                                        8

SEQ ID NO: 95           moltype = AA  length = 8
FEATURE                 Location/Qualifiers
source                  1..8
                        mol_type = protein
                        organism = synthetic construct
SEQUENCE: 95
GFSLNHYS                                                                        8

SEQ ID NO: 96           moltype = AA  length = 8
FEATURE                 Location/Qualifiers
source                  1..8
                        mol_type = protein
                        organism = synthetic construct
SEQUENCE: 96
GFSLNQYS                                                                        8

SEQ ID NO: 97           moltype = AA  length = 8
FEATURE                 Location/Qualifiers
source                  1..8
                        mol_type = protein
                        organism = synthetic construct
SEQUENCE: 97
GFSLNEYS                                                                        8

SEQ ID NO: 98           moltype = AA  length = 8
FEATURE                 Location/Qualifiers
source                  1..8
                        mol_type = protein
                        organism = synthetic construct
SEQUENCE: 98
GFSLNYYS                                                                        8

SEQ ID NO: 99           moltype = AA  length = 8
FEATURE                 Location/Qualifiers
source                  1..8
                        mol_type = protein
                        organism = synthetic construct
SEQUENCE: 99
GFSLNAES                                                                        8

SEQ ID NO: 100          moltype = AA  length = 16
FEATURE                 Location/Qualifiers
```

```
source                   1..16
                         mol_type = protein
                         organism = synthetic construct
SEQUENCE: 100
MIWGDGKIVY NSALKS                                            16

SEQ ID NO: 101           moltype = AA  length = 16
FEATURE                  Location/Qualifiers
source                   1..16
                         mol_type = protein
                         organism = synthetic construct
SEQUENCE: 101
YIYGDGKTNY NPALKS                                            16

SEQ ID NO: 102           moltype = AA  length = 16
FEATURE                  Location/Qualifiers
source                   1..16
                         mol_type = protein
                         organism = synthetic construct
SEQUENCE: 102
MIWSDGKIVY NSALKS                                            16

SEQ ID NO: 103           moltype = AA  length = 16
FEATURE                  Location/Qualifiers
source                   1..16
                         mol_type = protein
                         organism = synthetic construct
SEQUENCE: 103
MIWADGKIVY NSALKS                                            16

SEQ ID NO: 104           moltype = AA  length = 5
FEATURE                  Location/Qualifiers
source                   1..5
                         mol_type = protein
                         organism = synthetic construct
SEQUENCE: 104
WGDGK                                                         5

SEQ ID NO: 105           moltype = AA  length = 5
FEATURE                  Location/Qualifiers
source                   1..5
                         mol_type = protein
                         organism = synthetic construct
SEQUENCE: 105
YGDGK                                                         5

SEQ ID NO: 106           moltype = AA  length = 5
FEATURE                  Location/Qualifiers
source                   1..5
                         mol_type = protein
                         organism = synthetic construct
SEQUENCE: 106
WSDGK                                                         5

SEQ ID NO: 107           moltype = AA  length = 5
FEATURE                  Location/Qualifiers
source                   1..5
                         mol_type = protein
                         organism = synthetic construct
SEQUENCE: 107
WADGK                                                         5

SEQ ID NO: 108           moltype = AA  length = 7
FEATURE                  Location/Qualifiers
source                   1..7
                         mol_type = protein
                         organism = synthetic construct
SEQUENCE: 108
IWGDGKI                                                       7

SEQ ID NO: 109           moltype = AA  length = 7
FEATURE                  Location/Qualifiers
source                   1..7
                         mol_type = protein
                         organism = synthetic construct
SEQUENCE: 109
IYGDGKT                                                       7

SEQ ID NO: 110           moltype = AA  length = 7
```

```
FEATURE                 Location/Qualifiers
source                  1..7
                        mol_type = protein
                        organism = synthetic construct
SEQUENCE: 110
IWSDGKI                                                                    7

SEQ ID NO: 111          moltype = AA  length = 7
FEATURE                 Location/Qualifiers
source                  1..7
                        mol_type = protein
                        organism = synthetic construct
SEQUENCE: 111
IWADGKI                                                                    7

SEQ ID NO: 112          moltype = AA  length = 10
FEATURE                 Location/Qualifiers
source                  1..10
                        mol_type = protein
                        organism = synthetic construct
SEQUENCE: 112
DGYYPYAMDN                                                                10

SEQ ID NO: 113          moltype = AA  length = 10
FEATURE                 Location/Qualifiers
source                  1..10
                        mol_type = protein
                        organism = synthetic construct
SEQUENCE: 113
DGYYYYAMDV                                                                10

SEQ ID NO: 114          moltype = AA  length = 10
FEATURE                 Location/Qualifiers
source                  1..10
                        mol_type = protein
                        organism = synthetic construct
SEQUENCE: 114
HGYYPYAMDN                                                                10

SEQ ID NO: 115          moltype = AA  length = 10
FEATURE                 Location/Qualifiers
source                  1..10
                        mol_type = protein
                        organism = synthetic construct
SEQUENCE: 115
DLYYPYAMDN                                                                10

SEQ ID NO: 116          moltype = AA  length = 10
FEATURE                 Location/Qualifiers
source                  1..10
                        mol_type = protein
                        organism = synthetic construct
SEQUENCE: 116
DKYYPYAMDN                                                                10

SEQ ID NO: 117          moltype = AA  length = 10
FEATURE                 Location/Qualifiers
source                  1..10
                        mol_type = protein
                        organism = synthetic construct
SEQUENCE: 117
DGYYGYAMDN                                                                10

SEQ ID NO: 118          moltype = AA  length = 10
FEATURE                 Location/Qualifiers
source                  1..10
                        mol_type = protein
                        organism = synthetic construct
SEQUENCE: 118
DGYYAYAMDN                                                                10

SEQ ID NO: 119          moltype = AA  length = 10
FEATURE                 Location/Qualifiers
source                  1..10
                        mol_type = protein
                        organism = synthetic construct
SEQUENCE: 119
DGYYSYAMDN                                                                10
```

```
SEQ ID NO: 120          moltype = AA  length = 10
FEATURE                 Location/Qualifiers
source                  1..10
                        mol_type = protein
                        organism = synthetic construct
SEQUENCE: 120
DGYYTYAMDN                                                                   10

SEQ ID NO: 121          moltype = AA  length = 8
FEATURE                 Location/Qualifiers
source                  1..8
                        mol_type = protein
                        organism = synthetic construct
SEQUENCE: 121
GNSLNSYS                                                                      8

SEQ ID NO: 122          moltype =     length =
SEQUENCE: 122
000

SEQ ID NO: 123          moltype =     length =
SEQUENCE: 123
000

SEQ ID NO: 124          moltype =     length =
SEQUENCE: 124
000

SEQ ID NO: 125          moltype =     length =
SEQUENCE: 125
000

SEQ ID NO: 126          moltype =     length =
SEQUENCE: 126
000

SEQ ID NO: 127          moltype =     length =
SEQUENCE: 127
000

SEQ ID NO: 128          moltype =     length =
SEQUENCE: 128
000

SEQ ID NO: 129          moltype =     length =
SEQUENCE: 129
000

SEQ ID NO: 130          moltype = AA  length = 12
FEATURE                 Location/Qualifiers
source                  1..12
                        mol_type = protein
                        organism = synthetic construct
SEQUENCE: 130
AGDGYYPYAM DN                                                                12

SEQ ID NO: 131          moltype = AA  length = 12
FEATURE                 Location/Qualifiers
source                  1..12
                        mol_type = protein
                        organism = synthetic construct
SEQUENCE: 131
ARDGYYPYAM DN                                                                12

SEQ ID NO: 132          moltype = AA  length = 12
FEATURE                 Location/Qualifiers
source                  1..12
                        mol_type = protein
                        organism = synthetic construct
SEQUENCE: 132
ARDGYYYYAM DV                                                                12

SEQ ID NO: 133          moltype = AA  length = 12
FEATURE                 Location/Qualifiers
source                  1..12
                        mol_type = protein
                        organism = synthetic construct
SEQUENCE: 133
AGHGYYPYAM DN                                                                12
```

| | | |
|---|---|---|
| SEQ ID NO: 134<br>FEATURE<br>source | moltype = AA  length = 12<br>Location/Qualifiers<br>1..12<br>mol_type = protein<br>organism = synthetic construct | |
| SEQUENCE: 134<br>AGDLYYPYAM DN | | 12 |
| SEQ ID NO: 135<br>FEATURE<br>source | moltype = AA  length = 12<br>Location/Qualifiers<br>1..12<br>mol_type = protein<br>organism = synthetic construct | |
| SEQUENCE: 135<br>AGDKYYPYAM DN | | 12 |
| SEQ ID NO: 136<br>FEATURE<br>source | moltype = AA  length = 12<br>Location/Qualifiers<br>1..12<br>mol_type = protein<br>organism = synthetic construct | |
| SEQUENCE: 136<br>AGDGYYGYAM DN | | 12 |
| SEQ ID NO: 137<br>FEATURE<br>source | moltype = AA  length = 12<br>Location/Qualifiers<br>1..12<br>mol_type = protein<br>organism = synthetic construct | |
| SEQUENCE: 137<br>AGDGYYAYAM DN | | 12 |
| SEQ ID NO: 138<br>FEATURE<br>source | moltype = AA  length = 12<br>Location/Qualifiers<br>1..12<br>mol_type = protein<br>organism = synthetic construct | |
| SEQUENCE: 138<br>AGDGYYSYAM DN | | 12 |
| SEQ ID NO: 139<br>FEATURE<br>source | moltype = AA  length = 12<br>Location/Qualifiers<br>1..12<br>mol_type = protein<br>organism = synthetic construct | |
| SEQUENCE: 139<br>AGDGYYTYAM DN | | 12 |
| SEQ ID NO: 140<br>FEATURE<br>source | moltype = AA  length = 12<br>Location/Qualifiers<br>1..12<br>mol_type = protein<br>organism = synthetic construct | |
| SEQUENCE: 140<br>AGDGYYPYAM DN | | 12 |
| SEQ ID NO: 141<br>FEATURE<br>source | moltype = AA  length = 15<br>Location/Qualifiers<br>1..15<br>mol_type = protein<br>organism = synthetic construct | |
| SEQUENCE: 141<br>RASKSVDSYG NSFMH | | 15 |
| SEQ ID NO: 142<br>FEATURE<br>source | moltype = AA  length = 15<br>Location/Qualifiers<br>1..15<br>mol_type = protein<br>organism = synthetic construct | |
| SEQUENCE: 142<br>RASQSVDSNG NNFLH | | 15 |
| SEQ ID NO: 143<br>FEATURE<br>source | moltype = AA  length = 15<br>Location/Qualifiers<br>1..15<br>mol_type = protein<br>organism = synthetic construct | |
| SEQUENCE: 143 | | |

RASKSVDSYG NSRMH                                                                    15

SEQ ID NO: 144         moltype = AA  length = 15
FEATURE                Location/Qualifiers
source                 1..15
                       mol_type = protein
                       organism = synthetic construct
SEQUENCE: 144
RASKSVDSYG NSSMH                                                                    15

SEQ ID NO: 145         moltype =    length =
SEQUENCE: 145
000

SEQ ID NO: 146         moltype =    length =
SEQUENCE: 146
000

SEQ ID NO: 147         moltype =    length =
SEQUENCE: 147
000

SEQ ID NO: 148         moltype =    length =
SEQUENCE: 148
000

SEQ ID NO: 149         moltype = AA  length = 10
FEATURE                Location/Qualifiers
source                 1..10
                       mol_type = protein
                       organism = synthetic construct
SEQUENCE: 149
KSVDSYGNSF                                                                          10

SEQ ID NO: 150         moltype = AA  length = 10
FEATURE                Location/Qualifiers
source                 1..10
                       mol_type = protein
                       organism = synthetic construct
SEQUENCE: 150
QSVDSNGNNF                                                                          10

SEQ ID NO: 151         moltype = AA  length = 10
FEATURE                Location/Qualifiers
source                 1..10
                       mol_type = protein
                       organism = synthetic construct
SEQUENCE: 151
KSVDSYGNSR                                                                          10

SEQ ID NO: 152         moltype = AA  length = 10
FEATURE                Location/Qualifiers
source                 1..10
                       mol_type = protein
                       organism = synthetic construct
SEQUENCE: 152
KSVDSYGNSS                                                                          10

SEQ ID NO: 153         moltype = AA  length = 7
FEATURE                Location/Qualifiers
source                 1..7
                       mol_type = protein
                       organism = synthetic construct
SEQUENCE: 153
LASNLES                                                                              7

SEQ ID NO: 154         moltype = AA  length = 7
FEATURE                Location/Qualifiers
source                 1..7
                       mol_type = protein
                       organism = synthetic construct
SEQUENCE: 154
LASHLES                                                                              7

SEQ ID NO: 155         moltype = AA  length = 7
FEATURE                Location/Qualifiers
source                 1..7
                       mol_type = protein
                       organism = synthetic construct

```
SEQUENCE: 155
LASDLES                                                              7

SEQ ID NO: 156         moltype = AA  length = 7
FEATURE                Location/Qualifiers
source                 1..7
                       mol_type = protein
                       organism = synthetic construct
SEQUENCE: 156
LASQLES                                                              7

SEQ ID NO: 157         moltype = AA  length = 7
FEATURE                Location/Qualifiers
source                 1..7
                       mol_type = protein
                       organism = synthetic construct
SEQUENCE: 157
LASELES                                                              7

SEQ ID NO: 158         moltype = AA  length = 7
FEATURE                Location/Qualifiers
source                 1..7
                       mol_type = protein
                       organism = synthetic construct
SEQUENCE: 158
LASNRES                                                              7

SEQ ID NO: 159         moltype =     length =
SEQUENCE: 159
000

SEQ ID NO: 160         moltype =     length =
SEQUENCE: 160
000

SEQ ID NO: 161         moltype =     length =
SEQUENCE: 161
000

SEQ ID NO: 162         moltype =     length =
SEQUENCE: 162
000

SEQ ID NO: 163         moltype =     length =
SEQUENCE: 163
000

SEQ ID NO: 164         moltype =     length =
SEQUENCE: 164
000

SEQ ID NO: 165         moltype = AA  length = 9
FEATURE                Location/Qualifiers
source                 1..9
                       mol_type = protein
                       organism = synthetic construct
SEQUENCE: 165
QQNNEDPRT                                                            9

SEQ ID NO: 166         moltype = AA  length = 9
FEATURE                Location/Qualifiers
source                 1..9
                       mol_type = protein
                       organism = synthetic construct
SEQUENCE: 166
QQNNHTPRT                                                            9

SEQ ID NO: 167         moltype = AA  length = 9
FEATURE                Location/Qualifiers
source                 1..9
                       mol_type = protein
                       organism = synthetic construct
SEQUENCE: 167
QQNHEDPRT                                                            9

SEQ ID NO: 168         moltype = AA  length = 9
FEATURE                Location/Qualifiers
source                 1..9
                       mol_type = protein
```

```
SEQUENCE: 168                 organism = synthetic construct
QQNYEDPRT                                                                     9

SEQ ID NO: 169                moltype = AA   length = 9
FEATURE                       Location/Qualifiers
source                        1..9
                              mol_type = protein
                              organism = synthetic construct
SEQUENCE: 169
QQNSEDPRT                                                                     9

SEQ ID NO: 170                moltype = AA   length = 9
FEATURE                       Location/Qualifiers
source                        1..9
                              mol_type = protein
                              organism = synthetic construct
SEQUENCE: 170
QQNNRDPRT                                                                     9

SEQ ID NO: 171                moltype = AA   length = 9
FEATURE                       Location/Qualifiers
source                        1..9
                              mol_type = protein
                              organism = synthetic construct
SEQUENCE: 171
QQNNDDPRT                                                                     9

SEQ ID NO: 172                moltype = AA   length = 9
FEATURE                       Location/Qualifiers
source                        1..9
                              mol_type = protein
                              organism = synthetic construct
SEQUENCE: 172
QQNNQDPRT                                                                     9

SEQ ID NO: 173                moltype =    length =
SEQUENCE: 173
000

SEQ ID NO: 174                moltype =    length =
SEQUENCE: 174
000

SEQ ID NO: 175                moltype =    length =
SEQUENCE: 175
000

SEQ ID NO: 176                moltype =    length =
SEQUENCE: 176
000

SEQ ID NO: 177                moltype =    length =
SEQUENCE: 177
000

SEQ ID NO: 178                moltype =    length =
SEQUENCE: 178
000

SEQ ID NO: 179                moltype =    length =
SEQUENCE: 179
000

SEQ ID NO: 180                moltype =    length =
SEQUENCE: 180
000

SEQ ID NO: 181                moltype =    length =
SEQUENCE: 181
000

SEQ ID NO: 182                moltype =    length =
SEQUENCE: 182
000

SEQ ID NO: 183                moltype =    length =
SEQUENCE: 183
000
```

```
SEQ ID NO: 184         moltype =    length =
SEQUENCE: 184
000

SEQ ID NO: 185         moltype =    length =
SEQUENCE: 185
000

SEQ ID NO: 186         moltype =    length =
SEQUENCE: 186
000

SEQ ID NO: 187         moltype =    length =
SEQUENCE: 187
000

SEQ ID NO: 188         moltype =    length =
SEQUENCE: 188
000

SEQ ID NO: 189         moltype =    length =
SEQUENCE: 189
000

SEQ ID NO: 190         moltype =    length =
SEQUENCE: 190
000

SEQ ID NO: 191         moltype =    length =
SEQUENCE: 191
000

SEQ ID NO: 192         moltype =    length =
SEQUENCE: 192
000

SEQ ID NO: 193         moltype =    length =
SEQUENCE: 193
000

SEQ ID NO: 194         moltype =    length =
SEQUENCE: 194
000

SEQ ID NO: 195         moltype =    length =
SEQUENCE: 195
000

SEQ ID NO: 196         moltype =    length =
SEQUENCE: 196
000

SEQ ID NO: 197         moltype =    length =
SEQUENCE: 197
000

SEQ ID NO: 198         moltype = AA  length = 30
FEATURE                Location/Qualifiers
source                 1..30
                       mol_type = protein
                       organism = synthetic construct
SEQUENCE: 198
QVQLQESGPG LVAPSQSLSI TCTVSGFSLN                                30

SEQ ID NO: 199         moltype =    length =
SEQUENCE: 199
000

SEQ ID NO: 200         moltype = AA  length = 30
FEATURE                Location/Qualifiers
source                 1..30
                       mol_type = protein
                       organism = synthetic construct
SEQUENCE: 200
EVQLQESGPG LVKPSETLSL TCTVSGFSLN                                30

SEQ ID NO: 201         moltype = AA  length = 30
FEATURE                Location/Qualifiers
```

```
source                   1..30
                         mol_type = protein
                         organism = synthetic construct
SEQUENCE: 201
EVQLVQSGAE VKKPGASVKV SCKASGFSLN                                     30

SEQ ID NO: 202           moltype = AA  length = 30
FEATURE                  Location/Qualifiers
source                   1..30
                         mol_type = protein
                         organism = synthetic construct
SEQUENCE: 202
EVQLVQSGAE VKKPGSSVKV SCKASGFSLN                                     30

SEQ ID NO: 203           moltype = AA  length = 30
FEATURE                  Location/Qualifiers
source                   1..30
                         mol_type = protein
                         organism = synthetic construct
SEQUENCE: 203
EVQLVESGGG LVKPGGSLRL SCAASGFSLN                                     30

SEQ ID NO: 204           moltype = AA  length = 30
FEATURE                  Location/Qualifiers
source                   1..30
                         mol_type = protein
                         organism = synthetic construct
SEQUENCE: 204
EVQLLESGGG LVQPGGSLRL SCAASGFSLN                                     30

SEQ ID NO: 205           moltype = AA  length = 30
FEATURE                  Location/Qualifiers
source                   1..30
                         mol_type = protein
                         organism = synthetic construct
SEQUENCE: 205
EVQLQESGPG LVKPSETLSL TCTVSGGSLN                                     30

SEQ ID NO: 206           moltype = AA  length = 30
FEATURE                  Location/Qualifiers
source                   1..30
                         mol_type = protein
                         organism = synthetic construct
SEQUENCE: 206
QVQLQESGPG LVKPSETLSL TCTVSGGSLN                                     30

SEQ ID NO: 207           moltype = AA  length = 30
FEATURE                  Location/Qualifiers
source                   1..30
                         mol_type = protein
                         organism = synthetic construct
SEQUENCE: 207
EVQLLESGGG LVQPGGSLRL SCAASGYSLN                                     30

SEQ ID NO: 208           moltype = AA  length = 30
FEATURE                  Location/Qualifiers
source                   1..30
                         mol_type = protein
                         organism = synthetic construct
SEQUENCE: 208
EVQLLESGGG LVQPGGSLRL SCAASGFSLR                                     30

SEQ ID NO: 209           moltype = AA  length = 30
FEATURE                  Location/Qualifiers
source                   1..30
                         mol_type = protein
                         organism = synthetic construct
SEQUENCE: 209
EVQLLESGGG LVQPGGSLRL SCAASGFSLH                                     30

SEQ ID NO: 210           moltype = AA  length = 30
FEATURE                  Location/Qualifiers
source                   1..30
                         mol_type = protein
                         organism = synthetic construct
SEQUENCE: 210
EVQLLESGGG LVQPGGSLRL SCAASGFSLD                                     30

SEQ ID NO: 211           moltype = AA  length = 30
```

```
FEATURE               Location/Qualifiers
source                1..30
                      mol_type = protein
                      organism = synthetic construct
SEQUENCE: 211
EVQLLESGGG LVQPGGSLRL SCAASGFSLY                                    30

SEQ ID NO: 212        moltype = AA  length = 30
FEATURE               Location/Qualifiers
source                1..30
                      mol_type = protein
                      organism = synthetic construct
SEQUENCE: 212
EVQLLESGGG LVQPGGSLRL SCAASGFSLS                                    30

SEQ ID NO: 213        moltype =   length =
SEQUENCE: 213
000

SEQ ID NO: 214        moltype =   length =
SEQUENCE: 214
000

SEQ ID NO: 215        moltype =   length =
SEQUENCE: 215
000

SEQ ID NO: 216        moltype =   length =
SEQUENCE: 216
000

SEQ ID NO: 217        moltype =   length =
SEQUENCE: 217
000

SEQ ID NO: 218        moltype =   length =
SEQUENCE: 218
000

SEQ ID NO: 219        moltype =   length =
SEQUENCE: 219
000

SEQ ID NO: 220        moltype =   length =
SEQUENCE: 220
000

SEQ ID NO: 221        moltype =   length =
SEQUENCE: 221
000

SEQ ID NO: 222        moltype =   length =
SEQUENCE: 222
000

SEQ ID NO: 223        moltype =   length =
SEQUENCE: 223
000

SEQ ID NO: 224        moltype =   length =
SEQUENCE: 224
000

SEQ ID NO: 225        moltype =   length =
SEQUENCE: 225
000

SEQ ID NO: 226        moltype =   length =
SEQUENCE: 226
000

SEQ ID NO: 227        moltype =   length =
SEQUENCE: 227
000

SEQ ID NO: 228        moltype =   length =
SEQUENCE: 228
000
```

```
SEQ ID NO: 229          moltype =    length =
SEQUENCE: 229
000

SEQ ID NO: 230          moltype = AA   length = 23
FEATURE                 Location/Qualifiers
source                  1..23
                        mol_type = protein
                        organism = synthetic construct
SEQUENCE: 230
NIVLTQSPAS LAVSLGQRAT ISC                                          23

SEQ ID NO: 231          moltype = AA   length = 23
FEATURE                 Location/Qualifiers
source                  1..23
                        mol_type = protein
                        organism = synthetic construct
SEQUENCE: 231
DIQLTQSPSS LSASVGDRVT ITC                                          23

SEQ ID NO: 232          moltype =    length =
SEQUENCE: 232
000

SEQ ID NO: 233          moltype = AA   length = 23
FEATURE                 Location/Qualifiers
source                  1..23
                        mol_type = protein
                        organism = synthetic construct
SEQUENCE: 233
EIVLTQSPAT LSVSPGERAT LSC                                          23

SEQ ID NO: 234          moltype = AA   length = 23
FEATURE                 Location/Qualifiers
source                  1..23
                        mol_type = protein
                        organism = synthetic construct
SEQUENCE: 234
DIVLTQSPLS LPVTPGEPAS ISC                                          23

SEQ ID NO: 235          moltype = AA   length = 23
FEATURE                 Location/Qualifiers
source                  1..23
                        mol_type = protein
                        organism = synthetic construct
SEQUENCE: 235
DIVLTQSPDS LAVSLGERAT INC                                          23

SEQ ID NO: 236          moltype =    length =
SEQUENCE: 236
000

SEQ ID NO: 237          moltype =    length =
SEQUENCE: 237
000

SEQ ID NO: 238          moltype =    length =
SEQUENCE: 238
000

SEQ ID NO: 239          moltype = AA   length = 23
FEATURE                 Location/Qualifiers
source                  1..23
                        mol_type = protein
                        organism = synthetic construct
SEQUENCE: 239
DIVLTQSPAS LAVSPGERAT ISC                                          23

SEQ ID NO: 240          moltype = AA   length = 23
FEATURE                 Location/Qualifiers
source                  1..23
                        mol_type = protein
                        organism = synthetic construct
SEQUENCE: 240
DIVLTQSPAS LAVSPGERAT ISC                                          23

SEQ ID NO: 241          moltype =    length =
SEQUENCE: 241
000
```

| | | |
|---|---|---|
| SEQ ID NO: 242<br>SEQUENCE: 242<br>000 | moltype = length = | |
| SEQ ID NO: 243<br>SEQUENCE: 243<br>000 | moltype = length = | |
| SEQ ID NO: 244<br>SEQUENCE: 244<br>000 | moltype = length = | |
| SEQ ID NO: 245<br>SEQUENCE: 245<br>000 | moltype = length = | |
| SEQ ID NO: 246<br>SEQUENCE: 246<br>000 | moltype = length = | |
| SEQ ID NO: 247<br>SEQUENCE: 247<br>000 | moltype = length = | |
| SEQ ID NO: 248<br>SEQUENCE: 248<br>000 | moltype = length = | |
| SEQ ID NO: 249<br>SEQUENCE: 249<br>000 | moltype = length = | |
| SEQ ID NO: 250<br>SEQUENCE: 250<br>000 | moltype = length = | |
| SEQ ID NO: 251<br>SEQUENCE: 251<br>000 | moltype = length = | |
| SEQ ID NO: 252<br>SEQUENCE: 252<br>000 | moltype = length = | |
| SEQ ID NO: 253<br>SEQUENCE: 253<br>000 | moltype = length = | |
| SEQ ID NO: 254<br>SEQUENCE: 254<br>000 | moltype = length = | |
| SEQ ID NO: 255<br>FEATURE<br>source<br>SEQUENCE: 255<br>WIRQPPGKAL EWLA | moltype = AA  length = 14<br>Location/Qualifiers<br>1..14<br>mol_type = protein<br>organism = synthetic construct | 14 |
| SEQ ID NO: 256<br>FEATURE<br>source<br>SEQUENCE: 256<br>WVRQPPGKGL EWLG | moltype = AA  length = 14<br>Location/Qualifiers<br>1..14<br>mol_type = protein<br>organism = synthetic construct | 14 |
| SEQ ID NO: 257<br>SEQUENCE: 257<br>000 | moltype = length = | |
| SEQ ID NO: 258<br>FEATURE<br>source<br>SEQUENCE: 258 | moltype = AA  length = 14<br>Location/Qualifiers<br>1..14<br>mol_type = protein<br>organism = synthetic construct | |

```
                                                      -continued
WIRQPPGKGL EWLG                                                           14

SEQ ID NO: 259          moltype = AA  length = 14
FEATURE                 Location/Qualifiers
source                  1..14
                        mol_type = protein
                        organism = synthetic construct
SEQUENCE: 259
WVRQAPGQGL EWLG                                                           14

SEQ ID NO: 260          moltype =   length =
SEQUENCE: 260
000

SEQ ID NO: 261          moltype =   length =
SEQUENCE: 261
000

SEQ ID NO: 262          moltype = AA  length = 14
FEATURE                 Location/Qualifiers
source                  1..14
                        mol_type = protein
                        organism = synthetic construct
SEQUENCE: 262
WVRQAPGKGL EWLG                                                           14

SEQ ID NO: 263          moltype = AA  length = 14
FEATURE                 Location/Qualifiers
source                  1..14
                        mol_type = protein
                        organism = synthetic construct
SEQUENCE: 263
WVRQPPGKGL EWLG                                                           14

SEQ ID NO: 264          moltype =   length =
SEQUENCE: 264
000

SEQ ID NO: 265          moltype =   length =
SEQUENCE: 265
000

SEQ ID NO: 266          moltype =   length =
SEQUENCE: 266
000

SEQ ID NO: 267          moltype =   length =
SEQUENCE: 267
000

SEQ ID NO: 268          moltype =   length =
SEQUENCE: 268
000

SEQ ID NO: 269          moltype =   length =
SEQUENCE: 269
000

SEQ ID NO: 270          moltype =   length =
SEQUENCE: 270
000

SEQ ID NO: 271          moltype =   length =
SEQUENCE: 271
000

SEQ ID NO: 272          moltype =   length =
SEQUENCE: 272
000

SEQ ID NO: 273          moltype =   length =
SEQUENCE: 273
000

SEQ ID NO: 274          moltype =   length =
SEQUENCE: 274
000

SEQ ID NO: 275          moltype =   length =
```

```
SEQUENCE: 275
000

SEQ ID NO: 276           moltype =    length =
SEQUENCE: 276
000

SEQ ID NO: 277           moltype =    length =
SEQUENCE: 277
000

SEQ ID NO: 278           moltype =    length =
SEQUENCE: 278
000

SEQ ID NO: 279           moltype =    length =
SEQUENCE: 279
000

SEQ ID NO: 280           moltype =    length =
SEQUENCE: 280
000

SEQ ID NO: 281           moltype =    length =
SEQUENCE: 281
000

SEQ ID NO: 282           moltype =    length =
SEQUENCE: 282
000

SEQ ID NO: 283           moltype =    length =
SEQUENCE: 283
000

SEQ ID NO: 284           moltype =    length =
SEQUENCE: 284
000

SEQ ID NO: 285           moltype =    length =
SEQUENCE: 285
000

SEQ ID NO: 286           moltype = AA  length = 15
FEATURE                  Location/Qualifiers
source                   1..15
                         mol_type = protein
                         organism = synthetic construct
SEQUENCE: 286
WYQQKPGQPP KLLIY                                                      15

SEQ ID NO: 287           moltype =    length =
SEQUENCE: 287
000

SEQ ID NO: 288           moltype = AA  length = 15
FEATURE                  Location/Qualifiers
source                   1..15
                         mol_type = protein
                         organism = synthetic construct
SEQUENCE: 288
WYQQKPGKAP KLLIY                                                      15

SEQ ID NO: 289           moltype =    length =
SEQUENCE: 289
000

SEQ ID NO: 290           moltype = AA  length = 15
FEATURE                  Location/Qualifiers
source                   1..15
                         mol_type = protein
                         organism = synthetic construct
SEQUENCE: 290
WYQQKPGQAP RLLIY                                                      15

SEQ ID NO: 291           moltype = AA  length = 15
FEATURE                  Location/Qualifiers
source                   1..15
                         mol_type = protein
```

-continued

| | | |
|---|---|---|
| | organism = synthetic construct | |
| SEQUENCE: 291 | | |
| WYLQKPGQSP QLLIY | | 15 |
| SEQ ID NO: 292<br>SEQUENCE: 292<br>000 | moltype =   length = | |
| SEQ ID NO: 293<br>SEQUENCE: 293<br>000 | moltype =   length = | |
| SEQ ID NO: 294<br>SEQUENCE: 294<br>000 | moltype =   length = | |
| SEQ ID NO: 295<br>SEQUENCE: 295<br>000 | moltype =   length = | |
| SEQ ID NO: 296<br>SEQUENCE: 296<br>000 | moltype =   length = | |
| SEQ ID NO: 297<br>SEQUENCE: 297<br>000 | moltype =   length = | |
| SEQ ID NO: 298<br>SEQUENCE: 298<br>000 | moltype =   length = | |
| SEQ ID NO: 299<br>SEQUENCE: 299<br>000 | moltype =   length = | |
| SEQ ID NO: 300<br>FEATURE<br>source | moltype = AA  length = 15<br>Location/Qualifiers<br>1..15<br>mol_type = protein<br>organism = synthetic construct | |
| SEQUENCE: 300 | | |
| WYQQKPGKAP KLLIR | | 15 |
| SEQ ID NO: 301<br>FEATURE<br>source | moltype = AA  length = 15<br>Location/Qualifiers<br>1..15<br>mol_type = protein<br>organism = synthetic construct | |
| SEQUENCE: 301 | | |
| WYQQKPGKAP KLLIF | | 15 |
| SEQ ID NO: 302<br>SEQUENCE: 302<br>000 | moltype =   length = | |
| SEQ ID NO: 303<br>SEQUENCE: 303<br>000 | moltype =   length = | |
| SEQ ID NO: 304<br>SEQUENCE: 304<br>000 | moltype =   length = | |
| SEQ ID NO: 305<br>SEQUENCE: 305<br>000 | moltype =   length = | |
| SEQ ID NO: 306<br>SEQUENCE: 306<br>000 | moltype =   length = | |
| SEQ ID NO: 307<br>SEQUENCE: 307<br>000 | moltype =   length = | |
| SEQ ID NO: 308<br>SEQUENCE: 308<br>000 | moltype =   length = | |

-continued

```
SEQ ID NO: 309          moltype =    length =
SEQUENCE: 309
000

SEQ ID NO: 310          moltype =    length =
SEQUENCE: 310
000

SEQ ID NO: 311          moltype = AA   length = 32
FEATURE                 Location/Qualifiers
source                  1..32
                        mol_type = protein
                        organism = synthetic construct
SEQUENCE: 311
RLTISKDTSK NQVVLTMTNM DPVDTATYYC AG                              32

SEQ ID NO: 312          moltype = AA   length = 32
FEATURE                 Location/Qualifiers
source                  1..32
                        mol_type = protein
                        organism = synthetic construct
SEQUENCE: 312
RLNISKDSSK SQVFLKMSSL QSDDTARYYC AG                              32

SEQ ID NO: 313          moltype = AA   length = 32
FEATURE                 Location/Qualifiers
source                  1..32
                        mol_type = protein
                        organism = synthetic construct
SEQUENCE: 313
RLTISKDSSK SQVFLKMSSL QSDDTARYYC AG                              32

SEQ ID NO: 314          moltype = AA   length = 32
FEATURE                 Location/Qualifiers
source                  1..32
                        mol_type = protein
                        organism = synthetic construct
SEQUENCE: 314
RLTISKDSSK NQVSLKLSSV TAADTAVYYC AG                              32

SEQ ID NO: 315          moltype = AA   length = 32
FEATURE                 Location/Qualifiers
source                  1..32
                        mol_type = protein
                        organism = synthetic construct
SEQUENCE: 315
RLTITKDSST STVYMELSSL RSEDTAVYYC AG                              32

SEQ ID NO: 316          moltype =    length =
SEQUENCE: 316
000

SEQ ID NO: 317          moltype = AA   length = 32
FEATURE                 Location/Qualifiers
source                  1..32
                        mol_type = protein
                        organism = synthetic construct
SEQUENCE: 317
RLTISKDSSK NTVYLQMNSL KTEDTAVYYC AG                              32

SEQ ID NO: 318          moltype = AA   length = 32
FEATURE                 Location/Qualifiers
source                  1..32
                        mol_type = protein
                        organism = synthetic construct
SEQUENCE: 318
RLTISKDSSK NTVYLQMNSL RAEDTAVYYC AG                              32

SEQ ID NO: 319          moltype = AA   length = 32
FEATURE                 Location/Qualifiers
source                  1..32
                        mol_type = protein
                        organism = synthetic construct
SEQUENCE: 319
RLTISLDTSK SQVFLKMSSL TAADTAVYYC AR                              32

SEQ ID NO: 320          moltype =    length =
SEQUENCE: 320
```

000

SEQ ID NO: 321          moltype =      length =
SEQUENCE: 321
000

SEQ ID NO: 322          moltype =      length =
SEQUENCE: 322
000

SEQ ID NO: 323          moltype =      length =
SEQUENCE: 323
000

SEQ ID NO: 324          moltype =      length =
SEQUENCE: 324
000

SEQ ID NO: 325          moltype =      length =
SEQUENCE: 325
000

SEQ ID NO: 326          moltype =      length =
SEQUENCE: 326
000

SEQ ID NO: 327          moltype =      length =
SEQUENCE: 327
000

SEQ ID NO: 328          moltype =      length =
SEQUENCE: 328
000

SEQ ID NO: 329          moltype =      length =
SEQUENCE: 329
000

SEQ ID NO: 330          moltype =      length =
SEQUENCE: 330
000

SEQ ID NO: 331          moltype =      length =
SEQUENCE: 331
000

SEQ ID NO: 332          moltype =      length =
SEQUENCE: 332
000

SEQ ID NO: 333          moltype =      length =
SEQUENCE: 333
000

SEQ ID NO: 334          moltype =      length =
SEQUENCE: 334
000

SEQ ID NO: 335          moltype =      length =
SEQUENCE: 335
000

SEQ ID NO: 336          moltype =      length =
SEQUENCE: 336
000

SEQ ID NO: 337          moltype =      length =
SEQUENCE: 337
000

SEQ ID NO: 338          moltype =      length =
SEQUENCE: 338
000

SEQ ID NO: 339          moltype =      length =
SEQUENCE: 339
000

SEQ ID NO: 340          moltype =      length =

```
SEQUENCE: 340
000

SEQ ID NO: 341          moltype =    length =
SEQUENCE: 341
000

SEQ ID NO: 342          moltype =    length =
SEQUENCE: 342
000

SEQ ID NO: 343          moltype = AA   length = 32
FEATURE                 Location/Qualifiers
source                  1..32
                        mol_type = protein
                        organism = synthetic construct
SEQUENCE: 343
GVPDRFSGSG SGTDFTLTIS SLQAEDVAVY YC                                32

SEQ ID NO: 344          moltype = AA   length = 32
FEATURE                 Location/Qualifiers
source                  1..32
                        mol_type = protein
                        organism = synthetic construct
SEQUENCE: 344
GVPARFSGSG SRTDFTLTID PVEADDAASY YC                                32

SEQ ID NO: 345          moltype = AA   length = 32
FEATURE                 Location/Qualifiers
source                  1..32
                        mol_type = protein
                        organism = synthetic construct
SEQUENCE: 345
GVPSRFSGSG SRTDFTLTIS SLQPEDFATY YC                                32

SEQ ID NO: 346          moltype =    length =
SEQUENCE: 346
000

SEQ ID NO: 347          moltype = AA   length = 32
FEATURE                 Location/Qualifiers
source                  1..32
                        mol_type = protein
                        organism = synthetic construct
SEQUENCE: 347
GIPARFSGSG SRTEFTLTIS SLQSEDFAVY YC                                32

SEQ ID NO: 348          moltype = AA   length = 32
FEATURE                 Location/Qualifiers
source                  1..32
                        mol_type = protein
                        organism = synthetic construct
SEQUENCE: 348
GVPDRFSGSG SRTDFTLKIS RVEAEDVGVY YC                                32

SEQ ID NO: 349          moltype = AA   length = 32
FEATURE                 Location/Qualifiers
source                  1..32
                        mol_type = protein
                        organism = synthetic construct
SEQUENCE: 349
GVPSRFSGSG SGTDFTLTIS SLQPEDFATY YC                                32

SEQ ID NO: 350          moltype =    length =
SEQUENCE: 350
000

SEQ ID NO: 351          moltype = AA   length = 32
FEATURE                 Location/Qualifiers
source                  1..32
                        mol_type = protein
                        organism = synthetic construct
SEQUENCE: 351
GIPARFSGSG SGTEFTLTIS SLQSEDFAVY YC                                32

SEQ ID NO: 352          moltype = AA   length = 32
FEATURE                 Location/Qualifiers
source                  1..32
                        mol_type = protein
```

```
                         organism = synthetic construct
SEQUENCE: 352
GVPDRFSGSG SGTDFTLKIS RVEAEDVGVY YC                              32

SEQ ID NO: 353           moltype = AA   length = 32
FEATURE                  Location/Qualifiers
source                   1..32
                         mol_type = protein
                         organism = synthetic construct
SEQUENCE: 353
GVPDRFSGSG SGTDFTLTIS RVEADDVAVY YC                              32

SEQ ID NO: 354           moltype =   length =
SEQUENCE: 354
000

SEQ ID NO: 355           moltype =   length =
SEQUENCE: 355
000

SEQ ID NO: 356           moltype =   length =
SEQUENCE: 356
000

SEQ ID NO: 357           moltype =   length =
SEQUENCE: 357
000

SEQ ID NO: 358           moltype =   length =
SEQUENCE: 358
000

SEQ ID NO: 359           moltype =   length =
SEQUENCE: 359
000

SEQ ID NO: 360           moltype =   length =
SEQUENCE: 360
000

SEQ ID NO: 361           moltype =   length =
SEQUENCE: 361
000

SEQ ID NO: 362           moltype =   length =
SEQUENCE: 362
000

SEQ ID NO: 363           moltype =   length =
SEQUENCE: 363
000

SEQ ID NO: 364           moltype =   length =
SEQUENCE: 364
000

SEQ ID NO: 365           moltype =   length =
SEQUENCE: 365
000

SEQ ID NO: 366           moltype =   length =
SEQUENCE: 366
000

SEQ ID NO: 367           moltype =   length =
SEQUENCE: 367
000

SEQ ID NO: 368           moltype = AA   length = 11
FEATURE                  Location/Qualifiers
source                   1..11
                         mol_type = protein
                         organism = synthetic construct
SEQUENCE: 368
WGQGSLVTVS S                                                     11

SEQ ID NO: 369           moltype = AA   length = 11
FEATURE                  Location/Qualifiers
source                   1..11
```

```
                        mol_type = protein
                        organism = synthetic construct
SEQUENCE: 369
WGHGTSVTVS S                                                                11

SEQ ID NO: 370          moltype =   length =
SEQUENCE: 370
000

SEQ ID NO: 371          moltype = AA  length = 11
FEATURE                 Location/Qualifiers
source                  1..11
                        mol_type = protein
                        organism = synthetic construct
SEQUENCE: 371
WGQGTTVTVS S                                                                11

SEQ ID NO: 372          moltype =   length =
SEQUENCE: 372
000

SEQ ID NO: 373          moltype =   length =
SEQUENCE: 373
000

SEQ ID NO: 374          moltype =   length =
SEQUENCE: 374
000

SEQ ID NO: 375          moltype =   length =
SEQUENCE: 375
000

SEQ ID NO: 376          moltype =   length =
SEQUENCE: 376
000

SEQ ID NO: 377          moltype =   length =
SEQUENCE: 377
000

SEQ ID NO: 378          moltype =   length =
SEQUENCE: 378
000

SEQ ID NO: 379          moltype =   length =
SEQUENCE: 379
000

SEQ ID NO: 380          moltype =   length =
SEQUENCE: 380
000

SEQ ID NO: 381          moltype =   length =
SEQUENCE: 381
000

SEQ ID NO: 382          moltype =   length =
SEQUENCE: 382
000

SEQ ID NO: 383          moltype =   length =
SEQUENCE: 383
000

SEQ ID NO: 384          moltype =   length =
SEQUENCE: 384
000

SEQ ID NO: 385          moltype =   length =
SEQUENCE: 385
000

SEQ ID NO: 386          moltype =   length =
SEQUENCE: 386
000

SEQ ID NO: 387          moltype =   length =
SEQUENCE: 387
```

-continued

```
000

SEQ ID NO: 388            moltype =    length =
SEQUENCE: 388
000

SEQ ID NO: 389            moltype =    length =
SEQUENCE: 389
000

SEQ ID NO: 390            moltype =    length =
SEQUENCE: 390
000

SEQ ID NO: 391            moltype =    length =
SEQUENCE: 391
000

SEQ ID NO: 392            moltype =    length =
SEQUENCE: 392
000

SEQ ID NO: 393            moltype =    length =
SEQUENCE: 393
000

SEQ ID NO: 394            moltype =    length =
SEQUENCE: 394
000

SEQ ID NO: 395            moltype =    length =
SEQUENCE: 395
000

SEQ ID NO: 396            moltype =    length =
SEQUENCE: 396
000

SEQ ID NO: 397            moltype =    length =
SEQUENCE: 397
000

SEQ ID NO: 398            moltype =    length =
SEQUENCE: 398
000

SEQ ID NO: 399            moltype =    length =
SEQUENCE: 399
000

SEQ ID NO: 400            moltype = AA   length = 10
FEATURE                   Location/Qualifiers
source                    1..10
                          mol_type = protein
                          organism = synthetic construct
SEQUENCE: 400
FGGGTKVEIK                                                               10

SEQ ID NO: 401            moltype = AA   length = 10
FEATURE                   Location/Qualifiers
source                    1..10
                          mol_type = protein
                          organism = synthetic construct
SEQUENCE: 401
FGGGTKLEIK                                                               10

SEQ ID NO: 402            moltype =    length =
SEQUENCE: 402
000

SEQ ID NO: 403            moltype =    length =
SEQUENCE: 403
000

SEQ ID NO: 404            moltype =    length =
SEQUENCE: 404
000

SEQ ID NO: 405            moltype =    length =
```

| | | |
|---|---|---|
| SEQUENCE: 405 000 | | |
| SEQ ID NO: 406 SEQUENCE: 406 000 | moltype = | length = |
| SEQ ID NO: 407 SEQUENCE: 407 000 | moltype = | length = |
| SEQ ID NO: 408 SEQUENCE: 408 000 | moltype = | length = |
| SEQ ID NO: 409 SEQUENCE: 409 000 | moltype = | length = |
| SEQ ID NO: 410 SEQUENCE: 410 000 | moltype = | length = |
| SEQ ID NO: 411 SEQUENCE: 411 000 | moltype = | length = |
| SEQ ID NO: 412 SEQUENCE: 412 000 | moltype = | length = |
| SEQ ID NO: 413 SEQUENCE: 413 000 | moltype = | length = |
| SEQ ID NO: 414 SEQUENCE: 414 000 | moltype = | length = |
| SEQ ID NO: 415 SEQUENCE: 415 000 | moltype = | length = |
| SEQ ID NO: 416 SEQUENCE: 416 000 | moltype = | length = |
| SEQ ID NO: 417 SEQUENCE: 417 000 | moltype = | length = |
| SEQ ID NO: 418 SEQUENCE: 418 000 | moltype = | length = |
| SEQ ID NO: 419 SEQUENCE: 419 000 | moltype = | length = |
| SEQ ID NO: 420 SEQUENCE: 420 000 | moltype = | length = |
| SEQ ID NO: 421 SEQUENCE: 421 000 | moltype = | length = |
| SEQ ID NO: 422 SEQUENCE: 422 000 | moltype = | length = |
| SEQ ID NO: 423 SEQUENCE: 423 000 | moltype = | length = |
| SEQ ID NO: 424 SEQUENCE: 424 000 | moltype = | length = |

```
SEQ ID NO: 425          moltype = AA  length = 329
FEATURE                 Location/Qualifiers
source                  1..329
                        mol_type = protein
                        organism = synthetic construct
SEQUENCE: 425
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 426          moltype = AA  length = 327
FEATURE                 Location/Qualifiers
source                  1..327
                        mol_type = protein
                        organism = synthetic construct
SEQUENCE: 426
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTQ PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 427          moltype = AA  length = 327
FEATURE                 Location/Qualifiers
source                  1..327
                        mol_type = protein
                        organism = synthetic construct
SEQUENCE: 427
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTQ PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 428          moltype = AA  length = 327
FEATURE                 Location/Qualifiers
source                  1..327
                        mol_type = protein
                        organism = synthetic construct
SEQUENCE: 428
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEELGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 429          moltype = AA  length = 324
FEATURE                 Location/Qualifiers
source                  1..324
                        mol_type = protein
                        organism = synthetic construct
SEQUENCE: 429
ASTKGPSVFP LAPCSRSTSE STAALGCLVK DYFPEPVTVS WNSGALTSGV HTFPAVLQSS   60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSP                                        324

SEQ ID NO: 430          moltype = AA  length = 329
FEATURE                 Location/Qualifiers
source                  1..329
                        mol_type = protein
                        organism = synthetic construct
SEQUENCE: 430
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 431          moltype = AA  length = 329
```

| FEATURE | Location/Qualifiers |
|---|---|
| source | 1..329 |
| | mol_type = protein |
| | organism = synthetic construct |

SEQUENCE: 431

```
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329
```

| SEQ ID NO: 432 | moltype = AA length = 329 |
|---|---|
| FEATURE | Location/Qualifiers |
| source | 1..329 |
| | mol_type = protein |
| | organism = synthetic construct |

SEQUENCE: 432

```
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329
```

| SEQ ID NO: 433 | moltype = AA length = 329 |
|---|---|
| FEATURE | Location/Qualifiers |
| source | 1..329 |
| | mol_type = protein |
| | organism = synthetic construct |

SEQUENCE: 433

```
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329
```

| SEQ ID NO: 434 | moltype = AA length = 329 |
|---|---|
| FEATURE | Location/Qualifiers |
| source | 1..329 |
| | mol_type = protein |
| | organism = synthetic construct |

SEQUENCE: 434

```
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329
```

| SEQ ID NO: 435 | moltype = AA length = 329 |
|---|---|
| FEATURE | Location/Qualifiers |
| source | 1..329 |
| | mol_type = protein |
| | organism = synthetic construct |

SEQUENCE: 435

```
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329
```

| SEQ ID NO: 436 | moltype = AA length = 329 |
|---|---|
| FEATURE | Location/Qualifiers |
| source | 1..329 |
| | mol_type = protein |
| | organism = synthetic construct |

SEQUENCE: 436

```
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLYITREP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329
```

| SEQ ID NO: 437 | moltype = AA length = 329 |
|---|---|
| FEATURE | Location/Qualifiers |

```
source                  1..329
                        mol_type = protein
                        organism = synthetic construct
SEQUENCE: 437
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLYITREP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 438          moltype = AA   length = 329
FEATURE                 Location/Qualifiers
source                  1..329
                        mol_type = protein
                        organism = synthetic construct
SEQUENCE: 438
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLYITREP EVTCVVVAVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 439          moltype = AA   length = 329
FEATURE                 Location/Qualifiers
source                  1..329
                        mol_type = protein
                        organism = synthetic construct
SEQUENCE: 439
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 440          moltype = AA   length = 329
FEATURE                 Location/Qualifiers
source                  1..329
                        mol_type = protein
                        organism = synthetic construct
SEQUENCE: 440
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 441          moltype = AA   length = 329
FEATURE                 Location/Qualifiers
source                  1..329
                        mol_type = protein
                        organism = synthetic construct
SEQUENCE: 441
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 442          moltype = AA   length = 329
FEATURE                 Location/Qualifiers
source                  1..329
                        mol_type = protein
                        organism = synthetic construct
SEQUENCE: 442
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 443          moltype = AA   length = 329
FEATURE                 Location/Qualifiers
source                  1..329
```

```
                        mol_type = protein
                        organism = synthetic construct
SEQUENCE: 443
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                   329

SEQ ID NO: 444          moltype = AA  length = 329
FEATURE                 Location/Qualifiers
source                  1..329
                        mol_type = protein
                        organism = synthetic construct
SEQUENCE: 444
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                   329

SEQ ID NO: 445          moltype = AA  length = 329
FEATURE                 Location/Qualifiers
source                  1..329
                        mol_type = protein
                        organism = synthetic construct
SEQUENCE: 445
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                   329

SEQ ID NO: 446          moltype = AA  length = 329
FEATURE                 Location/Qualifiers
source                  1..329
                        mol_type = protein
                        organism = synthetic construct
SEQUENCE: 446
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                   329

SEQ ID NO: 447          moltype = AA  length = 329
FEATURE                 Location/Qualifiers
source                  1..329
                        mol_type = protein
                        organism = synthetic construct
SEQUENCE: 447
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                   329

SEQ ID NO: 448          moltype = AA  length = 329
FEATURE                 Location/Qualifiers
source                  1..329
                        mol_type = protein
                        organism = synthetic construct
SEQUENCE: 448
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                   329

SEQ ID NO: 449          moltype = AA  length = 329
FEATURE                 Location/Qualifiers
source                  1..329
                        mol_type = protein
```

```
                        organism = synthetic construct
SEQUENCE: 449
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV LHEALHSHYT QKSLSLSPG                                    329

SEQ ID NO: 450          moltype = AA  length = 329
FEATURE                 Location/Qualifiers
source                  1..329
                        mol_type = protein
                        organism = synthetic construct
SEQUENCE: 450
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VDHHDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHSHYT QKSLSLSPG                                    329

SEQ ID NO: 451          moltype = AA  length = 329
FEATURE                 Location/Qualifiers
source                  1..329
                        mol_type = protein
                        organism = synthetic construct
SEQUENCE: 451
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VDHHDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHSHYT QKSLSLSPG                                    329

SEQ ID NO: 452          moltype = AA  length = 329
FEATURE                 Location/Qualifiers
source                  1..329
                        mol_type = protein
                        organism = synthetic construct
SEQUENCE: 452
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVAVS HEDPEVKFNW YVDGVEVHNA KTKPREEQYN   180
STYRVVSVLT VDHHDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHSHYT QKSLSLSPG                                    329

SEQ ID NO: 453          moltype = AA  length = 328
FEATURE                 Location/Qualifiers
source                  1..328
                        mol_type = protein
                        organism = synthetic construct
SEQUENCE: 453
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VDHHDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHSHYT QKSLSLSP                                     328

SEQ ID NO: 454          moltype = AA  length = 329
FEATURE                 Location/Qualifiers
source                  1..329
                        mol_type = protein
                        organism = synthetic construct
SEQUENCE: 454
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLMISRTP EVTCVVVDVS HEDPEVKFNW YVDGVEVHNA KTKPREEQYN   180
STYRVVSVLT VDHHDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHSHYT QKSLSLSPG                                    329

SEQ ID NO: 455          moltype = AA  length = 329
FEATURE                 Location/Qualifiers
source                  1..329
                        mol_type = protein
                        organism = synthetic construct
```

```
SEQUENCE: 455
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLT VDHHDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHSHYT QKSLSLSPG                                    329

SEQ ID NO: 456             moltype = AA   length = 329
FEATURE                    Location/Qualifiers
source                     1..329
                           mol_type = protein
                           organism = synthetic construct
SEQUENCE: 456
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VDHHDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHSHYT QKSLSLSPG                                    329

SEQ ID NO: 457             moltype = AA   length = 327
FEATURE                    Location/Qualifiers
source                     1..327
                           mol_type = protein
                           organism = synthetic construct
SEQUENCE: 457
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LYITREPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 458             moltype = AA   length = 327
FEATURE                    Location/Qualifiers
source                     1..327
                           mol_type = protein
                           organism = synthetic construct
SEQUENCE: 458
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LYITREPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 459             moltype = AA   length = 327
FEATURE                    Location/Qualifiers
source                     1..327
                           mol_type = protein
                           organism = synthetic construct
SEQUENCE: 459
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEELGGPSV   120
FLFPPKPKDT LYITREPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 460             moltype = AA   length = 326
FEATURE                    Location/Qualifiers
source                     1..326
                           mol_type = protein
                           organism = synthetic construct
SEQUENCE: 460
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVLHE ALHSYTQKSL SLSLGK                                       326

SEQ ID NO: 461             moltype = AA   length = 327
FEATURE                    Location/Qualifiers
source                     1..327
                           mol_type = protein
                           organism = synthetic construct
SEQUENCE: 461
```

```
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVLHE ALHSHYTQKS LSLSLGK                                      327

SEQ ID NO: 462          moltype = AA  length = 327
FEATURE                 Location/Qualifiers
source                  1..327
                        mol_type = protein
                        organism = synthetic construct
SEQUENCE: 462
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEELGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVLHE ALHSHYTQKS LSLSLGK                                      327

SEQ ID NO: 463          moltype = AA  length = 327
FEATURE                 Location/Qualifiers
source                  1..327
                        mol_type = protein
                        organism = synthetic construct
SEQUENCE: 463
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVDH HDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHSHYTQKS LSLSLGK                                      327

SEQ ID NO: 464          moltype = AA  length = 327
FEATURE                 Location/Qualifiers
source                  1..327
                        mol_type = protein
                        organism = synthetic construct
SEQUENCE: 464
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVDH HDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHSHYTQKS LSLSLGK                                      327

SEQ ID NO: 465          moltype = AA  length = 327
FEATURE                 Location/Qualifiers
source                  1..327
                        mol_type = protein
                        organism = synthetic construct
SEQUENCE: 465
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEELGGPSV   120
FLFPPKPKDT LMISRTPEVT CVVVDVSQED PEVQFNWYVD GVEVHNAKTK PREEQFNSTY   180
RVVSVLTVDH HDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHSHYTQKS LSLSLGK                                      327

SEQ ID NO: 466          moltype = AA  length = 324
FEATURE                 Location/Qualifiers
source                  1..324
                        mol_type = protein
                        organism = synthetic construct
SEQUENCE: 466
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPCP APPVAGPSVF   120
LPPKPKDTL YITREPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDIAVEW ESNGQPENNY KTTPPMLDSD GSFFLYSKLT VDKSRWQQGN   300
VFSCSVLHEA LHSHYTQKSL SLSP                                         324

SEQ ID NO: 467          moltype = AA  length = 324
FEATURE                 Location/Qualifiers
source                  1..324
                        mol_type = protein
                        organism = synthetic construct
SEQUENCE: 467
ASTKGPSVFP LAPCSRSTSE STAALGCLVK DYFPEPVTVS WNSGALTSGV HTFPAVLQSS    60
```

```
GLYSLSSVVT VPSSNFGTQT YTCNVDHKPS NTKVDKTVER KCCVECPPCP APPVAGPSVF    120
LFPPKPKDTL MISRTPEVTC VVVDVSHEDP EVQFNWYVDG VEVHNAKTKP REEQFNSTFR    180
VVSVLTVVHQ DWLNGKEYKC KVSNKGLPAP IEKTISKTKG QPREPQVYTL PPSREEMTKN    240
QVSLTCLVKG FYPSDIAVEW ESNGQPENNY KTTPPMLDSD GSFFLYSKLT VDKSRWQQGN    300
VFSCSVMHEA LHNHYTQKSL SLSP                                          324

SEQ ID NO: 468           moltype = AA  length = 324
FEATURE                  Location/Qualifiers
source                   1..324
                         mol_type = protein
                         organism = synthetic construct
SEQUENCE: 468
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF    120
LFPPKPKDTL MISRTPEVTC VVVDVSHEDP EVQFNWYVDG VEVHNAKTKP REEQFNSTFR    180
VVSVLTVDHH DWLNGKEYKC KVSNKGLPAP IEKTISKTKG QPREPQVYTL PPSREEMTKN    240
QVSLTCLVKG FYPSDIAVEW ESNGQPENNY KTTPPMLDSD GSFFLYSKLT VDKSRWQQGN    300
VFSCSVMHEA LHSHYTQKSL SLSP                                          324

SEQ ID NO: 469           moltype = AA  length = 107
FEATURE                  Location/Qualifiers
source                   1..107
                         mol_type = protein
                         organism = synthetic construct
SEQUENCE: 469
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 470           moltype = AA  length = 118
FEATURE                  Location/Qualifiers
source                   1..118
                         mol_type = protein
                         organism = synthetic construct
SEQUENCE: 470
QVTLRESGPA LVKPTQTLTL TCTVSGFSLS AYSVNWIRQP PGKALEWLAM IWGDGKIVYN    60
SALKSRLTIS KDTSKNQVVL TMTNMDPVDT ATYYCAGDGY YPYAMDNWGQ GSLVTVSS     118

SEQ ID NO: 471           moltype = AA  length = 111
FEATURE                  Location/Qualifiers
source                   1..111
                         mol_type = protein
                         organism = synthetic construct
SEQUENCE: 471
DIVMTQSPDS LSVSLGERAT INCRASKSVD SYGNSFMHWY QQKPGQPPKL LIYLASNLES    60
GVPDRFSGSG SGTDFTLTIS SLQAEDVAVY YCQQNNEDPR TFGGGTKVEI K            111

SEQ ID NO: 472           moltype = AA  length = 146
FEATURE                  Location/Qualifiers
source                   1..146
                         mol_type = protein
                         organism = Homo sapiens
SEQUENCE: 472
MHPLLNPLLL ALGLMALLLT TVIALTCLGG FASPGPVPPS TALRELIEEL VNITQNQKAP    60
LCNGSMWWSI NLTAGMYCAA LESLINVSGC SAIEKTQRML SGFCPHKVSA GQFSSLHVRD   120
TKIEVAQFVK DLLLHLKKLF REGRFN                                        146

SEQ ID NO: 473           moltype = AA  length = 132
FEATURE                  Location/Qualifiers
source                   1..132
                         mol_type = protein
                         organism = Macaca fascicularis
SEQUENCE: 473
MALLLTMVIA LTCLGGFASP SPVPPSTALK ELIEELVNIT QNQKAPLCNG SMVWSINLTA    60
GVYCAALESL INVSGCSAIE KTQRMLNGFC PHKVSAGQFS SLRVRDTKIE VAQFVKDLLV   120
HLKKLFREGQ FN                                                       132

SEQ ID NO: 474           moltype = AA  length = 131
FEATURE                  Location/Qualifiers
source                   1..131
                         mol_type = protein
                         organism = Mus sp.
SEQUENCE: 474
MALWVTAVLA LACLGGLAAP GPVPRSVSLP LTLKELIEEL SNITQDQTPL CNGSMVWSVD    60
LAAGGFCVAL DSLTNISNCN AIYRTQRILH GLCNRKAPTT VSSLPDTKIE VAHFITKLLS   120
YTKQLFRHGP F                                                        131

SEQ ID NO: 475           moltype = AA  length = 131
FEATURE                  Location/Qualifiers
source                   1..131
```

```
                        mol_type = protein
                        organism = Rattus norvegicus
SEQUENCE: 475
MALWVTAVLA LACLGGLATP GPVRRSTSPP VALRELIEEL SNITQDQKTS LCNSSMVWSV    60
DLTAGGFCAA LESLTNISSC NAIHRTQRIL NGLCNQKASD VASSPPDTKI EVAQFISKLL   120
NYSKQLFRYG H                                                       131

SEQ ID NO: 476          moltype = AA  length = 24
FEATURE                 Location/Qualifiers
source                  1..24
                        mol_type = protein
                        organism = Homo sapiens
SEQUENCE: 476
MHPLLNPLLL ALGLMALLLT TVIA                                           24

SEQ ID NO: 477          moltype = AA  length = 18
FEATURE                 Location/Qualifiers
source                  1..18
                        mol_type = protein
                        organism = Macaca fascicularis
SEQUENCE: 477
MALLLTMVIA LTCLGGFA                                                  18

SEQ ID NO: 478          moltype = AA  length = 18
FEATURE                 Location/Qualifiers
source                  1..18
                        mol_type = protein
                        organism = Mus sp.
SEQUENCE: 478
MALWVTAVLA LACLGGLA                                                  18

SEQ ID NO: 479          moltype = AA  length = 18
FEATURE                 Location/Qualifiers
source                  1..18
                        mol_type = protein
                        organism = Rattus norvegicus
SEQUENCE: 479
MALWVTAVLA LACLGGLA                                                  18

SEQ ID NO: 480          moltype = AA  length = 122
FEATURE                 Location/Qualifiers
source                  1..122
                        mol_type = protein
                        organism = Homo sapiens
SEQUENCE: 480
LTCLGGFASP GPVPPSTALR ELIEELVNIT QNQKAPLCNG SMVWSINLTA GMYCAALESL    60
INVSGCSAIE KTQRMLSGFC PHKVSAGQFS SLHVRDTKIE VAQFVKDLLL HLKKLFREGR   120
FN                                                                 122

SEQ ID NO: 481          moltype = AA  length = 114
FEATURE                 Location/Qualifiers
source                  1..114
                        mol_type = protein
                        organism = Macaca fascicularis
SEQUENCE: 481
SPSPVPPSTA LKELIEELVN ITQNQKAPLC NGSMVWSINL TAGVYCAALE SLINVSGCSA    60
IEKTQRMLNG FCPHKVSAGQ FSSLRVRDTK IEVAQFVKDL LVHLKKLFRE GQFN         114

SEQ ID NO: 482          moltype = AA  length = 113
FEATURE                 Location/Qualifiers
source                  1..113
                        mol_type = protein
                        organism = Mus sp.
SEQUENCE: 482
APGPVPRSVS LPLTLKELIE ELSNITQDQT PLCNGSMVWS VDLAAGGFCV ALDSLTNISN    60
CNAIYRTQRI LHGLCNRKAP TTVSSLPDTK IEVAHFITKL LSYTKQLFRH GPF          113

SEQ ID NO: 483          moltype = AA  length = 113
FEATURE                 Location/Qualifiers
source                  1..113
                        mol_type = protein
                        organism = Rattus norvegicus
SEQUENCE: 483
TPGPVRRSTS PPVALRELIE ELSNITQDQK TSLCNSSMVW SVDLTAGGFC AALESLTNIS    60
SCNAIHRTQR ILNGLCNQKA SDVASSPPDT KIEVAQFISK LLNYSKQLFR YGH          113

SEQ ID NO: 484          moltype = AA  length = 329
FEATURE                 Location/Qualifiers
source                  1..329
```

```
                        mol_type = protein
                        organism = synthetic construct
SEQUENCE: 484
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                   329

SEQ ID NO: 485          moltype = AA  length = 329
FEATURE                 Location/Qualifiers
source                  1..329
                        mol_type = protein
                        organism = synthetic construct
SEQUENCE: 485
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                   329

SEQ ID NO: 486          moltype = AA  length = 329
FEATURE                 Location/Qualifiers
source                  1..329
                        mol_type = protein
                        organism = synthetic construct
SEQUENCE: 486
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                   329

SEQ ID NO: 487          moltype = AA  length = 329
FEATURE                 Location/Qualifiers
source                  1..329
                        mol_type = protein
                        organism = synthetic construct
SEQUENCE: 487
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                   329

SEQ ID NO: 488          moltype = AA  length = 329
FEATURE                 Location/Qualifiers
source                  1..329
                        mol_type = protein
                        organism = synthetic construct
SEQUENCE: 488
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                   329

SEQ ID NO: 489          moltype = AA  length = 329
FEATURE                 Location/Qualifiers
source                  1..329
                        mol_type = protein
                        organism = synthetic construct
SEQUENCE: 489
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                   329

SEQ ID NO: 490          moltype = AA  length = 329
FEATURE                 Location/Qualifiers
source                  1..329
                        mol_type = protein
```

```
                    organism = synthetic construct
SEQUENCE: 490
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV LHEALHAHYT QKSLSLSPG                                    329

SEQ ID NO: 491          moltype = AA   length = 329
FEATURE                 Location/Qualifiers
source                  1..329
                        mol_type = protein
                        organism = synthetic construct
SEQUENCE: 491
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                    329

SEQ ID NO: 492          moltype = AA   length = 329
FEATURE                 Location/Qualifiers
source                  1..329
                        mol_type = protein
                        organism = synthetic construct
SEQUENCE: 492
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                    329

SEQ ID NO: 493          moltype = AA   length = 329
FEATURE                 Location/Qualifiers
source                  1..329
                        mol_type = protein
                        organism = synthetic construct
SEQUENCE: 493
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVAVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                    329

SEQ ID NO: 494          moltype = AA   length = 329
FEATURE                 Location/Qualifiers
source                  1..329
                        mol_type = protein
                        organism = synthetic construct
SEQUENCE: 494
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                    329

SEQ ID NO: 495          moltype = AA   length = 329
FEATURE                 Location/Qualifiers
source                  1..329
                        mol_type = protein
                        organism = synthetic construct
SEQUENCE: 495
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                    329

SEQ ID NO: 496          moltype = AA   length = 329
FEATURE                 Location/Qualifiers
source                  1..329
                        mol_type = protein
                        organism = synthetic construct
```

```
SEQUENCE: 496
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                    329

SEQ ID NO: 497          moltype = AA   length = 329
FEATURE                 Location/Qualifiers
source                  1..329
                        mol_type = protein
                        organism = synthetic construct
SEQUENCE: 497
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                    329

SEQ ID NO: 498          moltype = AA   length = 329
FEATURE                 Location/Qualifiers
source                  1..329
                        mol_type = protein
                        organism = synthetic construct
SEQUENCE: 498
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                    329

SEQ ID NO: 499          moltype = AA   length = 329
FEATURE                 Location/Qualifiers
source                  1..329
                        mol_type = protein
                        organism = synthetic construct
SEQUENCE: 499
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                    329

SEQ ID NO: 500          moltype = AA   length = 329
FEATURE                 Location/Qualifiers
source                  1..329
                        mol_type = protein
                        organism = synthetic construct
SEQUENCE: 500
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVAVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                    329

SEQ ID NO: 501          moltype = AA   length = 329
FEATURE                 Location/Qualifiers
source                  1..329
                        mol_type = protein
                        organism = synthetic construct
SEQUENCE: 501
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                    329

SEQ ID NO: 502          moltype = AA   length = 329
FEATURE                 Location/Qualifiers
source                  1..329
                        mol_type = protein
                        organism = synthetic construct
SEQUENCE: 502
```

```
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                    329

SEQ ID NO: 503          moltype = AA   length = 329
FEATURE                 Location/Qualifiers
source                  1..329
                        mol_type = protein
                        organism = synthetic construct
SEQUENCE: 503
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                    329

SEQ ID NO: 504          moltype = AA   length = 329
FEATURE                 Location/Qualifiers
source                  1..329
                        mol_type = protein
                        organism = synthetic construct
SEQUENCE: 504
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                    329

SEQ ID NO: 505          moltype = AA   length = 329
FEATURE                 Location/Qualifiers
source                  1..329
                        mol_type = protein
                        organism = synthetic construct
SEQUENCE: 505
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRDP EVTCVVVDVS HEDPEVKFNW YVDGVEVHNA KTKPREEQYN   180
STYRVVSVLQ VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 506          moltype = AA   length = 329
FEATURE                 Location/Qualifiers
source                  1..329
                        mol_type = protein
                        organism = synthetic construct
SEQUENCE: 506
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRDP EVTCVVVDVS HEDPEVKFNW YVDGVEVHNA KTKPREEQYN   180
STYRVVSVLQ VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 507          moltype = AA   length = 329
FEATURE                 Location/Qualifiers
source                  1..329
                        mol_type = protein
                        organism = synthetic construct
SEQUENCE: 507
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRDP EVTCVVVAVS HEDPEVKFNW YVDGVEVHNA KTKPREEQYN   180
STYRVVSVLQ VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 508          moltype = AA   length = 329
FEATURE                 Location/Qualifiers
source                  1..329
                        mol_type = protein
                        organism = synthetic construct
SEQUENCE: 508
ASTKGPSVFP LAPSSKSTSG GTAALGCLVK DYFPEPVTVS WNSGALTSGV HTFPAVLQSS    60
```

```
GLYSLSSVVT VPSSSLGTQT YICNVNHKPS NTKVDKKVEP KSCDKTHTCP PCPAPEAAGG    120
PSVFLFPPKP KDTLMISRDP EVTCVVVDVS HEDPEVKFNW YVDGVEVHNA KTKPREEQYN    180
STYRVVSVLQ VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                     329

SEQ ID NO: 509            moltype = AA   length = 329
FEATURE                   Location/Qualifiers
source                    1..329
                          mol_type = protein
                          organism = synthetic construct
SEQUENCE: 509
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA    120
PSVFLFPPKP KDTLMISRDP EVTCVVVDVS HEDPEVKFNW YVDGVEVHNA KTKPREEQYN    180
STYRVVSVLQ VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                     329

SEQ ID NO: 510            moltype = AA   length = 329
FEATURE                   Location/Qualifiers
source                    1..329
                          mol_type = protein
                          organism = synthetic construct
SEQUENCE: 510
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA    120
PSVFLFPPKP KDTLMISRDP EVTCVVVDVS HEDPEVKFNW YVDGVEVHNA KTKPREEQYN    180
STYRVVSVLQ VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                     329

SEQ ID NO: 511            moltype = AA   length = 329
FEATURE                   Location/Qualifiers
source                    1..329
                          mol_type = protein
                          organism = synthetic construct
SEQUENCE: 511
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRDP EVTCVVVDVS HEDPEVKFNW YVDGVEVHNA KTKPREEQYN    180
STYRVVSVLQ VLHQDWLNGK EYKCKVSNKA LGAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                     329

SEQ ID NO: 512            moltype = AA   length = 329
FEATURE                   Location/Qualifiers
source                    1..329
                          mol_type = protein
                          organism = synthetic construct
SEQUENCE: 512
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRDP EVTCVVVDVS HEDPEVKFNW YVDGVEVHNA KTKPREEQYN    180
STYRVVSVLW VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                     329

SEQ ID NO: 513            moltype = AA   length = 329
FEATURE                   Location/Qualifiers
source                    1..329
                          mol_type = protein
                          organism = synthetic construct
SEQUENCE: 513
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRDP EVTCVVVDVS HEDPEVKFNW YVDGVEVHNA KTKPREEQYA    180
STYRVVSVLW VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                     329

SEQ ID NO: 514            moltype = AA   length = 329
FEATURE                   Location/Qualifiers
source                    1..329
                          mol_type = protein
                          organism = synthetic construct
SEQUENCE: 514
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
```

```
PSVFLFPPKP KDTLMISRDP EVTCVVVAVS HEDPEVKFNW YVDGVEVHNA KTKPREEQYN   180
STYRVVSVLW VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 515         moltype = AA   length = 329
FEATURE                Location/Qualifiers
source                 1..329
                       mol_type = protein
                       organism = synthetic construct
SEQUENCE: 515
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG   120
PSVFLFPPKP KDTLMISRDP EVTCVVVDVS HEDPEVKFNW YVDGVEVHNA KTKPREEQYN   180
STYRVVSVLW VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 516         moltype = AA   length = 329
FEATURE                Location/Qualifiers
source                 1..329
                       mol_type = protein
                       organism = synthetic construct
SEQUENCE: 516
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA   120
PSVFLFPPKP KDTLMISRDP EVTCVVVDVS HEDPEVKFNW YVDGVEVHNA KTKPREEQYN   180
STYRVVSVLW VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 517         moltype = AA   length = 329
FEATURE                Location/Qualifiers
source                 1..329
                       mol_type = protein
                       organism = synthetic construct
SEQUENCE: 517
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA   120
PSVFLFPPKP KDTLMISRDP EVTCVVVDVS HEDPEVKFNW YVDGVEVHNA KTKPREEQYN   180
STYRVVSVLW VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 518         moltype = AA   length = 329
FEATURE                Location/Qualifiers
source                 1..329
                       mol_type = protein
                       organism = synthetic construct
SEQUENCE: 518
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG   120
PSVFLFPPKP KDTLMISRDP EVTCVVVDVS HEDPEVKFNW YVDGVEVHNA KTKPREEQYN   180
STYRVVSVLW VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 519         moltype = AA   length = 329
FEATURE                Location/Qualifiers
source                 1..329
                       mol_type = protein
                       organism = synthetic construct
SEQUENCE: 519
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLYISRDP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 520         moltype = AA   length = 329
FEATURE                Location/Qualifiers
source                 1..329
                       mol_type = protein
                       organism = synthetic construct
SEQUENCE: 520
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLYISRDP EVTCVVVDVS HEDPEVKFNW YVDGVEVHNA KTKPREEQYA   180
```

```
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 521           moltype = AA  length = 329
FEATURE                  Location/Qualifiers
source                   1..329
                         mol_type = protein
                         organism = synthetic construct
SEQUENCE: 521
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLYISRDP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 522           moltype = AA  length = 329
FEATURE                  Location/Qualifiers
source                   1..329
                         mol_type = protein
                         organism = synthetic construct
SEQUENCE: 522
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLYISRDP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 523           moltype = AA  length = 329
FEATURE                  Location/Qualifiers
source                   1..329
                         mol_type = protein
                         organism = synthetic construct
SEQUENCE: 523
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLYISRDP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 524           moltype = AA  length = 329
FEATURE                  Location/Qualifiers
source                   1..329
                         mol_type = protein
                         organism = synthetic construct
SEQUENCE: 524
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAGGG  120
PSVFLFPPKP KDTLYISRDP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 525           moltype = AA  length = 329
FEATURE                  Location/Qualifiers
source                   1..329
                         mol_type = protein
                         organism = synthetic construct
SEQUENCE: 525
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLYISRDP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 526           moltype = AA  length = 329
FEATURE                  Location/Qualifiers
source                   1..329
                         mol_type = protein
                         organism = synthetic construct
SEQUENCE: 526
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLQ VLHVDWLNGK EYKCKVSNKA LPAPIEKTIS KAKGQPREPQ VYTLPPSRDE  240
```

```
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                     329

SEQ ID NO: 527           moltype = AA  length = 329
FEATURE                  Location/Qualifiers
source                   1..329
                         mol_type = protein
                         organism = synthetic construct
SEQUENCE: 527
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYA    180
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                     329

SEQ ID NO: 528           moltype = AA  length = 329
FEATURE                  Location/Qualifiers
source                   1..329
                         mol_type = protein
                         organism = synthetic construct
SEQUENCE: 528
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVAVS HEDPEVKFNW YVDGVEVHNA KTKPREEQYN    180
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                     329

SEQ ID NO: 529           moltype = AA  length = 329
FEATURE                  Location/Qualifiers
source                   1..329
                         mol_type = protein
                         organism = synthetic construct
SEQUENCE: 529
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRTP EVTCVVVDVS HEDPEVKFNW YVDGVEVHNA KTKPREEQYN    180
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                     329

SEQ ID NO: 530           moltype = AA  length = 329
FEATURE                  Location/Qualifiers
source                   1..329
                         mol_type = protein
                         organism = synthetic construct
SEQUENCE: 530
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA    120
PSVFLFPPKP KDTLMISRTP EVTCVVVDVS HEDPEVKFNW YVDGVEVHNA KTKPREEQYN    180
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                     329

SEQ ID NO: 531           moltype = AA  length = 329
FEATURE                  Location/Qualifiers
source                   1..329
                         mol_type = protein
                         organism = synthetic construct
SEQUENCE: 531
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA    120
PSVFLFPPKP KDTLMISRTP EVTCVVVDVS HEDPEVKFNW YVDGVEVHNA KTKPREEQYN    180
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                     329

SEQ ID NO: 532           moltype = AA  length = 329
FEATURE                  Location/Qualifiers
source                   1..329
                         mol_type = protein
                         organism = synthetic construct
SEQUENCE: 532
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRTP EVTCVVVDVS HEDPEVKFNW YVDGVEVHNA KTKPREEQYN    180
STYRVVSVLQ VLHVDWLNGK EYKCKVSNKA LGAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
```

```
QQGNVFSCSV MHEALHNHYT QKSLSLSPG                                         329

SEQ ID NO: 533              moltype = AA   length = 329
FEATURE                     Location/Qualifiers
source                      1..329
                            mol_type = protein
                            organism = synthetic construct
SEQUENCE: 533
ASTKGPSVFP LAPSSKSTSG GTAALGCLVK DYFPEPVTVS WNSGALTSGV HTFPAVLQSS        60
GLYSLSSVVT VPSSSLGTQT YICNVNHKPS NTKVDKKVEP KSCDKTHTCP PCPAPELLGG       120
PSVFLFPPKP KDTLMISRDP EVTCVVVDVS HEDPEVKFNW YVDGVEVDNA KTKPREEQYN       180
STYRVVSVLR VLHVDWLNGK EYKCKVSNKA LPAPIEKTIS KAKGQPREPQ VYTLPPSRDE       240
LTKNQVSLTC LVKGFYPSDI VVEWESNGQP ENNYKTTPPV LDSDGSFFLY SKLTVDKSRW       300
QQGNVFSCSV MHEALHNHYT QKSLSLSPG                                         329

SEQ ID NO: 534              moltype = AA   length = 329
FEATURE                     Location/Qualifiers
source                      1..329
                            mol_type = protein
                            organism = synthetic construct
SEQUENCE: 534
ASTKGPSVFP LAPSSKSTSG GTAALGCLVK DYFPEPVTVS WNSGALTSGV HTFPAVLQSS        60
GLYSLSSVVT VPSSSLGTQT YICNVNHKPS NTKVDKKVEP KSCDKTHTCP PCPAPELLGG       120
PSVFLFPPKP KDTLMISRDP EVTCVVVDVS HEDPEVKFNW YVDGVEVDNA KTKPREEQYA       180
STYRVVSVLR VLHVDWLNGK EYKCKVSNKA LPAPIEKTIS KAKGQPREPQ VYTLPPSRDE       240
LTKNQVSLTC LVKGFYPSDI VVEWESNGQP ENNYKTTPPV LDSDGSFFLY SKLTVDKSRW       300
QQGNVFSCSV MHEALHNHYT QKSLSLSPG                                         329

SEQ ID NO: 535              moltype = AA   length = 329
FEATURE                     Location/Qualifiers
source                      1..329
                            mol_type = protein
                            organism = synthetic construct
SEQUENCE: 535
ASTKGPSVFP LAPSSKSTSG GTAALGCLVK DYFPEPVTVS WNSGALTSGV HTFPAVLQSS        60
GLYSLSSVVT VPSSSLGTQT YICNVNHKPS NTKVDKKVEP KSCDKTHTCP PCPAPELLGG       120
PSVFLFPPKP KDTLMISRDP EVTCVVVAVS HEDPEVKFNW YVDGVEVDNA KTKPREEQYN       180
STYRVVSVLR VLHVDWLNGK EYKCKVSNKA LPAPIEKTIS KAKGQPREPQ VYTLPPSRDE       240
LTKNQVSLTC LVKGFYPSDI VVEWESNGQP ENNYKTTPPV LDSDGSFFLY SKLTVDKSRW       300
QQGNVFSCSV MHEALHNHYT QKSLSLSPG                                         329

SEQ ID NO: 536              moltype = AA   length = 329
FEATURE                     Location/Qualifiers
source                      1..329
                            mol_type = protein
                            organism = synthetic construct
SEQUENCE: 536
ASTKGPSVFP LAPSSKSTSG GTAALGCLVK DYFPEPVTVS WNSGALTSGV HTFPAVLQSS        60
GLYSLSSVVT VPSSSLGTQT YICNVNHKPS NTKVDKKVEP KSCDKTHTCP PCPAPEAAGG       120
PSVFLFPPKP KDTLMISRDP EVTCVVVDVS HEDPEVKFNW YVDGVEVDNA KTKPREEQYN       180
STYRVVSVLR VLHVDWLNGK EYKCKVSNKA LPAPIEKTIS KAKGQPREPQ VYTLPPSRDE       240
LTKNQVSLTC LVKGFYPSDI VVEWESNGQP ENNYKTTPPV LDSDGSFFLY SKLTVDKSRW       300
QQGNVFSCSV MHEALHNHYT QKSLSLSPG                                         329

SEQ ID NO: 537              moltype = AA   length = 329
FEATURE                     Location/Qualifiers
source                      1..329
                            mol_type = protein
                            organism = synthetic construct
SEQUENCE: 537
ASTKGPSVFP LAPSSKSTSG GTAALGCLVK DYFPEPVTVS WNSGALTSGV HTFPAVLQSS        60
GLYSLSSVVT VPSSSLGTQT YICNVNHKPS NTKVDKKVEP KSCDKTHTCP PCPAPELAGA       120
PSVFLFPPKP KDTLMISRDP EVTCVVVDVS HEDPEVKFNW YVDGVEVDNA KTKPREEQYN       180
STYRVVSVLR VLHVDWLNGK EYKCKVSNKA LPAPIEKTIS KAKGQPREPQ VYTLPPSRDE       240
LTKNQVSLTC LVKGFYPSDI VVEWESNGQP ENNYKTTPPV LDSDGSFFLY SKLTVDKSRW       300
QQGNVFSCSV MHEALHNHYT QKSLSLSPG                                         329

SEQ ID NO: 538              moltype = AA   length = 329
FEATURE                     Location/Qualifiers
source                      1..329
                            mol_type = protein
                            organism = synthetic construct
SEQUENCE: 538
ASTKGPSVFP LAPSSKSTSG GTAALGCLVK DYFPEPVTVS WNSGALTSGV HTFPAVLQSS        60
GLYSLSSVVT VPSSSLGTQT YICNVNHKPS NTKVDKKVEP KSCDKTHTCP PCPAPEAAGA       120
PSVFLFPPKP KDTLMISRDP EVTCVVVDVS HEDPEVKFNW YVDGVEVDNA KTKPREEQYN       180
STYRVVSVLR VLHVDWLNGK EYKCKVSNKA LPAPIEKTIS KAKGQPREPQ VYTLPPSRDE       240
LTKNQVSLTC LVKGFYPSDI VVEWESNGQP ENNYKTTPPV LDSDGSFFLY SKLTVDKSRW       300
QQGNVFSCSV MHEALHNHYT QKSLSLSPG                                         329
```

```
SEQ ID NO: 539          moltype = AA   length = 329
FEATURE                 Location/Qualifiers
source                  1..329
                        mol_type = protein
                        organism = synthetic construct
SEQUENCE: 539
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRDP EVTCVVVDVS HEDPEVKFNW YVDGVEVDNA KTKPREEQYN   180
STYRVVSVLR VLHVDWLNGK EYKCKVSNKA LGAPIEKTIS KAKGQPREPQ VYTLPPSRDE   240
LTKNQVSLTC LVKGFYPSDI VVEWESNGQP ENNYKTTPPV LDSDGSFFLY SKLTVDKSRW   300
QQGNVFSCSV MHEALHNHYT QKSLSLSPG                                    329

SEQ ID NO: 540          moltype = AA   length = 30
FEATURE                 Location/Qualifiers
source                  1..30
                        mol_type = protein
                        organism = synthetic construct
SEQUENCE: 540
QVTLRESGPA LVKPTQTLTL TCTVSGFSLS                                     30

SEQ ID NO: 541          moltype = AA   length = 5
FEATURE                 Location/Qualifiers
source                  1..5
                        mol_type = protein
                        organism = synthetic construct
SEQUENCE: 541
AYSWN                                                                5

SEQ ID NO: 542          moltype = AA   length = 25
FEATURE                 Location/Qualifiers
source                  1..25
                        mol_type = protein
                        organism = synthetic construct
SEQUENCE: 542
QVTLRESGPA LVKPTQTLTL TCTVS                                          25

SEQ ID NO: 543          moltype = AA   length = 25
FEATURE                 Location/Qualifiers
source                  1..25
                        mol_type = protein
                        organism = synthetic construct
SEQUENCE: 543
QVQLQESGPG LVAPSQSLSI TCTVS                                          25

SEQ ID NO: 544          moltype = AA   length = 25
FEATURE                 Location/Qualifiers
source                  1..25
                        mol_type = protein
                        organism = synthetic construct
SEQUENCE: 544
EVQLQESGPG LVKPSETLSL TCTVS                                          25

SEQ ID NO: 545          moltype = AA   length = 25
FEATURE                 Location/Qualifiers
source                  1..25
                        mol_type = protein
                        organism = synthetic construct
SEQUENCE: 545
EVQLVQSGAE VKKPGASVKV SCKAS                                          25

SEQ ID NO: 546          moltype = AA   length = 25
FEATURE                 Location/Qualifiers
source                  1..25
                        mol_type = protein
                        organism = synthetic construct
SEQUENCE: 546
EVQLVQSGAE VKKPGSSVKV SCKAS                                          25

SEQ ID NO: 547          moltype = AA   length = 25
FEATURE                 Location/Qualifiers
source                  1..25
                        mol_type = protein
                        organism = synthetic construct
SEQUENCE: 547
EVQLVESGGG LVKPGGSLRL SCAAS                                          25

SEQ ID NO: 548          moltype = AA   length = 25
```

```
FEATURE              Location/Qualifiers
source               1..25
                     mol_type = protein
                     organism = synthetic construct
SEQUENCE: 548
EVQLLESGGG LVQPGGSLRL SCAAS                                              25

SEQ ID NO: 549       moltype = AA  length = 25
FEATURE              Location/Qualifiers
source               1..25
                     mol_type = protein
                     organism = synthetic construct
SEQUENCE: 549
QVQLQESGPG LVKPSETLSL TCTVS                                              25

SEQ ID NO: 550       moltype = AA  length = 19
FEATURE              Location/Qualifiers
source               1..19
                     mol_type = protein
                     organism = synthetic construct
SEQUENCE: 550
SVNWIRQPPG KALEWLAMI                                                     19

SEQ ID NO: 551       moltype = AA  length = 19
FEATURE              Location/Qualifiers
source               1..19
                     mol_type = protein
                     organism = synthetic construct
SEQUENCE: 551
SVNWVRQPPG KGLEWLGMI                                                     19

SEQ ID NO: 552       moltype = AA  length = 19
FEATURE              Location/Qualifiers
source               1..19
                     mol_type = protein
                     organism = synthetic construct
SEQUENCE: 552
SVNWIRQPPG KGLEWLGMI                                                     19

SEQ ID NO: 553       moltype = AA  length = 19
FEATURE              Location/Qualifiers
source               1..19
                     mol_type = protein
                     organism = synthetic construct
SEQUENCE: 553
SVNWVRQAPG QGLEWLGMI                                                     19

SEQ ID NO: 554       moltype = AA  length = 19
FEATURE              Location/Qualifiers
source               1..19
                     mol_type = protein
                     organism = synthetic construct
SEQUENCE: 554
SVNWVRQAPG KGLEWLGMI                                                     19

SEQ ID NO: 555       moltype = AA  length = 19
FEATURE              Location/Qualifiers
source               1..19
                     mol_type = protein
                     organism = synthetic construct
SEQUENCE: 555
SWNWVRQPPG KGLEWLGYI                                                     19

SEQ ID NO: 556       moltype = AA  length = 41
FEATURE              Location/Qualifiers
source               1..41
                     mol_type = protein
                     organism = synthetic construct
SEQUENCE: 556
IVYNSALKSR LTISKDTSKN QVVLTMTNMD PVDTATYYCA G                            41

SEQ ID NO: 557       moltype = AA  length = 41
FEATURE              Location/Qualifiers
source               1..41
                     mol_type = protein
                     organism = synthetic construct
SEQUENCE: 557
IVYNSALKSR LNISKDSSKS QVFLKMSSLQ SDDTARYYCA G                            41
```

```
SEQ ID NO: 558            moltype = AA   length = 41
FEATURE                   Location/Qualifiers
source                    1..41
                          mol_type = protein
                          organism = synthetic construct
SEQUENCE: 558
IVYNSALKSR LTISKDSSKS QVFLKMSSLQ SDDTARYYCA G                    41

SEQ ID NO: 559            moltype = AA   length = 41
FEATURE                   Location/Qualifiers
source                    1..41
                          mol_type = protein
                          organism = synthetic construct
SEQUENCE: 559
IVYNSALKSR LTISKDSSKN QVSLKLSSVT AADTAVYYCA G                    41

SEQ ID NO: 560            moltype = AA   length = 41
FEATURE                   Location/Qualifiers
source                    1..41
                          mol_type = protein
                          organism = synthetic construct
SEQUENCE: 560
IVYNSALKSR LTITKDSSTS TVYMELSSLR SEDTAVYYCA G                    41

SEQ ID NO: 561            moltype = AA   length = 41
FEATURE                   Location/Qualifiers
source                    1..41
                          mol_type = protein
                          organism = synthetic construct
SEQUENCE: 561
IVYNSALKSR LTISKDSSKN TVYLQMNSLK TEDTAVYYCA G                    41

SEQ ID NO: 562            moltype = AA   length = 41
FEATURE                   Location/Qualifiers
source                    1..41
                          mol_type = protein
                          organism = synthetic construct
SEQUENCE: 562
IVYNSALKSR LTISKDSSKN TVYLQMNSLR AEDTAVYYCA G                    41

SEQ ID NO: 563            moltype = AA   length = 41
FEATURE                   Location/Qualifiers
source                    1..41
                          mol_type = protein
                          organism = synthetic construct
SEQUENCE: 563
IVYNSALKSR LTISLDTSKS QVFLKMSSLT AADTAVYYCA R                    41

SEQ ID NO: 564            moltype = AA   length = 41
FEATURE                   Location/Qualifiers
source                    1..41
                          mol_type = protein
                          organism = synthetic construct
SEQUENCE: 564
TNYNPALKSR LTISLDTSKS QVFLKMSSLT AADTAVYYCA R                    41

SEQ ID NO: 565            moltype = AA   length = 8
FEATURE                   Location/Qualifiers
source                    1..8
                          mol_type = protein
                          organism = synthetic construct
SEQUENCE: 565
GFSLNSYS                                                          8

SEQ ID NO: 566            moltype = AA   length = 17
FEATURE                   Location/Qualifiers
source                    1..17
                          mol_type = protein
                          organism = synthetic construct
SEQUENCE: 566
VNWIRQPPGK ALEWLAM                                               17

SEQ ID NO: 567            moltype = AA   length = 17
FEATURE                   Location/Qualifiers
source                    1..17
                          mol_type = protein
                          organism = synthetic construct
SEQUENCE: 567
VNWVRQPPGK GLEWLGM                                               17
```

```
SEQ ID NO: 568          moltype = AA   length = 17
FEATURE                 Location/Qualifiers
source                  1..17
                        mol_type = protein
                        organism = synthetic construct
SEQUENCE: 568
VNWIRQPPGK GLEWLGM                                                         17

SEQ ID NO: 569          moltype = AA   length = 17
FEATURE                 Location/Qualifiers
source                  1..17
                        mol_type = protein
                        organism = synthetic construct
SEQUENCE: 569
VNWVRQAPGQ GLEWLGM                                                         17

SEQ ID NO: 570          moltype = AA   length = 17
FEATURE                 Location/Qualifiers
source                  1..17
                        mol_type = protein
                        organism = synthetic construct
SEQUENCE: 570
VNWVRQAPGK GLEWLGM                                                         17

SEQ ID NO: 571          moltype = AA   length = 17
FEATURE                 Location/Qualifiers
source                  1..17
                        mol_type = protein
                        organism = synthetic construct
SEQUENCE: 571
WNWVRQPPGK GLEWLGY                                                         17

SEQ ID NO: 572          moltype = AA   length = 38
FEATURE                 Location/Qualifiers
source                  1..38
                        mol_type = protein
                        organism = synthetic construct
SEQUENCE: 572
VYNSALKSRL TISKDTSKNQ VVLTMTNMDP VDTATYYC                                   38

SEQ ID NO: 573          moltype = AA   length = 38
FEATURE                 Location/Qualifiers
source                  1..38
                        mol_type = protein
                        organism = synthetic construct
SEQUENCE: 573
VYNSALKSRL NISKDSSKSQ VFLKMSSLQS DDTARYYC                                   38

SEQ ID NO: 574          moltype = AA   length = 38
FEATURE                 Location/Qualifiers
source                  1..38
                        mol_type = protein
                        organism = synthetic construct
SEQUENCE: 574
VYNSALKSRL TISKDSSKSQ VFLKMSSLQS DDTARYYC                                   38

SEQ ID NO: 575          moltype = AA   length = 38
FEATURE                 Location/Qualifiers
source                  1..38
                        mol_type = protein
                        organism = synthetic construct
SEQUENCE: 575
VYNSALKSRL TISKDSSKNQ VSLKLSSVTA ADTAVYYC                                   38

SEQ ID NO: 576          moltype = AA   length = 38
FEATURE                 Location/Qualifiers
source                  1..38
                        mol_type = protein
                        organism = synthetic construct
SEQUENCE: 576
VYNSALKSRL TITKDSSTST VYMELSSLRS EDTAVYYC                                   38

SEQ ID NO: 577          moltype = AA   length = 38
FEATURE                 Location/Qualifiers
source                  1..38
                        mol_type = protein
                        organism = synthetic construct
SEQUENCE: 577
```

```
VYNSALKSRL TISKDSSKNT VYLQMNSLKT EDTAVYYC                            38

SEQ ID NO: 578          moltype = AA  length = 38
FEATURE                 Location/Qualifiers
source                  1..38
                        mol_type = protein
                        organism = synthetic construct
SEQUENCE: 578
VYNSALKSRL TISKDSSKNT VYLQMNSLRA EDTAVYYC                            38

SEQ ID NO: 579          moltype = AA  length = 38
FEATURE                 Location/Qualifiers
source                  1..38
                        mol_type = protein
                        organism = synthetic construct
SEQUENCE: 579
VYNSALKSRL TISLDTSKSQ VFLKMSSLTA ADTAVYYC                            38

SEQ ID NO: 580          moltype = AA  length = 38
FEATURE                 Location/Qualifiers
source                  1..38
                        mol_type = protein
                        organism = synthetic construct
SEQUENCE: 580
NYNPALKSRL TISLDTSKSQ VFLKMSSLTA ADTAVYYC                            38

SEQ ID NO: 581          moltype = AA  length = 23
FEATURE                 Location/Qualifiers
source                  1..23
                        mol_type = protein
                        organism = synthetic construct
SEQUENCE: 581
DIVMTQSPDS LSVSLGERAT INC                                            23

SEQ ID NO: 582          moltype = AA  length = 26
FEATURE                 Location/Qualifiers
source                  1..26
                        mol_type = protein
                        organism = synthetic construct
SEQUENCE: 582
DIVMTQSPDS LSVSLGERAT INCRAS                                         26

SEQ ID NO: 583          moltype = AA  length = 26
FEATURE                 Location/Qualifiers
source                  1..26
                        mol_type = protein
                        organism = synthetic construct
SEQUENCE: 583
NIVLTQSPAS LAVSLGQRAT ISCRAS                                         26

SEQ ID NO: 584          moltype = AA  length = 26
FEATURE                 Location/Qualifiers
source                  1..26
                        mol_type = protein
                        organism = synthetic construct
SEQUENCE: 584
DIQLTQSPSS LSASVGDRVT ITCRAS                                         26

SEQ ID NO: 585          moltype = AA  length = 26
FEATURE                 Location/Qualifiers
source                  1..26
                        mol_type = protein
                        organism = synthetic construct
SEQUENCE: 585
EIVLTQSPAT LSVSPGERAT LSCRAS                                         26

SEQ ID NO: 586          moltype = AA  length = 26
FEATURE                 Location/Qualifiers
source                  1..26
                        mol_type = protein
                        organism = synthetic construct
SEQUENCE: 586
DIVLTQSPLS LPVTPGEPAS ISCRAS                                         26

SEQ ID NO: 587          moltype = AA  length = 26
FEATURE                 Location/Qualifiers
source                  1..26
                        mol_type = protein
                        organism = synthetic construct
```

```
SEQUENCE: 587
DIVLTQSPDS LAVSLGERAT INCRAS                                                    26

SEQ ID NO: 588          moltype = AA  length = 26
FEATURE                 Location/Qualifiers
source                  1..26
                        mol_type = protein
                        organism = synthetic construct
SEQUENCE: 588
DIVLTQSPAS LAVSPGERAT ISCRAS                                                    26

SEQ ID NO: 589          moltype = AA  length = 17
FEATURE                 Location/Qualifiers
source                  1..17
                        mol_type = protein
                        organism = synthetic construct
SEQUENCE: 589
MHWYQQKPGQ PPKLLIY                                                              17

SEQ ID NO: 590          moltype = AA  length = 17
FEATURE                 Location/Qualifiers
source                  1..17
                        mol_type = protein
                        organism = synthetic construct
SEQUENCE: 590
MHWYQQKPGK APKLLIY                                                              17

SEQ ID NO: 591          moltype = AA  length = 17
FEATURE                 Location/Qualifiers
source                  1..17
                        mol_type = protein
                        organism = synthetic construct
SEQUENCE: 591
MHWYQQKPGQ APRLLIY                                                              17

SEQ ID NO: 592          moltype = AA  length = 17
FEATURE                 Location/Qualifiers
source                  1..17
                        mol_type = protein
                        organism = synthetic construct
SEQUENCE: 592
MHWYLQKPGQ SPQLLIY                                                              17

SEQ ID NO: 593          moltype = AA  length = 17
FEATURE                 Location/Qualifiers
source                  1..17
                        mol_type = protein
                        organism = synthetic construct
SEQUENCE: 593
LHWYQQKPGQ PPKLLIY                                                              17

SEQ ID NO: 594          moltype = AA  length = 17
FEATURE                 Location/Qualifiers
source                  1..17
                        mol_type = protein
                        organism = synthetic construct
SEQUENCE: 594
MHWYQQKPGK APKLLIR                                                              17

SEQ ID NO: 595          moltype = AA  length = 17
FEATURE                 Location/Qualifiers
source                  1..17
                        mol_type = protein
                        organism = synthetic construct
SEQUENCE: 595
MHWYQQKPGK APKLLIF                                                              17

SEQ ID NO: 596          moltype = AA  length = 36
FEATURE                 Location/Qualifiers
source                  1..36
                        mol_type = protein
                        organism = synthetic construct
SEQUENCE: 596
NLESGVPDRF SGSGSGTDFT LTISSLQAED VAVYYC                                         36

SEQ ID NO: 597          moltype = AA  length = 36
FEATURE                 Location/Qualifiers
source                  1..36
                        mol_type = protein
```

```
                          -continued organism = synthetic construct
SEQUENCE: 597
NLESGVPARF SGSGSRTDFT LTIDPVEADD AASYYC                           36

SEQ ID NO: 598            moltype = AA  length = 36
FEATURE                   Location/Qualifiers
source                    1..36
                          mol_type = protein
                          organism = synthetic construct
SEQUENCE: 598
NLESGVPSRF SGSGSRTDFT LTISSLQPED FATYYC                           36

SEQ ID NO: 599            moltype = AA  length = 36
FEATURE                   Location/Qualifiers
source                    1..36
                          mol_type = protein
                          organism = synthetic construct
SEQUENCE: 599
NLESGIPARF SGSGSRTEFT LTISSLQSED FAVYYC                           36

SEQ ID NO: 600            moltype = AA  length = 36
FEATURE                   Location/Qualifiers
source                    1..36
                          mol_type = protein
                          organism = synthetic construct
SEQUENCE: 600
NLESGVPDRF SGSGSRTDFT LKISRVEAED VGVYYC                           36

SEQ ID NO: 601            moltype = AA  length = 36
FEATURE                   Location/Qualifiers
source                    1..36
                          mol_type = protein
                          organism = synthetic construct
SEQUENCE: 601
NLESGVPSRF SGSGSGTDFT LTISSLQPED FATYYC                           36

SEQ ID NO: 602            moltype = AA  length = 36
FEATURE                   Location/Qualifiers
source                    1..36
                          mol_type = protein
                          organism = synthetic construct
SEQUENCE: 602
NLESGIPARF SGSGSGTEFT LTISSLQSED FAVYYC                           36

SEQ ID NO: 603            moltype = AA  length = 36
FEATURE                   Location/Qualifiers
source                    1..36
                          mol_type = protein
                          organism = synthetic construct
SEQUENCE: 603
NLESGVPDRF SGSGSGTDFT LKISRVEAED VGVYYC                           36

SEQ ID NO: 604            moltype = AA  length = 36
FEATURE                   Location/Qualifiers
source                    1..36
                          mol_type = protein
                          organism = synthetic construct
SEQUENCE: 604
NLESGVPDRF SGSGSGTDFT LTISRVEADD VAVYYC                           36

SEQ ID NO: 605            moltype = AA  length = 36
FEATURE                   Location/Qualifiers
source                    1..36
                          mol_type = protein
                          organism = synthetic construct
SEQUENCE: 605
NRESGVPDRF SGSGSGTDFT LTISRVEADD VAVYYC                           36

SEQ ID NO: 606            moltype = AA  length = 36
FEATURE                   Location/Qualifiers
source                    1..36
                          mol_type = protein
                          organism = synthetic construct
SEQUENCE: 606
HLESGVPSRF SGSGSGTDFT LTISSLQPED FATYYC                           36

SEQ ID NO: 607            moltype = AA  length = 36
FEATURE                   Location/Qualifiers
source                    1..36
```

```
                        mol_type = protein
                        organism = synthetic construct
SEQUENCE: 607
DLESGVPSRF SGSGSGTDFT LTISSLQPED FATYYC                              36

SEQ ID NO: 608          moltype = AA  length = 36
FEATURE                 Location/Qualifiers
source                  1..36
                        mol_type = protein
                        organism = synthetic construct
SEQUENCE: 608
QLESGVPSRF SGSGSGTDFT LTISSLQPED FATYYC                              36

SEQ ID NO: 609          moltype = AA  length = 36
FEATURE                 Location/Qualifiers
source                  1..36
                        mol_type = protein
                        organism = synthetic construct
SEQUENCE: 609
ELESGVPSRF SGSGSGTDFT LTISSLQPED FATYYC                              36
```

ANTIBODIES THAT BIND INTERLEUKIN 13 AND METHODS OF USE

CROSS REFERENCE TO RELATED APPLICATIONS

This application is a Continuation of International Application No. PCT/US2023/068621, filed on Jun. 16, 2023, which claims priority to, and the benefit to U.S. Provisional Application No. 63/353,367, filed Jun. 17, 2022, U.S. Provisional Application No. 63/462,822, filed Apr. 28, 2023, and U.S. Provisional Application No. 63/469,167, filed May 26, 2023, the entire disclosures of which are hereby incorporated by reference in their entirety for all purposes.

SEQUENCE LISTING

The instant application contains a Sequence Listing which has been submitted electronically in XML file format and is hereby incorporated by reference in its entirety. Said XML copy, created on Jun. 15, 2023, is named AOE-001WO_SL.xml and is 426,841 bytes in size.

BACKGROUND

Interleukin (IL)-13 is a T helper cell subclass 2 (Th2) cytokine and belongs to a family of type I cytokines, exhibiting pleiotropic effects across multiple cellular pathways. IL-13 is involved in the differentiation of naïve T cells into Th2 cells. IL-13 promotes B-cell proliferation and induces immunoglobulin isotype class switching to IgG4 and IgE when co-stimulated with CD40/CD40L. It also up-regulates FcεRI, and thus, helps in IgE priming of mast cells. In monocytes/macrophages, IL-13 up-regulates expression of CD23 and MHC class I and class II antigens, down-regulates the expression of CD14, inhibits antibody-dependent cytotoxicity, and promotes eosinophil survival, activation, and recruitment. IL-13 also manifests important functions on nonhematopoietic cells, such as smooth muscle cells, epithelial cells, endothelial cells, and fibroblast cells. IL-13 enhances proliferation and cholinergic-induced contractions of smooth muscles. In epithelial cells, IL-13 is a potent inducer of chemokine production, alters mucociliary differentiation, decreases ciliary beat frequency of ciliated epithelial cells, and results in goblet cell metaplasia. In endothelial cells, IL-13 is a potent inducer of vascular cell adhesion molecule 1 (VCAM-1), which is important for recruitment of eosinophils. In epithelial keratinocytes, IL-13 reduces the expression of barrier integrity molecules, such as filaggrin and loricrin, while stimulating CCL26 and CCL2 secretion responsible for the recruitment of several inflammatory cells of myeloid lineages. In human dermal fibroblasts, IL-13 induces type 1 collagen synthesis in human dermal fibroblasts.

The inhibition of IL-13 may be used to treat or prevent inflammatory diseases and conditions, such as those related to elevated levels of IgE, including but not limited to asthma, allergic rhinitis, urticaria, and allergic or atopic dermatitis. Thus, the development of potent and specific inhibitors of IL-13, for example, inhibitors that remain active for longer terms when administered to subjects, are needed for the prevention and/or treatment IL-13- and IgE-mediated diseases or conditions.

SUMMARY

In certain aspects, described herein is an isolated antibody that binds IL-13, i) comprising a variable heavy (VH) chain sequence comprising three heavy chain CDR sequences, CDR-H1, CDR-H2, and CDR-H3; and ii) a variable light (VL) chain sequence comprising three light chain CDR sequences, CDR-L1, CDR-L2, and CDR-L3; wherein: a) CDR-H1 comprises a sequence selected from the sequences set forth in SEQ ID NOs: 58-99 and 121; b) CDR-H2 comprises a sequence selected from the sequences set forth in SEQ ID NOs: 100-111; c) CDR-H3 comprises a sequence selected from the sequences set forth in SEQ ID NOs: 112-120 and 130-140; d) CDR-L1 comprises a sequence selected from the sequences set forth in SEQ ID NOs: 141-144 and 149-152; e) CDR-L2 comprises a sequence selected from the sequences set forth in SEQ ID NOs: 153-158 and the amino acid sequence LAS; and f) CDR-L3 comprises a sequence selected from the sequences set forth in SEQ ID NOs: 165-172.

In certain embodiments, the isolated antibody comprises: a) CDR-H1 comprising a sequence selected from the sequences set forth in SEQ ID NOs: 58-66; b) CDR-H2 comprises a sequence selected from the sequences set forth in SEQ ID NOs: 100-103; c) CDR-H3 comprises a sequence selected from the sequences set forth in SEQ ID NOs: 112-120; d) CDR-L1 comprises a sequence selected from the sequences set forth in SEQ ID NOs: 141-144; e) CDR-L2 comprises a sequence selected from the sequences set forth in SEQ ID NOs: 153-158; and f) CDR-L3 comprises a sequence selected from the sequences set forth in SEQ ID NOs: 165-172.

In certain embodiments, the isolated antibody comprises: a) CDR-H1 comprising a sequence selected from the sequences set forth in SEQ ID NOs: 67-83; b) CDR-H2 comprises a sequence selected from the sequences set forth in SEQ ID NOs: 104-107; c) CDR-H3 comprises a sequence selected from the sequences set forth in SEQ ID NOs: 112-120; d) CDR-L1 comprises a sequence selected from the sequences set forth in SEQ ID NOs: 141-144; e) CDR-L2 comprises a sequence selected from the sequences set forth in SEQ ID NOs: 153-158; and f) CDR-L3 comprises a sequence selected from the sequences set forth in SEQ ID NOs: 165-172.

In certain embodiments, the isolated antibody comprises: a) CDR-H1 comprising a sequence selected from the sequences set forth in SEQ ID NOs: 84-99 and 121; b) CDR-H2 comprises a sequence selected from the sequences set forth in SEQ ID NOs: 108-111; c) CDR-H3 comprises a sequence selected from the sequences set forth in SEQ ID NOs: 130-140; d) CDR-L1 comprises a sequence selected from the sequences set forth in SEQ ID NOs: 149-152; e) CDR-L2 comprises the amino acid sequence LAS; and f) CDR-L3 comprises a sequence selected from the sequences set forth in SEQ ID NOs: 165-172.

In certain embodiments, the isolated antibody does not comprise: a) CDR-H1 set forth in SEQ ID NO: 58; CDR-H2 set forth in SEQ ID NO: 100; CDR-H3 set forth in SEQ ID NO: 112; CDR-L1 set forth in SEQ ID NO: 141; CDR-L2 set forth in SEQ ID NO: 153; and CDR-L3 set forth in SEQ ID NO: 165; or b) CDR-H1 set forth in SEQ ID NO: 67; CDR-H2 set forth in SEQ ID NO: 104; CDR-H3 set forth in SEQ ID NO: 112; CDR-L1 set forth in SEQ ID NO: 141; CDR-L2 set forth in SEQ ID NO: 153; and CDR-L3 set forth in SEQ ID NO: 165; or c) CDR-H1 set forth in SEQ ID NO: 84; CDR-H2 set forth in SEQ ID NO: 108; CDR-H3 set forth in SEQ ID NO: 130; CDR-L1 set forth in SEQ ID NO: 149; CDR-L2 set forth by amino acid sequence LAS; and CDR-L3 set forth in SEQ ID NO: 165.

In certain embodiments, the antibody does not comprise any combination of: a) CDR-H1 set forth in any of SEQ ID NOs: 58, 67, or 84; b) a CDR-H2 set forth in any of SEQ ID NOs: 100, 104, or 108; c) a CDR-H3 set forth in any of SEQ ID NOs: 112 or 130; d) a CDR-L1 set forth in any of SEQ ID NOs: 141 or 149; e) a CDR-L2 set forth in any of SEQ ID NOs: 153 or 154; and f) a CDR-L3 set forth in SEQ ID NO: 165.

In certain embodiments, the isolated antibody comprises a CDR-H1 comprising the sequence set forth in any of SEQ ID NOs: 58, 67, or 68; a CDR-H2 comprising the sequence set forth in any of SEQ ID NOs: 100 or 104; a CDR-H3 comprising the sequence set forth in SEQ ID NO: 112; a CDR-L1 comprising the sequence set forth in any of SEQ ID NOs: 141 or 149; a CDR-L2 comprising the sequence set forth in any of SEQ ID NO: 153 or the amino acid sequence of LAS; and a CDR-L3 comprising the sequence set forth in SEQ ID NO: 165.

In certain embodiments, the isolated antibody comprises a CDR-H1 comprising the sequence set forth in SEQ ID NO: 58; a CDR-H2 comprising the sequence set forth in SEQ ID NO: 100; a CDR-H3 comprising the sequence set forth in SEQ ID NO: 112; a CDR-L1 comprising the sequence set forth in SEQ ID NO: 141; a CDR-L2 comprising the sequence set forth in SEQ ID NO: 153; and a CDR-L3 comprising the sequence set forth in SEQ ID NO: 165.

In certain embodiments, the isolated antibody comprises a CDR-H1 comprising the sequence set forth in SEQ ID NO: 67; a CDR-H2 comprising the sequence set forth in SEQ ID NO: 104; a CDR-H3 comprising the sequence set forth in SEQ ID NO: 112; a CDR-L1 comprising the sequence set forth in SEQ ID NO: 141; a CDR-L2 comprising the sequence set forth in SEQ ID NO: 153; and a CDR-L3 comprising the sequence set forth in SEQ ID NO: 165.

In certain embodiments, the isolated antibody comprises a CDR-H1 comprising the sequence set forth in SEQ ID NO: 68; a CDR-H2 comprising the sequence set forth in SEQ ID NO: 104; a CDR-H3 comprising the sequence set forth in SEQ ID NO: 112; a CDR-L1 comprising the sequence set forth in SEQ ID NO: 141; a CDR-L2 comprising the sequence set forth in SEQ ID NO: 153; and a CDR-L3 comprising the sequence set forth in SEQ ID NO: 165.

In certain embodiments, the isolated antibody comprises a CDR-H1 comprising the sequence set forth in SEQ ID NO: 67; a CDR-H2 comprising the sequence set forth in SEQ ID NO: 104; a CDR-H3 comprising the sequence set forth in SEQ ID NO: 112; a CDR-L1 comprising the sequence set forth in SEQ ID NO: 149; a CDR-L2 comprising the amino acid sequence LAS; and a CDR-L3 comprising the sequence set forth in SEQ ID NO: 165.

In certain embodiments, the isolated antibody comprises a CDR-H1 comprising the sequence set forth in SEQ ID NO: 68; a CDR-H2 comprising the sequence set forth in SEQ ID NO: 104; a CDR-H3 comprising the sequence set forth in SEQ ID NO: 112; a CDR-L1 comprising the sequence set forth in SEQ ID NO: 149; a CDR-L2 comprising the amino acid sequence LAS; and a CDR-L3 comprising the sequence set forth in SEQ ID NO: 165.

In certain embodiments, the isolated antibody comprises a CDR-H1 comprising the sequence set forth in any of SEQ ID NOs: 58, 67, 68, 84, or 85; a CDR-H2 comprising the sequence set forth in any of SEQ ID NOs: 100, 104, or 108; a CDR-H3 comprising the sequence set forth in any of SEQ ID NOs: 112 or 130; a CDR-L1 comprising the sequence set forth in any of SEQ ID NOs: 141 or 149; a CDR-L2 comprising the sequence set forth in any of SEQ ID NO: 153 or the amino acid sequence LAS; and a CDR-L3 comprising the sequence set forth in SEQ ID NO: 165.

In certain embodiments, the isolated antibody comprises a CDR-H1 comprising the sequence set forth in SEQ ID NO: 68; a CDR-H2 comprising the sequence set forth in SEQ ID NO: 104; a CDR-H3 comprising the sequence set forth in SEQ ID NO: 112; a CDR-L1 comprising the sequence set forth in SEQ ID NO: 141; a CDR-L2 comprising the sequence set forth in SEQ ID NO: 153; and a CDR-L3 comprising the sequence set forth in SEQ ID NO: 165.

In certain embodiments, the isolated antibody comprises a CDR-H1 comprising the sequence set forth in SEQ ID NO: 84; a CDR-H2 comprising the sequence set forth in SEQ ID NO: 108; a CDR-H3 comprising the sequence set forth in SEQ ID NO: 130; a CDR-L1 comprising the sequence set forth in SEQ ID NO: 149; a CDR-L2 comprising the amino acid sequence LAS; and a CDR-L3 comprising the sequence set forth in SEQ ID NO: 165.

In certain embodiments, the isolated antibody comprises a CDR-H1 comprising the sequence set forth in SEQ ID NO: 85; a CDR-H2 comprising the sequence set forth in SEQ ID NO: 108; a CDR-H3 comprising the sequence set forth in SEQ ID NO: 130; a CDR-L1 comprising the sequence set forth in SEQ ID NO: 149; a CDR-L2 comprising the amino acid sequence LAS; and a CDR-L3 comprising the sequence set forth in SEQ ID NO: 165.

In certain embodiments, the isolated antibody comprises a CDR-H1 comprising the sequence set forth in any of SEQ ID NOs: 58, 67, 68, 84, or 85; a CDR-H2 comprising the sequence set forth in any of SEQ ID NOs: 100, 104, or 108; a CDR-H3 comprising the sequence set forth in any of SEQ ID NOs: 112 or 130; a CDR-L1 comprising the sequence set forth in any of SEQ ID NOs: 141 or 149; a CDR-L2 comprising the sequence set forth in any of SEQ ID NO: 157 or the amino acid sequence LAS; and a CDR-L3 comprising the sequence set forth in SEQ ID NO: 165.

In certain embodiments, the isolated antibody comprises a CDR-H1 comprising the sequence set forth in SEQ ID NO: 58; a CDR-H2 comprising the sequence set forth in SEQ ID NO: 100; a CDR-H3 comprising the sequence set forth in SEQ ID NO: 112; a CDR-L1 comprising the sequence set forth in SEQ ID NO: 141; a CDR-L2 comprising the sequence set forth in SEQ ID NO: 157; and a CDR-L3 comprising the sequence set forth in SEQ ID NO: 165.

In certain embodiments, the isolated antibody comprises a CDR-H1 comprising the sequence set forth in SEQ ID NO: 68; a CDR-H2 comprising the sequence set forth in SEQ ID NO: 104; a CDR-H3 comprising the sequence set forth in SEQ ID NO: 112; a CDR-L1 comprising the sequence set forth in SEQ ID NO: 141; a CDR-L2 comprising the sequence set forth in SEQ ID NO: 157; and a CDR-L3 comprising the sequence set forth in SEQ ID NO: 165.

In certain embodiments, the isolated antibody comprises a CDR-H1 comprising the sequence set forth in any of SEQ ID NOs: 58, 67, 68, 84, or 85; a CDR-H2 comprising the sequence set forth in any of SEQ ID NOs: 100, 104, or 108; a CDR-H3 comprising the sequence set forth in any of SEQ ID NOs: 112 or 130; a CDR-L1 comprising the sequence set forth in any of SEQ ID NOs: 141 or 149; a CDR-L2 comprising the sequence set forth in any of SEQ ID NO: 157 or the amino acid sequence LAS; and a CDR-L3 comprising the sequence set forth in SEQ ID NO: 165.

In certain embodiments, the isolated antibody comprises a CDR-H1 comprising the sequence set forth in SEQ ID NO: 68; a CDR-H2 comprising the sequence set forth in SEQ ID NO: 104; a CDR-H3 comprising the sequence set forth in SEQ ID NO: 112; a CDR-L1 comprising the sequence set forth in SEQ ID NO: 141; a CDR-L2 comprising the sequence set forth in SEQ ID NO: 157; and a CDR-L3 comprising the sequence set forth in SEQ ID NO: 165.

In certain embodiments, the isolated antibody comprises a CDR-H1 comprising the sequence set forth in SEQ ID NO: 84; a CDR-H2 comprising the sequence set forth in SEQ ID NO: 108; a CDR-H3 comprising the sequence set forth in SEQ ID NO: 130; a CDR-L1 comprising the sequence set forth in SEQ ID NO: 149; a CDR-L2 comprising the amino acid sequence LAS; and a CDR-L3 comprising the sequence set forth in SEQ ID NO: 165.

In certain embodiments, the isolated antibody comprises a CDR-H1 comprising the sequence set forth in SEQ ID NO: 85; a CDR-H2 comprising the sequence set forth in SEQ ID NO: 108; a CDR-H3 comprising the sequence set forth in SEQ ID NO: 130; a CDR-L1 comprising the sequence set forth in SEQ ID NO: 149; a CDR-L2 comprising the amino acid sequence LAS; and a CDR-L3 comprising the sequence set forth in SEQ ID NO: 165.

In certain embodiments, the isolated antibody comprises a VH sequence selected from the sequences set forth in SEQ ID NOs: 1-32 and 470.

In certain embodiments, the isolated antibody comprises a VL sequence selected from the sequences set forth in SEQ ID NOs: 33-57 and 471.

In certain embodiments, the isolated antibody comprises a VH sequence selected from the sequences set forth in SEQ ID NOs: 1-32 and 470 and a VL sequence selected from the sequences set forth in SEQ ID NOs: 33-57 and 471.

In certain embodiments, the isolated antibody comprises a VH sequence selected from the sequences set forth in SEQ ID NOs: 1-32 and 470 and a VL sequence set forth in SEQ ID NO: 49.

In certain embodiments, the isolated antibody comprises a VH sequence selected from the sequences set forth in SEQ ID NOs: 1-32 and 470 and a VL sequence set forth in SEQ ID NO: 51.

In certain embodiments, the isolated antibody comprises a VH sequence set forth in SEQ ID NO: 1 and a VL sequence set forth in SEQ ID NO: 33.

In certain embodiments, the isolated antibody comprises a VH sequence set forth in SEQ ID NO: 2 and a VL sequence set forth in SEQ ID NO: 33.

In certain embodiments, the isolated antibody comprises a VH sequence set forth in SEQ ID NO: 3 and a VL sequence set forth in SEQ ID NO: 35.

In certain embodiments, the isolated antibody comprises a VH sequence set forth in SEQ ID NO: 4 and a VL sequence set forth in SEQ ID NO: 35.

In certain embodiments, the isolated antibody comprises a VH sequence set forth in SEQ ID NO: 5 and a VL sequence set forth in SEQ ID NO: 35.

In certain embodiments, the isolated antibody comprises a VH sequence set forth in SEQ ID NO: 6 and a VL sequence set forth in SEQ ID NO: 35.

In certain embodiments, the isolated antibody comprises a VH sequence set forth in SEQ ID NO: 7 and a VL sequence set forth in SEQ ID NO: 35.

In certain embodiments, the isolated antibody comprises a VH sequence set forth in SEQ ID NO: 3 and a VL sequence set forth in SEQ ID NO: 36.

In certain embodiments, the isolated antibody comprises a VH sequence set forth in SEQ ID NO: 4 and a VL sequence set forth in SEQ ID NO: 36.

In certain embodiments, the isolated antibody comprises a VH sequence set forth in SEQ ID NO: 5 and a VL sequence set forth in SEQ ID NO: 36.

In certain embodiments, the isolated antibody comprises a VH sequence set forth in SEQ ID NO: 6 and a VL sequence set forth in SEQ ID NO: 36.

In certain embodiments, the isolated antibody comprises a VH sequence set forth in SEQ ID NO: 7 and a VL sequence set forth in SEQ ID NO: 36.

In certain embodiments, the isolated antibody comprises a VH sequence set forth in SEQ ID NO: 3 and a VL sequence set forth in SEQ ID NO: 39.

In certain embodiments, the isolated antibody comprises a VH sequence set forth in SEQ ID NO: 4 and a VL sequence set forth in SEQ ID NO: 39.

In certain embodiments, the isolated antibody comprises a VH sequence set forth in SEQ ID NO: 5 and a VL sequence set forth in SEQ ID NO: 39.

In certain embodiments, the isolated antibody comprises a VH sequence set forth in SEQ ID NO: 6 and a VL sequence set forth in SEQ ID NO: 39.

In certain embodiments, the isolated antibody comprises a VH sequence set forth in SEQ ID NO: 7 and a VL sequence set forth in SEQ ID NO: 39.

In certain embodiments, the isolated antibody comprises a VH sequence set forth in SEQ ID NO: 3 and a VL sequence set forth in SEQ ID NO: 40.

In certain embodiments, the isolated antibody comprises a VH sequence set forth in SEQ ID NO: 4 and a VL sequence set forth in SEQ ID NO: 40.

In certain embodiments, the isolated antibody comprises a VH sequence set forth in SEQ ID NO: 5 and a VL sequence set forth in SEQ ID NO: 40.

In certain embodiments, the isolated antibody comprises a VH sequence set forth in SEQ ID NO: 6 and a VL sequence set forth in SEQ ID NO: 40.

In certain embodiments, the isolated antibody comprises a VH sequence set forth in SEQ ID NO: 7 and a VL sequence set forth in SEQ ID NO: 40.

In certain embodiments, the isolated antibody comprises a VH sequence set forth in SEQ ID NO: 8 and a VL sequence set forth in SEQ ID NO: 42.

In certain embodiments, the isolated antibody comprises a VH sequence set forth in SEQ ID NO: 9 and a VL sequence set forth in SEQ ID NO: 43.

In certain embodiments, the isolated antibody comprises a VH sequence set forth in SEQ ID NO: 7 and a VL sequence set forth in SEQ ID NO: 39.

In certain embodiments, the isolated antibody comprises a VH sequence set forth in SEQ ID NO: 7 and a VL sequence set forth in SEQ ID NO: 44.

In certain embodiments, the isolated antibody comprises a VH sequence set forth in SEQ ID NO: 7 and a VL sequence set forth in SEQ ID NO: 45.

In certain embodiments, the isolated antibody comprises a VH sequence set forth in SEQ ID NO: 7 and a VL sequence set forth in SEQ ID NO: 46.

In certain embodiments, the isolated antibody comprises a VH sequence set forth in SEQ ID NO: 7 and a VL sequence set forth in SEQ ID NO: 47.

In certain embodiments, the isolated antibody comprises a VH sequence set forth in SEQ ID NO: 7 and a VL sequence set forth in SEQ ID NO: 48.

In certain embodiments, the isolated antibody comprises a VH sequence set forth in SEQ ID NO: 7 and a VL sequence set forth in SEQ ID NO: 49.

In certain embodiments, the isolated antibody comprises a VH sequence set forth in SEQ ID NO: 7 and a VL sequence set forth in SEQ ID NO: 50.

In certain embodiments, the isolated antibody comprises a VH sequence set forth in SEQ ID NO: 3 and a VL sequence set forth in SEQ ID NO: 51.

In certain embodiments, the isolated antibody comprises a VH sequence set forth in SEQ ID NO: 7 and a VL sequence set forth in SEQ ID NO: 51.

In certain embodiments, the isolated antibody comprises a VH sequence set forth in SEQ ID NO: 7 and a VL sequence set forth in SEQ ID NO: 52.

In certain embodiments, the isolated antibody comprises a VH sequence set forth in SEQ ID NO: 7 and a VL sequence set forth in SEQ ID NO: 53.

In certain embodiments, the isolated antibody comprises a VH sequence set forth in SEQ ID NO: 7 and a VL sequence set forth in SEQ ID NO: 54.

In certain embodiments, the isolated antibody comprises a VH sequence set forth in SEQ ID NO: 7 and a VL sequence set forth in SEQ ID NO: 55.

In certain embodiments, the isolated antibody comprises a VH sequence set forth in SEQ ID NO: 7 and a VL sequence set forth in SEQ ID NO: 56.

In certain embodiments, the isolated antibody comprises a VH sequence set forth in SEQ ID NO: 7 and a VL sequence set forth in SEQ ID NO: 57.

In certain embodiments, the isolated antibody comprises a VH sequence set forth in SEQ ID NO: 10 and a VL sequence set forth in SEQ ID NO: 39.

In certain embodiments, the isolated antibody comprises a VH sequence set forth in SEQ ID NO: 11 and a VL sequence set forth in SEQ ID NO: 39.

In certain embodiments, the isolated antibody comprises a VH sequence set forth in SEQ ID NO: 12 and a VL sequence set forth in SEQ ID NO: 39.

In certain embodiments, the isolated antibody comprises a VH sequence set forth in SEQ ID NO: 13 and a VL sequence set forth in SEQ ID NO: 39.

In certain embodiments, the isolated antibody comprises a VH sequence set forth in SEQ ID NO: 14 and a VL sequence set forth in SEQ ID NO: 39.

In certain embodiments, the isolated antibody comprises a VH sequence set forth in SEQ ID NO: 15 and a VL sequence set forth in SEQ ID NO: 39.

In certain embodiments, the isolated antibody comprises a VH sequence set forth in SEQ ID NO: 16 and a VL sequence set forth in SEQ ID NO: 39.

In certain embodiments, the isolated antibody comprises a VH sequence set forth in SEQ ID NO: 17 and a VL sequence set forth in SEQ ID NO: 39.

In certain embodiments, the isolated antibody comprises a VH sequence set forth in SEQ ID NO: 18 and a VL sequence set forth in SEQ ID NO: 39.

In certain embodiments, the isolated antibody comprises a VH sequence set forth in SEQ ID NO: 19 and a VL sequence set forth in SEQ ID NO: 39.

In certain embodiments, the isolated antibody comprises a VH sequence set forth in SEQ ID NO: 20 and a VL sequence set forth in SEQ ID NO: 39.

In certain embodiments, the isolated antibody comprises a VH sequence set forth in SEQ ID NO: 21 and a VL sequence set forth in SEQ ID NO: 39.

In certain embodiments, the isolated antibody comprises a VH sequence set forth in SEQ ID NO: 22 and a VL sequence set forth in SEQ ID NO: 39.

In certain embodiments, the isolated antibody comprises a VH sequence set forth in SEQ ID NO: 23 and a VL sequence set forth in SEQ ID NO: 39.

In certain embodiments, the isolated antibody comprises a VH sequence set forth in SEQ ID NO: 24 and a VL sequence set forth in SEQ ID NO: 39.

The isolated antibody of claim 21, wherein the antibody comprises a VH sequence set forth in SEQ ID NO: 25 and a VL sequence set forth in SEQ ID NO: 39.

In certain embodiments, the isolated antibody comprises a VH sequence set forth in SEQ ID NO: 26 and a VL sequence set forth in SEQ ID NO: 39.

In certain embodiments, the isolated antibody comprises a VH sequence set forth in SEQ ID NO: 27 and a VL sequence set forth in SEQ ID NO: 39.

In certain embodiments, the isolated antibody comprises a VH sequence set forth in SEQ ID NO: 28 and a VL sequence set forth in SEQ ID NO: 39.

In certain embodiments, the isolated antibody comprises a VH sequence set forth in SEQ ID NO: 28 and a VL sequence set forth in SEQ ID NO: 39.

In certain embodiments, the isolated antibody comprises a VH sequence set forth in SEQ ID NO: 29 and a VL sequence set forth in SEQ ID NO: 39.

In certain embodiments, the isolated antibody comprises a VH sequence set forth in SEQ ID NO: 30 and a VL sequence set forth in SEQ ID NO: 39.

In certain embodiments, the isolated antibody comprises a VH sequence set forth in SEQ ID NO: 31 and a VL sequence set forth in SEQ ID NO: 39.

In certain embodiments, the isolated antibody comprises a VH sequence set forth in SEQ ID NO: 32 and a VL sequence set forth in SEQ ID NO: 39.

In certain embodiments, the isolated antibody comprises a VH sequence set forth in SEQ ID NO: 8 and a VL sequence set forth in SEQ ID NO: 39.

In certain embodiments, the isolated antibody comprises a VH sequence set forth in SEQ ID NO: 8 and a VL sequence set forth in SEQ ID NO: 51.

In certain embodiments, the isolated antibody comprises a VH sequence set forth in SEQ ID NO: 470 and a VL sequence set forth in SEQ ID NO: 471.

In certain embodiments, the isolated antibody is a humanized, human, or chimeric antibody. In certain embodiments, the isolated is a humanized antibody. In certain embodiments, the isolated antibody comprises a heavy chain human constant region of a class selected from IgG, IgA, IgD, IgE, and IgM. In certain embodiments, the human Fc region comprises a human heavy chain constant region of the class IgG and a subclass selected from IgG1, IgG2, IgG3, and IgG4. In certain embodiments, the human Fc region comprises a human IgG1 Fc. In certain embodiments, the human Fc region comprises a human IgG4 Fc. In certain embodiments, the human Fc region comprises a human IgG2 Fc.

In certain embodiments of the antibodies described herein, the heavy chain comprises a constant heavy chain sequence selected from the sequences set forth in SEQ ID NOs: 425-468 and 484-539.

In certain embodiments, the isolated antibody comprises a VH sequence set forth in SEQ ID NO: 1 and a VL sequence set forth in SEQ ID NO: 33; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 2 and a VL sequence set forth in SEQ ID NO: 33; and wherein the human Fc 436-468 and 484-539.

In certain embodiments, the isolated antibody comprises a VH sequence set forth in SEQ ID NO: 3 and a VL sequence set forth in SEQ ID NO: 35; and wherein the human Fc region comprises a human IgG sequence selected from a sequence set forth in SEQ ID NOS: 436-468 and 484-539.

In certain embodiments, the isolated antibody comprises a VH sequence set forth in SEQ ID NO: 4 and a VL sequence set forth in SEQ ID NO: 35; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 5 and a VL sequence set forth in SEQ ID NO: 35; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 6 and a VL sequence set forth in SEQ ID NO: 35; and wherein the human Fc region comprises a human IgG sequence selected from a sequence set forth in SEQ ID NOS: 436-468 and 484-539.

In certain embodiments, the isolated antibody comprises a VH sequence set forth in SEQ ID NO: 7 and a VL sequence set forth in SEQ ID NO: 35; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 3 and a VL sequence set forth in SEQ ID NO: 36; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 4 and a VL sequence set forth in SEQ ID NO: 36; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 5 and a VL sequence set forth in SEQ ID NO: 36; and wherein the human Fc 436-468 and 484-539.

In certain embodiments, the isolated antibody comprises a VH sequence set forth in SEQ ID NO: 6 and a VL sequence set forth in SEQ ID NO: 36; and wherein the human Fc region comprises a human IgG sequence selected from a sequence set forth in SEQ ID NOS: 436-468 and 484-539.

In certain embodiments, the isolated antibody comprises a VH sequence set forth in SEQ ID NO: 7 and a VL sequence set forth in SEQ ID NO: 36; and wherein the human Fc region comprises a human IgG sequence selected from a sequence set forth in SEQ ID NOs: 439, 440, 446, 457, and 460.

In certain embodiments, the isolated antibody comprises a VH sequence set forth in SEQ ID NO: 3 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 4 and a VL sequence set forth in SEQ ID NO: 39; and wherein the human Fc region comprises a human IgG sequence selected from a sequence set forth in SEQ ID NOS: 436-468 and 484-539.

In certain embodiments, the isolated antibody comprises a VH sequence set forth in SEQ ID NO: 5 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 6 and a VL sequence set forth in SEQ ID NO: 39; and wherein the human Fc region comprises a human IgG sequence selected from a sequence set forth in SEQ ID NOS: 436-468 and 484-539.

In certain embodiments, the isolated antibody comprises a VH sequence set forth in SEQ ID NO: 7 and a VL sequence set forth in SEQ ID NO: 39; and wherein the human Fc region comprises a human IgG sequence selected from a sequence set forth in SEQ ID NOS: 436-468 and 484-539.

In certain embodiments, the isolated antibody comprises a VH sequence set forth in SEQ ID NO: 3 and a VL sequence set forth in SEQ ID NO: 40; and wherein the human Fc 436-468 and 484-539.

In certain embodiments, the isolated antibody comprises a VH sequence set forth in SEQ ID NO: 4 and a VL sequence set forth in SEQ ID NO: 40; and wherein the human Fc region comprises a human IgG sequence selected from a sequence set forth in SEQ ID NOS: 436-468 and 484-539.

In certain embodiments, the isolated antibody comprises a VH sequence set forth in SEQ ID NO: 5 and a VL sequence set forth in SEQ ID NO: 40; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 6 and a VL sequence set forth in SEQ ID NO: 40; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 7 and a VL sequence set forth in SEQ ID NO: 40; and wherein the human Fc region comprises a human IgG sequence selected from a sequence set forth in SEQ ID NOS: 436-468 and 484-539.

In certain embodiments, the isolated antibody comprises a VH sequence set forth in SEQ ID NO: 8 and a VL sequence set forth in SEQ ID NO: 42; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 9 and a VL sequence set forth in SEQ ID NO: 43; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 7 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 7 and a VL sequence set forth in SEQ ID NO: 44; and wherein the human Fc 436-468 and 484-539.

In certain embodiments, the isolated antibody comprises a VH sequence set forth in SEQ ID NO: 7 and a VL sequence set forth in SEQ ID NO: 45; and wherein the human Fc region comprises a human IgG sequence selected from a sequence set forth in SEQ ID NOS: 436-468 and 484-539.

In certain embodiments, the isolated antibody comprises a VH sequence set forth in SEQ ID NO: 7 and a VL sequence set forth in SEQ ID NO: 46; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 7 and a VL sequence set forth in SEQ ID NO: 47; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 7 and a VL sequence set forth in SEQ ID NO: 48; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 7 and a VL sequence set forth in SEQ ID NO: 49; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 7 and a VL sequence set forth in SEQ ID NO: 50; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 3 and a VL sequence set forth in SEQ ID NO: 51; and wherein the human Fc region comprises a human IgG sequence selected from a sequence set forth in SEQ ID NOS: 436-468 and 484-539.

In certain embodiments, the isolated antibody comprises a VH sequence set forth in SEQ ID NO: 7 and a VL sequence set forth in SEQ ID NO: 51; and wherein the human Fc 436-468 and 484-539.

In certain embodiments, the isolated antibody comprises a VH sequence set forth in SEQ ID NO: 7 and a VL sequence set forth in SEQ ID NO: 52; and wherein the human Fc region comprises a human IgG sequence selected from a sequence set forth in SEQ ID NOS: 436-468 and 484-539.

In certain embodiments, the isolated antibody comprises a VH sequence set forth in SEQ ID NO: 7 and a VL sequence set forth in SEQ ID NO: 53; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 7 and a VL sequence set forth in SEQ ID NO: 54; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 7 and a VL sequence set forth in SEQ ID NO: 55; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 7 and a VL sequence set forth in SEQ ID NO: 56; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 7 and a VL sequence set forth in SEQ ID NO: 57; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 10 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 11 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 12 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 13 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated comprises a VH sequence set forth in SEQ ID NO: 14 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 15 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 16 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 17 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 18 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 19 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 20 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 21 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 22 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 23 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 24 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 25 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 26 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 27 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 28 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 28 and a VL sequence set forth in SEQ ID NO: 39; and wherein the human Fc region comprises a human IgG sequence set forth in SEQ ID NOs: 436-468 and 484-539.

In certain embodiments, the isolated antibody comprises a VH sequence set forth in SEQ ID NO: 29 and a VL sequence selected from a sequence set forth in SEQ ID NO: 39; and wherein the human Fc region comprises a human IgG sequence set forth in SEQ ID NOs: 436-468 and 484-539.

In certain embodiments, the isolated antibody comprises a VH sequence set forth in SEQ ID NO: 30 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 31 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 32 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 8 and a VL sequence set forth in SEQ ID NO: 39; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 8 and a VL sequence set forth in SEQ ID NO: 51; and wherein the human Fc region comprises a human IgG sequence selected from a sequence set forth in SEQ ID NOs: 436-468 and 484-539. In certain embodiments, the isolated antibody comprises a VH sequence set forth in SEQ ID NO: 470 and a VL sequence set forth in SEQ ID NO: 471; and wherein the human Fc region comprises a human IgG sequence selected from a sequence set forth in SEQ ID NOs: 436-468 and 484-539.

In certain embodiments, the isolated antibody comprises a VH sequence set forth in SEQ ID NO: 3 and a VL sequence set forth in SEQ ID NO: 39; and wherein the human Fc region comprises a human IgG sequence selected from a sequence set forth in SEQ ID NO: 439.

In certain embodiments, the isolated antibody comprises a VH sequence set forth in SEQ ID NO: 3 and a VL sequence set forth in SEQ ID NO: 39; and wherein the human Fc region comprises a human IgG sequence selected from a sequence set forth in SEQ ID NO: 446.

In certain embodiments, the isolated antibody comprises a VH sequence set forth in SEQ ID NO: 3 and a VL sequence set forth in SEQ ID NO: 39; and wherein the human Fc region comprises a human IgG sequence selected from a sequence set forth in SEQ ID NO: 457.

In certain embodiments, the isolated antibody comprises a VH sequence set forth in SEQ ID NO: 3 and a VL sequence set forth in SEQ ID NO: 39; and wherein the human Fc region comprises a human IgG sequence selected from a sequence set forth in SEQ ID NO: 460.

In certain embodiments, the isolated antibody comprises a VH sequence set forth in SEQ ID NO: 7 and a VL sequence set forth in SEQ ID NO: 39; and wherein the human Fc region comprises a human IgG sequence selected from a sequence set forth in SEQ ID NO: 439.

In certain embodiments, the isolated antibody comprises a VH sequence set forth in SEQ ID NO: 7 and a VL sequence set forth in SEQ ID NO: 39; and wherein the human Fc region comprises a human IgG sequence selected from a sequence set forth in SEQ ID NO: 446.

In certain embodiments, the isolated antibody comprises a VH sequence set forth in SEQ ID NO: 7 and a VL sequence set forth in SEQ ID NO: 39; and wherein the human Fc region comprises a human IgG sequence selected from a sequence set forth in SEQ ID NO: 457.

In certain embodiments, the isolated antibody comprises a VH sequence set forth in SEQ ID NO: 7 and a VL sequence set forth in SEQ ID NO: 39; and wherein the human Fc region comprises a human IgG sequence selected from a sequence set forth in SEQ ID NO: 460.

In certain embodiments, the isolated antibody comprises a VH sequence set forth in SEQ ID NO: 3 and a VL sequence set forth in SEQ ID NO: 51; and wherein the human Fc region comprises a human IgG sequence selected from a sequence set forth in SEQ ID NO: 439.

In certain embodiments, the isolated antibody comprises a VH sequence set forth in SEQ ID NO: 3 and a VL sequence set forth in SEQ ID NO: 51; and wherein the human Fc region comprises a human IgG sequence selected from a sequence set forth in SEQ ID NO: 446.

In certain embodiments, the isolated antibody comprises a VH sequence set forth in SEQ ID NO: 3 and a VL sequence set forth in SEQ ID NO: 51; and wherein the human Fc region comprises a human IgG sequence selected from a sequence set forth in SEQ ID NO: 457.

In certain embodiments, the isolated antibody comprises a VH sequence set forth in SEQ ID NO: 3 and a VL sequence set forth in SEQ ID NO: 51; and wherein the human Fc region comprises a human IgG sequence selected from a sequence set forth in SEQ ID NO: 460.

In certain embodiments, the isolated antibody comprises a VH sequence set forth in SEQ ID NO: 7 and a VL sequence set forth in SEQ ID NO: 51; and wherein the human Fc region comprises a human IgG sequence selected from a sequence set forth in SEQ ID NO: 439.

In certain embodiments, the isolated antibody comprises a VH sequence set forth in SEQ ID NO: 7 and a VL sequence set forth in SEQ ID NO: 51; and wherein the human Fc region comprises a human IgG sequence selected from a sequence set forth in SEQ ID NO: 446.

In certain embodiments, the isolated antibody comprises a VH sequence set forth in SEQ ID NO: 7 and a VL sequence set forth in SEQ ID NO: 51; and wherein the human Fc region comprises a human IgG sequence selected from a sequence set forth in SEQ ID NO: 457.

In certain embodiments, the isolated antibody comprises a VH sequence set forth in SEQ ID NO: 7 and a VL sequence set forth in SEQ ID NO: 51; and wherein the human Fc region comprises a human IgG sequence selected from a sequence set forth in SEQ ID NO: 460.

In certain embodiments, the isolated antibody comprises a VH sequence set forth in SEQ ID NO: 470 and a VL sequence set forth in SEQ ID NO: 471; and wherein the human Fc region comprises a human IgG sequence selected from a sequence set forth in SEQ ID NO: 439.

In certain embodiments, the isolated antibody comprises a VH sequence set forth in SEQ ID NO: 470 and a VL sequence set forth in SEQ ID NO: 471; and wherein the human Fc region comprises a human IgG sequence selected from a sequence set forth in SEQ ID NO: 446.

In certain embodiments, the isolated antibody comprises a VH sequence set forth in SEQ ID NO: 470 and a VL sequence set forth in SEQ ID NO: 471; and wherein the human Fc region comprises a human IgG sequence selected from a sequence set forth in SEQ ID NO: 457.

In certain embodiments, the isolated antibody comprises a VH sequence set forth in SEQ ID NO: 470 and a VL sequence set forth in SEQ ID NO: 471; and wherein the human Fc region comprises a human IgG sequence selected from a sequence set forth in SEQ ID NO: 460.

In certain embodiments, the isolated antibody comprises a VH sequence set forth in SEQ ID NO: 15 and a VL sequence set forth in SEQ ID NO: 39; and wherein the human Fc region comprises a human IgG sequence set forth in SEQ ID NO: 439.

In certain embodiments, the isolated antibody comprises a VH sequence set forth in SEQ ID NO: 15 and a VL sequence set forth in SEQ ID NO: 39; and wherein the human Fc region comprises a human IgG sequence set forth in SEQ ID NO: 457.

In certain embodiments, the isolated antibody comprises a VH sequence set forth in SEQ ID NO: 15 and a VL sequence set forth in SEQ ID NO: 39; and wherein the human Fc region comprises a human IgG sequence set forth in SEQ ID NO: 460.

In certain embodiments, the isolated antibody comprises a VH sequence set forth in SEQ ID NO: 15 and a VL sequence set forth in SEQ ID NO: 39; and wherein the human Fc region comprises a human IgG sequence set forth in SEQ ID NO: 446.

In certain embodiments, the isolated antibody comprises a VH sequence set forth in SEQ ID NO: 3 and a VL sequence set forth in SEQ ID NO: 39; and wherein the human Fc region comprises a human IgG sequence set forth in SEQ ID NO: 439.

In certain embodiments, the isolated antibody comprises a VH sequence set forth in SEQ ID NO: 3 and a VL sequence set forth in SEQ ID NO: 39; and wherein the human Fc region comprises a human IgG sequence set forth in SEQ ID NO: 457.

In certain embodiments, the isolated antibody comprises a VH sequence set forth in SEQ ID NO: 3 and a VL sequence set forth in SEQ ID NO: 39; and wherein the human Fc region comprises a human IgG sequence set forth in SEQ ID NO: 460.

In certain embodiments, the isolated antibody comprises a VH sequence set forth in SEQ ID NO: 3 and a VL sequence set forth in SEQ ID NO: 39; and wherein the human Fc region comprises a human IgG sequence set forth in SEQ ID NO: 446.

In certain embodiments, the isolated antibody comprises a VH sequence set forth in SEQ ID NO: 7 and a VL sequence set forth in SEQ ID NO: 51; and wherein the human Fc region comprises a human IgG sequence set forth in SEQ ID NO: 439.

In certain embodiments, the isolated antibody comprises a VH sequence set forth in SEQ ID NO: 7 and a VL sequence set forth in SEQ ID NO: 51; and wherein the human Fc region comprises a human IgG sequence set forth in SEQ ID NO: 457.

In certain embodiments, the isolated antibody comprises a VH sequence set forth in SEQ ID NO: 7 and a VL sequence set forth in SEQ ID NO: 51; and wherein the human Fc region comprises a human IgG sequence set forth in SEQ ID NO: 460.

In certain embodiments, the isolated antibody comprises a VH sequence set forth in SEQ ID NO: 7 and a VL sequence set forth in SEQ ID NO: 51; and wherein the human Fc region comprises a human IgG sequence set forth in SEQ ID NO: 446.

In certain embodiments, the isolated antibody comprises a VH sequence set forth in SEQ ID NO: 8 and a VL sequence set forth in SEQ ID NO: 39; and wherein the human Fc region comprises a human IgG sequence set forth in SEQ ID NO: 439.

In certain embodiments, the isolated antibody comprises a VH sequence set forth in SEQ ID NO: 8 and a VL sequence set forth in SEQ ID NO: 39; and wherein the human Fc region comprises a human IgG sequence set forth in SEQ ID NO: 457.

In certain embodiments, the isolated antibody comprises a VH sequence set forth in SEQ ID NO: 8 and a VL sequence set forth in SEQ ID NO: 51; and wherein the human Fc region comprises a human IgG sequence set forth in SEQ ID NO: 460.

In certain embodiments, the isolated antibody comprises a VH sequence set forth in SEQ ID NO: 8 and a VL sequence set forth in SEQ ID NO: 51; and wherein the human Fc region comprises a human IgG sequence set forth in SEQ ID NO: 446.

In certain embodiments, the isolated antibody comprises a VH sequence set forth in SEQ ID NO: 470 and a VL sequence set forth in SEQ ID NO: 471; and wherein the human Fc region comprises a human IgG sequence set forth in SEQ ID NO: 439.

In certain embodiments, the isolated antibody comprises a VH sequence set forth in SEQ ID NO: 470 and a VL sequence set forth in SEQ ID NO: 471; and wherein the human Fc region comprises a human IgG sequence set forth in SEQ ID NO: 457.

In certain embodiments, the isolated antibody comprises a VH sequence set forth in SEQ ID NO: 470 and a VL sequence set forth in SEQ ID NO: 471; and wherein the human Fc region comprises a human IgG sequence set forth in SEQ ID NO: 460.

In certain embodiments, the isolated antibody comprises a VH sequence set forth in SEQ ID NO: 470 and a VL sequence set forth in SEQ ID NO: 471; and wherein the human Fc region comprises a human IgG sequence set forth in SEQ ID NO: 446. In certain embodiments, the isolated antibody light chain comprises a constant light chain sequence set forth by SEQ ID NO: 469.

In certain embodiments, the isolated antibody Fc region comprises one or more amino acid substitutions, wherein the one or more substitutions result in a change (e.g., an increase or a decrease) in antibody half-life, ADCC activity, ADCP activity, or CDC activity as compared to an otherwise equivalent antibody comprising an Fc without the one or more substitutions. In certain embodiments, the change is an increase in antibody half-life, an increase or a decrease in ADCC activity, an increase in ADCP activity or an increase in CDC activity as compared to an otherwise equivalent antibody comprising an Fc without the one or more substitutions. In certain embodiments, the one or more amino acid substitutions results in increased antibody half-life compared to an antibody comprising a wild-type Fc region. In certain embodiments, the isolated antibody comprising an Fc region with one or more amino acid substitutions has a half-life of about 80 to 110 days in a human.

In certain embodiments, the change is an increase or a decrease in antibody half-life, an increase or a decrease in ADCC activity, an increase or a decrease in ADCP activity, or an increase or a decrease in CDC activity as compared to an otherwise equivalent antibody comprising an Fc without the one or more substitutions. In certain embodiments, the change is an increase in antibody half-life as compared to an otherwise equivalent antibody comprising an Fc without the one or more substitutions. In certain embodiments, the change is a decrease in antibody half-life as compared to an otherwise equivalent antibody comprising an Fc without the one or more substitutions. In certain embodiments, the change is an increase in ADCC activity as compared to an otherwise equivalent antibody comprising an Fc without the one or more substitutions. In certain embodiments, the change is a decrease in ADCC activity as compared to an otherwise equivalent antibody comprising an Fc without the one or more substitutions. In certain embodiments, the change is an increase in ADCP activity as compared to an otherwise equivalent antibody comprising an Fc without the one or more substitutions. In certain embodiments, the change is a decrease in ADCP activity as compared to an otherwise equivalent antibody comprising an Fc without the one or more substitutions. In certain embodiments, the change is an increase in CDC activity as compared to an otherwise equivalent antibody comprising an Fc without the one or more substitutions. In certain embodiments, the change is a decrease in CDC activity as compared to an otherwise equivalent antibody comprising an Fc without the one or more substitutions. In certain embodiments, the change is an increase in antibody half-life, an increase in ADCC activity, an increase in ADCP activity and an increase in CDC activity as compared to an otherwise equivalent antibody comprising an Fc without the one or more substitutions. In certain embodiments, the change is an increase in antibody half-life, a decrease in ADCC activity, an increase in ADCP activity and an increase in CDC activity as compared to an otherwise equivalent antibody comprising an Fc without the one or more substitutions.

In certain embodiments, the change is an increase in antibody half-life as compared to an otherwise equivalent antibody comprising an Fc without the one or more substitutions.

In certain embodiments, the change is an increase in ADCC activity as compared to an otherwise equivalent antibody comprising an Fc without the one or more substitutions.

In certain embodiments, the change is a decrease in ADCC activity as compared to an otherwise equivalent antibody comprising an Fc without the one or more substitutions.

In certain embodiments, the Fc region binds to Neonatal Fc receptor (FcRn). In certain embodiments, the Fc region binds an FcRn with higher affinity at pH 6.0 compared to an antibody comprising a wild-type Fc region. In certain embodiments, the Fc region binds to FcRn with a $K_D$ of $<1 \times 10^{-7}$ M at pH 6.0.

In certain embodiments, the isolated antibody is a monoclonal antibody.

In certain embodiments, the antibody binds an IL-13 sequence set forth in SEQ ID NOs: 472-475.

In certain embodiments, the isolated antibody binds to an IL-13 sequence set forth in SEQ ID NOs: 472-475 with a $K_D$ of less than or equal to about 1, 2, 3, 4, 5, 6, 7, 8, $9 \times 10^{-9}$ M, as measured by surface plasmon resonance (SPR). In certain embodiments, the isolated antibody binds to an IL-13 sequence set forth in SEQ ID NOs: 472-475 with a $K_D$ of less than or equal to about $1 \times 10^{-10}$ M, as measured by SPR. In certain embodiments, the antibody binds to human IL-13 with a $K_D$ of less than or equal to about $1 \times 10^{-9}$M, as measured by SPR.

In certain embodiments, the isolated antibody exhibits a melting temperature greater than 68° C. as measured by Differential Scanning Fluorometry (DSF). In certain embodiments, the antibody exhibits a melting temperature greater than 75° C. as measured by DSF. In certain embodiments, the antibody exhibits a aggregation temperature equal to or greater than 71.2° C. as measured by DSF.

In certain embodiments, the isolated antibody has a retention time of 15.2 minutes or less as measured by hydrophobic interaction chromatography.

In certain embodiments, the isolated antibody does not have a heavy chain variable region sequence set forth in SEQ ID NO: 470.

In certain embodiments, the isolated antibody is used in the treatment of an inflammatory disorder or disease. In certain embodiments, the isolated antibody is used in the treatment of atopic dermatitis. In certain embodiments, the treatment reduces disease severity in a subject and wherein disease severity is assessed by an Atopic Dermatitis Disease Severity Outcome Measure. In certain embodiments, the isolated antibody is used in the treatment of asthma. In certain embodiments, the isolated antibody is used in the treatment of idiopathic pulmonary fibrosis. In certain embodiments, the isolated antibody is used in the treatment of alopecia areata. In certain embodiments, the isolated antibody is used in the treatment of chronic sinusitis with nasal polyps. In certain embodiments, the isolated antibody is used in the treatment of Chronic Rhinosinusitis without Nasal Polyps (CRSsNP). In certain embodiments, the isolated antibody is used in the treatment of eosinophilic esophagitis (EoE). In certain embodiments, the isolated antibody is used in the treatment of an Eosinophilic gastro-intestinal disorder or disease (ENID) selected from the group consisting of Eosinophilic Gastritis (EoG), Eosinophilic Enteritis (EoN), Eosinophilic Colitis (EoC), and Eosinophilic Gastroenteritis (EGE). In certain embodiments, the isolated antibody is used in the treatment of Churg-Strauss syndrome/Eosinophilic granulomatosis with polyangiitis (EGPA). In certain embodiments, the isolated antibody is used in the treatment of Prurigo Nodularis (PN). In certain embodiments, the isolated antibody is used in the treatment of Chronic Spontaneous Urticaria (CSU). In certain embodiments, the isolated antibody is used in the treatment of Chronic Pruritis of Unknown Origin (CPUO). In certain embodiments, the isolated antibody is used in the treatment of Bullous Pemphigoid (BP). In certain embodiments, the isolated antibody is used in the treatment of Cold Inducible Urticaria (ColdU). In certain embodiments, the isolated antibody is used in the treatment of Allergic Fungal Rhinosinusitis (AFRS). In certain embodiments, the isolated antibody is used in the treatment of Allergic Bronchopulmonary Aspergillosis (ABPA). In certain embodiments, the isolated antibody is used in the treatment of Chronic Obstructive Pulmonary Disease (COPD). In certain embodiments, the isolated antibody is used in the treatment of inflammatory bowel disease, such as Crohn disease or ulcerative colitis. In certain embodiments, the isolated antibody is used in the treatment of psoriasis. In certain embodiments, the isolated antibody is used in the treatment of lupus. In certain embodiments, the isolated antibody is used in the treatment of rheumatoid arthritis.

In certain aspects, described herein is an isolated polynucleotide or set of polynucleotides encoding an antibody described herein, a VH thereof, a VL thereof, a light chain thereof, a heavy chain thereof, or an antigen-binding portion thereof, and optionally, wherein the polynucleotide or set of polynucleotides comprises cDNA. In certain aspects, described herein is a vector or set of vectors comprising the polynucleotide or set of polynucleotides. In certain aspects, described herein is a host cell comprising the polynucleotide or set of polynucleotides or the vector or set of vectors.

In certain aspects, described herein is a method of producing an antibody, the method comprising expressing the antibody with the host cell described herein and isolating the expressed antibody.

In certain aspects, described herein is a pharmaceutical composition comprising an antibody described herein and a pharmaceutically acceptable excipient.

In certain aspects, described herein is a kit comprising an antibody described herein or a pharmaceutical composition described herein and instructions for use.

In certain aspects, described herein is a method for treating an inflammatory disorder or disease in a mammalian subject in need thereof, the method comprising administering to the mammalian subject a therapeutically effective amount an antibody described herein or a pharmaceutical composition described herein. In certain embodiments of the methods described herein, the inflammatory disorder or disease is atopic dermatitis. In certain embodiments, the inflammatory disorder or disease is asthma. In certain embodiments, the inflammatory disorder or disease is idiopathic pulmonary fibrosis. In certain embodiments, the inflammatory disorder or disease is alopecia areata. In certain embodiments, the inflammatory disorder or disease is chronic sinusitis with nasal polyps. In certain embodiments, the inflammatory disorder or disease is Chronic Rhinosinusitis without Nasal Polyps (CRSsNP). In certain embodiments, the inflammatory disorder or disease is eosinophilic esophagitis (EoE). In certain embodiments, the inflammatory disorder or disease is an Eosinophilic gastrointestinal disorder or disease (ENID) selected from the group consisting of Eosinophilic Gastritis (EoG), Eosinophilic enteritis (EoN), Eosinophilic colitis (EoC), and Eosinophilic Gastroenteritis (EGE). In certain embodiments, the inflammatory disorder or disease is Churg-Strauss syndrome/Eosinophilic granulomatosis with polyangiitis (EGPA). In certain embodiments, the inflammatory disorder or disease is Prurigo Nodularis (PN). In certain embodiments, the inflammatory disorder or disease is Chronic Spontaneous Urticaria (CSU). In certain embodiments, the inflammatory disorder or disease is Chronic Pruritis of Unknown Origin (CPUO). In certain embodiments, the inflammatory disorder or disease is Bullous Pemphigoid (BP). In certain embodiments, the inflammatory disorder or disease is Cold Inducible Urticaria (ColdU). In certain embodiments, the inflammatory disorder or disease is Allergic Fungal Rhinosinusitis (AFRS). In certain embodiments, the inflammatory disorder or disease is Allergic Bronchopulmonary Aspergillosis (ABPA). In certain embodiments, the inflammatory disorder or disease is Chronic Obstructive Pulmonary Disease (COPD). In certain embodiments, the inflammatory disorder or disease is inflammatory bowel disease, such as Crohn disease or ulcerative colitis. In certain embodiments, the inflammatory disorder or disease is psoriasis. In certain embodiments, the inflammatory disorder or disease is lupus. In certain embodiments, the inflammatory disorder or disease is rheumatoid arthritis.

In certain aspects, described herein is a method for treating a pathology associated with elevated levels of IL-13 in a mammalian subject in need thereof, the method comprising administering to the mammalian subject a therapeutically effective amount an antibody described herein or a pharmaceutical composition described herein.

In certain aspects, described herein is a method of reducing biological activity of IL-13 in a mammalian subject in need thereof, the method comprising administering to the mammalian subject a therapeutically effective amount an antibody described herein or a pharmaceutical composition described herein.

In certain aspects, described herein is a method of inhibiting the TH2 type allergic response in a mammalian subject in need thereof, the method comprising administering to the mammalian subject a therapeutically effective amount an antibody described herein or a pharmaceutical composition described herein.

In certain aspects, described herein is a method of reducing levels of Thymus and Activation Regulated Chemokine (TARC)/CCL17 in a mammalian subject in need thereof, the method comprising administering to the mammalian subject a therapeutically effective amount an antibody described herein or a pharmaceutical composition described herein.

In certain aspects, described herein is a method of preventing an inflammatory disorder or disease in a mammalian subject in need thereof, the method comprising administering to the mammalian subject a therapeutically effective amount an antibody of described herein or a pharmaceutical composition described herein.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION

IL-13 signaling begins with the binding of IL-13 to IL-13Rα1, forming an inactive complex that then binds to IL-4Rα to form the complete, active receptor heterodimer. This active receptor heterodimer contributes to the pathogenesis of atopic dermatitis. The instant disclosure relates, in part, to anti-IL-13 antibodies that prevent the formation of this heterodimer.

Figure 1:
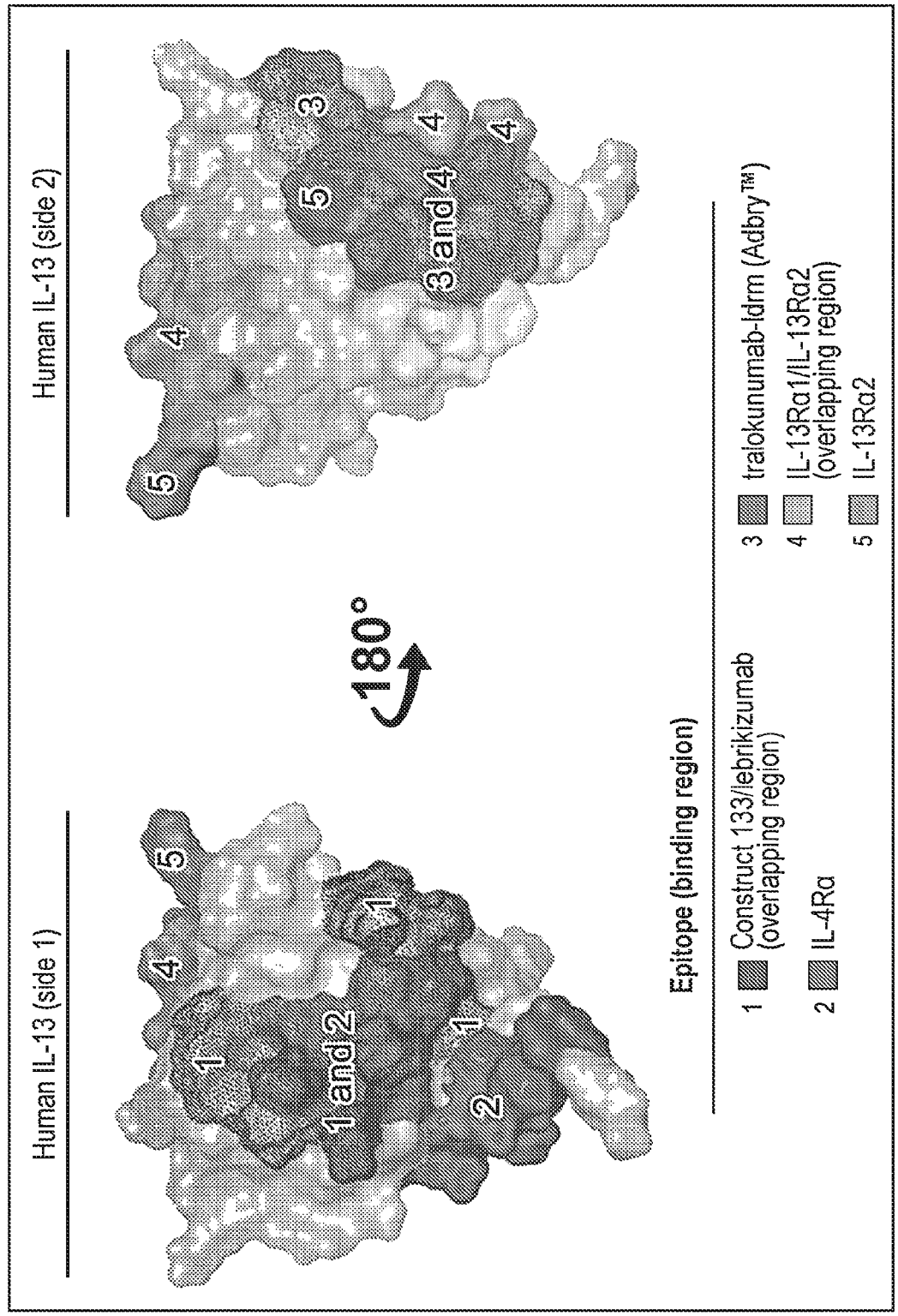
FIG. 1 is a three-dimensional rendering of human IL-13. The "1" gray highlights the epitope of lebrikizumab, which overlaps with the epitope of Construct 133 disclosed herein (see e.g., Tables 2-8). These epitopes also overlap with the IL-4Rα epitope on IL-13, shown in "2" gray. The epitope of tralokunumab-ldrm (Adbry™) is shown in "3" gray. The IL-13Rα1/IL-13Rα2 overlapping epitope is shown in "4" gray, and the IL-13Rα2 (non-overlapping) epitope is shown in "5" gray.

As shown in FIG. 1, a three-dimensional rendering of human IL-13, "1" gray highlights the epitope of lebrikizumab, which overlaps with the epitope of certain antibodies disclosed herein. Importantly, these epitopes also overlap with the IL-4Rα epitope on IL-13. Without wishing to be bound by theory, it is believed that antibodies that bind to this region are likely to prevent the formation of the IL-13Rα1-IL-4Rα heterodimer, limiting the inflammatory signaling that leads to atopic dermatitis. In contrast, the epitope of tralokunumab-ldrm (Adbry™), highlighted in "3" gray, does not overlap with the IL-4Rα epitope on IL-13 and therefore may have a more limited ability to prevent heterodimerization.

Definitions

Unless otherwise defined, all terms of art, notations and other scientific terminology used herein are intended to have the meanings commonly understood by those of skill in the art. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., Molecular Cloning: A Laboratory Manual 4th ed. (2012) Cold Spring Harbor Laboratory Press, Cold Spring Harbor, NY. As appropriate, procedures involving the use of commercially available kits and reagents are generally carried out in accordance with manufacturer-defined protocols and conditions unless otherwise noted.

As used herein, the singular form "a," "an," and "the" includes plural references unless indicated otherwise.

It is understood that aspects and embodiments of the invention described herein include "comprising," "consisting," and "consisting essentially of" aspects and embodiments.

For all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as "consisting essentially of" a component, the composition may additionally contain any amount of pharmaceutically acceptable carriers, vehicles, or diluents and other such components which do not substantially affect the condition being treated.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which an exogenous nucleic acid has been introduced, and the progeny of such cells. Host cells include "transformants" (or "transformed cells") and "transfectants" (or "transfected cells"), which each include the primary transformed or transfected cell and progeny derived therefrom. Such progeny may not be completely identical in nucleic acid content to a parent cell, and may contain mutations. A "recombinant host cell" or "host cell" refers to a cell that includes an exogenous polynucleotide, regardless of the method used for insertion, for example, direct uptake, transduction, f-mating, or other methods known in the art to create recombinant host cells.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

As used herein, the term "prokaryote" refers to prokaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, Methanococcus jannaschii, *Methanobacterium* thermoautotrophicum, *Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

An "effective amount" or "therapeutically effective amount" as used herein refers to an amount of therapeutic compound, such as an anti-IL-13 antibody, administered to an individual, either as a single dose or as part of a series of doses, which is effective to produce or contribute to a desired therapeutic effect, either alone or in combination with another therapeutic modality. Examples of a desired therapeutic effect is enhancing an immune response, slowing or delaying tumor development; stabilization of disease; amelioration of one or more symptoms. An effective amount may be given in one or more dosages.

The term "treating" (and variations thereof such as "treat" or "treatment") refers to clinical intervention in an attempt to alter the natural course of a disease or condition in a subject in need thereof. Treatment can be performed during the course of clinical pathology. Desirable effects of treatment include preventing recurrence of disease, alleviation of symptoms, diminishment of any direct or indirect pathological consequences of the disease, preventing metastasis, decreasing the rate of disease progression, amelioration or palliation of the disease state, and remission or improved prognosis.

The term "sufficient amount" means an amount sufficient to produce a desired effect, e.g., an amount sufficient to modulate an immune response in a subject.

As used herein, the term "subject" or "individual" means a mammalian subject. Exemplary subjects include humans, monkeys, dogs, cats, mice, rats, cows, horses, camels, goats, rabbits, and sheep. In certain embodiments, the subject is a human. In some embodiments the subject has a disease or condition that can be treated with an antibody provided herein. In some embodiments, the disease or condition is a cancer. In some embodiments, the disease or condition is a viral infection.

The term "in vitro" refers to processes that occur in a living cell growing separate from a living organism, e.g., growing in tissue culture.

The term "in vivo" refers to processes that occur in a living organism.

The term "package insert" is used to refer to instructions customarily included in commercial packages of therapeutic or diagnostic products (e.g., kits) that contain information about the indications, usage, dosage, administration, combination therapy, contraindications and/or warnings concerning the use of such therapeutic or diagnostic products.

The term "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The terms "co-administration," "co-administer," and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to the administration of a second therapeutic agent.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The term "about" indicates and encompasses an indicated value and a range above and below that value. In certain embodiments, the term "about" indicates the designated value±10%, ±5%, or ±1%. In certain embodiments, where applicable, the term "about" indicates the designated value(s)±one standard deviation of that value(s).

The term "agonize" refers to the activation of receptor signaling to induce a biological response associated with activation of the receptor. An "agonist" is an entity that binds to and agonizes a receptor.

The term "antagonize" refers to the inhibition of receptor signaling to inhibit a biological response associated with activation of the receptor. An "antagonist" is an entity that binds to and antagonizes a receptor.

For any of the structural and functional characteristics described herein, methods of determining these characteristics are known in the art.

The term "optionally" is meant, when used sequentially, to include from one to all of the enumerated combinations and contemplates all sub-combinations.

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The term "affinity" refers to the strength of the sum total of non-covalent interactions between a single binding site of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope).

The term "kd" (sec-1), as used herein, refers to the dissociation rate constant of a particular antibody-antigen interaction. This value is also referred to as the koff value.

The term "ka" (M-1×sec-1), as used herein, refers to the association rate constant of a particular antibody-antigen interaction. This value is also referred to as the kon value.

The term "KD" (M), as used herein, refers to the dissociation equilibrium constant of a particular antibody-antigen interaction. KD=kd/ka. In some embodiments, the affinity of an antibody is described in terms of the KD for an interaction between such antibody and its antigen. For clarity, as known in the art, a smaller KD value indicates a higher affinity interaction, while a larger KD value indicates a lower affinity interaction.

The term "KA" (M-1), as used herein, refers to the association equilibrium constant of a particular antibody-antigen interaction. KA=ka/kd.

The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies.

A "anti-IL-13 antibody," "IL-13 antibody," or "IL-13 specific antibody" is an antibody, as provided herein, which specifically binds to the antigen IL-13.

The term "epitope" means a portion of an antigen that specifically binds to an antibody.

The term "hypervariable region" or "HVR," as used herein, refers to each of the regions of an antibody variable domain which are hypervariable in sequence and/or form structurally defined loops ("hypervariable loops").

The term "antigen-binding domain" means the portion of an antibody that is capable of specifically binding to an antigen or epitope.

The term "chimeric antibody" refers to an antibody in which a portion of the heavy and/or light chain is derived from a particular source or species, while the remainder of the heavy and/or light chain is derived from a different source or species.

The term "human antibody" refers to an antibody which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

The term "humanized antibody" refers to a protein having a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject.

The term "multispecific antibody" refers to an antibody that comprises two or more different antigen-binding domains that collectively specifically bind two or more different epitopes.

A "monospecific antibody" is an antibody that comprises one or more binding sites that specifically bind to a single epitope. An example of a monospecific antibody is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "single-chain" refers to a molecule comprising amino acid monomers linearly linked by peptide bonds. In a particular such embodiment, the C-terminus of the Fab light chain is connected to the N-terminus of the Fab heavy chain in the single-chain Fab molecule. As described in more detail herein, an scFv has a variable domain of light chain (VL) connected from its C-terminus to the N-terminal end of a variable domain of heavy chain (VH) by a polypeptide chain. Alternately the scFv comprises of polypeptide chain where in the C-terminal end of the VH is connected to the N-terminal end of VL by a polypeptide chain.

The "Fab fragment" (also referred to as fragment antigen-binding) contains the constant domain (CL) of the light chain and the first constant domain (CH1) of the heavy chain along with the variable domains VL and VH on the light and heavy chains respectively. The variable domains comprise the complementarity determining loops (CDR, also referred to as hypervariable region) that are involved in antigen-binding. Fab' fragments differ from Fab fragments by the addition of a few residues at the carboxy terminus of the heavy chain CH1 domain including one or more cysteines from the antibody hinge region.

"F(ab')2" fragments contain two Fab' fragments joined, near the hinge region, by disulfide bonds. F(ab')2 fragments may be generated, for example, by recombinant methods or by pepsin digestion of an intact antibody. The F(ab') fragments can be dissociated, for example, by treatment with β-mercaptoethanol.

"Fv" fragments comprise a non-covalently-linked dimer of one heavy chain variable domain and one light chain variable domain.

"Single-chain Fv" or "sFv" or "scFv" includes the VH and VL domains of an antibody, wherein these domains are present in a single polypeptide chain. In one embodiment, the Fv polypeptide further comprises a polypeptide linker between the VH and VL domains which enables the scFv to form the desired structure for antigen-binding. For a review of scFv see Pluckthun in The Pharmacology of Monoclonal Antibodies, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

"scFv-Fc" fragments comprise an scFv attached to an Fc domain. For example, an Fc domain may be attached to the C-terminal of the scFv. The Fc domain may follow the VH or VL, depending on the orientation of the variable domains in the scFv (i.e., VH-VL or VL-VH). Any suitable Fc domain known in the art or described herein may be used. In some cases, the Fc domain comprises an IgG4 Fc domain.

The term "single domain antibody" or "sdAb" refers to a molecule in which one variable domain of an antibody specifically binds to an antigen without the presence of the other variable domain. Single domain antibodies, and fragments thereof, are described in Arabi Ghahroudi et al., *FEBS Letters,* 1998, 414:521-526 and Muyldermans et al., *Trends in Biochem. Sci.,* 2001, 26:230-245, each of which is incorporated by reference in its entirety. Single domain antibodies are also known as sdAbs or nanobodies. Sdabs are fairly stable and easy to express as fusion partner with the Fc chain of an antibody (Harmsen M M, De Haard H J (2007). "Properties, production, and applications of camelid single-domain antibody fragments". *Appl. Microbiol Biotechnol.* 77 (1): 13-22).

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

The term "antibody fragment" refers to an antibody that comprises a portion of an intact antibody, such as the antigen-binding or variable region of an intact antibody. Antibody fragments include, for example, Fv fragments, Fab fragments, F(ab')2 fragments, Fab' fragments, scFv (sFv) fragments, and scFv-Fc fragments.

The term "Fc domain" or "Fc region" herein is used to define a C-terminal region of an immunoglobulin heavy chain that contains at least a portion of the constant region. The term includes native sequence Fc regions and variant Fc regions.

The term "substantially purified" refers to a construct described herein, or variant thereof that may be substantially or essentially free of components that normally accompany or interact with the protein as found in its naturally occurring environment, i.e. a native cell, or host cell in the case of recombinantly produced antibody that in certain embodiments, is substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., using publicly available computer software such as BLAST, BLASTP, BLASTN, BLAST-2, ALIGN, MEGALIGN (DNASTAR), CLUSTALW, CLUSTAL OMEGA, or MUSCLE software or other algorithms available to persons of skill) or by visual inspection. Software for performing BLAST analyses is publicly available through the National Center for Biotechnology Information (ncbi.nlm.nih.gov). Those skilled in the art can determine appropriate parameters for aligning sequences, including any algorithms needed to achieve maximal alignment over the full length of the sequences being compared. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

It must be noted that, as used in the specification and the appended claims, the singular forms "a," "an" and "the" include plural referents unless the context clearly dictates otherwise.

Anti-IL-13 Antibodies

Antibody Structure

The present application provides antibodies and compositions comprising an antibody which binds IL-13.

The recognized immunoglobulin genes include the kappa, lambda, alpha, gamma, delta, epsilon, and mu constant region genes, as well as the myriad immunoglobulin variable region genes. Light chains are classified as either kappa or lambda. The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

An exemplary immunoglobulin (antibody) structural unit is composed of two pairs of polypeptide chains, each pair having one "light" (about 25 kD) and one "heavy" chain (about 50-70 kD). The N-terminal domain of each chain defines a variable region of about 100 to 110 or more amino acids primarily responsible for antigen recognition. The terms variable light chain (VL) and variable heavy chain (VH) refer to these light and heavy chain domains respectively. The IgG1 heavy chain comprises of the VH, CH1, CH2, and CH3 domains respectively from the N- to C-terminus. The light chain comprises of the VL and CL domains from N- to C-terminus. The IgG1 heavy chain comprises a hinge between the CH1 and CH2 domains. In certain embodiments, the immunoglobulin constructs comprise at least one immunoglobulin domain from IgG, IgM, IgA, IgD, or IgE connected to a therapeutic polypeptide. In some embodiments, the immunoglobulin domain found in an antibody provided herein, is from or derived from an immunoglobulin based construct such as a diabody or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody, or any chimeric antibody.

In some embodiments, the antibodies provided herein comprise a heavy chain. In one embodiment, the heavy chain is an IgA. In one embodiment, the heavy chain is an IgD. In one embodiment, the heavy chain is an IgE. In one embodiment, the heavy chain is an IgG. In one embodiment, the heavy chain is an IgM. In one embodiment, the heavy chain is an IgG1. In one embodiment, the heavy chain is an IgG2. In one embodiment, the heavy chain is an IgG3. In one embodiment, the heavy chain is an IgG4. In one embodiment, the heavy chain is an IgA1. In one embodiment, the heavy chain is an IgA2.

In some embodiments, an antibody is an IgG1 antibody. In some embodiments, an antibody is an IgG3 antibody. In some embodiments, an antibody is an IgG2 antibody. In some embodiments, an antibody is an IgG4 antibody.

Generally, native four-chain antibodies comprise six hypervariable regions (HVRs); three in the VH (H1, H2, and H3), and three in the VL (L1, L2, and L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. HVRs are also referred to as CDRs, and these terms are used herein interchangeably in reference to portions of the variable region that form the antigen-binding regions. This particular region has been described by Kabat et al., U.S. Dept. of Health and Human Services, Sequences of Proteins of Immunological Interest (1983) and by Chothia et al., *J Mol Biol* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme); each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

CDRs may be assigned, for example, using antibody numbering software, such as Abnum, available at www.bioinf.org.uk/abs/abnum/, and described in Abhinandan and Martin, *Immunology*, 2008, 45:3832-3839, incorporated by reference in its entirety.

TABLE 1

Table 1. Residues in CDRs according to Kabat and Chothia numbering schemes.

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

One example of an antigen-binding domain is an antigen-binding domain formed by a VH-VL dimer of an antibody. Another example of an antigen-binding domain is an antigen-binding domain formed by diversification of certain loops from the tenth fibronectin type III domain of an Adnectin. An antigen-binding domain can include CDRs 1, 2, and 3 from a heavy chain in that order; and CDRs 1, 2, and 3 from a light chain in that order.

Epitopes frequently consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding and other amino acid residues, which are not directly involved in the binding. The epitope to which an antibody binds can be determined using known techniques for epitope determination such as, for example, testing for antibody binding to IL-13 variants with different point-mutations or to chimeric IL-13 variants.

To screen for antibodies which bind to an epitope on a target antigen bound by an antibody of interest (e.g., IL-13), a routine cross-blocking assay such as that described in Antibodies, A Laboratory Manual, Cold Spring Harbor Laboratory, Ed Harlow and David Lane (1988), can be performed. Alternatively, or additionally, epitope mapping can be performed by methods known in the art.

Chimeric antibodies are antibodies in which a portion of the heavy and/or light chain is derived from a particular source or species, while the remainder of the heavy and/or light chain is derived from a different source or species.

Human antibodies are antibodies which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies can be found in U.S. Pat. Nos. 6,054,297, 5,886,152 and 5,877,293. For further details, see Jones et al., *Nature*, 1986, 321:522-525; Riechmann et al., *Nature*, 1988, 332:323-329; and Presta, *Curr. Op. Struct. Biol.*, 1992, 2:593-596, each of which is incorporated by reference in its entirety.

The two or more different epitopes may be epitopes on the same antigen (e.g., a single IL-13) or on different antigens (e.g., different IL-13 molecules, or a IL-13 molecule and a non-IL-13 molecule). In some embodiments, a multi-specific antibody binds two different epitopes (i.e., a "bispecific antibody"). In some embodiments, a multi-specific antibody binds three different epitopes (i.e., a "trispecific antibody").

Anti-IL-13 antibodies can include those described herein such as the clones set forth in the drawings and/or tables. In some embodiments, the antibody comprises an alternative scaffold. In some embodiments, the antibody consists of an alternative scaffold. In some embodiments, the antibody consists essentially of an alternative scaffold. In some embodiments, the antibody comprises an antibody fragment. In some embodiments, the antibody consists of an antibody fragment. In some embodiments, the antibody consists essentially of an antibody fragment.

In some embodiments the antibodies are monoclonal antibodies.

In some embodiments the antibodies are polyclonal antibodies.

In some embodiments the antibodies are produced by hybridomas. In other embodiments, the antibodies are produced by recombinant cells engineered to express the desired variable and constant domains.

In some embodiments the antibodies may be single chain antibodies or other antibody derivatives retaining the antigen specificity and the lower hinge region or a variant thereof.

In some embodiments the antibodies may be polyfunctional antibodies, recombinant antibodies, human antibodies, humanized antibodies, fragments or variants thereof. In particular embodiments, the antibody fragment or a derivative thereof is selected from a Fab fragment, a Fab'2 fragment, a CDR, and ScFv.

In some embodiments, the antibodies are capable of forming an immune complex. For example, an immune complex can be a tumor cell covered by antibodies.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (www.ncbi.nlm.nih.gov/).

Sequences of IL-13 Antibodies
VH Domains

In some embodiments, an antibody provided herein comprises a VH sequence selected from SEQ ID NOs: 1-32 and 470.

In some embodiments, an antibody provided herein comprises a VH sequence having at least about 80%, 90%, 91%, 92%, 93%, 94%, 95%, 96%, 97%, 98% or 99% identity to an illustrative VH sequence provided in SEQ ID NOs: 1-32 and 470. In some embodiments, an antibody provided herein comprises a VH sequence provided in SEQ ID NOs: 1-32 and 470, with up to 1, 2, 3, 4, 5, 6, 7, 8, 9, 10, 11, 12, 13, 14, 15, 16, 17, 18, 19, or 20 amino acid substitutions. In some embodiments, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

VL Domains

In some embodiments, an antibody provided herein comprises a VL sequence selected from SEQ ID NOs: 33-57 and 471.

In some embodiments, an antibody provided herein comprises a VL sequence having at least about 80%, 90%, 91%, 92%, 93%, 94%, 95%, 96%, 97%, 98% or 99% identity to an illustrative VL sequence provided in SEQ ID NOs: 33-57 and 471. In some embodiments, an antibody provided herein comprises a VL sequence provided in SEQ ID NOs: 33-57 and 471 with up to 1, 2, 3, 4, 5, 6, 7, 8, 9, 10, 11, 12, 13, 14, 15, 16, 17, 18, 19, or 20 amino acid substitutions. In some embodiments, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

VH-VL Combinations

In some embodiments, an antibody provided herein comprises a VH sequence selected from SEQ ID NOs: 1-32 and 470; and a VL sequence selected from SEQ ID NOS: 33-57 and 471, such as the VH-VL combination set forth in Table 2, below.

In certain aspects, any of SEQ ID NOs: 1-32 and 470 can be combined with any of SEQ ID NOs: 33-57 and 471.

In certain embodiments, the antibody comprises a VH sequence selected from the sequences set forth in SEQ ID NOs: 1-32 and 470 and a VL sequence set forth in SEQ ID NO: 49.

In certain embodiments, the antibody comprises a VH sequence selected from the sequences set forth in SEQ ID NOs: 1-32 and 470 and a VL sequence set forth in SEQ ID NO: 51.

In some embodiments, an antibody provided herein comprises a VH sequence having at least about 80%, 90%, 91%, 92%, 93%, 94%, 95%, 96%, 97%, 98% or 99% identity to an illustrative VH sequence provided in SEQ ID NOs: 1-32 and 470; and a VL sequence having at least about 80%, 90%, 91%, 92%, 93%, 94%, 95%, 96%, 97%, 98% or 99% identity to an illustrative VL sequence provided in SEQ ID NOs: 33-57 and 471. In some embodiments, an antibody provided herein comprises a VH sequence provided in SEQ ID NOs: 1-32 and 470, with up to 1, 2, 3, 4, 5, 6, 7, 8, 9, 10, 11, 12, 13, 14, 15, 16, 17, 18, 19, or 20 amino acid substitutions; and a VL sequence provided in SEQ ID NOs: 33-57 and 471, with up to 1, 2, 3, 4, 5, 6, 7, 8, 9, 10, 11, 12, 13, 14, 15, 16, 17, 18, 19, or 20 amino acid substitutions. In some embodiments, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a VH sequence and a VL sequence selected from combinations set forth in Table 2, below. In certain embodiments, the antibody comprises a VH sequence set forth in SEQ ID NO: 1 and a VL sequence set forth in SEQ ID NO: 33. In certain embodiments, the antibody comprises a VH sequence set forth in SEQ ID NO: 2 and a VL sequence set forth in SEQ ID NO: 33. In certain embodiments, the antibody comprises a VH sequence set forth in SEQ ID NO: 3 and a VL sequence set forth in SEQ ID NO: 35. In certain embodiments, the antibody comprises a VH sequence set forth in SEQ ID NO: 4 and a VL sequence set forth in SEQ ID NO: 35. In certain embodiments, the antibody comprises a VH sequence set forth in SEQ ID NO: 5 and a VL sequence set forth in SEQ ID NO: 35. In certain embodiments, the antibody comprises a VH sequence set forth in SEQ ID NO: 6 and a VL sequence set forth in SEQ ID NO: 35. In certain embodiments, the antibody comprises a VH sequence set forth in SEQ ID NO: 7 and a VL sequence set forth in SEQ ID NO: 35. In certain embodiments, the antibody comprises a VH sequence set forth in SEQ ID NO: 3 and a VL sequence set forth in SEQ ID NO: 36. In certain embodiments, the antibody comprises a VH sequence set forth in SEQ ID NO: 4 and a VL sequence set forth in SEQ ID NO: 36. In certain embodiments, the antibody comprises a VH sequence set forth in SEQ ID NO: 5 and a VL sequence set forth in SEQ ID NO: 36. In certain embodiments, the antibody comprises a VH sequence set forth in SEQ ID NO: 6 and a VL sequence set forth in SEQ ID NO: 36. In certain embodiments, the antibody comprises a VH sequence set forth in SEQ ID NO: 7 and a VL sequence set forth in SEQ ID NO: 36. In certain embodiments, the antibody comprises a VH sequence set forth in SEQ ID NO: 3 and a VL sequence set forth in SEQ ID NO: 39. In certain embodiments, the antibody comprises a VH sequence set forth in SEQ ID NO: 4 and a VL sequence set forth in SEQ ID NO: 39. In certain embodiments, the antibody comprises a VH sequence set forth in SEQ ID NO: 5 and a VL sequence set forth in SEQ ID NO: 39. In certain embodiments, the antibody comprises a VH sequence set forth in SEQ ID NO: 6 and a VL sequence set forth in SEQ ID NO: 39. In certain embodiments, the antibody comprises a VH sequence set forth in SEQ ID NO: 7 and a VL sequence set forth in SEQ ID NO: 39. In certain embodiments, the antibody comprises a VH sequence set forth in SEQ ID NO: 3 and a VL sequence set forth in SEQ ID NO: 40. In certain embodiments, the antibody comprises a VH sequence set forth in SEQ ID NO: 4 and a VL sequence set forth in SEQ ID NO: 40. In certain embodiments, the antibody comprises a VH sequence set forth in SEQ ID NO: 5 and a VL sequence set forth in SEQ ID NO: 40. In certain embodiments, the antibody comprises a VH sequence set forth in SEQ ID NO: 6 and a VL sequence set forth in SEQ ID NO: 40. In certain embodiments, the antibody comprises a VH sequence set forth in SEQ ID NO: 7 and a VL sequence set forth in SEQ ID NO: 40. In certain embodiments, the antibody comprises a VH sequence set forth in SEQ ID NO: 8 and a VL sequence set forth in SEQ ID NO: 42. In certain embodiments, the antibody comprises a VH sequence set forth in SEQ ID NO: 9 and a VL sequence set forth in SEQ ID NO: 43. In certain embodiments, the antibody comprises a VH sequence set forth in SEQ ID NO: 7 and a VL sequence set forth in SEQ ID NO: 39. In certain embodiments, the antibody comprises a VH sequence set forth in SEQ ID NO: 7 and a VL sequence set forth in SEQ ID NO: 44. In certain embodiments, the antibody comprises a VH sequence set forth in SEQ ID NO: 7 and a VL sequence set forth in SEQ ID NO: 45. In certain embodiments, the antibody comprises a VH sequence set forth in SEQ ID NO: 7 and a VL sequence set forth in SEQ ID NO: 46. In certain embodiments, the antibody comprises a VH sequence set forth in SEQ ID NO: 7 and a VL sequence set forth in SEQ ID NO: 47. In certain embodiments, the antibody comprises a VH sequence set forth in SEQ ID NO: 7 and a VL sequence set forth in SEQ ID NO: 48. In certain embodiments, the antibody comprises a VH sequence set forth in SEQ ID NO: 7 and a VL sequence set forth in SEQ ID NO: 49. In certain embodiments, the antibody comprises a VH sequence set forth in SEQ ID NO: 7 and a VL sequence set forth in SEQ ID NO: 50. In certain embodiments, the antibody comprises a VH sequence set forth in SEQ ID NO: 7 and a VL sequence set forth in SEQ ID NO: 51. In certain embodiments, the antibody comprises a VH sequence set forth in SEQ ID NO: 7 and a VL sequence set forth in SEQ ID NO: 52. In certain embodiments, the antibody comprises a VH sequence set forth in SEQ ID NO: 7 and a VL sequence set forth in SEQ ID NO: 53. In certain embodiments, the antibody comprises a VH sequence set forth in SEQ ID NO: 7 and a VL sequence set forth in SEQ ID NO: 54. In certain embodiments, the antibody comprises a VH sequence set forth in SEQ ID NO: 7 and a VL sequence set forth in SEQ ID NO: 55. In certain embodiments, the antibody comprises a VH sequence set forth in SEQ ID NO: 7 and a VL sequence set forth in SEQ ID NO: 56. In certain embodiments, the antibody comprises a VH sequence set forth in SEQ ID NO: 7 and a VL sequence set forth in SEQ ID NO: 57. In certain embodiments, the antibody comprises a VH sequence set forth in SEQ ID NO: 10 and a VL sequence set forth in SEQ ID NO: 39. In certain embodiments, the antibody comprises a VH sequence set forth in SEQ ID NO: 11 and a VL sequence set forth in SEQ ID NO: 39. In certain embodiments, the antibody comprises a VH sequence set forth in SEQ ID NO: 12 and a VL sequence set forth in SEQ ID NO: 39. In certain embodiments, the antibody comprises a VH sequence set forth in SEQ ID NO: 13 and a VL sequence set forth in SEQ ID NO: 39; and wherein the human Fc region comprises a human IgG sequence selected from a sequence set forth in SEQ ID NO: 436-468 and 484-539. In certain embodiments, the antibody comprises a VH sequence set forth in SEQ ID NO: 14 and a VL sequence set forth in SEQ ID NO: 39. In certain embodiments, the antibody comprises a VH sequence set forth in SEQ ID NO: 15 and a VL sequence set forth in SEQ ID NO: 39. In certain embodiments, the antibody comprises a VH sequence set forth in SEQ ID NO: 16 and a VL sequence set forth in SEQ ID NO: 39. In certain embodiments, the antibody comprises a VH sequence set forth in SEQ ID NO: 17 and a VL sequence set forth in SEQ ID NO: 39. In certain embodiments, the antibody comprises a VH sequence set forth in SEQ ID NO: 18 and a VL sequence set forth in SEQ ID NO: 39. In certain embodiments, the antibody comprises a VH sequence set forth in SEQ ID NO: 19 and a VL sequence set forth in SEQ ID NO: 39. In certain embodiments, the antibody comprises a VH sequence set forth in SEQ ID NO: 20 and a VL sequence set forth in SEQ ID NO: 39. In certain embodiments, the antibody comprises a VH sequence set forth in SEQ ID NO: 21 and a VL sequence set forth in SEQ ID NO: 39. In certain embodiments, the antibody comprises a VH sequence set forth in SEQ ID NO: 22 and a VL sequence set forth in SEQ ID NO: 39. In certain embodiments, the antibody comprises a VH sequence set forth in SEQ ID NO: 23 and a VL sequence set forth in SEQ ID NO: 39. In certain embodiments, the antibody comprises a VH sequence set forth in SEQ ID NO: 24 and a VL sequence set forth in SEQ ID NO: 39. In certain embodiments, the antibody comprises a VH sequence set forth in SEQ ID NO: 25 and a VL sequence set forth in SEQ ID NO: 39. In certain embodiments, the antibody comprises a VH sequence set forth in SEQ ID NO: 26 and a VL sequence set forth in SEQ ID NO: 39. In certain embodiments, the antibody comprises a VH sequence set forth in SEQ ID NO: 27 and a VL sequence set forth in SEQ ID NO: 39. In certain embodiments, the antibody comprises a VH sequence set forth in SEQ ID NO: 28 and a VL sequence set forth in SEQ ID NO: 39. In certain embodiments, the antibody comprises a VH sequence set forth in SEQ ID NO: 28 and a VL sequence set forth in SEQ ID NO: 39. In certain embodiments, the antibody comprises a VH sequence set forth in SEQ ID NO: 29 and a VL sequence set forth in SEQ ID NO: 39. In certain embodiments, the antibody comprises a VH sequence set forth in SEQ ID NO: 30 and a VL sequence set forth in SEQ ID NO: 39. In certain embodiments, the antibody comprises a VH sequence set forth in SEQ ID NO: 31 and a VL sequence set forth in SEQ ID NO: 39. In certain embodiments, the antibody comprises a VH sequence set forth in SEQ ID NO: 32 and a VL sequence set forth in SEQ ID NO: 39. In certain embodiments, the antibody comprises a VH sequence set forth in SEQ ID NO: 8 and a VL sequence set forth in SEQ ID NO: 39. In certain embodiments, the antibody comprises a VH sequence set forth in SEQ ID NO: 8 and a VL sequence set forth in SEQ ID NO: 51. In certain embodiments, the antibody comprises a VH sequence set forth in SEQ ID NO: 3 and a VL sequence set forth in SEQ ID NO: 51. In certain embodiments, the antibody comprises a VH sequence set forth in SEQ ID NO: 470 and a VL sequence set forth in SEQ ID NO: 471.

In certain embodiments, the isolated antibody comprises a heavy chain variable domain comprising a framework region sequence selected from a sequence set forth in SEQ ID NOs: 198-229, 255-256, 258-259, 261-285, 311-315, 317-342, 368-369, 371-399, and 540-580. In certain embodiments, the isolated antibody comprises a heavy chain variable domain comprising 1, 2, 3, or 4 framework region sequences selected from a sequence set forth in SEQ ID NOs: 198-229, 255-256, 258-259, 261-285, 311-315, 317-342, 368-369, 371-399, and 540-580.

In certain embodiments, the isolated antibody comprises a light chain variable domain comprising a framework region sequence selected from a sequence set forth in SEQ ID NOs: 230-231, 233-235, 239, 241-254, 286, 288, 290-291, 293, 296-310, 343-345, 347, 400-424, and 581-609. In certain embodiments, the isolated antibody comprises a light chain variable domain comprising 1, 2, 3, or 4 framework region sequences selected from a sequence set forth in SEQ ID NOs: 230-231, 233-235, 239, 241-254, 286, 288, 290-291, 293, 296-310, 343-345, 347, 400-424, and 581-609.

In certain embodiments, the isolated antibody comprises a heavy chain variable domain comprising 1, 2, 3, or 4 framework region sequences selected from a sequence set forth in SEQ ID NOs: 198-229, 255-256, 258-259, 261-285, 311-315, 317-342, 368-369, 371-399, and 540-580, and comprises a light chain variable domain comprising 1, 2, 3, or 4 framework region sequences selected from a sequence set forth in SEQ ID NOs: 230-231, 233-235, 239, 241-254, 286, 288, 290-291, 293, 296-310, 343-345, 347, 400-424, and 581-609.

TABLE 2

Anti-interleukin (IL)-13 antibody VH-VL sequences

| Construct ID | VH; VL; HC constant; and LC constant names, respectively* | VH sequence | VL sequence |
|---|---|---|---|
| 1 (Lebrikizumab) | Lebrikizumab-HC; Lebrikizumab-LC; IgG4-SP; Human kappa LC | QVTLRESGPALVKPTQTLTLTCTVSGFSLSAYSVNWIRQPPGKALEWLAMIWGDGKIVYNSALKSRLTISKDTSKNQVVLTMTNMDPVDTATYYCAGDGYYPYAMDNWGQGSLVTVSS (SEQ ID NO: 470) | DIVMTQSPDSLSVSLGERATINCRASKSVDSYGNSFMHWYQQKPGQPPKLLIYLASNLESGVPDRFSGSGSGTDFTLTISSLQAEDVAVYYCQQNNEDPRTFGGGTKVEIK (SEQ ID NO: 471) |
| 2 | Lebrikizumab-HC; Lebrikizumab-LC; hIgG1-LAGA YTE; Human kappa LC | QVTLRESGPALVKPTQTLTLTCTVSGFSLSAYSVNWIRQPPGKALEWLAMIWGDGKIVYNSALKSRLTISKDTSKNQVVLTMTNMDPVDTATYYCAGDGYYPYAMDNWGQGSLVTVSS (SEQ ID NO: 470) | DIVMTQSPDSLSVSLGERATINCRASKSVDSYGNSFMHWYQQKPGQPPKLLIYLASNLESGVPDRFSGSGSGTDFTLTISSLQAEDVAVYYCQQNNEDPRTFGGGTKVEIK (SEQ ID NO: 471) |
| 3 | HC0; LC0; hIgG1-LAGA YTE; Human kappa LC | QVQLQESGPGLVAPSQSLSITCTVSGFSLNAYSVNWVRQPPGKGLEWLGMIWGDGKIVYNSALKSRLNISKDSSKSQVFLKMSSLQSDDTARYYCAGDGYYPYAMDNWGHGTSVTVSS (SEQ ID NO: 1) | NIVLTQSPASLAVSLGQRATISCRASKSVDSYGNSFMHWYQQKPGQPPKLLIYLASNLESGVPARFSGSGSRTDFTLTIDPVEADDAASYYCQQNNEDPRTFGGGTKLEIK (SEQ ID NO: 33) |
| 4 | HC0_M; LC0; hIgG1-LAGA YTE; Human kappa LC | QVQLQESGPGLVAPSQSLSITCTVSGFSLNAYSVNWVRQPPGKGLEWLGMIWGDGKIVYNSALKSRLTISKDSSKSQVFLKMSSLQSDDTARYYCAGDGYYPYAMDNWGHGTSVTVSS (SEQ ID NO: 2) | NIVLTQSPASLAVSLGQRATISCRASKSVDSYGNSFMHWYQQKPGQPPKLLIYLASNLESGVPARFSGSGSRTDFTLTIDPVEADDAASYYCQQNNEDPRTFGGGTKLEIK (SEQ ID NO: 33) |
| 5 | HC1; LC2; hIgG1-LAGA YTE; Human kappa LC | EVQLQESGPGLVKPSETLSLTCTVSGFSLNAYSVNWIRQPPGKGLEWLGMIWGDGKIVYNSALKSRLTISKDSSKNQVSLKLSSVTAADTAVYYCAGDGYYPYAMDNWGQGTTVTVSS (SEQ ID NO: 3) | DIQLTQSPSSLSASVGDRVTITCRASKSVDSYGNSFMHWYQQKPGKAPKLLIYLASNLESGVPSRFSGSGSRTDFTLTISSLQPEDFATYYCQQNNEDPRTFGGGTKVEIK (SEQ ID NO: 35) |
| 6 | HC2; LC2; hIgG1-LAGA YTE; Human kappa LC | EVQLVQSGAEVKKPGASVKVSCKASGFSLNAYSVNWVRQAPGQGLEWLGMIWGDGKIVYNSALKSRLTITKDSSTSTVYMELSSLRSEDTAVYYCAGDGYYPYAMDNWGQGTTVTVSS (SEQ ID NO: 4) | DIQLTQSPSSLSASVGDRVTITCRASKSVDSYGNSFMHWYQQKPGKAPKLLIYLASNLESGVPSRFSGSGSRTDFTLTISSLQPEDFATYYCQQNNEDPRTFGGGTKVEIK (SEQ ID NO: 35) |
| 7 | HC3; LC2; hIgG1-LAGA YTE; Human kappa LC | EVQLVQSGAEVKKPGSSVKVSCKASGFSLNAYSVNWVRQAPGQGLEWLGMIWGDGKIVYNSALKSRLTITKDSSTSTVYMELSSLRSEDTAVYYCAGDGYYPYAMDNWGQGTTVTVSS (SEQ ID NO: 5) | DIQLTQSPSSLSASVGDRVTITCRASKSVDSYGNSFMHWYQQKPGKAPKLLIYLASNLESGVPSRFSGSGSRTDFTLTISSLQPEDFATYYCQQNNEDPRTFGGGTKVEIK (SEQ ID NO: 35) |
| 8 | HC4; LC2; hIgG1-LAGA YTE; Human | EVQLVESGGGLVKPGGSLRLSCAASGFSLNAYSVNWVRQAPGKGLEWLGMIWGDGKIVYNSALK | DIQLTQSPSSLSASVGDRVTITCRASKSVDSYGNSFMHWYQQKPGKAPKLLIYLASNLESGVPSRFSGSGSRT |

TABLE 2-continued

Anti-interleukin (IL)-13 antibody VH-VL sequences

| Construct ID | VH; VL; HC constant; and LC constant names, respectively* | VH sequence | VL sequence |
|---|---|---|---|
| | kappa LC | SRLTISKDSSKNTVYLQ MNSLKTEDTAVYYCA GDGYYPYAMDNWGQ GTTVTVSS (SEQ ID NO: 6) | DFTLTISSLQPEDFATYYC QQNNEDPRTFGGGTKVEI K (SEQ ID NO: 35) |
| 9 | HC5; LC2; hIgG1-LAGA YTE; Human kappa LC | EVQLLESGGGLVQPGG SLRLSCAASGFSLNAYS VNWVRQAPGKGLEWL GMIWGDGKIVYNSALK SRLTISKDSSKNTVYLQ MNSLRAEDTAVYYCA GDGYYPYAMDNWGQ GTTVTVSS (SEQ ID NO: 7) | DIQLTQSPSSLSASVGDRV TITCRASKSVDSYGNSFM HWYQQKPGKAPKLLIYL ASNLESGVPSRFSGSGSRT DFTLTISSLQPEDFATYYC QQNNEDPRTFGGGTKVEI K (SEQ ID NO: 35) |
| 10 | HC1; LC3; hIgG1-LAGA YTE; Human kappa LC | EVQLQESGPGLVKPSET LSLTCTVSGFSLNAYSV NWIRQPPGKGLEWLG MIWGDGKIVYNSALKS RLTISKDSSKNQVSLKL SSVTAADTAVYYCAGD GYYPYAMDNWGQGTT VTVSS (SEQ ID NO: 3) | EIVLTQSPATLSVSPGERA TLSCRASKSVDSYGNSFM HWYQQKPGQAPRLLIYL ASNLESGIPARFSGSGSRT EFTLTISSLQSEDFAVYYC QQNNEDPRTFGGGTKVEI K (SEQ ID NO: 36) |
| 11 | HC2; LC3; hIgG1-LAGA YTE; Human kappa LC | EVQLVQSGAEVKKPGA SVKVSCKASGFSLNAY SVNWVRQAPGQGLEW LGMIWGDGKIVYNSAL KSRLTITKDSSTSTVYM ELSSLRSEDTAVYYCA GDGYYPYAMDNWGQ GTTVTVSS (SEQ ID NO: 4) | EIVLTQSPATLSVSPGERA TLSCRASKSVDSYGNSFM HWYQQKPGQAPRLLIYL ASNLESGIPARFSGSGSRT EFTLTISSLQSEDFAVYYC QQNNEDPRTFGGGTKVEI K (SEQ ID NO: 36) |
| 12 | HC3; LC3; hIgG1-LAGA YTE; Human kappa LC | EVQLVQSGAEVKKPGS SVKVSCKASGFSLNAY SVNWVRQAPGQGLEW LGMIWGDGKIVYNSAL KSRLTITKDSSTSTVYM ELSSLRSEDTAVYYCA GDGYYPYAMDNWGQ GTTVTVSS (SEQ ID NO: 5) | EIVLTQSPATLSVSPGERA TLSCRASKSVDSYGNSFM HWYQQKPGQAPRLLIYL ASNLESGIPARFSGSGSRT EFTLTISSLQSEDFAVYYC QQNNEDPRTFGGGTKVEI K (SEQ ID NO: 36) |
| 13 | HC4; LC3; hIgG1-LAGA YTE; Human kappa LC | EVQLVESGGGLVKPGG SLRLSCAASGFSLNAYS VNWVRQAPGKGLEWL GMIWGDGKIVYNSALK SRLTISKDSSKNTVYLQ MNSLKTEDTAVYYCA GDGYYPYAMDNWGQ GTTVTVSS (SEQ ID NO: 6) | EIVLTQSPATLSVSPGERA TLSCRASKSVDSYGNSFM HWYQQKPGQAPRLLIYL ASNLESGIPARFSGSGSRT EFTLTISSLQSEDFAVYYC QQNNEDPRTFGGGTKVEI K (SEQ ID NO: 36) |
| 14 | HC5; LC3; hIgG1-LAGA YTE; Human kappa LC | EVQLLESGGGLVQPGG SLRLSCAASGFSLNAYS VNWVRQAPGKGLEWL GMIWGDGKIVYNSALK SRLTISKDSSKNTVYLQ MNSLRAEDTAVYYCA GDGYYPYAMDNWGQ GTTVTVSS (SEQ ID NO: 7) | EIVLTQSPATLSVSPGERA TLSCRASKSVDSYGNSFM HWYQQKPGQAPRLLIYL ASNLESGIPARFSGSGSRT EFTLTISSLQSEDFAVYYC QQNNEDPRTFGGGTKVEI K (SEQ ID NO: 36) |

TABLE 2-continued

Anti-interleukin (IL)-13 antibody VH-VL sequences

| Construct ID | VH; VL; HC constant; and LC constant names, respectively* | VH sequence | VL sequence |
| --- | --- | --- | --- |
| 15 | HC1; LC6; hIgG1-LAGA YTE; Human kappa LC | EVQLQESGPGLVKPSETLSLTCTVSGFSLNAYSVNWIRQPPGKGLEWLGMIWGDGKIVYNSALKSRLTISKDSSKNQVSLKLSSVTAADTAVYYCAGDGYYPYAMDNWGQGTTVTVSS (SEQ ID NO: 3) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 16 | HC2; LC6; hIgG1-LAGA YTE; Human kappa LC | EVQLVQSGAEVKKPGSSVKVSCKASGFSLNAYSVNWVRQAPGQGLEWLGMIWGDGKIVYNSALKSRLTITKDSSTSTVYMELSSLRSEDTAVYYCAGDGYYPYAMDNWGQGTTVTVSS (SEQ ID NO: 4) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 17 | HC3; LC6; hIgG1-LAGA YTE; Human kappa LC | EVQLVQSGAEVKKPGSSVKVSCKASGFSLNAYSVNWVRQAPGQGLEWLGMIWGDGKIVYNSALKSRLTITKDSSTSTVYMELSSLRSEDTAVYYCAGDGYYPYAMDNWGQGTTVTVSS (SEQ ID NO: 5) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 18 | HC4; LC6; hIgG1-LAGA YTE; Human kappa LC | EVQLVESGGGLVKPGGSLRLSCAASGFSLNAYSVNWVRQAPGKGLEWLGMIWGDGKIVYNSALKSRLTISKDSSKNTVYLQMNSLKTEDTAVYYCAGDGYYPYAMDNWGQGTTVTVSS (SEQ ID NO: 6) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 19 | HC5; LC6; hIgG1-LAGA YTE; Human kappa LC | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 7) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 20 | HC1; LC7; hIgG1-LAGA YTE; Human kappa LC | EVQLQESGPGLVKPSETLSLTCTVSGFSLNAYSVNWIRQPPGKGLEWLGMIWGDGKIVYNSALKSRLTISKDSSKNQVSLKLSSVTAADTAVYYCAGDGYYPYAMDNWGQGTTVTVSS (SEQ ID NO: 3) | EIVLTQSPATLSVSPGERATLSCRASKSVDSYGNSFMHWYQQKPGQAPRLLIYLASNLESGIPARFSGSGSGTEFTLTISSLQSEDFAVYYCQQNNEDPRTFGGGTKVEIK (SEQ ID NO: 40) |
| 21 | HC2; LC7; hIgG1-LAGA YTE; Human kappa LC | EVQLVQSGAEVKKPGSSVKVSCKASGFSLNAYSVNWVRQAPGQGLEWLGMIWGDGKIVYNSALKSRLTITKDSSTSTVYMELSSLRSEDTAVYYCAGDGYYPYAMDNWGQGTTVTVSS (SEQ ID NO: 4) | EIVLTQSPATLSVSPGERATLSCRASKSVDSYGNSFMHWYQQKPGQAPRLLIYLASNLESGIPARFSGSGSGTEFTLTISSLQSEDFAVYYCQQNNEDPRTFGGGTKVEIK (SEQ ID NO: 40) |
| 22 | HC3; LC7; hIgG1-LAGA YTE; | EVQLVQSGAEVKKPGSSVKVSCKASGFSLNAYSVNWVRQAPGQGLEW | EIVLTQSPATLSVSPGERATLSCRASKSVDSYGNSFMHWYQQKPGQAPRLLIYL |

TABLE 2-continued

Anti-interleukin (IL)-13 antibody VH-VL sequences

| Construct ID | VH; VL; HC constant; and LC constant names, respectively* | VH sequence | VL sequence |
| --- | --- | --- | --- |
| | Human kappa LC | LGMIWGDGKIVYNSAL KSRLTITKDSSTSTVYM ELSSLRSEDTAVYYCA GDGYYPYAMDNWGQ GTTVTVSS (SEQ ID NO: 5) | ASNLESGIPARFSGSGSGT EFTLTISSLQSEDFAVYC QQNNEDPRTFGGGTKVEI K (SEQ ID NO: 40) |
| 23 | HC4; LC7; hIgG1-LAGA YTE; Human kappa LC | EVQLVESGGGLVKPGG SLRLSCAASGFSLNAYS VNWVRQAPGKGLEWL GMIWGDGKIVYNSALK SRLTISKDSSKNTVYLQ MNSLKTEDTAVYYCA GDGYYPYAMDNWGQ GTTVTVSS (SEQ ID NO: 6) | EIVLTQSPATLSVSPGERA TLSCRASKSVDSYGNSFM HWYQQKPGQAPRLLIYL ASNLESGIPARFSGSGSGT EFTLTISSLQSEDFAVYYC QQNNEDPRTFGGGTKVEI K (SEQ ID NO: 40) |
| 24 | HC5; LC7; hIgG1-LAGA YTE; Human kappa LC | EVQLLESGGGLVQPGG SLRLSCAASGFSLNAYS VNWVRQAPGKGLEWL GMIWGDGKIVYNSALK SRLTISKDSSKNTVYLQ MNSLRAEDTAVYYCA GDGYYPYAMDNWGQ GTTVTVSS (SEQ ID NO: 7) | EIVLTQSPATLSVSPGERA TLSCRASKSVDSYGNSFM HWYQQKPGQAPRLLIYL ASNLESGIPARFSGSGSGT EFTLTISSLQSEDFAVYYC QQNNEDPRTFGGGTKVEI K (SEQ ID NO: 40) |
| 25 | HC6; LC9; hIgG1-LAGA YTE; Human kappa LC | EVQLQESGPGLVKPSET LSLTCTVSGGSLNAYSV NWVRQPPGKGLEWLG MIWGDGKIVYNSALKS RLTISLDTSKSQVFLKM SSLTAADTAVYYCARD GYYPYAMDNWGQGTT VTVSS (SEQ ID NO: 8) | DIVLTQSPASLAVSPGERA TISCRASKSVDSYGNSFM HWYQQKPGQPPKLLIYLA SNLESGVPDRFSGSGSGT DFTLTISRVEADDVAVYY CQQNNEDPRTFGGGTKLE IK (SEQ ID NO: 42) |
| 26 | HC7; LC10; hIgG1-LAGA YTE; Human kappa LC | QVQLQESGPGLVKPSE TLSLTCTVSGGSLNAYS WNWVRQPPGKGLEWL GYIYGDGKTNYNPALK SRLTISLDTSKSQVFLK MSSLTAADTAVYYCAR DGYYYYAMDVWGQG TTVTVSS (SEQ ID NO: 9) | DIVLTQSPASLAVSPGERA TISCRASQSVDSNGNNFL HWYQQKPGQPPKLLIYLA SNRESGVPDRFSGSGSGT DFTLTISRVEADDVAVYY CQQNNHTPRTFGGGTKLE IK (SEQ ID NO: 43) |
| 90 | HC5; LC6; hIgG1-LAGA YTE; Human kappa LC | EVQLLESGGGLVQPGG SLRLSCAASGFSLNAYS VNWVRQAPGKGLEWL GMIWGDGKIVYNSALK SRLTISKDSSKNTVYLQ MNSLRAEDTAVYYCA GDGYYPYAMDNWGQ GTTVTVSS (SEQ ID NO: 7) | DIQLTQSPSSLSASVGDRV TITCRASKSVDSYGNSFM HWYQQKPGKAPKLLIYL ASNLESGVPSRFSGSGSGT DFTLTISSLQPEDFATYYC QQNNEDPRTFGGGTKVEI K (SEQ ID NO: 39) |
| 91 | HC5; LC6_m1; hIgG1-LAGA YTE; Human kappa LC | EVQLLESGGGLVQPGG SLRLSCAASGFSLNAYS VNWVRQAPGKGLEWL GMIWGDGKIVYNSALK SRLTISKDSSKNTVYLQ MNSLRAEDTAVYYCA GDGYYPYAMDNWGQ GTTVTVSS (SEQ ID NO: 7) | DIQLTQSPSSLSASVGDRV TITCRASKSVDSYGNSRM HWYQQKPGKAPKLLIYL ASNLESGVPSRFSGSGSGT DFTLTISSLQPEDFATYYC QQNNEDPRTFGGGTKVEI K (SEQ ID NO: 44) |
| 92 | HC5; LC6_m2; hIgG1-LAGA YTE; Human | EVQLLESGGGLVQPGG SLRLSCAASGFSLNAYS VNWVRQAPGKGLEWL GMIWGDGKIVYNSALK SRLTISKDSSKNTVYLQ | DIQLTQSPSSLSASVGDRV TITCRASKSVDSYGNSSM HWYQQKPGKAPKLLIYL ASNLESGVPSRFSGSGSGT DFTLTISSLQPEDFATYYC |

TABLE 2-continued

Anti-interleukin (IL)-13 antibody VH-VL sequences

| Construct ID | VH; VL; HC constant; and LC constant names, respectively* | VH sequence | VL sequence |
| --- | --- | --- | --- |
| | kappa LC | MNSLRAEDTAVYYCA GDGYYPYAMDNWGQ GTTVTVSS (SEQ ID NO: 7) | QQNNEDPRTFGGGTKVEI K (SEQ ID NO: 45) |
| 93 | HC5; LC6_m3; hIgG1-LAGA YTE; Human kappa LC | EVQLLESGGGLVQPGG SLRLSCAASGFSLNAYS VNWVRQAPGKGLEWL GMIWGDGKIVYNSALK SRLTISKDSSKNTVYLQ MNSLRAEDTAVYYCA GDGYYPYAMDNWGQ GTTVTVSS (SEQ ID NO: 7) | DIQLTQSPSSLSASVGDRV TITCRASKSVDSYGNSFM HWYQQKPGKAPKLLIRL ASNLESGVPSRFSGSGSGT DFTLTISSLQPEDFATYYC QQNNEDPRTFGGGTKVEI K (SEQ ID NO: 46) |
| 94 | HC5; LC6_m4; hIgG1-LAGA YTE; Human kappa LC | EVQLLESGGGLVQPGG SLRLSCAASGFSLNAYS VNWVRQAPGKGLEWL GMIWGDGKIVYNSALK SRLTISKDSSKNTVYLQ MNSLRAEDTAVYYCA GDGYYPYAMDNWGQ GTTVTVSS (SEQ ID NO: 7) | DIQLTQSPSSLSASVGDRV TITCRASKSVDSYGNSFM HWYQQKPGKAPKLLIFLA SNLESGVPSRFSGSGSGTD FTLTISSLQPEDFATYYCQ QNNEDPRTFGGGTKVEIK (SEQ ID NO: 47) |
| 95 | HC5; LC6_m5; hIgG1-LAGA YTE; Human kappa LC | EVQLLESGGGLVQPGG SLRLSCAASGFSLNAYS VNWVRQAPGKGLEWL GMIWGDGKIVYNSALK SRLTISKDSSKNTVYLQ MNSLRAEDTAVYYCA GDGYYPYAMDNWGQ GTTVTVSS (SEQ ID NO: 7) | DIQLTQSPSSLSASVGDRV TITCRASKSVDSYGNSFM HWYQQKPGKAPKLLIYL ASHLESGVPSRFSGSGSGT DFTLTISSLQPEDFATYYC QQNNEDPRTFGGGTKVEI K (SEQ ID NO: 48) |
| 96 | HC5; LC6_m6; hIgG1-LAGA YTE; Human kappa LC | EVQLLESGGGLVQPGG SLRLSCAASGFSLNAYS VNWVRQAPGKGLEWL GMIWGDGKIVYNSALK SRLTISKDSSKNTVYLQ MNSLRAEDTAVYYCA GDGYYPYAMDNWGQ GTTVTVSS (SEQ ID NO: 7) | DIQLTQSPSSLSASVGDRV TITCRASKSVDSYGNSFM HWYQQKPGKAPKLLIYL ASDLESGVPSRFSGSGSGT DFTLTISSLQPEDFATYYC QQNNEDPRTFGGGTKVEI K (SEQ ID NO: 49) |
| 97 | HC5; LC6_m7; hIgG1-LAGA YTE; Human kappa LC | EVQLLESGGGLVQPGG SLRLSCAASGFSLNAYS VNWVRQAPGKGLEWL GMIWGDGKIVYNSALK SRLTISKDSSKNTVYLQ MNSLRAEDTAVYYCA GDGYYPYAMDNWGQ GTTVTVSS (SEQ ID NO: 7) | DIQLTQSPSSLSASVGDRV TITCRASKSVDSYGNSFM HWYQQKPGKAPKLLIYL ASQLESGVPSRFSGSGSGT DFTLTISSLQPEDFATYYC QQNNEDPRTFGGGTKVEI K (SEQ ID NO: 50) |
| 98 | HC5; LC6_m8; hIgG1-LAGA YTE; Human kappa LC | EVQLLESGGGLVQPGG SLRLSCAASGFSLNAYS VNWVRQAPGKGLEWL GMIWGDGKIVYNSALK SRLTISKDSSKNTVYLQ MNSLRAEDTAVYYCA GDGYYPYAMDNWGQ GTTVTVSS (SEQ ID NO: 7) | DIQLTQSPSSLSASVGDRV TITCRASKSVDSYGNSFM HWYQQKPGKAPKLLIYL ASELESGVPSRFSGSGSGT DFTLTISSLQPEDFATYYC QQNNEDPRTFGGGTKVEI K (SEQ ID NO: 51) |
| 99 | HC5; LC6_m9; hIgG1-LAGA YTE; Human kappa LC | EVQLLESGGGLVQPGG SLRLSCAASGFSLNAYS VNWVRQAPGKGLEWL GMIWGDGKIVYNSALK SRLTISKDSSKNTVYLQ MNSLRAEDTAVYYCA | DIQLTQSPSSLSASVGDRV TITCRASKSVDSYGNSFM HWYQQKPGKAPKLLIYL ASNLESGVPSRFSGSGSGT DFTLTISSLQPEDFATYYC QQNHEDPRTFGGGTKVEI |

TABLE 2-continued

Anti-interleukin (IL)-13 antibody VH-VL sequences

| Construct ID | VH; VL; HC constant; and LC constant names, respectively* | VH sequence | VL sequence |
| --- | --- | --- | --- |
| | | GDGYYPYAMDNWGQGTTVTVSS (SEQ ID NO: 7) | K (SEQ ID NO: 52) |
| 100 | HC5; LC6_m10; hIgG1-LAGA YTE; Human kappa LC | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 7) | DIQLTQSPSSLSASVGDRVTITCRASKSVDSYGNSFMHWYQQKPGKAPKLLIYLASNLESGVPSRFSGSGSTDFTLTISSLQPEDFATYYCQQNYEDPRTFGGGTKVEIK (SEQ ID NO: 53) |
| 101 | HC5; LC6_m11; hIgG1-LAGA YTE; Human kappa LC | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 7) | DIQLTQSPSSLSASVGDRVTITCRASKSVDSYGNSFMHWYQQKPGKAPKLLIYLASNLESGVPSRFSGSGSTDFTLTISSLQPEDFATYYCQQNSEDPRTFGGGTKVEIK (SEQ ID NO: 54) |
| 102 | HC5; LC6_m12; hIgG1-LAGA YTE; Human kappa LC | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 7) | DIQLTQSPSSLSASVGDRVTITCRASKSVDSYGNSFMHWYQQKPGKAPKLLIYLASNLESGVPSRFSGSGSTDFTLTISSLQPEDFATYYCQQNNRDPRTFGGGTKVEIK (SEQ ID NO: 55) |
| 103 | HC5; LC6_m13; hIgG1-LAGA YTE; Human kappa LC | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 7) | DIQLTQSPSSLSASVGDRVTITCRASKSVDSYGNSFMHWYQQKPGKAPKLLIYLASNLESGVPSRFSGSGSTDFTLTISSLQPEDFATYYCQQNNDDPRTFGGGTKVEIK (SEQ ID NO: 56) |
| 104 | HC5; LC6_m14; hIgG1-LAGA YTE; Human kappa LC | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 7) | DIQLTQSPSSLSASVGDRVTITCRASKSVDSYGNSFMHWYQQKPGKAPKLLIYLASNLESGVPSRFSGSGSTDFTLTISSLQPEDFATYYCQQNNQDPRTFGGGTKVEIK (SEQ ID NO: 57) |
| 105 | HC5_m1; LC6; hIgG1-LAGA YTE; Human kappa LC | EVQLLESGGGLVQPGGSLRLSCAASGYSLNAYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 10) | DIQLTQSPSSLSASVGDRVTITCRASKSVDSYGNSFMHWYQQKPGKAPKLLIYLASNLESGVPSRFSGSGSTDFTLTISSLQPEDFATYYCQQNNEDPRTFGGGTKVEIK (SEQ ID NO: 39) |

TABLE 2-continued

Anti-interleukin (IL)-13 antibody VH-VL sequences

| Construct ID | VH; VL; HC constant; and LC constant names, respectively* | VH sequence | VL sequence |
| --- | --- | --- | --- |
| 106 | HC5_m2; LC6; hIgG1-LAGA YTE; Human kappa LC | EVQLLESGGGLVQPGGSLRLSCAASGFSLRAYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 11) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 107 | HC5_m3; LC6; hIgG1-LAGA YTE; Human kappa LC | EVQLLESGGGLVQPGGSLRLSCAASGFSLHAYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 12) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 108 | HC5_m4; LC6; hIgG1-LAGA YTE; Human kappa LC | EVQLLESGGGLVQPGGSLRLSCAASGFSLDAYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 13) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 109 | HC5_m5; LC6; hIgG1-LAGA YTE; Human kappa LC | EVQLLESGGGLVQPGGSLRLSCAASGFSLYAYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 14) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 110 | HC5_m6; LC6; hIgG1-LAGA YTE; Human kappa LC | EVQLLESGGGLVQPGGSLRLSCAASGFSLSAYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 15) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 111 | HC5_m7; LC6; hIgG1-LAGA YTE; Human kappa LC | EVQLLESGGGLVQPGGSLRLSCAASGFSLNRYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 16) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 112 | HC5_m8; LC6; hIgG1-LAGA YTE; Human kappa LC | EVQLLESGGGLVQPGGSLRLSCAASGFSLNKYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 17) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |

TABLE 2-continued

Anti-interleukin (IL)-13 antibody VH-VL sequences

| Construct ID | VH; VL; HC constant; and LC constant names, respectively* | VH sequence | VL sequence |
|---|---|---|---|
| 113 | HC5_m9; LC6; hIgG1-LAGA YTE; Human kappa LC | EVQLLESGGGLVQPGGSLRLSCAASGFSLNHYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 18) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 114 | HC5_m10; LC6; hIgG1-LAGA YTE; Human kappa LC | EVQLLESGGGLVQPGGSLRLSCAASGFSLNQYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 19) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 115 | HC5_m11; LC6; hIgG1-LAGA YTE; Human kappa LC | EVQLLESGGGLVQPGGSLRLSCAASGFSLNEYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 20) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 116 | HC5_m12; LC6; hIgG1-LAGA YTE; Human kappa LC | EVQLLESGGGLVQPGGSLRLSCAASGFSLNSYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 21) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 117 | HC5_m13; LC6; hIgG1-LAGA YTE; Human kappa LC | EVQLLESGGGLVQPGGSLRLSCAASGFSLNYYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 22) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 118 | HC5_m14; LC6; hIgG1-LAGA YTE; Human kappa LC | EVQLLESGGGLVQPGGSLRLSCAASGFSLNAESVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 23) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 119 | HC5_m15; LC6; hIgG1-LAGA YTE; Human kappa LC | EVQLLESGGGLVQPGGSLRLSCAASGFSLNAYSVNWVRQAPGKGLEWLGMIWSDGKIVYNSALKSRLTISKDSSKNTVYLQMNSLRAEDTAVYYCAGDGYYPYAMDNWGQGTTVTVSS (SEQ ID NO: 24) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |

TABLE 2-continued

Anti-interleukin (IL)-13 antibody VH-VL sequences

| Construct ID | VH; VL; HC constant; and LC constant names, respectively* | VH sequence | VL sequence |
|---|---|---|---|
| 120 | HC5_m16; LC6; hIgG1-LAGA YTE; Human kappa LC | EVQLLESGGGLVQPGGSLRLSCAASGFSLNAYSVNWVRQAPGKGLEWLGMIWADGKIVYNSALKSRLTISKDSSKNTVYLQMNSLRAEDTAVYYCAGDGYYPYAMDNWGQGTTVTVSS (SEQ ID NO: 25) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 121 | HC5_m17; LC6; hIgG1-LAGA YTE; Human kappa LC | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGHGYYPYAMDNWGQGTTVTVSS (SEQ ID NO: 26) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 122 | HC5_m18; LC6; hIgG1-LAGA YTE; Human kappa LC | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDLYYPYAMDNWGQGTTVTVSS (SEQ ID NO: 27) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 123 | HC5_m19; LC6; hIgG1-LAGA YTE; Human kappa LC | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDKYYPYAMDNWGQGTTVTVSS (SEQ ID NO: 28) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 124 | HC5_m20; LC6; hIgG1-LAGA YTE; Human kappa LC | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDGYYGYAMDNWGQGTTVTVSS (SEQ ID NO: 29) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 125 | HC5_m21; LC6; hIgG1-LAGA YTE; Human kappa LC | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDGYYAYAMDNWGQGTTVTVSS (SEQ ID NO: 30) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |
| 126 | HC5_m22; LC6; hIgG1-LAGA YTE; Human kappa LC | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDGYYSYAMDNWGQGTTVTVSS (SEQ ID NO: 31) | DIQLTQSPSSLSASVGDRVTITCRASKSVDSYGNSFMHWYQQKPGKAPKLLIYLASNLESGVPSRFSGSGSGTDFTLTISSLQPEDFATYYCQQNNEDPRTFGGGTKVEIK (SEQ ID NO: 39) |

TABLE 2-continued

Anti-interleukin (IL)-13 antibody VH-VL sequences

| Construct ID | VH; VL; HC constant; and LC constant names, respectively* | VH sequence | VL sequence |
|---|---|---|---|
| 127 | HC5_m23; LC6; hIgG1-LAGA YTE; Human kappa LC | EVQLLESGGGLVQPGG SLRLSCAASGFSLNAYS VNWVRQAPGKGLEWL GMIWGDGKIVYNSALK SRLTISKDSSKNTVYLQ MNSLRAEDTAVYYCA GDGYYTYAMDNWGQ GTTVTVSS (SEQ ID NO: 32) | DIQLTQSPSSLSASVGDRV TITCRASKSVDSYGNSFM HWYQQKPGKAPKLLIYL ASNLESGVPSRFSGSGSGT DFTLTISSLQPEDFATYYC QQNNEDPRTFGGGTKVEI K (SEQ ID NO: 39) |
| 128 | Lebrikizumab-HC; Lebrikizumab-LC; hIgG4-YTE; Human kappa LC | QVTLRESGPALVKPTQ TLTLTCTVSGFSLSAYS VNWIRQPPGKALEWL AMIWGDGKIVYNSAL KSRLTISKDTSKNQVV LTMTNMDPVDTATYY CAGDGYYPYAMDNW GQGSLVTVSS (SEQ ID NO: 470) | DIVMTQSPDSL SVSLGERATIN CRASKSVDSY GNSFMHWYQ QKPGQPPKLLI YLASNLESGVP DRFSGSGSGTD FTLTISSLQAED VAVYYCQQNN EDPRTFGGGTK VEIK (SEQ ID NO: 471) |
| 129 | Lebrikizumab-HC; Lebrikizumab-LC; hIgG4-LS; Human kappa LC | QVTLRESGPALVKPTQ TLTLTCTVSGFSLSAYS VNWIRQPPGKALEWL AMIWGDGKIVYNSAL KSRLTISKDTSKNQVV LTMTNMDPVDTATYY CAGDGYYPYAMDNW GQGSLVTVSS (SEQ ID NO: 470) | DIVMTQSPDSL SVSLGERATIN CRASKSVDSY GNSFMHWYQ QKPGQPPKLLI YLASNLESGVP DRFSGSGSGTD FTLTISSLQAED VAVYYCQQNN EDPRTFGGGTK VEIK (SEQ ID NO: 471) |
| 130 | Lebrikizumab-HC; Lebrikizumab-LC; hIgG1-LALA-YTE; Human kappa LC | QVTLRESGPALVKPTQ TLTLTCTVSGFSLSAYS VNWIRQPPGKALEWL AMIWGDGKIVYNSAL KSRLTISKDTSKNQVV LTMTNMDPVDTATYY CAGDGYYPYAMDNW GQGSLVTVSS (SEQ ID NO: 470) | DIVMTQSPDSL SVSLGERATIN CRASKSVDSY GNSFMHWYQ QKPGQPPKLLI YLASNLESGVP DRFSGSGSGTD FTLTISSLQAED VAVYYCQQNN EDPRTFGGGTK VEIK (SEQ ID NO: 471) |
| 131 | Lebrikizumab-HC; Lebrikizumab-LC; hIgG1-LALA-LS; Human kappa LC | QVTLRESGPALVKPTQ TLTLTCTVSGFSLSAYS VNWIRQPPGKALEWL AMIWGDGKIVYNSAL KSRLTISKDTSKNQVV LTMTNMDPVDTATYY CAGDGYYPYAMDNW GQGSLVTVSS (SEQ ID NO: 470) | DIVMTQSPDSL SVSLGERATIN CRASKSVDSY GNSFMHWYQ QKPGQPPKLLI YLASNLESGVP DRFSGSGSGTD FTLTISSLQAED VAVYYCQQNN EDPRTFGGGTK VEIK (SEQ ID NO: 471) |
| 132 | HC5; LC6; hIgG1-LALA YTE; Human kappa LC | EVQLLESGGGLVQPGG SLRLSCAASGFSLNAY SVNWVRQAPGKGLEW LGMIWGDGKIVYNSA LKSRLTISKDSSKNTVY LQMNSLRAEDTAVYY CAGDGYYPYAMDNW GQGTTVTVSS (SEQ ID NO: 7) | DIQLTQSPSSLS ASVGDRVTITC RASKSVDSYG NSFMHWYQQ KPGKAPKLLIY LASNLESGVPS RFSGSGSGTDF TLTISSLQPEDF ATYYCQQNNE |

TABLE 2-continued

Anti-interleukin (IL)-13 antibody VH-VL sequences

| Construct ID | VH; VL; HC constant; and LC constant names, respectively* | VH sequence | VL sequence |
| --- | --- | --- | --- |
| | | | DPRTFGGGTK VEIK (SEQ ID NO: 39) |
| 133 | HC1; LC6; hIgG1-LALA YTE; Human kappa LC | EVQLQESGPGLVKPSE TLSLTCTVSGFSLNAYS VNWIRQPPGKGLEWL GMIWGDGKIVYNSAL KSRLTISKDSSKNQVSL KLSSVTAADTAVYYC AGDGYYPYAMDNWG QGTTVTVSS (SEQ ID NO: 3) | DIQLTQSPSSLS ASVGDRVTITC RASKSVDSYG NSFMHWYQQ KPGKAPKLLIY LASNLESGVPS RFSGSGSGTDF TLTISSLQPEDF ATYYCQQNNE DPRTFGGGTK VEIK (SEQ ID NO: 39) |
| 134 | HC1; LC6; hIgG4-YTE; Human kappa LC | EVQLQESGPGLVKPSE TLSLTCTVSGFSLNAYS VNWIRQPPGKGLEWL GMIWGDGKIVYNSAL KSRLTISKDSSKNQVSL KLSSVTAADTAVYYC AGDGYYPYAMDNWG QGTTVTVSS (SEQ ID NO: 3) | DIQLTQSPSSLS ASVGDRVTITC RASKSVDSYG NSFMHWYQQ KPGKAPKLLIY LASNLESGVPS RFSGSGSGTDF TLTISSLQPEDF ATYYCQQNNE DPRTFGGGTK VEIK (SEQ ID NO: 39) |
| 135 | HC1; LC6; hIgG4-LS; Human kappa LC | EVQLQESGPGLVKPSE TLSLTCTVSGFSLNAYS VNWIRQPPGKGLEWL GMIWGDGKIVYNSAL KSRLTISKDSSKNQVSL KLSSVTAADTAVYYC AGDGYYPYAMDNWG QGTTVTVSS (SEQ ID NO: 3) | DIQLTQSPSSLS ASVGDRVTITC RASKSVDSYG NSFMHWYQQ KPGKAPKLLIY LASNLESGVPS RFSGSGSGTDF TLTISSLQPEDF ATYYCQQNNE DPRTFGGGTK VEIK (SEQ ID NO: 39) |
| 136 | HC1; LC6; hIgG1-LALA LS; Human kappa LC | EVQLQESGPGLVKPSE TLSLTCTVSGFSLNAYS VNWIRQPPGKGLEWL GMIWGDGKIVYNSAL KSRLTISKDSSKNQVSL KLSSVTAADTAVYYC AGDGYYPYAMDNWG QGTTVTVSS (SEQ ID NO: 3) | DIQLTQSPSSLS ASVGDRVTITC RASKSVDSYG NSFMHWYQQ KPGKAPKLLIY LASNLESGVPS RFSGSGSGTDF TLTISSLQPEDF ATYYCQQNNE DPRTFGGGTK VEIK (SEQ ID NO: 39) |
| 137 | HC5; LC6_m8; hIgG1-LALA YTE; Human kappa LC | EVQLLESGGGLVQPGG SLRLSCAASGFSLNAY SVNWVRQAPGKGLEW LGMIWGDGKIVYNSA LKSRLTISKDSSKNTVY LQMNSLRAEDTAVYY CAGDGYYPYAMDNW GQGTTVTVSS (SEQ ID NO: 7) | DIQLTQSPSSLS ASVGDRVTITC RASKSVDSYG NSFMHWYQQ KPGKAPKLLIY LASELESGVPS RFSGSGSGTDF TLTISSLQPEDF ATYYCQQNNE DPRTFGGGTK VEIK (SEQ ID NO: 51) |
| 138 | HC5; LC6_m8; | EVQLLESGGGLVQPGG SLRLSCAASGFSLNAY | DIQLTQSPSSLS ASVGDRVTITC |

TABLE 2-continued

Anti-interleukin (IL)-13 antibody VH-VL sequences

| Construct ID | VH; VL; HC constant; and LC constant names, respectively* | VH sequence | VL sequence |
|---|---|---|---|
| | hIgG4-YTE; Human kappa LC | SVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 7) | RASKSVDSYGNSFMHWYQQKPGKAPKLLIYLASELESGVPSRFSGSGSGTDFTLTISSLQPEDFATYYCQQNNEDPRTFGGGTKVEIK (SEQ ID NO: 51) |
| 139 | HC5; LC6_m8; hIgG4-LS; Human kappa LC | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 7) | DIQLTQSPSSLSASVGDRVTITCRASKSVDSYGNSFMHWYQQKPGKAPKLLIYLASELESGVPSRFSGSGSGTDFTLTISSLQPEDFATYYCQQNNEDPRTFGGGTKVEIK (SEQ ID NO: 51) |
| 140 | HC5; LC6_m8; hIgG1-LALA LS; Human kappa LC | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDGYYPYAMDNWGQGTTVTVSS (SEQ ID NO: 7) | DIQLTQSPSSLSASVGDRVTITCRASKSVDSYGNSFMHWYQQKPGKAPKLLIYLASELESGVPSRFSGSGSGTDFTLTISSLQPEDFATYYCQQNNEDPRTFGGGTKVEIK (SEQ ID NO: 51) |
| 141 | HC1; LC6_m8; hIgG1-LALA YTE; Human kappa LC | EVQLQESGPGLVKPSETLSLTCTVSGFSLNAYSVNWIRQPPGKGLEWLGMIWGDGKIVYNSALKSRLTISKDSSKNQVSLKLSSVTAADTAVYYCAGDGYYPYAMDNWGQGTTVTVSS (SEQ ID NO: 3) | DIQLTQSPSSLSASVGDRVTITCRASKSVDSYGNSFMHWYQQKPGKAPKLLIYLASELESGVPSRFSGSGSGTDFTLTISSLQPEDFATYYCQQNNEDPRTFGGGTKVEIK (SEQ ID NO: 51) |
| 142 | HC1; LC6_m8; hIgG4 YTE; Human kappa LC | EVQLQESGPGLVKPSETLSLTCTVSGFSLNAYSVNWIRQPPGKGLEWLGMIWGDGKIVYNSALKSRLTISKDSSKNQVSLKLSSVTAADTAVYYCAGDGYYPYAMDNWGQGTTVTVSS (SEQ ID NO: 3) | DIQLTQSPSSLSASVGDRVTITCRASKSVDSYGNSFMHWYQQKPGKAPKLLIYLASELESGVPSRFSGSGSGTDFTLTISSLQPEDFATYYCQQNNEDPRTFGGGTKVEIK (SEQ ID NO: 51) |
| 143 | HC1; LC6_m8; hIgG4 LS; Human kappa LC | EVQLQESGPGLVKPSETLSLTCTVSGFSLNAYSVNWIRQPPGKGLEWLGMIWGDGKIVYNSALKSRLTISKDSSKNQVSLKLSSVTAADTAVYYCAGDGYYPYAMDNWGQGTTVTVSS (SEQ ID | DIQLTQSPSSLSASVGDRVTITCRASKSVDSYGNSFMHWYQQKPGKAPKLLIYLASELESGVPSRFSGSGSGTDFTLTISSLQPEDF |

TABLE 2-continued

Anti-interleukin (IL)-13 antibody VH-VL sequences

| Construct ID | VH; VL; HC constant; and LC constant names, respectively* | VH sequence | VL sequence |
| --- | --- | --- | --- |
| | | NO: 3) | ATYYCQQNNE DPRTFGGGTK VEIK (SEQ ID NO: 51) |
| 144 | HC1; LC6_m8; hIgG1-LALA LS; Human kappa LC | EVQLQESGPGLVKPSE TLSLTCTVSGFSLNAYS VNWIRQPPGKGLEWL GMIWGDGKIVYNSAL KSRLTISKDSSKNQVSL KLSSVTAADTAVYYC AGDGYYPYAMDNWG QGTTVTVSS (SEQ ID NO: 3) | DIQLTQSPSSLS ASVGDRVTITC RASKSVDSYG NSFMHWYQQ KPGKAPKLLIY LASELESGVPS RFSGSGSGTDF TLTISSLQPEDF ATYYCQQNNE DPRTFGGGTK VEIK (SEQ ID NO: 51) |

*Names correspond with name in informal sequence listing

In some embodiments, such a IgG4-SP HC constant domain has the sequence:

(SEQ ID NO: 427)
ASTKGPSVFPLAPCSRSTSESTAALGCLVKDYFPEPVTVSWNSGA

LTSGVHTFPAVLQSSGLYSLSSVVTVPSSSLGTKTYTCNVDHKPS

NTKVDKRVESKYGPPCPPCPAPEFLGGPSVFLFPPKPKDTLMISR

TPEVTCVVVDVSQEDPEVQFNWYVDGVEVHNAKTKPREEQFNSTY

RVVSVLTVLHQDWLNGKEYKCKVSNKGLPSSIEKTISKAKGQPRE

PQVYTLPPSQEEMTKNQVSLTCLVKGFYPSDIAVEWESNGQPENN

YKTTPPVLDSDGSFFLYSRLTVDKSRWQEGNVFSCSVMHEALHNH

YTQKSLSLSLGK.

In some embodiments, such a hIgG1-LALA-YTE HC constant domain has the sequence:

(SEQ ID NO: 439)
ASTKGPSVFPLAPSSKSTSGGTAALGCLVKDYFPEPVTVSWNSGA

LTSGVHTFPAVLQSSGLYSLSSVVTVPSSSLGTQTYICNVNHKPS

NTKVDKKVEPKSCDKTHTCPPCPAPEAAGGPSVFLFPPKPKDTLY

ITREPEVTCVVVDVSHEDPEVKFNWYVDGVEVHNAKTKPREEQYN

STYRVVSVLTVLHQDWLNGKEYKCKVSNKALPAPIEKTISKAKGQ

PREPQVYTLPPSRDELTKNQVSLTCLVKGFYPSDIAVEWESNGQP

ENNYKTTPPVLDSDGSFFLYSKLTVDKSRWQQGNVFSCSVMHEAL

HNHYTQKSLSLSPG.

In some embodiments, such a hIgG1-LAGA YTE HC constant domain has the sequence:

(SEQ ID NO: 440)
ASTKGPSVFPLAPSSKSTSGGTAALGCLVKDYFPEPVTVSWNSGA

LTSGVHTFPAVLQSSGLYSLSSVVTVPSSSLGTQTYICNVNHKPS

NTKVDKKVEPKSCDKTHTCPPCPAPELAGAPSVFLFPPKPKDTLY

ITREPEVTCVVVDVSHEDPEVKFNWYVDGVEVHNAKTKPREEQYN

STYRVVSVLTVLHQDWLNGKEYKCKVSNKALPAPIEKTISKAKGQ

PREPQVYTLPPSRDELTKNQVSLTCLVKGFYPSDIAVEWESNGQP

ENNYKTTPPVLDSDGSFFLYSKLTVDKSRWQQGNVFSCSVMHEAL

HNHYTQKSLSLSPG.

In some embodiments, such a hIgG1-LALA-LS constant domain has the sequence:

(SEQ ID NO: 446)
ASTKGPSVFPLAPSSKSTSGGTAALGCLVKDYFPEPVTVSWNSGA

LTSGVHTFPAVLQSSGLYSLSSVVTVPSSSLGTQTYICNVNHKPS

NTKVDKKVEPKSCDKTHTCPPCPAPEAAGGPSVFLFPPKPKDTLM

ISRTPEVTCVVVDVSHEDPEVKFNWYVDGVEVHNAKTKPREEQYN

STYRVVSVLTVLHQDWLNGKEYKCKVSNKALPAPIEKTISKAKGQ

PREPQVYTLPPSRDELTKNQVSLTCLVKGFYPSDIAVEWESNGQP

ENNYKTTPPVLDSDGSFFLYSKLTVDKSRWQQGNVFSCSVLHEAL

HSHYTQKSLSLSPG.

In some embodiments, such a IgG4-YTE HC constant domain has the sequence:

(SEQ ID NO: 457)
ASTKGPSVFPLAPCSRSTSESTAALGCLVKDYFPEPVTVSWNSGA

LTSGVHTFPAVLQSSGLYSLSSVVTVPSSSLGTKTYTCNVDHKPS

NTKVDKRVESKYGPPCPSCPAPEFLGGPSVFLFPPKPKDTLYITR

EPEVTCVVVDVSQEDPEVQFNWYVDGVEVHNAKTKPREEQFNSTY

RVVSVLTVLHQDWLNGKEYKCKVSNKGLPSSIEKTISKAKGQPRE

PQVYTLPPSQEEMTKNQVSLTCLVKGFYPSDIAVEWESNGQPENN

YKTTPPVLDSDGSFFLYSRLTVDKSRWQEGNVFSCSVMHEALHNH

YTQKSLSLSLGK.

In some embodiments, such a IgG4-LS HC constant domain has the sequence:

(SEQ ID NO: 460)
ASTKGPSVFPLAPCSRSTSESTAALGCLVKDYFPEPVTVSWNSGA

LTSGVHTFPAVLQSSGLYSLSSVVTVPSSSLGTKTYTCNVDHKPS

NTKVDKRVESKYGPPCPSCPAPEFLGGPSVFLFPPKPKDTLMISR

TPEVTCVVVDVSQEDPEVQFNWYVDGVEVHNAKTKPREEQFNSTY

RVVSVLTVLHQDWLNGKEYKCKVSNKGLPSSIEKTISKAKGQPRE

PQVYTLPPSQEEMTKNQVSLTCLVKGFYPSDIAVEWESNGQPENN

YKTTPPVLDSDGSFFLYSRLTVDKSRWQEGNVFSCSVLHEALHSY

TQKSLSLSLGK.

In some embodiments, such a human kappa LC constant domain has the sequence:

(SEQ ID NO: 469)
RTVAAPSVFIFPPSDEQLKSGTASVVCLLNNFYPREAKVQWKVDN

ALQSGNSQESVTEQDSKDSTYSLSSTLTLSKADYEKHKVYACEVT

HQGLSSPVTKSFNRGEC.

CDRs

In some embodiments, an antibody provided herein comprises one to three CDRs of a VH domain selected from SEQ ID NOs: 1-32 and 470, such as any of the CDRs listed in Table 3, Table 4, or Table 5, below. In some embodiments, an antibody provided herein comprises two to three CDRs of a VH domain selected from SEQ ID NOs: 1-32 and 470. In some embodiments, an antibody provided herein comprises three CDRs of a VH domain selected from SEQ ID NOs: 1-32 and 470. In some embodiments, the CDRs are Exemplary CDRs. In some embodiments, the CDRs are Kabat CDRs. In some embodiments, the CDRs are Chothia CDRs. In some embodiments, the CDRs are IMGT CDRs. In some embodiments, the CDRs are AbM CDRs. In some embodiments, the CDRs are Contact CDRs.

In some embodiments, the CDRs are CDRs having at least about 80%, 90%, 91%, 92%, 93%, 94%, 95%, 96%, 97%, 98%, 99% or 100% identity with a CDR-H1, CDR-H2, or CDR-H3 of SEQ ID NOs: 58-140. In some embodiments, the CDR-H1 is a CDR-H1 of a VH domain selected from SEQ ID NOs: 1-32 and 470, with up to 1, 2, 3, 4, or 5 amino acid substitutions. In some embodiments, the CDR-H2 is a CDR-H2 of a VH domain of SEQ ID NO: 1-32 and 470, with up to 1, 2, 3, 4, 5, 6, 7, or 8 amino acid substitutions. In some embodiments, the CDR-H3 is a CDR-H3 of a VH domain selected from SEQ ID NOs: 1-32 and 470, with up to 1, 2, 3, 4, 5, 6, 7, or 8 amino acid substitutions. In some embodiments, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a VL domain of SEQ ID NOs: 33-57 and 471, such as any of the CDRs listed in Table 6, Table 7, or Table 8, below. In some embodiments, an antibody provided herein comprises two to three CDRs of a VL domain of SEQ ID NOs: 33-57 and 471. In some embodiments, an antibody provided herein comprises three CDRs of a VL domain of SEQ ID NOs: 33-57 and 471. In some embodiments, the CDRs are Exemplary CDRs. In some embodiments, the CDRs are Kabat CDRs. In some embodiments, the CDRs are Chothia CDRs. In some embodiments, the CDRs are IMGT CDRs. In some embodiments, the CDRs are AbM CDRs. In some embodiments, the CDRs are Contact CDRs.

In some embodiments, the CDRs are CDRs having at least about 80%, 90%, 91%, 92%, 93%, 94%, 95%, 96%, 97%, 98%, 99% or 100% identity with a CDR-L1, CDR-L2, or CDR-L3 of SEQ ID NOs: 141-188. In some embodiments, the CDR-L1 is a CDR-L1 of a VL domain of SEQ ID NOs: 33-57 and 471, with up to 1, 2, 3, 4, or 5 amino acid substitutions. In some embodiments, the CDR-L2 is a CDR-L2 of a VL domain of SEQ ID NOs: 33-57 and 471, with up to 1, 2, 3, 4, 5, 6, 7, or 8 amino acid substitutions. In some embodiments, the CDR-L3 is a CDR-L3 of a VL domain of SEQ ID NOs: 33-57 and 471, with up to 1, 2, 3, 4, 5, 6, 7, or 8 amino acid substitutions. In some embodiments, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a VH domain selected from SEQ ID NOs: 1-32 and 470 and one to three CDRs of a VL domain of SEQ ID NOs: 33-57 and 471. In some embodiments, an antibody provided herein comprises two to three CDRs of a VH domain selected from SEQ ID NOs: 1-32 and 470 and two to three CDRs of a VL domain of SEQ ID NOs: 33-57 and 471. In some embodiments, an antibody provided herein comprises three CDRs of a VH domain selected from SEQ ID NOs: 1-32 and 470 and three CDRs of a VL domain of SEQ ID NOs: 33-57 and 471. In some embodiments, the CDRs are Exemplary CDRs. In some embodiments, the CDRs are Kabat CDRs. In some embodiments, the CDRs are Chothia CDRs. In some embodiments, the CDRs are IMGT CDRs. In some embodiments, the CDRs are AbM CDRs. In some embodiments, the CDRs are Contact CDRs.

In some embodiments, an antibody provided herein comprises a CDR-H3 selected of SEQ ID NOs: 112-120 and 130-40. In some embodiments, the CDR-H3 has at least about 80%, 90%, 91%, 92%, 93%, 94%, 95%, 96%, 97%, 98% or 99% identity with a CDR-H3 of SEQ ID NOs: 112-120 or 130-40. In some embodiments, the CDR-H3 is a CDR-H3 selected of SEQ ID NOs: 112-120 and 130-40, with up to 1, 2, 3, 4, 5, 6, 7, or 8 amino acid substitutions. In some embodiments, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H1 of SEQ ID NOs: 58-99 and 121. In some embodiments, the CDR-H1 has at least about 80%, 90%, 91%, 92%, 93%, 94%, 95%, 96%, 97%, 98% or 99% identity with a CDR-H1 of SEQ ID NOs: 58-99 or 121. In some embodiments, the CDR-H1 is a CDR-H1 of SEQ ID NOs: 58-99 or 121, with up to 1, 2, 3, 4, 5, 6, 7, or 8 amino acid substitutions. In some embodiments, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H2 of any one of SEQ ID NOs: 100-111. In some embodiments, the CDR-H2 has at least about 80%, 90%, 91%, 92%, 93%, 94%, 95%, 96%, 97%, 98% or 99% identity with a CDR-H2 of any one of SEQ ID NOs: 100-111. In some embodiments, the CDR-H2 is a CDR-H2 of any one of SEQ ID NOs: 100-111, with up to 1, 2, 3, 4, 5, 6, 7, or 8 amino acid substitutions. In some embodiments, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L3 selected from SEQ ID NOs: 165-172. In some embodiments, the CDR-L3 has at least about 80%, 90%, 91%, 92%, 93%, 94%, 95%, 96%, 97%, 98% or 99% identity with a CDR-L3 of SEQ ID NOs: 165-172. In some embodiments, the CDR-L3 is a CDR-L3 of SEQ ID NOs: 165-172, with up to 1, 2, 3, 4, 5, 6, 7, or 8 amino acid substitutions. In some embodiments, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L2 selected from SEQ ID NOs: 153-158 and the amino acid sequence LAS. In some embodiments, the CDR-L2 has at least about 80%, 90%, 91%, 92%, 93%, 94%, 95%, 96%, 97%, 98% or 99% identity with a CDR-L2 selected from SEQ ID NOs: 153-158 and the amino acid sequence LAS. In some embodiments, the CDR-L2 is a CDR-L2 selected from SEQ ID NOs: 153-158 and the amino acid sequence LAS, with up to 1, 2, 3, 4, 5, 6, 7, or 8 amino acid substitutions. In some embodiments, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L1 selected from SEQ ID NOs: 141-144 and 149-152. In some embodiments, the CDR-L1 has at least about 80%, 90%, 91%, 92%, 93%, 94%, 95%, 96%, 97%, 98% or 99% identity with a CDR-L1 selected from SEQ ID NOs: 141-144 and 149-152. In some embodiments, the CDR-L1 is a CDR-L1 selected from SEQ ID NOs: 141-144 and 149-152, with up to 1, 2, 3, 4, 5, 6, 7, or 8 amino acid substitutions. In some embodiments, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected from SEQ ID NOs: 112-120 and 130-140, a CDR-H2 of SEQ ID NOs: 100-111, a CDR-H1 selected from SEQ ID NOs: 58-99 and 121, a CDR-L3 selected from SEQ ID NOs: 165-172, a CDR-L2 selected from SEQ ID NOs: 153-158 and the amino acid sequence LAS, and a CDR-L1 selected from SEQ ID NOs: 141-144 and 149-152. In some embodiments, the CDR-H3 has at least about 80%, 90%, 91%, 92%, 93%, 94%, 95%, 96%, 97%, 98% or 99% identity with a CDR-H3 selected from SEQ ID NOs: 112-120 and 130-140, the CDR-H2 has at least about 80%, 90%, 91%, 92%, 93%, 94%, 95%, 96%, 97%, 98% or 99% identity with a CDR-H2 of SEQ ID NOs: 100-111, the CDR-H1 has at least about 80%, 90%, 91%, 92%, 93%, 94%, 95%, 96%, 97%, 98% or 99% identity with a CDR-H1 selected from SEQ ID NOs: 58-99 and 121, the CDR-L3 has at least about 80%, 90%, 91%, 92%, 93%, 94%, 95%, 96%, 97%, 98% or 99% identity with a CDR-L3 selected from SEQ ID NOs: 165-172, the CDR-L2 has at least about 80%, 90%, 91%, 92%, 93%, 94%, 95%, 96%, 97%, 98% or 99% identity with a CDR-L2 selected from SEQ ID NOs: 153-158 and the amino acid sequence LAS, and the CDR-L1 has at least about 80%, 90%, 91%, 92%, 93%, 94%, 95%, 96%, 97%, 98% or 99% identity with a CDR-L1 selected from SEQ ID NOs: 141-144 and 149-152. In some embodiments, the CDR-H3 is a CDR-H3 selected from SEQ ID NOs: 112-120 and 130-140, with up to 1, 2, 3, 4, 5, 6, 7, or 8 amino acid substitutions; the CDR-H2 is a CDR-H2 of SEQ ID NOs: 100-111, with up to 1, 2, 3, 4, 5, 6, 7, or 8 amino acid substitutions; the CDR-H1 is a CDR-H1 selected from SEQ ID NOs: 58-99 and 121, with up to 1, 2, 3, 4, or 5 amino acid substitutions; the CDR-L3 is a CDR-L3 selected from SEQ ID NOs: 165-172, with up to 1, 2, 3, 4, or 5 amino acid substitutions; the CDR-L2 is a CDR-L2 selected from SEQ ID NOs: 153-158 and the amino acid sequence LAS, with up to 1, 2, 3, or 4 amino acid substitutions; and the CDR-L1 is a CDR-L1 selected from SEQ ID NOs: 141-144 and 149-152, with up to 1, 2, 3, 4, 5, or 6 amino acid substitutions.

In some embodiments, an antibody provided herein comprises a CDR-H3 of SEQ ID NOs: 112, 121, and 130, a CDR-H2 of SEQ ID NOs: 100, 104, and 108, a CDR-H1 of SEQ ID NOs: 58, 68, and 85, a CDR-L3 of SEQ ID NOs: 168, 173, and 181, a CDR-L2 of SEQ ID NOs: 153 and the amino acid sequence LAS, and a CDR-L1 of SEQ ID NOs: 141 and 149. In some embodiments, the CDR-H3 has at least about 80%, 90%, 91%, 92%, 93%, 94%, 95%, 96%, 97%, 98% or 99% identity with a CDR-H3 of SEQ ID NOs: 112 or 130, the CDR-H2 has at least about 80%, 90%, 91%, 92%, 93%, 94%, 95%, 96%, 97%, 98% or 99% identity with a CDR-H2 of SEQ ID NOs: 100, 104 or 108, the CDR-H1 has at least about 80%, 90%, 91%, 92%, 93%, 94%, 95%, 96%, 97%, 98% or 99% identity with a CDR-H1 of SEQ ID NOs: 58, 68 or 85, the CDR-L3 has at least about 80%, 90%, 91%, 92%, 93%, 94%, 95%, 96%, 97%, 98% or 99% identity with a CDR-L3 of SEQ ID NO: 168, the CDR-L2 has at least about 80%, 90%, 91%, 92%, 93%, 94%, 95%, 96%, 97%, 98% or 99% identity with a CDR-L2 of SEQ ID NOs: 153 or the amino acid sequence LAS, and the CDR-L1 has at least about 80%, 90%, 91%, 92%, 93%, 94%, 95%, 96%, 97%, 98% or 99% identity with a CDR-L1 of SEQ ID NOs: 141 or 149. In some embodiments, the CDR-H3 is a CDR-H3 of SEQ ID NOs: 112 or 130, with up to 1, 2, 3, 4, 5, 6, 7, or 8 amino acid substitutions; the CDR-H2 is a CDR-H2 of SEQ ID NOs: 100, 104 or 108, with up to 1, 2, 3, 4, 5, 6, 7, or 8 amino acid substitutions; the CDR-H1 is a CDR-H1 of SEQ ID NOs: 58, 68 or 85, with up to 1, 2, 3, 4, or 5 amino acid substitutions; the CDR-L3 is a CDR-L3 of SEQ ID NO: 168 with up to 1, 2, 3, 4, or 5 amino acid substitutions; the CDR-L2 is a CDR-L2 of SEQ ID NOs: 153 or the amino acid sequence LAS, with up to 1, 2, 3, or 4 amino acid substitutions; and the CDR-L1 is a CDR-L1 of SEQ ID NOs: 141 or 149, with up to 1, 2, 3, 4, 5, or 6 amino acid substitutions.

In some embodiments, an antibody provided herein comprises a CDR-H3 of SEQ ID NOs: 112, 121 or 130, a CDR-H2 of SEQ ID NOs: 100, 104 or 108, a CDR-H1 of SEQ ID NOs: 58, 68, or 85, a CDR-L3 of SEQ ID NO: 165, a CDR-L2 of SEQ ID NOs: 153 or the amino acid sequence LAS, and a CDR-L1 of SEQ ID NOs: 141 or 149. In some embodiments, the CDR-H3 has at least about 80%, 90%, 91%, 92%, 93%, 94%, 95%, 96%, 97%, 98% or 99% identity with a CDR-H3 of SEQ ID NOs: 112 or 130, the CDR-H2 has at least about 80%, 90%, 91%, 92%, 93%, 94%, 95%, 96%, 97%, 98% or 99% identity with a CDR-H2 of SEQ ID NOs: 100, 104 or 108, the CDR-H1 has at least about 80%, 90%, 91%, 92%, 93%, 94%, 95%, 96%, 97%, 98% or 99% identity with a CDR-H1 of SEQ ID NOs: 58, 68 or 85, the CDR-L3 has at least about 80%, 90%, 91%, 92%, 93%, 94%, 95%, 96%, 97%, 98% or 99% identity with a CDR-L3 of SEQ ID NO: 165, the CDR-L2 has at least about 80%, 90%, 91%, 92%, 93%, 94%, 95%, 96%, 97%, 98% or 99% identity with a CDR-L2 of SEQ ID NOs: 153 or the amino acid sequence LAS, and the CDR-L1 has at least about 80%, 90%, 91%, 92%, 93%, 94%, 95%, 96%, 97%, 98% or 99% identity with a CDR-L1 of SEQ ID NOs: 141 or 149. In some embodiments, the CDR-H3 is a CDR-H3 of SEQ ID NOs: 112 or 130, with up to 1, 2, 3, 4, 5, 6, 7, or 8 amino acid substitutions; the CDR-H2 is a CDR-H2 of SEQ ID NOs: 100, 104 or 108, with up to 1, 2, 3, 4, 5, 6, 7, or 8 amino acid substitutions; the CDR-H1 is a CDR-H1 of SEQ ID NOs: 58, 68 or 85, with up to 1, 2, 3, 4, or 5 amino acid substitutions; the CDR-L3 is a CDR-L3 of SEQ ID NO: 165, with up to 1, 2, 3, 4, or 5 amino acid substitutions; the CDR-L2 is a CDR-L2 of SEQ ID NO: 153 or the amino acid sequence LAS, with up to 1, 2, 3, or 4 amino acid substitutions; and the CDR-L1 is a CDR-L1 of SEQ ID NOs: 141 or 149, with up to 1, 2, 3, 4, 5, or 6 amino acid substitutions.

In some embodiments, an antibody provided herein comprises a CDR-H3 of SEQ ID NOs: 112 or 130, a CDR-H2 of SEQ ID NOs: 100, 104, or 108, a CDR-H1 of SEQ ID NOs: 58, 68, or 85, a CDR-L3 of SEQ ID NO: 165, a CDR-L2 of SEQ ID NO: 158 or the amino acid sequence LAS, and a CDR-L1 of SEQ ID NOs: 141 or 149. In some embodiments, the CDR-H3 has at least about 80%, 90%, 91%, 92%, 93%, 94%, 95%, 96%, 97%, 98% or 99% identity with a CDR-H3 of SEQ ID NOs: 112 or 130, the CDR-H2 has at least about 80%, 90%, 91%, 92%, 93%, 94%, 95%, 96%, 97%, 98% or 99% identity with a CDR-H2 of SEQ ID NOs: 100, 104, or 108, the CDR-H1 has at least about 80%, 90%, 91%, 92%, 93%, 94%, 95%, 96%, 97%, 98% or 99% identity with a CDR-H1 of SEQ ID NOs: 58, 68 or 85, the CDR-L3 has at least about 80%, 90%, 91%, 92%, 93%, 94%, 95%, 96%, 97%, 98% or 99% identity with a CDR-L3 of SEQ ID NO: 165, the CDR-L2 has at least about 80%, 90%, 91%, 92%, 93%, 94%, 95%, 96%, 97%, 98% or 99% identity with a CDR-L2 of SEQ ID NO: 158 or the amino acid sequence LAS, and the CDR-L1 has at least about 80%, 90%, 91%, 92%, 93%, 94%, 95%, 96%, 97%, 98% or 99% identity with a CDR-L1 of SEQ ID NOs: 141 or 149. In some embodiments, the CDR-H3 is a CDR-H3 of SEQ ID NOs: 112 or 130, with up to 1, 2, 3, 4, 5, 6, 7, or 8 amino acid substitutions; the CDR-H2 is a CDR-H2 of SEQ ID NOs: 100, 104, or 108, with up to 1, 2, 3, 4, 5, 6, 7, or 8 amino acid substitutions; the CDR-H1 is a CDR-H1 of SEQ ID NOs: 58, 68, or 85, with up to 1, 2, 3, 4, or 5 amino acid substitutions; the CDR-L3 is a CDR-L3 of SEQ ID NO: 165, with up to 1, 2, 3, 4, or 5 amino acid substitutions; the CDR-L2 is a CDR-L2 of SEQ ID NO: 158 or the amino acid sequence LAS, with up to 1, 2, 3, or 4 amino acid substitutions; and the CDR-L1 is a CDR-L1 of SEQ ID NOs: 141 or 149, with up to 1, 2, 3, 4, 5, or 6 amino acid substitutions.

In some embodiments, an antibody provided herein comprises a CDR-H3 of SEQ ID NOs: 112, 121 or 130, a CDR-H2 of SEQ ID NOs: 100, 104 or 108, a CDR-H1 of SEQ ID NOs: 58, 67, or 84, a CDR-L3 of SEQ ID NO: 165, a CDR-L2 of SEQ ID NOs: 153 or the amino acid sequence LAS, and a CDR-L1 of SEQ ID NOs: 141 or 149. In some embodiments, the CDR-H3 has at least about 80%, 90%, 91%, 92%, 93%, 94%, 95%, 96%, 97%, 98% or 99% identity with a CDR-H3 of SEQ ID NOs: 112 or 130, the CDR-H2 has at least about 80%, 90%, 91%, 92%, 93%, 94%, 95%, 96%, 97%, 98% or 99% identity with a CDR-H2 of SEQ ID NOs: 100, 104 or 108, the CDR-H1 has at least about 80%, 90%, 91%, 92%, 93%, 94%, 95%, 96%, 97%, 98% or 99% identity with a CDR-H1 of SEQ ID NOs: 58, 67 or 84, the CDR-L3 has at least about 80%, 90%, 91%, 92%, 93%, 94%, 95%, 96%, 97%, 98% or 99% identity with a CDR-L3 of SEQ ID NO: 165, the CDR-L2 has at least about 80%, 90%, 91%, 92%, 93%, 94%, 95%, 96%, 97%, 98% or 99% identity with a CDR-L2 of SEQ ID NOs: 153 or the amino acid sequence LAS, and the CDR-L1 has at least about 80%, 90%, 91%, 92%, 93%, 94%, 95%, 96%, 97%, 98% or 99% identity with a CDR-L1 of SEQ ID NOs: 141 or 149. In some embodiments, the CDR-H3 is a CDR-H3 of SEQ ID NOs: 112 or 130, with up to 1, 2, 3, 4, 5, 6, 7, or 8 amino acid substitutions; the CDR-H2 is a CDR-H2 of SEQ ID NOs: 100, 104 or 108, with up to 1, 2, 3, 4, 5, 6, 7, or 8 amino acid substitutions; the CDR-H1 is a CDR-H1 of SEQ ID NOs: 58, 67 or 84, with up to 1, 2, 3, 4, or 5 amino acid substitutions; the CDR-L3 is a CDR-L3 of SEQ ID NO: 165, with up to 1, 2, 3, 4, or 5 amino acid substitutions; the CDR-L2 is a CDR-L2 of SEQ ID NO: 153 or the amino acid sequence LAS, with up to 1, 2, 3, or 4 amino acid substitutions; and the CDR-L1 is a CDR-L1 of SEQ ID NOs: 141 or 149, with up to 1, 2, 3, 4, 5, or 6 amino acid substitutions.

In some embodiments, an antibody provided herein comprises a CDR-H3 of SEQ ID NOs: 112 or 130, a CDR-H2 of SEQ ID NOs: 100, 104, or 108, a CDR-H1 of SEQ ID NOs: 58, 67, or 84, a CDR-L3 of SEQ ID NO: 165, a CDR-L2 of SEQ ID NO: 158 or the amino acid sequence LAS, and a CDR-L1 of SEQ ID NOs: 141 or 149. In some embodiments, the CDR-H3 has at least about 80%, 90%, 91%, 92%, 93%, 94%, 95%, 96%, 97%, 98% or 99% identity with a CDR-H3 of SEQ ID NOs: 112 or 130, the CDR-H2 has at least about 80%, 90%, 91%, 92%, 93%, 94%, 95%, 96%, 97%, 98% or 99% identity with a CDR-H2 of SEQ ID NOs: 100, 104, or 108, the CDR-H1 has at least about 80%, 90%, 91%, 92%, 93%, 94%, 95%, 96%, 97%, 98% or 99% identity with a CDR-H1 of SEQ ID NOs: 58, 67 or 84, the CDR-L3 has at least about 80%, 90%, 91%, 92%, 93%, 94%, 95%, 96%, 97%, 98% or 99% identity with a CDR-L3 of SEQ ID NO: 165, the CDR-L2 has at least about 80%, 90%, 91%, 92%, 93%, 94%, 95%, 96%, 97%, 98% or 99% identity with a CDR-L2 of SEQ ID NO: 158 or the amino acid sequence LAS, and the CDR-L1 has at least about 80%, 90%, 91%, 92%, 93%, 94%, 95%, 96%, 97%, 98% or 99% identity with a CDR-L1 of SEQ ID NOs: 141 or 149. In some embodiments, the CDR-H3 is a CDR-H3 of SEQ ID NOs: 112 or 130, with up to 1, 2, 3, 4, 5, 6, 7, or 8 amino acid substitutions; the CDR-H2 is a CDR-H2 of SEQ ID NOs: 100, 104, or 108, with up to 1, 2, 3, 4, 5, 6, 7, or 8 amino acid substitutions; the CDR-H1 is a CDR-H1 of SEQ ID NOs: 58, 67, or 84, with up to 1, 2, 3, 4, or 5 amino acid substitutions; the CDR-L3 is a CDR-L3 of SEQ ID NO: 165, with up to 1, 2, 3, 4, or 5 amino acid substitutions; the CDR-L2 is a CDR-L2 of SEQ ID NO: 158 or the amino acid sequence LAS, with up to 1, 2, 3, or 4 amino acid substitutions; and the CDR-L1 is a CDR-L1 of SEQ ID NOs: 141 or 149, with up to 1, 2, 3, 4, 5, or 6 amino acid substitutions.

In some embodiments, the amino acid substitutions are conservative amino acid substitutions. In some embodiments, the antibodies described in this disclosure are referred to herein as "variants" or "clones". In some embodiments, such variants or clones are derived from a sequence provided herein, for example, by affinity maturation, site directed mutagenesis, random mutagenesis, or any other method known in the art or described herein. In some embodiments, such variants or cones are not derived from a sequence provided herein and may, for example, be isolated de novo according to the methods provided herein for obtaining antibodies.

In certain aspects, the antibodies disclosed herein do not include antibodies disclosed in U.S. Pat. No. 9,067,994.

TABLE 3

Anti-interleukin (IL)-13 antibody Heavy Chain Kabat CDRs

| Construct ID | VH Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 1 (lebrikizumab), 2, and 128-131 | Lebrikizumab-HC | QVTLR ESGPA LVKPT QTLTL TCTVS GFSLS | 540 | AYSVN | 58 | WIRQP PGKAL EWLA | 255 | MIWGD GKIVY NSALK S | 100 | RLTIS KDTSK NQVVL TMTNM DPVDT ATYYC AG | 311 | DGYYP YAMDN | 112 | WGQGS LVTVS S | 368 |
| 3 | HC0 | QVQLQ ESGPG LVAPS QSLSI TCTVS GFSLN | 198 | AYSVN | 58 | WVRQP PGKGL EWLG | 256 | MIWGD GKIVY NSALK S | 100 | RLNIS KDSSK SQVFL KMSSL QSDDT ARYYC AG | 312 | DGYYP YAMDN | 112 | WGHGT SVTVS S | 369 |
| 4 | HC0_M | QVQLQ ESGPG LVAPS QSLSI TCTVS GFSLN | 198 | AYSVN | 58 | WVRQP PGKGL EWLG | 256 | MIWGD GKIVY NSALK S | 100 | RLTIS KDSSK SQVFL KMSSL QSDDT ARYYC AG | 313 | DGYYP YAMDN | 112 | WGHGT SVTVS S | 369 |
| 5, 10, 15, 20, 133- | HC1 | EVQLQ ESGPG | 200 | AYSVN | 58 | WIRQP PGKGL | 258 | MIWGD GKIVY | 100 | RLTIS KDSSK | 314 | DGYYP YAMDN | 112 | WGQGT TVTVS | 371 |

TABLE 3-continued

Anti-interleukin (IL)-13 antibody Heavy Chain Kabat CDRs

| Construct ID | VH Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 136, and 141-144 | | LVKPS ETLSL TCTVS GFSLN | | | | EWLG | | NSALK S | | NQVSL KLSSV TAADT AVYYC AG | | | | S | |
| 6, 11, 16, and 21 | HC2 | EVQLV QSGAE VKKPG ASVKV SCKAS GFSLN | | AYSVN | 201 | WVRQA PGQGL EWLG | 58 | MIWGD GKIVY NSALK S | 259 | RLTIT KDSST STVYM ELSSL RSEDT AVYYC AG | 100 | DGYYP YAMDN | 315 | WGQGT TVTVS S | 112 | 371 |
| 7, 12, 17, and 22 | HC3 | EVQLV QSGAE VKKPG SSVKV SCKAS GFSLN | | AYSVN | 202 | WVRQA PGQGL EWLG | 58 | MIWGD GKIVY NSALK S | 259 | RLTIT KDSST STVYM ELSSL RSEDT AVYYC AG | 100 | DGYYP YAMD N | 315 | WGQG TTVTV SS | 112 | 371 |
| 8, 13, 18, and 23 | HC4 | EVQLV ESGGG LVKPG GSLRL SCAAS GFSLN | | AYSVN | 203 | WVRQA PGKGL EWLG | 58 | MIWGD GKIVY NSALK S | 262 | RLTIS KDSSK NTVYL QMNSL KTEDT AVYYC AG | 100 | DGYYP YAMDN | 317 | WGQGT TVTVS S | 112 | 371 |
| 9, 14, 19, 24, 90-104, 132, and 137-140 | HC5 | EVQLL ESGGG LVQPG GSLRL SCAAS GFSLN | | AYSVN | 204 | WVRQA PGKGL EWLG | 58 | MIWGD GKIVY NSALK S | 262 | RLTIS KDSSK NTVYL QMNSL RAEDT AVYYC AG | 100 | DGYYP YAMDN | 318 | WGQGT TVTVS S | 112 | 371 |
| 25 | HC6 | EVQLQ ESGPG LVKPS ETLSL TCTVS GGSLN | | AYSVN | 205 | WVRQP PGKGL EWLG | 58 | MIWGD GKIVY NSALK S | 256 | RLTIS LDTSK SQVFL KMSSL TAADT AVYYC AR | 100 | DGYYP YAMDN | 319 | WGQGT TVTVS S | 112 | 371 |
| 26 | HC7 | QVQLQ ESGPG LVKPS ETLSL TCTVS GGSLN | | AYSWN | 206 | WVRQP PGKGL EWLG | 541 | YIYGD GKTNY NPALK S | 256 | RLTIS LDTSK SQVFL KMSSL TAADT AVYYC AR | 101 | DGYYY YAMDV | 319 | WGQGT TVTVS S | 113 | 371 |
| 105 | HC5_m1 | EVQLL ESGGG LVQPG GSLRL SCAAS GYSLN | | AYSVN | 207 | WVRQA PGKGL EWLG | 58 | MIWGD GKIVY NSALK S | 262 | RLTIS KDSSK NTVYL QMNSL RAEDT AVYYC AG | 100 | DGYYP YAMDN | 318 | WGQGT TVTVS S | 112 | 371 |
| 106 | HC5_m2 | EVQLL ESGGG LVQPG GSLRL SCAAS GFSLR | | AYSVN | 208 | WVRQA PGKGL EWLG | 58 | MIWGD GKIVY NSALK S | 262 | RLTIS KDSSK NTVYL QMNSL RAEDT AVYYC AG | 100 | DGYYP YAMDN | 318 | WGQGT TVTVS S | 112 | 371 |
| 107 | HC5_m3 | EVQLL ESGGG LVQPG GSLRL | | AYSVN | 209 | WVRQA PGKGL EWLG | 58 | MIWGD GKIVY NSALK S | 262 | RLTIS KDSSK NTVYL QMNSL | 100 | DGYYP YAMDN | 318 | WGQGT TVTVS S | 112 | 371 |

TABLE 3-continued

Anti-interleukin (IL)-13 antibody Heavy Chain Kabat CDRs

| Construct ID | VH Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| | | SCAAS GFSLH | | | | | | | | RAEDT AVYYC AG | | | | | |
| 108 | HC5_m4 | EVQLLESGGGLVQPGGSLRLSCAASGFSLD | | AYSVN | 210 | WVRQAPGKGLEWLG | 58 | MIWGDGKIVYNSALKS | 262 | RLTISKDSSKNTVYLQMNSLRAEDTAVYYCAG | 100 | DGYYPYAMDN | 318 | WGQGTTVTVSS | 112 | 371 |
| 109 | HC5_m5 | EVQLLESGGGLVQPGGSLRLSCAASGFSLY | | AYSVN | 211 | WVRQAPGKGLEWLG | 58 | MIWGDGKIVYNSALKS | 262 | RLTISKDSSKNTVYLQMNSLRAEDTAVYYCAG | 100 | DGYYPYAMDN | 318 | WGQGTTVTVSS | 112 | 371 |
| 110 | HC5_m6 | EVQLLESGGGLVQPGGSLRLSCAASGFSLS | | AYSVN | 212 | WVRQAPGKGLEWLG | 58 | MIWGDGKIVYNSALKS | 262 | RLTISKDSSKNTVYLQMNSLRAEDTAVYYCAG | 100 | DGYYPYAMDN | 318 | WGQGTTVTVSS | 112 | 371 |
| 111 | HC5_m7 | EVQLLESGGGLVQPGGSLRLSCAASGFSLN | | RYSVN | 204 | WVRQAPGKGLEWLG | 59 | MIWGDGKIVYNSALKS | 262 | RLTISKDSSKNTVYLQMNSLRAEDTAVYYCAG | 100 | DGYYPYAMDN | 318 | WGQGTTVTVSS | 112 | 371 |
| 112 | HC5_m8 | EVQLLESGGGLVQPGGSLRLSCAASGFSLN | | KYSVN | 204 | WVRQAPGKGLEWLG | 60 | MIWGDGKIVYNSALKS | 262 | RLTISKDSSKNTVYLQMNSLRAEDTAVYYCAG | 100 | DGYYPYAMDN | 318 | WGQGTTVTVSS | 112 | 371 |
| 113 | HC5_m9 | EVQLLESGGGLVQPGGSLRLSCAASGFSLN | | HYSVN | 204 | WVRQAPGKGLEWLG | 61 | MIWGDGKIVYNSALKS | 262 | RLTISKDSSKNTVYLQMNSLRAEDTAVYYCAG | 100 | DGYYPYAMDN | 318 | WGQGTTVTVSS | 112 | 371 |
| 114 | HC5_m10 | EVQLLESGGGLVQPGGSLRLSCAASGFSLN | | QYSVN | 204 | WVRQAPGKGLEWLG | 62 | MIWGDGKIVYNSALKS | 262 | RLTISKDSSKNTVYLQMNSLRAEDTAVYYCAG | 100 | DGYYPYAMDN | 318 | WGQGTTVTVSS | 112 | 371 |
| 115 | HC5_m11 | EVQLLESGGGLVQPGGSLRLSCAASGFSLN | | EYSVN | 204 | WVRQAPGKGLEWLG | 63 | MIWGDGKIVYNSALKS | 262 | RLTISKDSSKNTVYLQMNSLRAEDTAVYYCAG | 100 | DGYYPYAMDN | 318 | WGQGTTVTVSS | 112 | 371 |

TABLE 3-continued

Anti-interleukin (IL)-13 antibody Heavy Chain Kabat CDRs

| Construct ID | VH Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 116 | HC5_m12 | EVQLLESGGGLVQPGGSLRLSCAASGFSLN | 204 | SYSVN | 64 | WVRQAPGKGLEWLG | 262 | MIWGDGKIVYNSALKS | 100 | RLTISKDSSKNTVYLQMNSLRAEDTAVYYCAG | 318 | DGYYPYAMDN | 112 | WGQGTTVTVSS | 371 |
| 117 | HC5_m13 | EVQLLESGGGLVQPGGSLRLSCAASGFSLN | 204 | YYSVN | 65 | WVRQAPGKGLEWLG | 262 | MIWGDGKIVYNSALKS | 100 | RLTISKDSSKNTVYLQMNSLRAEDTAVYYCAG | 318 | DGYYPYAMDN | 112 | WGQGTTVTVSS | 371 |
| 118 | HC5_m14 | EVQLLESGGGLVQPGGSLRLSCAASGFSLN | 204 | AESVN | 66 | WVRQAPGKGLEWLG | 262 | MIWGDGKIVYNSALKS | 100 | RLTISKDSSKNTVYLQMNSLRAEDTAVYYCAG | 318 | DGYYPYAMDN | 112 | WGQGTTVTVSS | 371 |
| 119 | HC5_m15 | EVQLLESGGGLVQPGGSLRLSCAASGFSLN | 204 | AYSVN | 58 | WVRQAPGKGLEWLG | 262 | MIWSDGKIVYNSALKS | 102 | RLTISKDSSKNTVYLQMNSLRAEDTAVYYCAG | 318 | DGYYPYAMDN | 112 | WGQGTTVTVSS | 371 |
| 120 | HC5_m16 | EVQLLESGGGLVQPGGSLRLSCAASGFSLN | 204 | AYSVN | 58 | WVRQAPGKGLEWLG | 262 | MIWADGKIVYNSALKS | 103 | RLTISKDSSKNTVYLQMNSLRAEDTAVYYCAG | 318 | DGYYPYAMDN | 112 | WGQGTTVTVSS | 371 |
| 121 | HC5_m17 | EVQLLESGGGLVQPGGSLRLSCAASGFSLN | 204 | AYSVN | 58 | WVRQAPGKGLEWLG | 262 | MIWGDGKIVYNSALKS | 100 | RLTISKDSSKNTVYLQMNSLRAEDTAVYYCAG | 318 | HGYYPYAMDN | 114 | WGQGTTVTVSS | 371 |
| 122 | HC5_m18 | EVQLLESGGGLVQPGGSLRLSCAASGFSLN | 204 | AYSVN | 58 | WVRQAPGKGLEWLG | 262 | MIWGDGKIVYNSALKS | 100 | RLTISKDSSKNTVYLQMNSLRAEDTAVYYCAG | 318 | DLYYPYAMDN | 115 | WGQGTTVTVSS | 371 |
| 123 | HC5_m19 | EVQLLESGGGLVQPGGSLRLSCAASGFSLN | 204 | AYSVN | 58 | WVRQAPGKGLEWLG | 262 | MIWGDGKIVYNSALKS | 100 | RLTISKDSSKNTVYLQMNSLRAEDTAVYYCAG | 318 | DKYYPYAMDN | 116 | WGQGTTVTVSS | 371 |
| 124 | HC5_m20 | EVQLLESGGGLVQPGGSLRLSCAASGFSLN | 204 | AYSVN | 58 | WVRQAPGKGLEWLG | 262 | MIWGDGKIVYNSALKS | 100 | RLTISKDSSKNTVYLQMNSLRAEDTAVYYCAG | 318 | DGYYGYAMDN | 117 | WGQGTTVTVSS | 371 |

TABLE 3-continued

Anti-interleukin (IL)-13 antibody Heavy Chain Kabat CDRs

| Construct ID | VH Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 125 | HC5_m21 | EVQLLESGGGLVQPGGSLRLSCAASGFSLN | 204 | AYSVN | 58 | WVRQAPGKGLEWLG | 262 | MIWGDGKIVYNSALKS | 100 | RLTISKDSSKNTVYLQMNSLRAEDTAVYYCAG | 318 | DGYYAYAMDN | 118 | WGQGTTVTVSS | 371 |
| 126 | HC5_m22 | EVQLLESGGGLVQPGGSLRLSCAASGFSLN | 204 | AYSVN | 58 | WVRQAPGKGLEWLG | 262 | MIWGDGKIVYNSALKS | 100 | RLTISKDSSKNTVYLQMNSLRAEDTAVYYCAG | 318 | DGYYSYAMDN | 119 | WGQGTTVTVSS | 371 |
| 127 | HC5_m24 | EVQLLESGGGLVQPGGSLRLSCAASGFSLN | 204 | AYSVN | 58 | WVRQAPGKGLEWLG | 262 | MIWGDGKIVYNSALKS | 100 | RLTISKDSSKNTVYLQMNSLRAEDTAVYYCAG | 318 | DGYYTYAMDN | 120 | WGQGTTVTVSS | 371 |

*Names correspond with name in informal sequence listing.

TABLE 4

Anti-interleukin (IL)-13 antibody Heavy Chain Chothia CDRs

| Construct ID | VH Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 1 (lebrikizumab), 2, and 128-131 | Lebrikizumab-HC | QVTLRESGPALVKPTQTLTLTCTVS | 542 | GFSLSAY | 67 | SVNWIRQPPGKALEWLAMI | 550 | WGDGK | 104 | IVYNSALKSRLTISKDTSKNQVVLTMTNMDPVDTATYYCAG | 556 | DGYYPYAMDN | 112 | WGQGSLVTVSS | 368 |
| 3 | HC0 | QVQLQESGPGLVAPSQSLSITCTVS | 543 | GFSLNAY | 68 | SVNWVRQPPGKGLEWLGMI | 551 | WGDGK | 104 | IVYNSALKSRLNISKDSSKSQVFLKMSSLQSDDTARYYCAG | 557 | DGYYPYAMDN | 112 | WGHGTSVTVSS | 369 |
| 4 | HC0_M | QVQLQESGPGLVAPSQSLSITCTVS | 543 | GFSLNAY | 68 | SVNWVRQPPGKGLEWLGMI | 551 | WGDGK | 104 | IVYNSALKSRLTISKDSSKSQVFLKMSSLQSDDTARYYCAG | 558 | DGYYPYAMDN | 112 | WGHGTSVTVSS | 369 |
| 5, 10, 15, 20, 133-136, and 141-144 | HC1 | EVQLQESGPGLVKPSETLSLTCTVS | 544 | GFSLNAY | 68 | SVNWIRQPPGKGLEWLGMI | 552 | WGDGK | 104 | IVYNSALKSRLTISKDSSKNQVSLKLSSVTAADTAVYYCAG | 559 | DGYYPYAMDN | 112 | WGQGTTVTVSS | 371 |

TABLE 4-continued

Anti-interleukin (IL)-13 antibody Heavy Chain Chothia CDRs

| Construct ID | VH Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 6, 11, 16, and 21 | HC2 | EVQLVQSGAEVKKPGASVKVSCKAS | 545 | GFSLNAY | 68 | SVNWVRQAPGQGLEWLGMI | 553 | WGDGK | 104 | IVYNSALKSRLTITKDSSTSTVYMELSSLRSEDTAVYYCAG | 560 | DGYYPYAMDN | 112 | WGQGTTVTVSS | 371 |
| 7, 12, 17, and 22 | HC3 | EVQLVQSGAEVKKPGSSVKVSCKAS | 546 | GFSLNAY | 68 | SVNWVRQAPGQGLEWLGMI | 553 | WGDGK | 104 | IVYNSALKSRLTITKDSSTSTVYMELSSLRSEDTAVYYCAG | 560 | DGYYPYAMDN | 112 | WGQGTTVTVSS | 371 |
| 8, 13, 18, and 23 | HC4 | EVQLVESGGGLVKPGGSLRLSCAAS | 547 | GFSLNAY | 68 | SVNWVRQAPGKGLEWLGMI | 554 | WGDGK | 104 | IVYNSALKSRLTISKDSSKNTVYLQMNSLKTEDTAVYYCAG | 561 | DGYYPYAMDN | 112 | WGQGTTVTVSS | 371 |
| 9, 14, 19, 24, 90-104, 132, and 137-140 | HC5 | EVQLLESGGGLVQPGGSLRLSCAAS | 548 | GFSLNAY | 68 | SVNWVRQAPGKGLEWLGMI | 554 | WGDGK | 104 | IVYNSALKSRLTISKDSSKNTVYLQMNSLRAEDTAVYYCAG | 562 | DGYYPYAMDN | 112 | WGQGTTVTVSS | 371 |
| 25 | HC6 | EVQLQESGPGLVKPSETLSLTCTVS | 544 | GGSLNAY | 69 | SVNWVRQPPGKGLEWLGMI | 551 | WGDGK | 104 | IVYNSALKSRLTISLDTSKSQVFLKMSSLTAADTAVYYCAR | 563 | DGYYPYAMDN | 112 | WGQGTTVTVSS | 371 |
| 26 | HC7 | QVQLQESGPGLVKPSETLSLTCTVS | 549 | GGSLNAY | 69 | SWNWVRQPPGKGLEWLGYI | 555 | YGDGK | 105 | TNYNPALKSRLTISLDTSKSQVFLKMSSLTAADTAVYYCAR | 564 | DGYYYAMDV | 113 | WGQGTTVTVSS | 371 |
| 105 | HC5_m1 | EVQLLESGGGLVQPGGSLRLSCAAS | 548 | GYSLNAY | 71 | SVNWVRQAPGKGLEWLGMI | 554 | WGDGK | 104 | IVYNSALKSRLTISKDSSKNTVYLQMNSLRAEDTAVYYCAG | 562 | DGYYPYAMDN | 112 | WGQGTTVTVSS | 371 |
| 106 | HC5_m2 | EVQLLESGGGLVQPGGSLRLSCAAS | 548 | GFSLRAY | 72 | SVNWVRQAPGKGLEWLGMI | 554 | WGDGK | 104 | IVYNSALKSRLTISKDSSKNTVYLQMNSLRAEDTAVYYCAG | 562 | DGYYPYAMDN | 112 | WGQGTTVTVSS | 371 |

TABLE 4-continued

Anti-interleukin (IL)-13 antibody Heavy Chain Chothia CDRs

| Construct ID | VH Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 107 | HC5_m3 | EVQLLESGGGLVQPGGSLRLSCAAS | 548 | GFSLHAY | 73 | SVNWVRQAPGKGLEWLGMI | 554 | WGDGK | 104 | IVYNSALKSRLTISKDSSKNTVYLQMNSLRAEDTAVYYCAG | 562 | DGYYPYAMDN | 112 | WGQGTTVTVSS | 371 |
| 108 | HC5_m4 | EVQLLESGGGLVQPGGSLRLSCAAS | 548 | GFSLDAY | 74 | SVNWVRQAPGKGLEWLGMI | 554 | WGDGK | 104 | IVYNSALKSRLTISKDSSKNTVYLQMNSLRAEDTAVYYCAG | 562 | DGYYPYAMDN | 112 | WGQGTTVTVSS | 371 |
| 109 | HC5_m5 | EVQLLESGGGLVQPGGSLRLSCAAS | 548 | GFSLYAY | 75 | SVNWVRQAPGKGLEWLGMI | 554 | WGDGK | 104 | IVYNSALKSRLTISKDSSKNTVYLQMNSLRAEDTAVYYCAG | 562 | DGYYPYAMDN | 112 | WGQGTTVTVSS | 371 |
| 110 | HC5_m6 | EVQLLESGGGLVQPGGSLRLSCAAS | 548 | GFSLSAY | 67 | SVNWVRQAPGKGLEWLGMI | 554 | WGDGK | 104 | IVYNSALKSRLTISKDSSKNTVYLQMNSLRAEDTAVYYCAG | 562 | DGYYPYAMDN | 112 | WGQGTTVTVSS | 371 |
| 111 | HC5_m7 | EVQLLESGGGLVQPGGSLRLSCAAS | 548 | GFSLNRY | 76 | SVNWVRQAPGKGLEWLGMI | 554 | WGDGK | 104 | IVYNSALKSRLTISKDSSKNTVYLQMNSLRAEDTAVYYCAG | 562 | DGYYPYAMDN | 112 | WGQGTTVTVSS | 371 |
| 112 | HC5_m8 | EVQLLESGGGLVQPGGSLRLSCAAS | 548 | GFSLNKY | 77 | SVNWVRQAPGKGLEWLGMI | 554 | WGDGK | 104 | IVYNSALKSRLTISKDSSKNTVYLQMNSLRAEDTAVYYCAG | 562 | DGYYPYAMDN | 112 | WGQGTTVTVSS | 371 |
| 113 | HC5_m9 | EVQLLESGGGLVQPGGSLRLSCAAS | 548 | GFSLNHY | 78 | SVNWVRQAPGKGLEWLGMI | 554 | WGDGK | 104 | IVYNSALKSRLTISKDSSKNTVYLQMNSLRAEDTAVYYCAG | 562 | DGYYPYAMDN | 112 | WGQGTTVTVSS | 371 |

TABLE 4-continued

Anti-interleukin (IL)-13 antibody Heavy Chain Chothia CDRs

| Construct ID | VH Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 114 | HC5_m10 | EVQLLESGGGLVQPGGSLRLSCAAS | 548 | GFSLNQY | 79 | SVNWVRQAPGKGLEWLGMI | 554 | WGDGK | 104 | IVYNSALKSRLTISKDSSKNTVYLQMNSLRAEDTAVYYCAG | 562 | DGYYPYAMDN | 112 | WGQGTTVTVSS | 371 |
| 115 | HC5_m11 | EVQLLESGGGLVQPGGSLRLSCAAS | 548 | GFSLNEY | 80 | SVNWVRQAPGKGLEWLGMI | 554 | WGDGK | 104 | IVYNSALKSRLTISKDSSKNTVYLQMNSLRAEDTAVYYCAG | 562 | DGYYPYAMDN | 112 | WGQGTTVTVSS | 371 |
| 116 | HC5_m12 | EVQLLESGGGLVQPGGSLRLSCAAS | 548 | GFSLNSY | 81 | SVNWVRQAPGKGLEWLGMI | 554 | WGDGK | 104 | IVYNSALKSRLTISKDSSKNTVYLQMNSLRAEDTAVYYCAG | 562 | DGYYPYAMDN | 112 | WGQGTTVTVSS | 371 |
| 117 | HC5_m13 | EVQLLESGGGLVQPGGSLRLSCAAS | 548 | GFSLNYY | 82 | SVNWVRQAPGKGLEWLGMI | 554 | WGDGK | 104 | IVYNSALKSRLTISKDSSKNTVYLQMNSLRAEDTAVYYCAG | 562 | DGYYPYAMDN | 112 | WGQGTTVTVSS | 371 |
| 118 | HC5_m14 | EVQLLESGGGLVQPGGSLRLSCAAS | 548 | GFSLNAE | 83 | SVNWVRQAPGKGLEWLGMI | 554 | WGDGK | 104 | IVYNSALKSRLTISKDSSKNTVYLQMNSLRAEDTAVYYCAG | 562 | DGYYPYAMDN | 112 | WGQGTTVTVSS | 371 |
| 119 | HC5_m15 | EVQLLESGGGLVQPGGSLRLSCAAS | 548 | GFSLNAY | 68 | SVNWVRQAPGKGLEWLGMI | 554 | WSDGK | 106 | IVYNSALKSRLTISKDSSKNTVYLQMNSLRAEDTAVYYCAG | 562 | DGYYPYAMDN | 112 | WGQGTTVTVSS | 371 |
| 120 | HC5_m16 | EVQLLESGGGLVQPGGSLRLSCAAS | 548 | GFSLNAY | 68 | SVNWVRQAPGKGLEWLGMI | 554 | WADGK | 107 | IVYNSALKSRLTISKDSSKNTVYLQMNSLRAEDTAVYYCAG | 562 | DGYYPYAMDN | 112 | WGQGTTVTVSS | 371 |

TABLE 4-continued

Anti-interleukin (IL)-13 antibody Heavy Chain Chothia CDRs

| Construct ID | VH Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 121 | HC5_m17 | EVQLLESGGGLVQPGGSLRLSCAAS | | GFSLNAY | 548 | SVNWVRQAPGKGLEWLGMI | 68 | WGDGK | 554 | IVYNSALKSRLTISKDSSKNTVYLQMNSLRAEDTAVYYCAG | 104 | HGYYPYAMDN | 562 | WGQGTTVTVSS | 114 | 371 |
| 122 | HC5_m18 | EVQLLESGGGLVQPGGSLRLSCAAS | | GFSLNAY | 548 | SVNWVRQAPGKGLEWLGMI | 68 | WGDGK | 554 | IVYNSALKSRLTISKDSSKNTVYLQMNSLRAEDTAVYYCAG | 104 | DLYYPYAMDN | 562 | WGQGTTVTVSS | 115 | 371 |
| 123 | HC5_m19 | EVQLLESGGGLVQPGGSLRLSCAAS | | GFSLNAY | 548 | SVNWVRQAPGKGLEWLGMI | 68 | WGDGK | 554 | IVYNSALKSRLTISKDSSKNTVYLQMNSLRAEDTAVYYCAG | 104 | DKYYPYAMDN | 562 | WGQGTTVTVSS | 116 | 371 |
| 124 | HC5_m20 | EVQLLESGGGLVQPGGSLRLSCAAS | | GFSLNAY | 548 | SVNWVRQAPGKGLEWLGMI | 68 | WGDGK | 554 | IVYNSALKSRLTISKDSSKNTVYLQMNSLRAEDTAVYYCAG | 104 | DGYYGYAMDN | 562 | WGQGTTVTVSS | 117 | 371 |
| 125 | HC5_m21 | EVQLLESGGGLVQPGGSLRLSCAAS | | GFSLNAY | 548 | SVNWVRQAPGKGLEWLGMI | 68 | WGDGK | 554 | IVYNSALKSRLTISKDSSKNTVYLQMNSLRAEDTAVYYCAG | 104 | DGYYAYAMDN | 562 | WGQGTTVTVSS | 118 | 371 |
| 126 | HC5_m22 | EVQLLESGGGLVQPGGSLRLSCAAS | | GFSLNAY | 548 | SVNWVRQAPGKGLEWLGMI | 68 | WGDGK | 554 | IVYNSALKSRLTISKDSSKNTVYLQMNSLRAEDTAVYYCAG | 104 | DGYYSYAMDN | 562 | WGQGTTVTVSS | 119 | 371 |
| 127 | HC5_m24 | EVQLLESGGGLVQPGGSLRLSCAAS | | GFSLNAY | 548 | SVNWVRQAPGKGLEWLGMI | 68 | WGDGK | 554 | IVYNSALKSRLTISKDSSKNTVYLQMNSLRAEDTAVYYCAG | 104 | DGYYTYAMDN | 562 | WGQGTTVTVSS | 120 | 371 |

*Names correspond with name in informal sequence listing.

TABLE 5

Anti-interleukin (IL)-13 antibody Heavy Chain IMGT CDRs

| Construct ID | VH Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 1 (lebrikizumab - HC umab), 2, and 128-131 | Lebrikiz- | QVTLRESGPALVKPTQTLTLTCTVS | 542 | GFSLSAYS | 84 | VNWIRQPPGKALEWLAM | 566 | IWGDGKI | 108 | VYNSALKSRLTISKDTSKNQVVLTMTNMDPVDTATYYC | 572 | AGDGYYPYAMDN | 130 | WGQGSLVTVSS | 368 |
| 3 | HC0 | QVQLQESGPGLVAPSQSLSITCTVS | 543 | GFSLNAYS | 85 | VNWVRQPPGKGLEWLGM | 567 | IWGDGKI | 108 | VYNSALKSRLNISKDSSKSQVFLKMSSLQSDDTARYYC | 573 | AGDGYYPYAMDN | 130 | WGHGTSVTVSS | 369 |
| 4 | HC0_M | QVQLQESGPGLVAPSQSLSITCTVS | 543 | GFSLNAYS | 85 | VNWVRQPPGKGLEWLGM | 567 | IWGDGKI | 108 | VYNSALKSRLTISKDSSKSQVFLKMSSLQSDDTARYYC | 574 | AGDGYYPYAMDN | 130 | WGHGTSVTVSS | 369 |
| 5, 10, 15, 20, and 133-136 | HC1 | EVQLQESGPGLVKPSETLSLTCTVS | 544 | GFSLNAYS | 85 | VNWIRQPPGKGLEWLGM | 568 | IWGDGKI | 108 | VYNSALKSRLTISKDSSKNQVSLKLSSVTAADTAVYYC | 575 | AGDGYYPYAMDN | 130 | WGQGTTVTVSS | 371 |
| 6, 11, 16, and 21 | HC2 | EVQLVQSGAEVKKPGASVKVSCKAS | 545 | GFSLNAYS | 85 | VNWVRQAPGQGLEWLGM | 569 | IWGDGKI | 108 | VYNSALKSRLTITKDSSTSTVYMELSSLRSEDTAVYYC | 576 | AGDGYYPYAMDN | 130 | WGQGTTVTVSS | 371 |
| 7, 12, 17, and 22 | HC3 | EVQLVQSGAEVKKPGSSVKVSCKAS | 546 | GFSLNAYS | 85 | VNWVRQAPGQGLEWLGM | 569 | IWGDGKI | 108 | VYNSALKSRLTITKDSSTSTVYMELSSLRSEDTAVYYC | 576 | AGDGYYPYAMDN | 130 | WGQGTTVTVSS | 371 |
| 8, 13, 18, and 23 | HC4 | EVQLVESGGGLVKPGGSLRLSCAAS | 547 | GFSLNAYS | 85 | VNWVRQAPGKGLEWLGM | 570 | IWGDGKI | 108 | VYNSALKSRLTISKDSSKNTVYLQMNSLKTEDTAVYYC | 577 | AGDGYYPYAMDN | 130 | WGQGTTVTVSS | 371 |
| 9, 14, 19, 24, 90-104, 132, and 137-140 | HC5 | EVQLLESGGGLVQPGGSLRLSCAAS | 548 | GFSLNAYS | 85 | VNWVRQAPGKGLEWLGM | 570 | IWGDGKI | 108 | VYNSALKSRLTISKDSSKNTVYLQMNSLRAEDTAVYYC | 578 | AGDGYYPYAMDN | 130 | WGQGTTVTVSS | 371 |

TABLE 5-continued

Anti-interleukin (IL)-13 antibody Heavy Chain IMGT CDRs

| Construct ID | VH Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 25 | HC6 | EVQLQESGPGLVKPSETLSLTCTVS | 544 | GGSLNAYS | 86 | VNWVRQPPGKGLEWLGM | 567 | IWGDGKI | 108 | VYNSALKSRLTISLDTSKSQVFLKMSSLTAADTAVYYC | 579 | ARDGYPYAMDN | 131 | WGQGTTVTVSS | 371 |
| 26 | HC7 | QVQLQESGPGLVKPSETLSLTCTVS | 549 | GGSLNAYS | 86 | WNWVRQPPGKGLEWLGY | 571 | IYGDGKT | 109 | NYNPALKSRLTISLDTSKSQVFLKMSSLTAADTAVYYC | 580 | ARDGYYYYAMDV | 132 | WGQGTTVTVSS | 371 |
| 105 | HC5_m1 | EVQLLESGGGLVQPGGSLRLSCAAS | 548 | GYSLNAYS | 87 | VNWVRQAPGKGLEWLGM | 570 | IWGDGKI | 108 | VYNSALKSRLTISKDSSKNTVYLQMNSLRAEDTAVYYC | 578 | AGDGYPYAMDN | 130 | WGQGTTVTVSS | 371 |
| 106 | HC5_m2 | EVQLLESGGGLVQPGGSLRLSCAAS | 548 | GFSLRAYS | 88 | VNWVRQAPGKGLEWLGM | 570 | IWGDGKI | 108 | VYNSALKSRLTISKDSSKNTVYLQMNSLRAEDTAVYYC | 578 | AGDGYPYAMDN | 130 | WGQGTTVTVSS | 371 |
| 107 | HC5_m3 | EVQLLESGGGLVQPGGSLRLSCAAS | 548 | GFSLHAYS | 89 | VNWVRQAPGKGLEWLGM | 570 | IWGDGKI | 108 | VYNSALKSRLTISKDSSKNTVYLQMNSLRAEDTAVYYC | 578 | AGDGYPYAMDN | 130 | WGQGTTVTVSS | 371 |
| 108 | HC5_m4 | EVQLLESGGGLVQPGGSLRLSCAAS | 548 | GFSLDAYS | 90 | VNWVRQAPGKGLEWLGM | 570 | IWGDGKI | 108 | VYNSALKSRLTISKDSSKNTVYLQMNSLRAEDTAVYYC | 578 | AGDGYPYAMDN | 130 | WGQGTTVTVSS | 371 |
| 109 | HC5_m5 | EVQLLESGGGLVQPGGSLRLSCAAS | 548 | GFSLYAYS | 91 | VNWVRQAPGKGLEWLGM | 570 | IWGDGKI | 108 | VYNSALKSRLTISKDSSKNTVYLQMNSLRAEDTAVYYC | 578 | AGDGYPYAMDN | 130 | WGQGTTVTVSS | 371 |
| 110 | HC5_m6 | EVQLLESGGGLVQPGGSLRLSCAAS | 548 | GFSLSAYS | 84 | VNWVRQAPGKGLEWLGM | 570 | IWGDGKI | 108 | VYNSALKSRLTISKDSSKNTVYLQMNSLRAEDTAVYYC | 578 | AGDGYPYAMDN | 130 | WGQGTTVTVSS | 371 |

TABLE 5-continued

Anti-interleukin (IL)-13 antibody Heavy Chain IMGT CDRs

| Construct ID | VH Name* | FR1 | SEQ ID NO:CDR1 | CDR1 | SEQ ID NO:FR2 | FR2 | SEQ ID NO:CDR2 | CDR2 | SEQ ID NO:FR3 | FR3 | SEQ ID NO:CDR3 | CDR3 | SEQ ID NO:FR4 | FR4 | SEQ ID NO: |
|---|---|---|---|---|---|---|---|---|---|---|---|---|---|---|---|
| 111 | HC5_m7 | EVQLLESGGGLVQPGGSLRLSCAAS | 548 | GFSLNRYS | 93 | VNWVRQAPGKGLEWLGM | 570 | IWGDGKI | 108 | VYNSALKSRLTISKDSSKNTVYLQMNSLRAEDTAVYYC | 578 | AGDGYYPYAMDN | 130 | WGQGTTVTVSS | 371 |
| 112 | HC5_m8 | EVQLLESGGGLVQPGGSLRLSCAAS | 548 | GFSLNKYS | 94 | VNWVRQAPGKGLEWLGM | 570 | IWGDGKI | 108 | VYNSALKSRLTISKDSSKNTVYLQMNSLRAEDTAVYYC | 578 | AGDGYYPYAMDN | 130 | WGQGTTVTVSS | 371 |
| 113 | HC5_m9 | EVQLLESGGGLVQPGGSLRLSCAAS | 548 | GFSLNHYS | 95 | VNWVRQAPGKGLEWLGM | 570 | IWGDGKI | 108 | VYNSALKSRLTISKDSSKNTVYLQMNSLRAEDTAVYYC | 578 | AGDGYYPYAMDN | 130 | WGQGTTVTVSS | 371 |
| 114 | HC5_m10 | EVQLLESGGGLVQPGGSLRLSCAAS | 548 | GFSLNQYS | 96 | VNWVRQAPGKGLEWLGM | 570 | IWGDGKI | 108 | VYNSALKSRLTISKDSSKNTVYLQMNSLRAEDTAVYYC | 578 | AGDGYYPYAMDN | 130 | WGQGTTVTVSS | 371 |
| 115 | HC5_m11 | EVQLLESGGGLVQPGGSLRLSCAAS | 548 | GFSLNEYS | 97 | VNWVRQAPGKGLEWLGM | 570 | IWGDGKI | 108 | VYNSALKSRLTISKDSSKNTVYLQMNSLRAEDTAVYYC | 578 | AGDGYYPYAMDN | 130 | WGQGTTVTVSS | 371 |
| 116 | HC5_m12 | EVQLLESGGGLVQPGGSLRLSCAAS | 548 | GFSLNSYS | 565 | VNWVRQAPGKGLEWLGM | 570 | IWGDGKI | 108 | VYNSALKSRLTISKDSSKNTVYLQMNSLRAEDTAVYYC | 578 | AGDGYYPYAMDN | 130 | WGQGTTVTVSS | 371 |
| 117 | HC5_m13 | EVQLLESGGGLVQPGGSLRLSCAAS | 548 | GFSLNYYS | 98 | VNWVRQAPGKGLEWLGM | 570 | IWGDGKI | 108 | VYNSALKSRLTISKDSSKNTVYLQMNSLRAEDTAVYYC | 578 | AGDGYYPYAMDN | 130 | WGQGTTVTVSS | 371 |
| 118 | HC5_m14 | EVQLLESGGGLVQPGGSLRLSCAAS | 548 | GFSLNAES | 99 | VNWVRQAPGKGLEWLGM | 570 | IWGDGKI | 108 | VYNSALKSRLTISKDSSKNTVYLQMNSLRAEDTAVYYC | 578 | AGDGYYPYAMDN | 130 | WGQGTTVTVSS | 371 |

TABLE 5-continued

Anti-interleukin (IL)-13 antibody Heavy Chain IMGT CDRs

| Construct ID | VH Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 119 | HC5_m15 | EVQLLESGGGLVQPGGSLRLSCAAS | 548 | GFSLNAYS | 85 | VNWVRQAPGKGLEWLGM | 570 | IWSDGKI | 110 | VYNSALKSRLTISKDSSKNTVYLQMNSLRAEDTAVYYC | 578 | AGDGYYPYAMDN | 130 | WGQGTTVTVSS | 371 |
| 120 | HC5_m16 | EVQLLESGGGLVQPGGSLRLSCAAS | 548 | GFSLNAYS | 85 | VNWVRQAPGKGLEWLGM | 570 | IWADGKI | 111 | VYNSALKSRLTISKDSSKNTVYLQMNSLRAEDTAVYYC | 578 | AGDGYYPYAMDN | 130 | WGQGTTVTVSS | 371 |
| 121 | HC5_m17 | EVQLLESGGGLVQPGGSLRLSCAAS | 548 | GFSLNAYS | 85 | VNWVRQAPGKGLEWLGM | 570 | IWGDGKI | 108 | VYNSALKSRLTISKDSSKNTVYLQMNSLRAEDTAVYYC | 578 | AGHGYYPYAMDN | 133 | WGQGTTVTVSS | 371 |
| 122 | HC5_m18 | EVQLLESGGGLVQPGGSLRLSCAAS | 548 | GFSLNAYS | 85 | VNWVRQAPGKGLEWLGM | 570 | IWGDGKI | 108 | VYNSALKSRLTISKDSSKNTVYLQMNSLRAEDTAVYYC | 578 | AGDLYYPYAMDN | 134 | WGQGTTVTVSS | 371 |
| 123 | HC5_m19 | EVQLLESGGGLVQPGGSLRLSCAAS | 548 | GFSLNAYS | 85 | VNWVRQAPGKGLEWLGM | 570 | IWGDGKI | 108 | VYNSALKSRLTISKDSSKNTVYLQMNSLRAEDTAVYYC | 578 | AGDKYYPYAMDN | 135 | WGQGTTVTVSS | 371 |
| 124 | HC5_m20 | EVQLLESGGGLVQPGGSLRLSCAAS | 548 | GFSLNAYS | 85 | VNWVRQAPGKGLEWLGM | 570 | IWGDGKI | 108 | VYNSALKSRLTISKDSSKNTVYLQMNSLRAEDTAVYYC | 578 | AGDGYYGYAMDN | 136 | WGQGTTVTVSS | 371 |
| 125 | HC5_m21 | EVQLLESGGGLVQPGGSLRLSCAAS | 548 | GFSLNAYS | 85 | VNWVRQAPGKGLEWLGM | 570 | IWGDGKI | 108 | VYNSALKSRLTISKDSSKNTVYLQMNSLRAEDTAVYYC | 578 | AGDGYYAYAMDN | 137 | WGQGTTVTVSS | 371 |
| 126 | HC5_m22 | EVQLLESGGGLVQPGGSLRLSCAAS | 548 | GFSLNAYS | 85 | VNWVRQAPGKGLEWLGM | 570 | IWGDGKI | 108 | VYNSALKSRLTISKDSSKNTVYLQMNSLRAEDTAVYYC | 578 | AGDGYYSYAMDN | 138 | WGQGTTVTVSS | 371 |
| 127 | HC5_m24 | EVQLLESGGG | 548 | GFSLNAYS | 85 | VNWVRQAP | 570 | IWGDGKI | 108 | VYNSALKSRL | 578 | AGDGYYTY | 139 | WGQGTTVT | 371 |

TABLE 5-continued

Anti-interleukin (IL)-13 antibody Heavy Chain IMGT CDRs

| Construct ID | VH Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| | | LVQPGGSLRLSCAAS | | | | GKGLEWLGM | | | | TISKDSSKNTVYLQMNSLRAEDTAVYYC | | AMDN | | VSS | |

*Names correspond with name in informal sequence listing.

TABLE 6

Anti-interleukin (IL)-13 antibody Light Chain Kabat CDRs

| Construct ID | VL Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 1 (lebrikizumab), 2, and 128-131 | Lebrikizumab-LC | DIVMT QSPDS LSVSL GERAT INC | 581 | RASKS VDSYG NSFMH | 141 | WYQQ KPGQP PKLLIY | 286 | LASNL ES | 153 | GVPDR FSGSG SGTDF TLTISS LQAED VAVY YC | 343 | QQNNE DPRT | 165 | FGGGT KVEIK | 400 |
| 3 and 4 | LC0 | NIVLT QSPAS LAVSL GQRAT ISC | 230 | RASKS VDSYG NSFMH | 141 | WYQQ KPGQP PKLLIY | 286 | LASNL ES | 153 | GVPAR FSGSG SRTDF TLTIDP VEADD AASYY C | 344 | QQNNE DPRT | 165 | FGGGT KLEIK | 401 |
| — | LC1 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SRTDF TLTISS LQPED FATYY C | 345 | QQNNE DPRT | 165 | FGGGT KVEIK | 400 |
| 5-9 | LC2 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SRTDF TLTISS LQPED FATYY C | 345 | QQNNE DPRT | 165 | FGGGT KVEIK | 400 |
| 10-14 | LC3 | EIVLT QSPAT LSVSP GERAT LSC | 233 | RASKS VDSYG NSFMH | 141 | WYQQ KPGQA PRLLIY | 290 | LASNL ES | 153 | GIPARF SGSGS RTEFT LTISSL QSEDF AVYYC | 347 | QQNNE DPRT | 165 | FGGGT KVEIK | 400 |
| — | LC4 | DIVLT QSPLS LPVTP GEPASI SC | 234 | RASKS VDSYG NSFMH | 141 | WYLQ KPGQS PQLLIY | 291 | LASNL ES | 153 | GVPDR FSGSG SRTDF TLKISR VEAED VGVY | 348 | QQNNE DPRT | 165 | FGGGT KVEIK | 400 |

TABLE 6-continued

Anti-interleukin (IL)-13 antibody Light Chain Kabat CDRs

| Construct ID | VL Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| — | LC5 | DIVLT QSPDS LAVSL GERAT INC | 235 | RASKS VDSYG NSFMH | 141 | WYQQ KPGQP PKLLIY | 286 | LASNL ES | 153 | GVPDR FSGSG SGTDF TLTISS LQAED VAVY YC | 343 | QQNNE DPRT | 165 | FGGGT KVEIK | 400 |
| 15-19, 90, 105-127, and 132-136 | LC6 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SGTDF TLTISS LQPED FATYY C | 349 | QQNNE DPRT | 165 | FGGGT KVEIK | 400 |
| 20-24 | LC7 | EIVLT QSPAT LSVSP GERAT LSC | 233 | RASKS VDSYG NSFMH | 141 | WYQQ KPGQA PRLLIY | 290 | LASNL ES | 153 | GIPARF SGSGS GTEFT LTISSL QSEDF AVYYC | 351 | QQNNE DPRT | 165 | FGGGT KVEIK | 400 |
| — | LC8 | DIVLT QSPLS LPVTP GEPASI SC | 234 | RASKS VDSYG NSFMH | 141 | WYLQ KPGQS PQLLIY | 291 | LASNL ES | 153 | GVPDR FSGSG SGTDF TLKISR VEAED VGVY YC | 352 | QQNNE DPRT | 165 | FGGGT KVEIK | 400 |
| 25 | LC9 | DIVLT QSPAS LAVSP GERAT ISC | 239 | RASKS VDSYG NSFMH | 141 | WYQQ KPGQP PKLLIY | 286 | LASNL ES | 153 | GVPDR FSGSG SGTDF TLTISR VEADD VAVY YC | 353 | QQNNE DPRT | 165 | FGGGT KLEIK | 401 |

TABLE 6-continued

Anti-interleukin (IL)-13 antibody Light Chain Kabat CDRs

| Construct ID | VL Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 26 | LC10 | DIVLT QSPAS LAVSP GERAT ISC | 239 | RASQS VDSNG NNFLH | 142 | WYQQ KPGQP PKLLIY | 286 | LASNR ES | 158 | GVPDR FSGSG SGTDF TLTISR VEADD VAVY YC | 353 | QQNN HTPRT | 166 | FGGGT KLEIK | 401 |
| 91 | LC6_m1 | DIQLT QSPSSL SASVG DRVTI TC | 231 | RASKS VDSYG NSRMH | 143 | WYQQ KPGKA PKLLIY | 288 | LASNL ES | 153 | GVPSR FSGSG SGTDF TLTISS LQPED FATYY C | 349 | QQNNE DPRT | 165 | FGGGT KVEIK | 400 |
| 92 | LC6_m2 | DIQLT QSPSSL SASVG DRVTI TC | 231 | RASKS VDSYG NSSMH | 144 | WYQQ KPGKA PKLLIY | 288 | LASNL ES | 153 | GVPSR FSGSG SGTDF TLTISS LQPED FATYY C | 349 | QQNNE DPRT | 165 | FGGGT KVEIK | 400 |
| 93 | LC6_m3 | DIQLT QSPSSL SASVG DRVTI TC | 231 | RASKS VDSYG NSFMH | 141 | WYQQ KPGKA PKLLIR | 300 | LASNL ES | 153 | GVPSR FSGSG SGTDF TLTISS LQPED FATYY C | 349 | QQNNE DPRT | 165 | FGGGT KVEIK | 400 |
| 94 | LC6_m4 | DIQLT QSPSSL SASVG DRVTI TC | 231 | RASKS VDSYG NSFMH | 141 | WYQQ KPGKA PKLLIF | 301 | LASNL ES | 153 | GVPSR FSGSG SGTDF TLTISS LQPED FATYY C | 349 | QQNNE DPRT | 165 | FGGGT KVEIK | 400 |
| 95 | LC6_m5 | DIQLT QSPSSL SASVG DRVTI TC | 231 | RASKS VDSYG NSFMH | 141 | WYQQ KPGKA PKLLIY | 288 | LASHL ES | 154 | GVPSR FSGSG SGTDF TLTISS LQPED FATYY C | 349 | QQNNE DPRT | 165 | FGGGT KVEIK | 400 |

TABLE 6-continued

Anti-interleukin (IL)-13 antibody Light Chain Kabat CDRs

| Construct ID | VL Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 96 | LC6_m6 | DIQLT QSPSSL SASVG DRVTI TC | 231 | RASKS VDSYG NSFMH | 141 | WYQQ KPGKA PKLLIY | 288 | LASDL ES | 155 | GVPSR FSGSG SGTDF TLTISS LQPED FATYY C | 349 | QQNNE DPRT | 165 | FGGGT KVEIK | 400 |
| 97 | LC6_m7 | DIQLT QSPSSL SASVG DRVTI TC | 231 | RASKS VDSYG NSFMH | 141 | WYQQ KPGKA PKLLIY | 288 | LASQL ES | 156 | GVPSR FSGSG SGTDF TLTISS LQPED FATYY C | 349 | QQNNE DPRT | 165 | FGGGT KVEIK | 400 |
| 98 and 137-140 | LC6_m8 | DIQLT QSPSSL SASVG DRVTI TC | 231 | RASKS VDSYG NSFMH | 141 | WYQQ KPGKA PKLLIY | 288 | LASEL ES | 157 | GVPSR FSGSG SGTDF TLTISS LQPED FATYY C | 349 | QQNNE DPRT | 165 | FGGGT KVEIK | 400 |
| 99 | LC6_m9 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SGTDF TLTISS LQPED FATYY C | 349 | QQNHE DPRT | 167 | FGGGT KVEIK | 400 |
| 100 | LC6_m10 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SGTDF TLTISS LQPED FATYY C | 349 | QQNYE DPRT | 168 | FGGGT KVEIK | 400 |

TABLE 6-continued

Anti-interleukin (IL)-13 antibody Light Chain Kabat CDRs

| Construct ID | VL Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 101 | LC6_m11 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SGTDF TLTISS LQPED FATYY C | 349 | QQNSE DPRT | 169 | FGGGT KVEIK | 400 |
| 102 | LC6_m12 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SGTDF TLTISS LQPED FATYY C | 349 | QQNNR DPRT | 170 | FGGGT KVEIK | 400 |
| 103 | LC6_m13 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SGTDF TLTISS LQPED FATYY C | 349 | QQNN DDPRT | 171 | FGGGT KVEIK | 400 |
| 104 | LC6_m14 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SGTDF TLTISS LQPED FATYY C | 349 | QQNN QDPRT | 172 | FGGGT KVEIK | 400 |

*Names correspond with name in informal sequence listing.

TABLE 7

Anti-interleukin (IL)-13 antibody Light Chain Chothia CDRs

| Construct ID | VL Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 1 (lebrikizumab), 2, and 128-131 | Lebrikizumab-LC | DIVMT QSPDS LSVSL GERAT INC | 581 | RASKS VDSYG NSFMH | 141 | WYQQ KPGQP PKLLIY | 286 | LASNL ES | 153 | GVPDR FSGSG SGTDF TLTISS LQAED VAVY YC | 343 | QQNNE DPRT | 165 | FGGGT KVEIK | 400 |
| 3 and 4 | LC0 | NIVLT QSPAS LAVSL GQRAT ISC | 230 | RASKS VDSYG NSFMH | 141 | WYQQ KPGQP PKLLIY | 286 | LASNL ES | 153 | GVPAR FSGSG SRTDF TLTIDP VEADD AASYY C | 344 | QQNNE DPRT | 165 | FGGGT KLEIK | 401 |
| — | LC1 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SRTDF TLTISS LQPED FATYY C | 345 | QQNNE DPRT | 165 | FGGGT KVEIK | 400 |
| 5-9 | LC2 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SRTDF TLTISS LQPED FATYY C | 345 | QQNNE DPRT | 165 | FGGGT KVEIK | 400 |
| 10-14 | LC3 | EIVLT QSPAT LSVSP GERAT LSC | 233 | RASKS VDSYG NSFMH | 141 | WYQQ KPGQA PRLLIY | 290 | LASNL ES | 153 | GIPARF SGSGS RTEFT LTISSL QSEDF AVYYC | 347 | QQNNE DPRT | 165 | FGGGT KVEIK | 400 |

TABLE 7-continued

Anti-interleukin (IL)-13 antibody Light Chain Chothia CDRs

| Construct ID | VL Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| — | LC4 | DIVLT QSPLS LPVTP GEPASI SC | 234 | RASKS VDSYG NSFMH | 141 | WYLQ KPGQS PQLLIY | 291 | LASNL ES | 153 | GVPDR FSGSG SRTDF TLKISR VEAED VGVY YC | 348 | QQNNE DPRT | 165 | FGGGT KVEIK | 400 |
| — | LC5 | DIVLT QSPDS LAVSL GERAT INC | 235 | RASKS VDSYG NSFMH | 141 | WYQQ KPGQP PKLLIY | 286 | LASNL ES | 153 | GVPDR FSGSG SGTDF TLTISS LQAED VAVY YC | 343 | QQNNE DPRT | 165 | FGGGT KVEIK | 400 |
| 15-19, 90, 105-127, and 132-136 | LC6 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SGTDF TLTISS LQPED FATYY C | 349 | QQNNE DPRT | 165 | FGGGT KVEIK | 400 |
| 20-24 | LC7 | EIVLT QSPAT LSVSP GERAT LSC | 233 | RASKS VDSYG NSFMH | 141 | WYLQ KPGQA PRLLIY | 290 | LASNL ES | 153 | GIP ARF SGSGS GTEFT LTISSL QSEDF AVYYC | 351 | QQNNE DPRT | 165 | FGGGT KVEIK | 400 |
| — | LC8 | DIVLT QSPLS LPVTP GEPASI SC | 234 | RASKS VDSYG NSFMH | 141 | WYLQ KPGQS PQLLIY | 291 | LASNL ES | 153 | GVPDR FSGSG SGTDF TLKISR VEAED VGVY YC | 352 | QQNNE DPRT | 165 | FGGGT KVEIK | 400 |
| 25 | LC9 | DIVLT QSPAS LAVSP GERAT ISC | 239 | RASKS VDSYG NSFMH | 141 | WYQQ KPGQP PKLLIY | 286 | LASNL ES | 153 | GVPDR FSGSG SGTDF TLTISR VEADD VAVY YC | 353 | QQNNE DPRT | 165 | FGGGT KLEIK | 401 |

TABLE 7-continued

Anti-interleukin (IL)-13 antibody Light Chain Chothia CDRs

| IDConstruct | VL Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 26 | LC10 | DIVLT QSPAS LAVSP GERAT ISC | 239 | RASQS VDSNG NNFLH | 142 | WYQQ KPGQP PKLLIY | 286 | LASNR ES | 158 | GVPDR FSGSG SGTDF TLTISR VEADD VAVY YC | 353 | QQNN HTPRT | 166 | FGGGT KLEIK | 401 |
| 91 | LC6_m1 | DIQLT QSPSSL SASVG DRVTI TC | 231 | RASKS VDSYG NSRMH | 143 | WYQQ KPGKA PKLLIY | 288 | LASNL ES | 153 | GVPSR FSGSG SGTDF TLTISS LQPED FATYY C | 349 | QQNNE DPRT | 165 | FGGGT KVEIK | 400 |
| 92 | LC6_m2 | DIQLT QSPSSL SASVG DRVTI TC | 231 | RASKS VDSYG NSSMH | 144 | WYQQ KPGKA PKLLIY | 288 | LASNL ES | 153 | GVPSR FSGSG SGTDF TLTISS LQPED FATYY C | 349 | QQNNE DPRT | 165 | FGGGT KVEIK | 400 |
| 93 | LC6_m3 | DIQLT QSPSSL SASVG DRVTI TC | 231 | RASKS VDSYG NSFMH | 141 | WYQQ KPGKA PKLLIR | 300 | LASNL ES | 153 | GVPSR FSGSG SGTDF TLTISS LQPED FATYY C | 349 | QQNNE DPRT | 165 | FGGGT KVEIK | 400 |
| 94 | LC6_m4 | DIQLT QSPSSL SASVG DRVTI TC | 231 | RASKS VDSYG NSFMH | 141 | WYQQ KPGKA PKLLIF | 301 | LASNL ES | 153 | GVPSR FSGSG SGTDF TLTISS LQPED FATYY C | 349 | QQNNE DPRT | 165 | FGGGT KVEIK | 400 |
| 95 | LC6_m5 | DIQLT QSPSSL SASVG DRVTI TC | 231 | RASKS VDSYG NSFMH | 141 | WYQQ KPGKA PKLLIY | 288 | LASHL ES | 154 | GVPSR FSGSG SGTDF TLTISS LQPED FATYY C | 349 | QQNNE DPRT | 165 | FGGGT KVEIK | 400 |

TABLE 7-continued

Anti-interleukin (IL)-13 antibody Light Chain Chothia CDRs

| IDConstruct | VL Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 96 | LC6_m6 | DIQLT QSPSSL SASVG DRVTI TC | 231 | RASKS VDSYG NSFMH | 141 | WYQQ KPGKA PKLLIY | 288 | LASDL ES | 155 | GVPSR FSGSG SGTDF TLTISS LQPED FATYY C | 349 | QQNNE DPRT | 165 | FGGGT KVEIK | 400 |
| 97 | LC6_m7 | DIQLT QSPSSL SASVG DRVTI TC | 231 | RASKS VDSYG NSFMH | 141 | WYQQ KPGKA PKLLIY | 288 | LASQL ES | 156 | GVPSR FSGSG SGTDF TLTISS LQPED FATYY C | 349 | QQNNE DPRT | 165 | FGGGT KVEIK | 400 |
| 98 and 137-144 | LC6_m8 | DIQLT QSPSSL SASVG DRVTI TC | 231 | RASKS VDSYG NSFMH | 141 | WYQQ KPGKA PKLLIY | 288 | LASEL ES | 157 | GVPSR FSGSG SGTDF TLTISS LQPED FATYY C | 349 | QQNNE DPRT | 165 | FGGGT KVEIK | 400 |
| 99 | LC6_m9 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SGTDF TLTISS LQPED FATYY C | 349 | QQNHE DPRT | 167 | FGGGT KVEIK | 400 |
| 100 | LC6_m10 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SGTDF TLTISS LQPED FATYY C | 349 | QQNYE DPRT | 168 | FGGGT KVEIK | 400 |
| 101 | LC6_m11 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SGTDF TLTISS LQPED FATYY C | 349 | QQNSE DPRT | 169 | FGGGT KVEIK | 400 |

TABLE 7-continued

Anti-interleukin (IL)-13 antibody Light Chain Chothia CDRs

| IDConstruct | VL Name* | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|---|
| 102 | LC6_m12 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SGTDF TLTISS LQPED FATYY C | 349 | QQNNR DPRT | 170 | FGGGT KVEIK | 400 |
| 103 | LC6_m13 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SGTDF TLTISS LQPED FATYY C | 349 | QQNN DDPRT | 171 | FGGGT KVEIK | 400 |
| 104 | LC6_m14 | DIQLT QSPSSL SASVG DRVTI TC | 231 | RASKS VDSYG NSFMH | 141 | WYQQ KPGKA PKLLIY | 288 | LASNL ES | 153 | GVPSR FSGSG SGTDF TLTISS LQPED FATYY C | 349 | QQNN QDPRT | 172 | FGGGT KVEIK | 400 |

*Names correspond with name in informal sequence listing.

TABLE 8

Anti-interleukin (IL)-13 antibody Light Chain IMGT CDRs

| Construct ID | VL Name* | FR1 | SEQ ID NO: | CDR1 | SEQ ID NO: | FR2 | SEQ ID NO: | CDR2 | FR3 | SEQ ID NO: | CDR3 | SEQ ID NO: | FR4 | SEQ ID NO: |
|---|---|---|---|---|---|---|---|---|---|---|---|---|---|---|
| 1 (lebrikizumab), 2, and 128-131 | Lebrikizumab-LC | DIVMTQSPDSLSVSLGERATINCRAS | 582 | KSVDSYGNSF | 149 | MHWYQQKPGQPPKLLIY | 589 | LAS | NLESGVPDRFSGSGSGTDFTLTISSLQAEDVAVYYC | 596 | QQNNEDPRT | 165 | FGGGTKVEIK | 400 |
| 3 and 4 | LC0 | NIVLTQSPASLAVSLGQRATISCRAS | 583 | KSVDSYGNSF | 149 | MHWYQQKPGQPPKLLIY | 589 | LAS | NLESGVPARFSGSGSRTDFTLTIDPVEADDAASYYC | 597 | QQNNEDPRT | 165 | FGGGTKLEIK | 401 |
| — | LC1 | DIQLTQSPSSLSASVGDRVTITCRAS | 584 | KSVDSYGNSF | 149 | MHWYQQKPGKAPKLLIY | 590 | LAS | NLESGVPSRFSGSGSRTDFTLTISSLQPEDFATYYC | 598 | QQNNEDPRT | 165 | FGGGTKVEIK | 400 |
| 5-9 | LC2 | DIQLTQSPSSLSASVGDRVTITCRAS | 584 | KSVDSYGNSF | 149 | MHWYQQKPGKAPKLLIY | 590 | LAS | NLESGVPSRFSGSGSRTDFTLTISSLQPEDFATYYC | 598 | QQNNEDPRT | 165 | FGGGTKVEIK | 400 |
| 10-14 | LC3 | EIVLTQSPATLSVSPGERATLSCRAS | 585 | KSVDSYGNSF | 149 | MHWYQQKPGQAPRLLIY | 591 | LAS | NLESGIPARFSGSGSRTEFTLTISSLQSEDFAVYYC | 599 | QQNNEDPRT | 165 | FGGGTKVEIK | 400 |
| — | LC4 | DIVLTQSPLSLPVTPGEPASISCRAS | 586 | KSVDSYGNSF | 149 | MHWLQQKPGQSPQLLIY | 592 | LAS | NLESGVPDRFSGSGSRTDFTLKISR | 600 | QQNNEDPRT | 165 | FGGGTKVEIK | 400 |

TABLE 8-continued

Anti-interleukin (IL)-13 antibody Light Chain IMGT CDRs

| Construct ID | VL Name* | FR1 | SEQ ID NO: | CDR1 | SEQ ID NO: | FR2 | SEQ ID NO: | CDR2 | FR3 | SEQ ID NO: | CDR3 | SEQ ID NO: | FR4 | SEQ ID NO: |
|---|---|---|---|---|---|---|---|---|---|---|---|---|---|---|
| — | LC5 | DIVLT QSPDS LAVSL GERAT INCRA S | 587 | KSVDS YGNSF | 149 | MHWY QQKPG QPPKL LIY | 589 | LAS | NLESG VPDRF SGSGS GTDFT LTISSL QAEDV AVYYC | 596 | QQNNE DPRT | 165 | FGGGT KVEIK | 400 |
| 15-19, 90, 105-127, and 132-136 | LC6 | DIQLT QSPSSL SASVG DRVTI TCRAS | 584 | KSVDS YGNSF | 149 | MHWY QQKPG KAPKL LIY | 590 | LAS | NLESG VPSRF SGSGS GTDFT LTISSL QPEDF ATYYC | 601 | QQNNE DPRT | 165 | FGGGT KVEIK | 400 |
| 20-24 | LC7 | EIVLT QSPAT LSVSP GERAT LSCRA S | 585 | KSVDS YGNSF | 149 | MHWY QQKPG QAPRL LIY | 591 | LAS | NLESGI PARFS GSGSG TEFTL TISLQ SEDFA VYYC | 602 | QQNNE DPRT | 165 | FGGGT KVEIK | 400 |
| — | LC8 | DIVLT QSPLS LPVTP GEPASI SCRAS | 586 | KSVDS YGNSF | 149 | MHWY LQKPG QSPQL LIY | 592 | LAS | NLESG VPDRF SGSGS GTDFT LKISR VEAED VGVY YC | 603 | QQNNE DPRT | 165 | FGGGT KVEIK | 400 |
| 25 | LC9 | DIVLT QSPAS LAVSP GERAT ISCRAS | 588 | KSVDS YGNSF | 149 | MHWY QQKPG QPPKL LIY | 589 | LAS | NLESG VPDRF SGSGS GTDFT LTISRV EADDV AVYYC | 604 | QQNNE DPRT | 165 | FGGGT KLEIK | 401 |
| 26 | LC10 | DIVLT QSPAS | 588 | QSVDS NGNNF | 150 | LHWY QQKPG | 593 | LAS | NRESG VPDRF | 605 | QQNN HTPRT | 166 | FGGGT KLEIK | 401 |

TABLE 8-continued

Anti-interleukin (IL)-13 antibody Light Chain IMGT CDRs

| Construct ID | VL Name* | FR1 | SEQ ID NO: | CDR1 | SEQ ID NO: | FR2 | SEQ ID NO: | CDR2 | FR3 | SEQ ID NO: | CDR3 | SEQ ID NO: | FR4 | SEQ ID NO: |
|---|---|---|---|---|---|---|---|---|---|---|---|---|---|---|
| | | LAVSP GERAT ISCRAS | | | | QPPKL LIY | | | SGSGS GTDFT LTISRV EADDV AVYYC | | | | | |
| 91 | LC6_m1 | DIQLT QSPSSL SASVG DRVTI TCRAS | 584 | KSVDS YGNSR | 151 | MHWY QQKPG KAPKL LIY | 590 | LAS | NLESG VPSRF SGSGS GTDFT LTISSL QPEDF ATYYC | 601 | QQNNE DPRT | 165 | FGGGT KVEIK | 400 |
| 92 | LC6_m2 | DIQLT QSPSSL SASVG DRVTI TCRAS | 584 | KSVDS YGNSS | 152 | MHWY QQKPG KAPKL LIY | 590 | LAS | NLESG VPSRF SGSGS GTDFT LTISSL QPEDF ATYYC | 601 | QQNNE DPRT | 165 | FGGGT KVEIK | 400 |
| 93 | LC6_m3 | DIQLT QSPSSL SASVG DRVTI TCRAS | 584 | KSVDS YGNSF | 149 | MHWY QQKPG KAPKL LIR | 594 | LAS | NLESG VPSRF SGSGS GTDFT LTISSL QPEDF ATYYC | 601 | QQNNE DPRT | 165 | FGGGT KVEIK | 400 |
| 94 | LC6_m4 | DIQLT QSPSSL SASVG DRVTI TCRAS | 584 | KSVDS YGNSF | 149 | MHWY QQKPG KAPKL LIF | 595 | LAS | NLESG VPSRF SGSGS GTDFT LTISSL QPEDF ATYYC | 601 | QQNNE DPRT | 165 | FGGGT KVEIK | 400 |
| 95 | LC6_m5 | DIQLT QSPSSL SASVG DRVTI TCRAS | 584 | KSVDS YGNSF | 149 | MHWY QQKPG KAPKL LIY | 590 | LAS | HLESG VPSRF SGSGS GTDFT LTISSL QPEDF ATYYC | 606 | QQNNE DPRT | 165 | FGGGT KVEIK | 400 |

TABLE 8-continued

Anti-interleukin (IL)-13 antibody Light Chain IMGT CDRs

| Construct ID | VL Name* | FR1 | SEQ ID NO: | CDR1 | SEQ ID NO: | FR2 | SEQ ID NO: | CDR2 | FR3 | SEQ ID NO: | CDR3 | SEQ ID NO: | FR4 | SEQ ID NO: |
|---|---|---|---|---|---|---|---|---|---|---|---|---|---|---|
| 96 | LC6_m6 | DIQLT QSPSSL SASVG DRVTI TCRAS | 584 | KSVDS YGNSF | 149 | MHWY QQKPG KAPKL LIY | 590 | LAS | DLESG VPSRF SGSGS GTDFT LTISSL QPEDF ATYYC | 607 | QQNNE DPRT | 165 | FGGGT KVEIK | 400 |
| 97 | LC6_m7 | DIQLT QSPSSL SASVG DRVTI TCRAS | 584 | KSVDS YGNSF | 149 | MHWY QQKPG KAPKL LIY | 590 | LAS | QLESG VPSRF SGSGS GTDFT LTISSL QPEDF ATYYC | 608 | QQNNE DPRT | 165 | FGGGT KVEIK | 400 |
| 98 and 137-144 | LC6_m8 | DIQLT QSPSSL SASVG DRVTI TCRAS | 584 | KSVDS YGNSF | 149 | MHWY QQKPG KAPKL LIY | 590 | LAS | ELESG VPSRF SGSGS GTDFT LTISSL QPEDF ATYYC | 609 | QQNNE DPRT | 165 | FGGGT KVEIK | 400 |
| 99 | LC6_m9 | DIQLT QSPSSL SASVG DRVTI TCRAS | 584 | KSVDS YGNSF | 149 | MHWY QQKPG KAPKL LIY | 590 | LAS | NLESG VPSRF SGSGS GTDFT LTISSL QPEDF ATYYC | 601 | QQNHE DPRT | 167 | FGGGT KVEIK | 400 |
| 100 | LC6_m10 | DIQLT QSPSSL SASVG DRVTI TCRAS | 584 | KSVDS YGNSF | 149 | MHWY QQKPG KAPKL LIY | 590 | LAS | NLESG VPSRF SGSGS GTDFT LTISSL QPEDF ATYYC | 601 | QQNYE DPRT | 168 | FGGGT KVEIK | 400 |
| 101 | LC6_m11 | DIQLT QSPSSL SASVG DRVTI TCRAS | 584 | KSVDS YGNSF | 149 | MHWY QQKPG KAPKL LIY | 590 | LAS | NLESG VPSRF SGSGS GTDFT LTISSL QPEDF ATYYC | 601 | QQNSE DPRT | 169 | FGGGT KVEIK | 400 |

TABLE 8-continued

Anti-interleukin (IL)-13 antibody Light Chain IMGT CDRs

| Construct ID | VL Name* | FR1 | SEQ ID NO: | CDR1 | SEQ ID NO: | FR2 | SEQ ID NO: | CDR2 | FR3 | SEQ ID NO: | CDR3 | SEQ ID NO: | FR4 | SEQ ID NO: |
|---|---|---|---|---|---|---|---|---|---|---|---|---|---|---|
| 102 | LC6_m12 | DIQLT QSPSSL SASVG DRVTI TCRAS | 584 | KSVDS YGNSF | 149 | MHWY QQKPG KAPKL LIY | 590 | LAS | NLESG VPSRF SGSGS GTDFT LTISSL QPEDF ATYYC | 601 | QQNNR DPRT | 170 | FGGGT KVEIK | 400 |
| 103 | LC6_m13 | DIQLT QSPSSL SASVG DRVTI TCRAS | 584 | KSVDS YGNSF | 149 | MHWY QQKPG KAPKL LIY | 590 | LAS | NLESG VPSRF SGSGS GTDFT LTISSL QPEDF ATYYC | 601 | QQNN DDPRT | 171 | FGGGT KVEIK | 400 |
| 104 | LC6_m14 | DIQLT QSPSSL SASVG DRVTI TCRAS | 584 | KSVDS YGNSF | 149 | MHWY QQKPG KAPKL LIY | 590 | LAS | NLESG VPSRF SGSGS GTDFT LTISSL QPEDF ATYYC | 601 | QQNN QDPRT | 172 | FGGGT KVEIK | 400 |

*Names correspond with name in informal sequence listing.

Fc Region

The structures of the Fc regions of various immunoglobulins, and the glycosylation sites contained therein, are known in the art. See Schroeder and Cavacini, J. Allergy Clin. Immunol., 2010, 125: S41-52, incorporated by reference in its entirety. The Fc region may be a naturally occurring Fc region or an Fc region modified as described in the art or elsewhere in this disclosure.

Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991. An "Fc polypeptide" of a dimeric Fc as used herein refers to one of the two polypeptides forming the dimeric Fc domain, i.e., a polypeptide comprising C-terminal constant regions of an immunoglobulin heavy chain, capable of stable self-association. For example, an Fc polypeptide of a dimeric IgG Fc comprises an IgG CH2 and an IgG CH3 constant domain sequence. An Fc can be of the class IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$.

The terms "Fc receptor" and "FcR" are used to describe a receptor that binds to the Fc region of an antibody. For example, an FcR can be a native sequence human FcR. Generally, an FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., Immuno Biology: the immune system in health and disease, (Elsevier Science Ltd., NY) (4th ed., 1999)). Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976); and Kim et al., J. Immunol. 24:249 (1994)).

Modifications in the CH2 domain can affect the binding of FcRs to the Fc. A number of amino acid modifications in the Fc region are known in the art for selectively altering the affinity of the Fc for different Fcgamma receptors. In some embodiments, the Fc comprises one or more modifications to promote selective binding of Fc-gamma receptors.

Exemplary mutations that alter the binding of FcRs to the Fc are listed below:

S298A/E333A/K334A, S298A/E333A/K334A/K326A (Lu Y, Vernes J M, Chiang N, et al. J Immunol Methods. 2011 Feb. 28; 365 (1-2): 132-41);

F243L/R292P/Y300L/V305I/P396L, F243L/R292P/Y300L/L235V/P396L (Stavenhagen J B, Gorlatov S, Tuaillon N, et al. Cancer Res. 2007 Sep. 15; 67 (18): 8882-90; Nordstrom J L, Gorlatov S, Zhang W, et al. Breast Cancer Res. 2011 Nov. 30; 13 (6): R123);

F243L (Stewart R, Thom G, Levens M, et al. Protein Eng Des Sel. 2011 September; 24 (9): 671-8.), S298A/E333A/K334A (Shields R L, Namenuk A K, Hong K, et al. J Biol Chem. 2001 Mar. 2; 276 (9): 6591-604);

S239D/I332E/A330L, S239D/I332E (Lazar G A, Dang W, Karki S, et al. Proc Natl Acad Sci USA. 2006 Mar. 14; 103 (11): 4005-10);

S239D/S267E, S267E/L328F (Chu S Y, Vostiar I, Karki S, et al. Mol Immunol. 2008 September; 45 (15): 3926-33); and S239D/D265S/S298A/I332E, S239E/S298A/K326A/A327H, G237F/S298A/A330L/I332E, S239D/I332E/S298A, S239D/K326E/A330L/I332E/S298A, G236A/S239D/D270L/I332E, S239E/S267E/H268D, L234F/S267E/N325L, G237F/V266L/S267D and other mutations listed in WO2011/120134 and WO2011/120135, herein incorporated by reference. Therapeutic Antibody Engineering (by William R. Strohl and Lila M. Strohl, Woodhead Publishing series in Biomedicine No 11, ISBN 1 907568 37 9, October 2012) lists mutations on page 283.

In some embodiments an antibody described herein includes modifications to improve its ability to mediate effector function. Such modifications are known in the art and include afucosylation, or engineering of the affinity of the Fc towards an activating receptor, mainly FCGR3a for ADCC, and towards C1q for CDC. The following Table 9 summarizes various designs reported in the literature for effector function engineering.

Methods of producing antibodies with little or no fucose on the Fc glycosylation site (Asn 297 EU numbering) without altering the amino acid sequence are well known in the art. The GlymaX® technology (ProBioGen AG) is based on the introduction of a gene for an enzyme which deflects the cellular pathway of fucose biosynthesis into cells used for antibody production. This prevents the addition of the sugar "fucose" to the N-linked antibody carbohydrate part by antibody-producing cells (von Horsten et al. (2010) Glycobiology. 2010 December; 20 (12): 1607-18). Another approach to obtaining antibodies with lowered levels of fucosylation can be found in U.S. Pat. No. 8,409,572, which teaches selecting cell lines for antibody production for their ability to yield lower levels of fucosylation on antibodies can be fully afucosylated (meaning they contain no detectable fucose) or they can be partially afucosylated, meaning that the isolated antibody contains less than 95%, less than 85%, less than 75%, less than 65%, less than 55%, less than 45%, less than 35%, less than 25%, less than 15%, or less than 5% of the amount of fucose normally detected for a similar antibody produced by a mammalian expression system.

Thus, in one embodiment, an antibody described herein can include a dimeric Fc that comprises one or more amino acid modifications as noted in Table 9 that confer improved effector function. In another embodiment, the antibody can be afucosylated to improve effector function.

TABLE 9

CH2 domains and effector function engineering

| Reference | Mutations | Effect |
|---|---|---|
| Lu, 2011, Ferrara 2011, Mizushima 2011 | Afucosylated | Increased ADCC |

TABLE 9-continued

CH2 domains and effector function engineering

| Reference | Mutations | Effect |
|---|---|---|
| Lu, 2011 | S298A/E333A/K334A | Increased ADCC |
| Lu, 2011 | S298A/E333A/K334A/K326A | Increased ADCC |
| Stavenhagen, 2007 | F243L/R292P/Y300L/V305I/P396L | Increased ADCC |
| Nordstrom, 2011 | F243L/R292P/Y300L/L235V/P396L | Increased ADCC |
| Stewart, 2011 | F243L | Increased ADCC |
| Shields, 2001 | S298A/E333A/K334A | Increased ADCC |
| Lazar, 2006 | S239D/I332E/A330L | Increased ADCC |
| Lazar, 2006 | S239D/I332E | Increased ADCC |
| Bowles, 2006 | AME-D, not specified mutations | Increased ADCC |
| Heider, 2011 | 37.1, mutations not disclosed | Increased ADCC |
| Moore, 2010 | S267E/H268F/S324T | Increased CDC |

Fc modifications reducing FcgR and/or complement binding and/or effector function are known in the art. Recent publications describe strategies that have been used to engineer antibodies with reduced or silenced effector activity (see Strohl, W R (2009), Curr Opin Biotech 20:685-691, and Strohl, W R and Strohl L M, "Antibody Fc engineering for optimal antibody performance" In Therapeutic Antibody Engineering, Cambridge: Woodhead Publishing (2012), pp 225-249). These strategies include reduction of effector function through modification of glycosylation, use of IgG2/IgG4 scaffolds, or the introduction of mutations in the hinge or CH2 regions of the Fc. For example, U.S. Patent Publication No. 2011/0212087 (Strohl), International Patent Publication No. WO 2006/105338 (Xencor), U.S. Patent Publication No. 2012/0225058 (Xencor), U.S. Patent Publication No. 2012/0251531 (Genentech), and Strop et al. ((2012) J. Mol. Biol. 420:204-219) describe specific modifications to reduce FcgR or complement binding to the Fc.

Specific, non-limiting examples of known amino acid modifications to reduce FcgR or complement binding to the Fc include those identified in the following Table 10:

TABLE 10

Modifications to reduce FcgR or complement binding to the Fc

| Company | Mutations |
|---|---|
| GSK | N297A |
| Ortho Biotech | L234A/L235A |
| Protein Design labs | IGG2 V234A/G237A |
| Wellcome Labs | IGG4 L235A/G237A/E318A |
| GSK | IGG4 S228P/L236E |
| Alexion | IGG2/IGG4combo |
| Merck | IGG2 H268Q/V309L/A330S/A331S |
| Bristol-Myers | C220S/C226S/C229S/P238S |
| Seattle Genetics | C226S/C229S/E3233P/L235V/L235A |
| Amgen | E. coli production, non glyco |
| Medimune | L234F/L235E/P331S |
| Trubion | Hinge mutant, possibly C226S/P230S |

Examples of cell lines capable of producing defucosylated antibody include CHO-DG44 with stable overexpression of the bacterial oxidoreductase GDP-6-deoxy-D-lyxo-4-hexylose reductase (RMD) (see Henning von Horsten et al., Glycobiol 2010, 20:1607-1618) or Lec13 CHO cells, which are deficient in protein fucosylation (see Ripka et al., Arch. Biochem. Biophys., 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., Biotech. Bioeng., 2004, 87:614-622; Kanda et al., Biotechnol. Bioeng., 2006, 94:680-688; and WO 2003/085107; each of which is incorporated by reference in its entirety). Another approach to obtaining antibodies with lowered levels of fucosylation can be found in U.S. Pat. No. 8,409,572, which teaches selecting cell lines for antibody production for their ability to yield lower levels of fucosylation on antibodies.

Antibodies can be fully afucosylated (meaning they contain no detectable fucose) or they can be partially afucosylated, meaning that the isolated antibody contains less than 95%, less than 85%, less than 75%, less than 65%, less than 55%, less than 45%, less than 35%, less than 25%, less than 15%, or less than 5% of the amount of fucose normally detected for a similar antibody produced by a mammalian expression system.

In some embodiments, an antibody provided herein comprises an IgG1 domain with reduced fucose content at position Asn 297 compared to a naturally occurring IgG1 domain. Such Fc domains are known to have improved ADCC. See Shields et al., J. Biol. Chem., 2002, 277:26733-26740, incorporated by reference in its entirety. In some embodiments, such antibodies do not comprise any fucose at position Asn 297. The amount of fucose may be determined using any suitable method, for example as described in WO 2008/077546, incorporated by reference in its entirety.

In certain embodiments, an antibody provided herein comprises an Fc region with one or more amino acid substitutions which improve ADCC, such as a substitution at one or more of positions 298, 333, and 334 of the Fc region. In some embodiments, an antibody provided herein comprises an Fc region with one or more amino acid substitutions at positions 239, 332, and 330, as described in Lazar et al., Proc. Natl. Acad. Sci. USA, 2006,103:4005-4010, incorporated by reference in its entirety.

Other illustrative glycosylation variants which may be incorporated into the antibodies provided herein are described, for example, in U.S. Pat. Pub. Nos. 2003/0157108, 2004/0093621, 2003/0157108, 2003/0115614, 2002/0164328, 2004/0093621, 2004/0132140, 2004/0110704, 2004/0110282, 2004/0109865; International Pat. Pub. Nos. 2000/61739, 2001/29246, 2003/085119, 2003/084570, 2005/035586, 2005/035778; 2005/053742, 2002/031140; Okazaki et al., J. Mol. Biol., 2004, 336:1239-1249; and Yamane-Ohnuki et al., Biotech. Bioeng., 2004, 87:614-622; each of which is incorporated by reference in its entirety.

In some embodiments, an antibody provided herein comprises an Fc region with at least one galactose residue in the oligosaccharide attached to the Fc region. Such antibody variants may have improved CDC function. Examples of such antibody variants are described, for example, in WO 1997/30087; WO 1998/58964; and WO 1999/22764; each of which his incorporated by reference in its entirety.

In some embodiments, an antibody provided herein comprises one or more alterations that improves or diminishes C1q binding and/or CDC. See U.S. Pat. No. 6,194,551; WO 99/51642; and Idusogie et al., J. Immunol., 2000, 164:4178-4184; each of which is incorporated by reference in its entirety.

In certain embodiments, an antibody provided herein comprises a heavy chain comprising a constant heavy chain sequence selected from the sequences set forth in SEQ ID NOs: 425-468 and 484-539.

In certain embodiments, the antibody comprises a VH sequence set forth in SEQ ID NO: 1 and a VL sequence set forth in SEQ ID NO: 33; and wherein the human Fc region comprises a human IgG sequence selected from a sequence set forth in SEQ ID NOs: 436-468 and 484-539. In certain embodiments, the antibody comprises a VH sequence set forth in SEQ ID NO: 2 and a VL sequence set forth in SEQ ID NO: 33; and wherein the human Fc 436-468 and 484-539. In certain embodiments, the antibody comprises a VH sequence set forth in SEQ ID NO: 3 and a VL sequence set forth in SEQ ID NO: 35; and wherein the human Fc region comprises a human IgG sequence selected from a sequence set forth in SEQ ID NOs: 436-468 and 484-539. In certain embodiments, the antibody comprises a VH sequence set forth in SEQ ID NO: 4 and a VL sequence set forth in SEQ ID NO: 35; and wherein the human Fc region comprises a human IgG sequence selected from a sequence set forth in SEQ ID NOs: 436-468 and 484-539. In certain embodiments, the antibody comprises a VH sequence set forth in SEQ ID NO: 5 and a VL sequence set forth in SEQ ID NO: 35; and wherein the human Fc region comprises a human IgG sequence selected from a sequence set forth in SEQ ID NOs: 436-468 and 484-539. In certain embodiments, the antibody comprises a VH sequence set forth in SEQ ID NO: 6 and a VL sequence set forth in SEQ ID NO: 35; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 35; and wherein the human Fc region comprises a human IgG sequence selected from a sequence set forth in SEQ ID NOs: 436-468 and 484-539. In certain embodiments, the antibody comprises a VH sequence set forth in SEQ ID NO: 3 and a VL sequence set forth in SEQ ID NO: 36; and wherein the human Fc region comprises a human IgG sequence selected from a sequence set forth in SEQ ID NOs: 436-468 and 484-539. In certain embodiments, the antibody comprises a VH sequence set forth in SEQ ID NO: 4 and a VL sequence set forth in SEQ ID NO: 36; and wherein the human Fc region comprises a human IgG sequence selected from a sequence set forth in SEQ ID NOs: 436-468 and 484-539. In certain embodiments, the antibody comprises a VH sequence set forth in SEQ ID NO: 5 and a VL sequence set forth in SEQ ID NO: 36; and wherein the human Fc region comprises a human IgG sequence selected from a sequence set forth in SEQ ID NOs: 436-468 and 484-539. In certain embodiments, the antibody comprises a VH sequence set forth in SEQ ID NO: 6 and a VL sequence set forth in SEQ ID NO: 36; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 36; and wherein the human Fc region comprises a human IgG sequence selected from a sequence set forth in SEQ ID NOs: 439, 440, 446, 457 and 460. In certain embodiments, the antibody comprises a VH sequence set forth in SEQ ID NO: 3 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 4 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 5 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 6 and a VL sequence set forth in SEQ ID NO: 39; and wherein the human Fc region comprises a human IgG sequence selected from a sequence set forth in SEQ ID NOs: 436-468. In certain embodiments, the antibody comprises a VH sequence set forth in SEQ ID NO: 7 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 3 and a VL sequence set forth in SEQ ID NO: 40; and wherein the human Fc region comprises a human IgG sequence selected from a sequence set forth in SEQ ID NOs: 436-468 and 484-539. In certain embodiments, the antibody comprises a VH sequence set forth in SEQ ID NO: 4 and a VL sequence set forth in SEQ ID NO: 40; and wherein the human Fc region comprises a human IgG sequence selected from a sequence set forth in SEQ ID NOs: 436-468 and 484-539. In certain embodiments, the antibody comprises a VH sequence set forth in SEQ ID NO: 5, and a VL sequence set forth in SEQ ID NO: 40; and wherein the human Fc region comprises a human IgG sequence selected from a sequence set forth in SEQ ID NOs: 436-468 and 484-539. In certain embodiments, the antibody comprises a VH sequence set forth in SEQ ID NO: 6 and a VL sequence set forth in SEQ ID NO: 40; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 40; and wherein the human Fc region comprises a human IgG sequence selected from a sequence set forth in SEQ ID NOs: 436-468 and 484-539. In certain embodiments, the antibody comprises a VH sequence set forth in SEQ ID NO: 8 and a VL sequence set forth in SEQ ID NO: 42; and wherein the human Fc region comprises a human IgG sequence selected from a sequence set forth in SEQ ID NOs: 436-468 and 484-539. In certain embodiments, the antibody comprises a VH sequence set forth in SEQ ID NO: 9 and a VL sequence set forth in SEQ ID NO: 43; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7, and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 44; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 45; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 46; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 47; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 48; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 49; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 50; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 51; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 52; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 53; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 54; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 55; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 56; and wherein the human Fc region comprises a human IgG sequence selected from a sequence set forth in SEQ ID NOs: 436-468 and 484-539. In certain embodiments, the antibody comprises a VH sequence set forth in SEQ ID NO: 7 and a VL sequence set forth in SEQ ID NO: 57; and wherein the human Fc region comprises a human IgG sequence selected from a sequence set forth in SEQ ID NOs: 436-468 and 484-539. In certain embodiments, the antibody comprises a VH sequence set forth in SEQ ID NO: 10 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 11 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 12 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 13 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 14 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 15 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 16 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 17 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 18 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 19 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 20 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 21 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 22 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 23 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 24 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 25 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 26 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 27 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 28 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 28 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 29 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 30 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 31 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 32 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 8 and a VL sequence set forth in SEQ ID NO: 39; and wherein the human Fc region comprises a human IgG sequence selected from a sequence set forth in SEQ ID NOs: 436-468 and 484-539. In certain embodiments, the antibody comprises a VH sequence set forth in SEQ ID NO: 8 and a VL sequence set forth in SEQ ID NO: 51; and wherein the human Fc region comprises a human IgG sequence selected from a sequence set forth in SEQ ID NOs: 436-468 and 484-539. In certain embodiments, the antibody comprises a VH sequence set forth in SEQ ID NO: 3 and a VL sequence set forth in SEQ ID NO: 51; and wherein the human Fc region comprises a human IgG sequence selected from a sequence set forth in SEQ ID NOs: 436-468 and 484-539. In certain embodiments, the antibody comprises a VH sequence set forth in SEQ ID NO: 470 and a VL sequence set forth in SEQ ID NO: 471; and wherein the human Fc region comprises a human IgG sequence selected from a sequence set forth in SEQ ID NOs: 436-468 and 484-539.

In certain embodiments, the antibody comprises a VH sequence set forth in SEQ ID NO: 15 and a VL sequence set forth in SEQ ID NO: 39; and wherein the human Fc region comprises a human IgG sequence set forth in SEQ ID NO: 439. In certain embodiments, the antibody comprises a VH sequence set forth in SEQ ID NO: 15 and a VL sequence set forth in SEQ ID NO: 39; and wherein the human Fc region comprises a human IgG sequence set forth in SEQ ID NO: 457. In certain embodiments, the antibody comprises a VH sequence set forth in SEQ ID NO: 15 and a VL sequence set forth in SEQ ID NO: 39; and wherein the human Fc region comprises a human IgG sequence set forth in SEQ ID NO: 460. In certain embodiments, the antibody comprises a VH sequence set forth in SEQ ID NO: 15 and a VL sequence set forth in SEQ ID NO: 39; and wherein the human Fc region comprises a human IgG sequence set forth in SEQ ID NO: 446. In certain embodiments, the antibody comprises a VH sequence set forth in SEQ ID NO: 3 and a VL sequence set forth in SEQ ID NO: 39; and wherein the human Fc region comprises a human IgG sequence set forth in SEQ ID NO: 439. In certain embodiments, the antibody comprises a VH sequence set forth in SEQ ID NO: 3 and a VL sequence set forth in SEQ ID NO: 39; and wherein the human Fc region comprises a human IgG sequence set forth in SEQ ID NO: 457. In certain embodiments, the antibody comprises a VH sequence set forth in SEQ ID NO: 3 and a VL sequence set forth in SEQ ID NO: 39; and wherein the human Fc region comprises a human IgG sequence set forth in SEQ ID NO: 460. In certain embodiments, the antibody comprises a VH sequence set forth in SEQ ID NO: 3 and a VL sequence set forth in SEQ ID NO: 39; and wherein the human Fc region comprises a human IgG sequence set forth in SEQ ID NO: 446. In certain embodiments, the antibody comprises a VH sequence set forth in SEQ ID NO: 7 and a VL sequence set forth in SEQ ID NO: 51; and wherein the human Fc region comprises a human IgG sequence set forth in SEQ ID NO: 439. In certain embodiments, the antibody comprises a VH sequence set forth in SEQ ID NO: 7 and a VL sequence set forth in SEQ ID NO: 51; and wherein the human Fc region comprises a human IgG sequence set forth in SEQ ID NO: 457. In certain embodiments, the antibody comprises a VH sequence set forth in SEQ ID NO: 7 and a VL sequence set forth in SEQ ID NO: 51; and wherein the human Fc region comprises a human IgG sequence set forth in SEQ ID NO: 460. In certain embodiments, the antibody comprises a VH sequence set forth in SEQ ID NO: 7 and a VL sequence set forth in SEQ ID NO: 51; and wherein the human Fc region comprises a human IgG sequence set forth in SEQ ID NO: 446. In certain embodiments, the antibody comprises a VH sequence set forth in SEQ ID NO: 8 and a VL sequence set forth in SEQ ID NO: 39; and wherein the human Fc region comprises a human IgG sequence set forth in SEQ ID NO: 439. In certain embodiments, the antibody comprises a VH sequence set forth in SEQ ID NO: 8 and a VL sequence set forth in SEQ ID NO: 39; and wherein the human Fc region comprises a human IgG sequence set forth in SEQ ID NO: 457. In certain embodiments, the antibody comprises a VH sequence set forth in SEQ ID NO: 8 and a VL sequence set forth in SEQ ID NO: 51; and wherein the human Fc region comprises a human IgG sequence set forth in SEQ ID NO: 460. In certain embodiments, the antibody comprises a VH sequence set forth in SEQ ID NO: 8 and a VL sequence set forth in SEQ ID NO: 51; and wherein the human Fc region comprises a human IgG sequence set forth in SEQ ID NO: 446. In certain embodiments, the antibody comprises a VH sequence set forth in SEQ ID NO: 470 and a VL sequence set forth in SEQ ID NO: 471; and wherein the human Fc region comprises a human IgG sequence set forth in SEQ ID NO: 439. In certain embodiments, the antibody comprises a VH sequence set forth in SEQ ID NO: 470 and a VL sequence set forth in SEQ ID NO: 471; and wherein the human Fc region comprises a human IgG sequence set forth in SEQ ID NO: 457. In certain embodiments, the antibody comprises a VH sequence set forth in SEQ ID NO: 470 and a VL sequence set forth in SEQ ID NO: 471; and wherein the human Fc region comprises a human IgG sequence set forth in SEQ ID NO: 460. In certain embodiments, the antibody comprises a VH sequence set forth in SEQ ID NO: 470 and a VL sequence set forth in SEQ ID NO: 471; and wherein the human Fc region comprises a human IgG sequence set forth in SEQ ID NO: 446. In certain embodiments, the antibody comprises a VH sequence set forth in SEQ ID NO: 3 and a VL sequence set forth in SEQ ID NO: 39; and wherein the human Fc region comprises a human IgG sequence selected from a sequence set forth in SEQ ID NO: 439. In certain embodiments, the antibody comprises a VH sequence set forth in SEQ ID NO: 3 and a VL sequence set forth in SEQ ID NO: 39; and wherein the human Fc region comprises a human IgG sequence selected from a sequence set forth in SEQ ID NO: 446. In certain embodiments, the antibody comprises a VH sequence set forth in SEQ ID NO: 3 and a VL sequence set forth in SEQ ID NO: 39; and wherein the human Fc region comprises a human IgG sequence selected from a sequence set forth in SEQ ID NO: 457. In certain embodiments, the antibody comprises a VH sequence set forth in SEQ ID NO: 3 and a VL sequence set forth in SEQ ID NO: 39; and wherein the human Fc region comprises a human IgG sequence selected from a sequence set forth in SEQ ID NO: 460. In certain embodiments, the antibody comprises a VH sequence set forth in SEQ ID NO: 7 and a VL sequence set forth in SEQ ID NO: 39; and wherein the human Fc region comprises a human IgG sequence selected from a sequence set forth in SEQ ID NO: 439. In certain embodiments, the antibody comprises a VH sequence set forth in SEQ ID NO: 7 and a VL sequence set forth in SEQ ID NO: 39; and wherein the human Fc region comprises a human IgG sequence selected from a sequence set forth in SEQ ID NO: 446. In certain embodiments, the antibody comprises a VH sequence set forth in SEQ ID NO: 7 and a VL sequence set forth in SEQ ID NO: 39; and wherein the human Fc region comprises a human IgG sequence selected from a sequence set forth in SEQ ID NO: 457. In certain embodiments, the antibody comprises a VH sequence set forth in SEQ ID NO: 7 and a VL sequence set forth in SEQ ID NO: 39; and wherein the human Fc region comprises a human IgG sequence selected from a sequence set forth in SEQ ID NO: 460. In certain embodiments, the antibody comprises a VH sequence set forth in SEQ ID NO: 3 and a VL sequence set forth in SEQ ID NO: 51; and wherein the human Fc region comprises a human IgG sequence selected from a sequence set forth in SEQ ID NO: 439. In certain embodiments, the antibody comprises a VH sequence set forth in SEQ ID NO: 3 and a VL sequence set forth in SEQ ID NO: 51; and wherein the human Fc region comprises a human IgG sequence selected from a sequence set forth in SEQ ID NO: 446. In certain embodiments, the antibody comprises a VH sequence set forth in SEQ ID NO: 3 and a VL sequence set forth in SEQ ID NO: 51; and wherein the human Fc region comprises a human IgG sequence selected from a sequence set forth in SEQ ID NO: 457. In certain embodiments, the antibody comprises a VH sequence set forth in SEQ ID NO: 3 and a VL sequence set forth in SEQ ID NO: 51; and wherein the human Fc region comprises a human IgG sequence selected from a sequence set forth in SEQ ID NO: 460. In certain embodiments, the antibody comprises a VH sequence set forth in SEQ ID NO: 7 and a VL sequence set forth in SEQ ID NO: 51; and wherein the human Fc region comprises a human IgG sequence selected from a sequence set forth in SEQ ID NO: 439. In certain embodiments, the antibody comprises a VH sequence set forth in SEQ ID NO: 7 and a VL sequence set forth in SEQ ID NO: 51; and wherein the human Fc region comprises a human IgG sequence selected from a sequence set forth in SEQ ID NO: 446. In certain embodiments, the antibody comprises a VH sequence set forth in SEQ ID NO: 7 and a VL sequence set forth in SEQ ID NO: 51; and wherein the human Fc region comprises a human IgG sequence selected from a sequence set forth in SEQ ID NO: 457. In certain embodiments, the antibody comprises a VH sequence set forth in SEQ ID NO: 7 and a VL sequence set forth in SEQ ID NO: 51; and wherein the human Fc region comprises a human IgG sequence selected from a sequence set forth in SEQ ID NO: 460. In certain embodiments, the antibody comprises a VH sequence set forth in SEQ ID NO: 470 and a VL sequence set forth in SEQ ID NO: 471; and wherein the human Fc region comprises a human IgG sequence selected from a sequence set forth in SEQ ID NO: 439. In certain embodiments, the antibody comprises a VH sequence set forth in SEQ ID NO: 470 and a VL sequence set forth in SEQ ID NO: 471; and wherein the human Fc region comprises a human IgG sequence selected from a sequence set forth in SEQ ID NO: 446. In certain embodiments, the antibody comprises a VH sequence set forth in SEQ ID NO: 470 and a VL sequence set forth in SEQ ID NO: 471; and wherein the human Fc region comprises a human IgG sequence selected from a sequence set forth in SEQ ID NO: 457. In certain embodiments, the antibody comprises a VH sequence set forth in SEQ ID NO: 470 and a VL sequence set forth in SEQ ID NO: 471; and wherein the human Fc region comprises a human IgG sequence selected from a sequence set forth in SEQ ID NO: 460.

In certain embodiments, the isolated antibody described herein comprises a constant light chain sequence set forth by SEQ ID NO: 469.

In certain embodiments, the Fc region comprises one or more amino acid substitutions, wherein the one or more substitutions result in increased antibody half-life, increased ADCC activity, increased ADCP activity, or increased CDC activity compared with the Fc without the one or more substitutions. In certain embodiments, the one or more amino acid substitutions results in increased antibody half-life at pH 6.0 compared to an antibody comprising a wild-type Fc region. In certain embodiments, the isolated antibody comprising an Fc region with one or more amino acid substitutions has a half-life of about 80 to 110 days in a human.

In certain embodiments, the antibody has an increased half-life that is about 10,000-fold, 1,000-fold, 500-fold, 100-fold, 50-fold, 20-fold, 10-fold, 9-fold, 8-fold, 7-fold, 6-fold, 5-fold, 4.5-fold, 4-fold, 3.5-fold, 3-fold, 2.5-fold, 2-fold, 1.95-fold, 1.9-fold, 1.85-fold, 1.8-fold, 1.75-fold, 1.7-fold, 1.65-fold, 1.6-fold, 1.55-fold, 1.50-fold, 1.45-fold, 1.4-fold, 1.35-fold, 1.3-fold, 1.25-fold, 1.2-fold, 1.15-fold, 1.1-fold, or 1.05-fold longer compared to an antibody comprising a wild-type Fc region. In certain embodiments, the antibody has an increased half-life that is about 10,000-fold, 1,000-fold, 500-fold, 100-fold, 50-fold, 20-fold, 10-fold, 9-fold, 8-fold, 7-fold, 6-fold, 5-fold, 4.5-fold, 4-fold, 3.5-fold, 3-fold, 2.5-fold, 2-fold, 1.95-fold, 1.9-fold, 1.85-fold, 1.8-fold, 1.75-fold, 1.7-fold, 1.65-fold, 1.6-fold, 1.55-fold, 1.50-fold, 1.45-fold, 1.4-fold, 1.35-fold, 1.3-fold, 1.25-fold, 1.2-fold, 1.15-fold, 1.1-fold, or 1.05-fold longer compared to lebrikizumab.

In certain embodiments, the Fc region comprises one or more amino acid substitutions, wherein the one or more substitutions result in increased antibody half-life, a decrease in one or more of ADCC activity, ADCP activity, or CDC activity compared with the Fc without the one or more substitutions. In certain embodiments, the one or more amino acid substitutions results in increased antibody half-life at pH 6.0 compared to an antibody comprising a wild-type Fc region. In certain embodiments, the isolated antibody comprising an Fc region with one or more amino acid substitutions has a half-life of about 80 to 110 days in a human.

In certain embodiments, the one or more amino acid substitutions is selected from the group consisting of S228P (SP); M252Y, S254T, T256E, T256D, T250Q, H285D, T307A, T307Q, T307R, T307W, L309D, Q411H, Q311V, A378V, E380A, M428L, N434A, N434S, N297A, D265A, L234A, L235A, and N434W. In certain embodiments, the one or more amino acid substitutions comprises a plurality of amino acid substitutions selected from the group consisting of M428L/N434S (LS); M252Y/S254T/T256E (YTE); T250Q/M428L; T307A/E380A/N434A; T256D/T307Q (DQ); T256D/T307W (DW); M252Y/T256D (YD); T307Q/Q311V/A378V (QVV); T256D/H285D/T307R/Q311V/A378V (DDRVV); L309D/Q311H/N434S (DHS); S228P/L235E (SPLE); L234A/L235A (LALA), M428L/N434A (LA), L234A/G237A (LAGA), L234A/L235A/G237A (LALAGA), L234A/L235A/P329G (LALAPG), N297A, D265A/YTE, LALA/YTE, LAGA/YTE, LALAGA/YTE, LALAPG/YTE, N297A/LS; D265A/LS; LALA/LS; LALAGA/LS; LALAPG/LS; N297A/DHS; D265A/DHS; LALA/DHS; LAGA/DHS; LALAGA/DHS; LALAPG/DHS; SP/YTE; SPLE/YTE; SP/LS; SPLE/LS, SP/DHS; SPLE/DHS; N297A/LA; D265A/LA, LALA/LA, LAGA/LA, LALAGA/LA, LALAPG/LA, N297A/N434A; D265A/N434A; LALA/N434A, LAGA/N434A, LALAGA/N434A, LALAPG/N434A, N297A/N434W, D265A/N434W, LALA/N434W, LAGA/N434W, LALAGA/N434W, LALAPG/N434W, N297A/DQ, D265A/DQ, LALA/DQ, LAGA/DQ, LALAGA/DQ, LALAPG/DQ, N297A/DW, D265A/DW, LALA/DW, LAGA/DW, LALAGA/DW, LALAPG/DW N297A/YD, D265A/YD, LALA/YD, LAGA/YD, LALAGA/YD, LALAPG/YD, T307Q/Q311V/A378V (QVV), N297A/QVV, D265A/QVV, LALA/QVV, LAGA/QVV, LALAGA/QVV, LALAPG/QVV, DDRVV, N297A/DDRVV, D265A/DDRVV, LALA/DDRVV, LAGA/DDRVV, LALAGA/DDRVV, and LALAPG/DDRVV.

In certain embodiments, the one or more amino acid substitutions is selected from the group consisting of LALA/YTE, LAGA/YTE, LALA/LS, YTE, and LS.

In certain embodiments, the one or more amino acid substitutions comprises or consists of LALA/YTE. In certain embodiments, the one or more amino acid substitutions comprises or consists of LAGA/YTE. In certain embodiments, the one or more amino acid substitutions comprises or consists of LALA/LS. In certain embodiments, the one or more amino acid substitutions comprises or consists of YTE. In certain embodiments, the one or more amino acid substitutions comprises or consists of LS.

In certain embodiments, the Fc region binds an Fcγ Receptor selected from the group consisting of: FcγRI, FcγRIIa, FcγRIIb, FcγRIIc, FcγRIIIa, and FcγRIIIb. In certain embodiments, the Fc region binds an Fcγ Receptor with higher affinity at pH 6.0 compared to an antibody comprising a wild-type Fc region.

Binding

The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

With regard to the binding of an antibody to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule (i.e., IL-13) and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule. In some embodiments, the affinity of an anti-IL-13 antibody for a non-target molecule is less than about 50% of the affinity for IL-13. In some embodiments, the affinity of an anti-IL-13 antibody for a non-target molecule is less than about 40% of the affinity for IL-13. In some embodiments, the affinity of an anti-IL-13 antibody for a non-target molecule is less than about 30% of the affinity for IL-13. In some embodiments, the affinity of an anti-IL-13 antibody for a non-target molecule is less than about 20% of the affinity for IL-13. In some embodiments, the affinity of an anti-IL-13 antibody for a non-target molecule is less than about 10% of the affinity for IL-13. In some embodiments, the affinity of an anti-IL-13 antibody for a non-target molecule is less than about 1% of the affinity for IL-13. In some embodiments, the affinity of an anti-IL-13 antibody for a non-target molecule is less than about 0.1% of the affinity for IL-13.

When used herein in the context of two or more antibodies, the term "competes with" or "cross-competes with" indicates that the two or more antibodies compete for binding to an antigen (e.g., IL-13). In one exemplary assay, IL-13 is coated on a surface and contacted with a first anti-IL-13 antibody, after which a second anti-IL-13 antibody is added. In another exemplary assay, a first anti-IL-13 antibody is coated on a surface and contacted with IL-13, and then a second anti-IL-13 antibody is added. If the presence of the first anti-IL-13 antibody reduces binding of the second anti-IL-13 antibody, in either assay, then the antibodies compete with each other. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 25%, at least 50%, at least 60%, at least 70%, at least 80%, at least 85%, at least 90%, at least 95%, or at least 99% as measured in a competitive binding assay. A skilled artisan can select the concentrations of the antibodies used in the competition assays based on the affinities of the antibodies for IL-13 and the valency of the antibodies. The assays described in this definition are illustrative, and a skilled artisan can utilize any suitable assay to determine if antibodies compete with each other. Suitable assays are described, for example, in Cox et al., "Immunoassay Methods," in Assay Guidance Manual [Internet], Updated Dec. 24, 2014 (ncbi.nlm.nih.gov/books/NBK92434/; accessed Sep. 29, 2015); Silman et al., *Cytometry*, 2001, 44:30-37; and Finco et al., J. Pharm. Biomed. Anal., 2011, 54:351-358; each of which is incorporated by reference in its entirety.

A test antibody competes with a reference antibody if an excess of a test antibody (e.g., at least 2×, 5×, 10×, 20×, or 100×) inhibits or blocks binding of the reference antibody by, e.g., at least 50%, 60%, 70%, 75%, 80%, 85%, 90%, 95%, or 99% as measured in a competitive binding assay. Antibodies identified by competition assay (competing antibody) include antibodies binding to the same epitope as the reference antibody and antibodies binding to an adjacent epitope sufficiently proximal to the epitope bound by the reference antibody for steric hindrance to occur. For example, a second, competing antibody can be identified that competes for binding to IL-13 with a first antibody described herein. In certain instances, the second antibody can block or inhibit binding of the first antibody by, e.g., at least 50%, 60%, 70%, 75%, 80%, 85%, 90%, 95%, or 99% as measured in a competitive binding assay. In certain instances, the second antibody can displace the first antibody by greater than 50%, 60%, 70%, 75%, 80%, 85%, 90%, 95%, or 99%.

In certain embodiments, the antibody binds a human IL-13.

In certain embodiments, the antibody binds an IL-13 sequence set forth in SEQ ID NOs: 472-475.

In certain embodiments, the antibody is cross-reactive to cynomolgus monkey IL-13.

In certain embodiments, the antibody binds to an IL-13 sequence set forth in SEQ ID NOs: 472-475 with a $K_D$ of less than or equal to about 1, 2, 3, 4, 5, 6, 7, 8, $9 \times 10^{-9}$ M, as measured by SPR. In certain embodiments, the antibody binds to an IL-13 sequence set forth in SEQ ID NOs: 472-475 with a $K_D$ of less than or equal to about $1 \times 10^{-10}$ M, as measured by SPR. In certain embodiments, the antibody binds to human IL-13 with a $K_D$ of less than or equal to about $1 \times 10^{-9}$ M, as measured by SPR.

In some embodiments, an antibody provided herein binds IL-13 with a $K_D$ of less than or equal to about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 1.95, 2, 2.5, 3, 3.5, 4, 4.5, 5, 6, 7, 8, 9, or $10 \times 10^{-8}$ M, as measured by ELISA or any other suitable method known in the art. In some embodiments, an antibody provided herein binds IL-13 with a $K_D$ of less than or equal to about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 1.95, 2, 2.5, 3, 3.5, 4, 4.5, 5, 6, 7, 8, 9, or $10 \times 10^{-9}$ M, as measured by ELISA or any other suitable method known in the art.

In some embodiments, the $K_D$ of the antibody provided herein for the binding of IL-13 is between about 0.001-0.01, 0.01-0.1, 0.01-0.05, 0.05-0.1, 0.1-0.5, 0.5-1, 0.25-0.75, 0.25-0.5, 0.5-0.75, 0.75-1, 0.75-2, 1.1-1.2, 1.2-1.3, 1.3-1.4, 1.4-1.5, 1.5-1.6, 1.6-1.7, 1.7-1.8, 1.8-1.9, 1.9-2, 1-2, 1-5, 2-7, 3-8, 3-5, 4-6, 5-7, 6-8, 7-9, 7-10, or $5-10 \times 10^{-8}$ M, as measured by ELISA or any other suitable method known in the art. In some embodiments, an antibody provided herein binds IL-13 with a $K_D$ of less than or equal to about $1 \times 10^{-8}$ M, or less than or equal to above $1 \times 10^{-9}$ M as measured by ELISA or any other suitable method known in the art.

In some embodiments, the antibody provided herein binds IL-13 with a $K_D$ of less than or equal to about 10, 9, 8, 7, 6, 5, 4.5, 4, 3.5, 3, 2.5, 2, 1.98, 1.95, 1.9, 1.85, 1.8, 1.75, 1.7, 1.65, 1.6, 1.55, 1.50, 1.45, 1.4, 1.3, 1.2, 1.1, 1, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05, 0.01, 0.005, 0.001, 0.0005, or $0.0001 \times 10^{-8}$ M, or less, as measured by ELISA or any other suitable method known in the art. In some embodiments, the antibody provided herein binds IL-13 with a $K_D$ between 5-3, 4-2, 3-1, 1.9-1.8, 1.8-1.7, 1.7-1.6, 1.6-1.5, 1.9-1.5, 1.5-1, 1-0.8, 1-0.5, 0.9-0.6, 0.7-0.4, 0.6-0.2, 0.5-0.3, 0.3-0.2, 0.2-0.1, 0.1-0.01, 0.01-0.001, or $0.001-0.0001 \times 10^{-8}$ M as measured by ELISA or any other suitable method known in the art.

Function

"Effector functions" refer to those biological activities mediated by the Fc region of an antibody, which activities may vary depending on the antibody isotype. Examples of antibody effector functions include receptor ligand blocking, agonism, or antagonism, C1q binding to activate complement dependent cytotoxicity (CDC), Fc receptor binding to activate antibody-dependent cellular cytotoxicity (ADCC), and antibody dependent cellular phagocytosis (ADCP). In some embodiments, the effector function of the anti-IL-13 antibody described herein is antagonism and blocks the IL-13 receptor binding to IL-13.

Pharmaceutical Compositions

The present application provides compositions comprising the antibodies including pharmaceutical compositions comprising any one or more of the antibodies described herein with one or more pharmaceutically acceptable excipients. In some embodiments the composition is sterile. The pharmaceutical compositions generally comprise an effective amount of an antibody.

These compositions can comprise, in addition to one or more of the antibodies disclosed herein, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g., oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

The anti-IL-13 antibody that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, $16^{th}$ edition, Osol, A. (ed), 1980.

A composition can be administered alone or in combination with other treatments, either simultaneously or sequentially dependent upon the condition to be treated.

Methods

Methods of Preparation

Antibodies described herein can be produced using recombinant methods and compositions, e.g., as described in U.S. Pat. No. 4,816,567. In one embodiment, an isolated nucleic acid encoding an antibody described herein is provided. Such a nucleic acid may encode an amino acid sequence comprising the VL and/or an amino acid sequence comprising the VH of the antibody (e.g., the light and/or heavy chains of the antibody) or an amino acid sequence comprising the VHH of a single domain antibody. In a further embodiment, one or more vectors (e.g., expression vectors) comprising such nucleic acid are provided. In one embodiment, the nucleic acid is provided in a multicistronic vector. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antigen-binding polypeptide construct, or (2) a first vector comprising a nucleic acid that encodes an amino acid sequence comprising the VL of the antigen-binding polypeptide construct and a second vector comprising a nucleic acid that encodes an amino acid sequence comprising the VH of the antigen-binding polypeptide construct. In one embodiment, the host cell is eukaryotic, e.g., a Chinese Hamster Ovary (CHO) cell, or human embryonic kidney (HEK) cell, or lymphoid cell (e.g., Y0, NS0, Sp20 cell). In one embodiment, a method of making an antibody is provided, wherein the method comprises culturing a host cell comprising nucleic acid encoding the antibody, as provided above, under conditions suitable for expression of the antibody, and optionally recovering the antibody from the host cell (or host cell culture medium).

For recombinant production of the antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

When an antibody or variant thereof is recombinantly produced by the host cells, the protein in certain embodiments is present at about 30%, about 25%, about 20%, about 15%, about 10%, about 5%, about 4%, about 3%, about 2%, or about 1% or less of the dry weight of the cells. When the antibody or variant thereof is recombinantly produced by the host cells, the protein, in certain embodiments, is present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. In certain embodiments, "substantially purified" antibody produced by the methods described herein, has a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

Suitable host cells for cloning or expression of antibody-encoding vectors include prokaryotic or eukaryotic cells described herein.

Recombinant host cells or host cells are cells that include an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome. Host cells can include CHO, derivatives of CHO, NS0, Sp20, CV-1, VERO-76, HeLa, HepG2, Per.C6, or BHK.

For example, antibody may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibodies are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

In one embodiment, the antibodies described herein are produced in stable mammalian cells, by a method comprising: transfecting at least one stable mammalian cell with: nucleic acid encoding the antibody, in a predetermined ratio; and expressing the nucleic acid in the at least one mammalian cell. In some embodiments, the predetermined ratio of nucleic acid is determined in transient transfection experiments to determine the relative ratio of input nucleic acids that results in the highest percentage of the antibody in the expressed product.

In some embodiments, is the method of producing an antibody in stable mammalian cells as described herein wherein the expression product of the at least one stable mammalian cell comprises a larger percentage of the desired glycosylated antibody as compared to the monomeric heavy or light chain polypeptides, or other antibodies.

In some embodiments, is the method of producing a glycosylated antibody in stable mammalian cells described herein, said method comprising identifying and purifying the desired glycosylated antibody. In some embodiments, the said identification is by one or both of liquid chromatography and mass spectrometry.

If required, the antibodies can be purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of antibodies. For example, the bacterial proteins A and G bind to the Fc region. Likewise, the bacterial protein L binds to the Fab region of some antibodies. Purification can often be enabled by a particular fusion partner. For example, antibodies may be purified using glutathione resin if a GST fusion is employed, $Ni^{+2}$ affinity chromatography if a His-tag is employed or immobilized anti-flag antibody if a flag-tag is used. For general guidance in suitable purification techniques, see, e.g., incorporated entirely by reference Protein Purification: Principles and Practice, $3^{rd}$ Ed., Scopes, Springer-Verlag, NY, 1994, incorporated entirely by reference. The degree of purification necessary will vary depending on the use of the antibodies. In some instances, no purification is necessary.

In certain embodiments, the antibodies are purified using Anion Exchange Chromatography including, but not limited to, chromatography on Q-sepharose, DEAE sepharose, poros HQ, poros DEAF, Toyopearl Q, Toyopearl QAE, Toyopearl DEAE, Resource/Source Q and DEAE, Fractogel Q and DEAE columns.

In specific embodiments, the proteins described herein are purified using Cation Exchange Chromatography including, but not limited to, SP-sepharose, CM sepharose, poros HS, poros CM, Toyopearl SP, Toyopearl CM, Resource/Source S and CM, Fractogel S and CM columns and their equivalents and comparables.

In addition, antibodies described herein can be chemically synthesized using techniques known in the art (e.g., see Creighton, 1983, Proteins: Structures and Molecular Principles, W. H. Freeman & Co., N.Y and Hunkapiller et al., *Nature*, 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4diaminobutyric acid, alpha-amino isobutyric acid, 4aminobutyric acid, Abu, 2-amino butyric acid, g-Abu, e-Ahx, 6amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, alanine, fluoro-amino acids, designer amino acids such as methyl amino acids, C-methyl amino acids, N-methyl amino acids, and amino acid analogs in general. Furthermore, the amino acid can be D (dextrorotary) or L (levorotary).

In certain embodiments, an antibody described herein has an aggregation temperature greater than about 69° C., greater than about 70° C., greater than about 71° C., greater than about 72° C., greater than about 73° C., greater than about 74° C., greater than about 75° C., or greater than about 76° C., for example, between about 69° C. and about 77° C., between about 70° C. and about 76° C., between about 71° C. and about 75° C. In certain embodiments, aggregation temperature is measured using DSF.

In certain embodiments, an antibody described herein has reduced hydrophobicity as compared to lebrikizumab as measured by hydrophobic interaction chromatography (HIC). In certain embodiments, the antibody exhibits an HIC retention time that is less than about 15.2 min. In certain embodiments, the antibody exhibits an HIC retention time that is between about 13 min and about 15 min.

Methods of Use

In an aspect, the present application provides methods of contacting IL-13 with an anti-IL-13 antibody, such as a human or humanized antibody, which results in inhibition of IL-13 binding to an IL-13 receptor expressed on a cell.

In an aspect, the present application provides methods of using the isolated anti-IL-13 antibodies described herein for treatment of a disorder or disease in a subject. In certain aspects, described herein is a method for treating a subject in need thereof with an anti-IL-13 antibody, the method comprising administering to a mammalian subject a therapeutically effective amount of an anti-IL-13 antibody or pharmaceutical composition comprising an anti-IL-13 antibody described herein. In certain embodiments, the present application provides methods of treating a disorder or disease associated with elevated levels of IL-13 and/or IgE in a subject.

In certain aspects, described herein are methods for treating a pathology associated with IL-13 activity, the method comprising administering to a mammalian subject a therapeutically effective amount an isolated anti-IL-13 antibody or a pharmaceutical composition comprising an isolated anti-IL-13 antibody described herein.

In certain aspects, described herein is a method for treating an inflammatory disorder or disease in a mammalian subject in need thereof, the method comprising administering to the mammalian subject a therapeutically effective amount an antibody described herein or a pharmaceutical composition described herein. In certain embodiments of the methods described herein, the inflammatory disorder or disease is atopic dermatitis. In certain embodiments, the inflammatory disorder or disease is asthma. In certain embodiments, the inflammatory disorder or disease is idiopathic pulmonary fibrosis. In certain embodiments of the methods described herein, the inflammatory disorder or disease is alopecia areata. In certain embodiments, the inflammatory disorder or disease is chronic sinusitis with nasal polyps. In certain embodiments, the inflammatory disorder or disease is Chronic Rhinosinusitis without Nasal Polyps (CRSsNP). In certain embodiments, the inflammatory disorder or disease is eosinophilic esophagitis (EoE). In certain embodiments, the inflammatory disorder or disease is an Eosinophilic gastrointestinal disorder or disease (ENID) selected from the group consisting of Eosinophilic Gastritis (EoG), Eosinophilic enteritis (EN), Eosinophilic colitis (EoC), and Eosinophilic Gastroenteritis (EGE). In certain embodiments, the inflammatory disorder or disease is Churg-Strauss syndrome/Eosinophilic granulomatosis with polyangiitis (EGPA). In certain embodiments, the inflammatory disorder or disease is Prurigo Nodularis (PN). In certain embodiments, the inflammatory disorder or disease is Chronic Spontaneous Urticaria (CSU). In certain embodiments, the inflammatory disorder or disease is Chronic Pruritis of Unknown Origin (CPUO). In certain embodiments, the inflammatory disorder or disease is Bullous Pemphigoid (BP). In certain embodiments, the inflammatory disorder or disease is Cold Inducible Urticaria (ColdU). In certain embodiments, the inflammatory disorder or disease is Allergic Fungal Rhinosinusitis (AFRS). In certain embodiments, the inflammatory disorder or disease is Allergic Bronchopulmonary Aspergillosis (ABPA). In certain embodiments, the inflammatory disorder or disease is Chronic Obstructive Pulmonary Disease (COPD). In certain embodiments, the inflammatory disorder or disease is inflammatory bowel disease, such as Crohn disease or ulcerative colitis. In certain embodiments, the inflammatory disorder or disease is psoriasis. In certain embodiments, the inflammatory disorder or disease is lupus. In certain embodiments, the inflammatory disorder or disease is rheumatoid arthritis.

In certain aspects, described herein are methods for treating a pathology associated with elevated levels of IL-13 in a mammalian subject in need thereof, the method comprising administering to the mammalian subject a therapeutically effective amount an antibody or a pharmaceutical composition described herein.

In certain aspects, described herein are methods of reducing biological activity of IL-13 in a mammalian subject in need thereof, the method comprising administering to the mammalian subject a therapeutically effective amount an antibody or a pharmaceutical composition described herein.

In certain aspects, described herein are methods for inhibiting the TH2 type allergic response in a mammalian subject in need thereof, the method comprising administering to the mammalian subject a therapeutically effective amount an antibody or a pharmaceutical composition described herein.

In certain aspects, described herein are methods for inhibiting IL-13-induced phosphorylation of STAT6 in a cell, the method comprising contacting the cell with an antibody described herein.

In certain aspects, described herein are methods for inhibiting IL-13-induced CD23 expression in a cell, the method comprising contacting the cell with an antibody described herein.

In certain aspects, described herein are methods for inhibiting IL-13-induced secretion of CCL2 and CCL26 from a cell, the method comprising contacting the cell with an antibody described herein.

In certain aspects, described herein are methods for inhibiting IL-13-induced NTRK1 expression in a cell, the method comprising contacting the cell with an antibody described herein.

In certain aspects, described herein are methods for reducing levels of Thymus and Activation Regulated Chemokine (TARC)/CCL17 in a mammalian subject in need thereof, the method comprising administering to the mammalian subject a therapeutically effective amount an antibody or a pharmaceutical composition described herein.

In certain aspects, described herein are methods of preventing an inflammatory disorder or disease in a mammalian subject in need thereof, the method comprising administering to the mammalian subject a therapeutically effective amount an antibody or a pharmaceutical composition described herein.

Methods of Administration

In some embodiments, the methods provided herein are useful for the treatment of a disease or disorder in an individual. In an embodiment, the individual is a human and the antibody is an anti-IL-13 antibody described herein.

In some embodiments, an antibody is administered intravenously, intramuscularly, subcutaneously, topically, orally, transdermally, intraperitoneally, intraorbitally, by implantation, by inhalation, intrathecally, intraventricularly, or intranasally. An effective amount of an anti-IL-13 antibody may be administered for the treatment of a disease or disorder. The appropriate dosage of the anti-IL-13 antibody may be determined based on the type of disease or disorder to be treated, the type of the anti-IL-13 antibody, the severity and course of the disease or disorder, the clinical condition of the individual, the individual's clinical history and response to the treatment, and the discretion of the attending physician.

In some embodiments, an antibody provided herein is administered with at least one additional therapeutic agent. Any suitable additional therapeutic or immunotherapeutic agent may be administered with an antibody provided herein. Additional therapeutic agents include agents that are used to treat or prevent a disease or disorder such as, but not limited to, an inflammatory disease or disorder associated with elevated levels of IL-13 and/or IgE.

The additional therapeutic agent can be administered by any suitable means. In some embodiments, an antibody provided herein and the additional therapeutic agent are included in the same pharmaceutical composition. In some embodiments, an antibody provided herein and the additional therapeutic agent are included in different pharmaceutical compositions.

In embodiments where an antibody provided herein and the additional therapeutic agent are included in different pharmaceutical compositions, administration of the antibody can occur prior to, simultaneously, and/or following, administration of the additional therapeutic agent. In some embodiments, administration of an antibody provided herein and the additional therapeutic agent occur within about one month of each other. In some embodiments, administration of an antibody provided herein and the additional therapeutic agent occur within about one week of each other. In some embodiments, administration of an antibody provided herein and the additional therapeutic agent occur within about one day of each other. In some embodiments, administration of an antibody provided herein and the additional therapeutic agent occur within about twelve hours of each other. In some embodiments, administration of an antibody provided herein and the additional therapeutic agent occur within about one hour of each other.

Kits and Articles of Manufacture

The present application provides kits comprising any one or more of the antibody compositions described herein and instructions for use. In some embodiments, the kits further contain a component selected from any of secondary antibodies, reagents for immunohistochemistry analysis, pharmaceutically acceptable excipient and instruction manual and any combination thereof. In one specific embodiment, the kit comprises a pharmaceutical composition comprising any one or more of the antibody compositions described herein, with one or more pharmaceutically acceptable excipients.

The present application also provides articles of manufacture comprising any one of the antibody compositions or kits described herein. Examples of an article of manufacture include vials (including sealed vials).

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual ($2^{nd}$ Edition, 1989); Methods In Enzymology (S. Colowick and N. Kaplan eds., Academic Press, Inc.); Remington's Pharmaceutical Sciences, $18^{th}$ Edition (Easton, Pennsylvania: Mack Publishing Company, 1990); Carey and Sundberg *Advanced Organic Chemistry* $3^{rd}$ Ed. (Plenum Press) Vols A and B (1992).

Methods
Humanization of Mouse Hybridoma Sequence of Anti-IL-13 Antibody 228B/C-1

Complementarity-determining region (CDR) grafting technology was used to humanize the parental mouse anti-human IL-13 228B/C-1, the parental monoclonal antibody of Lebrikizumab. The parental mouse heavy and light sequences were modeled onto a human antibody framework as described below. A set of human heavy and light chains were selected for humanization. The goal was to design pairs of these heavy and light chains that resulted in improved biophysical properties of the parental antibody while retaining binding. These humanized molecules were designed for improved developability profile during scale up in bioprocess.

Humanization of Light Chains

The parental mAb light chain sequence of mouse hybridoma sequence of anti-IL13 antibody (Lebrikizumab) was compared to a group of human variable region light chain (VK) germlines amino acid sequences (Lefranc, M.-P. IMGT, the international ImMunoGeneTics database *Nucleic Acids Res.*, 29, D207-209 (2001). DOI:10.1093/nar/29.1.207. PMID:11125093.). A total of 4 human VK germlines were selected. Of these, one belonged to Vk4 family (IGKV4-1), two belonged to VK1 family (IGKV1-39 and IGKV3-15) and one belonged to VK2 family (IGKV2-28). One substitution on light chain framework 3, R to G was also designed. This back mutation from human to mouse can alter binding. Human germline KJ4 was selected for the J region based on sequence similarity with the mouse sequence. The humanized VL domains were cloned into a vector encoding for a kappa light chain constant domain.

The following nomenclature was used for the light chains: "LC0" corresponds to the mouse hybridoma sequence. "LC1" corresponds to IGKV4-1_KJ4. "LC2" corresponds to IGKV1-39_KJ4. "LC3" corresponds to IGKV3-15_KJ4. "LC4" corresponds to IGKV2-28_KJ4. "LC5" corresponds to IGKV4-1_R to G_KJ. "LC6" corresponds to IGK V1-39_R to G_KJ4. "LC7" corresponds to IGKV3-15_R to G_KJ4. "LC8" corresponds to IGKV2-28_R to G_KJ4.

Humanization of Heavy Chain

The parental mAb heavy chain sequence of mouse hybridoma sequence of anti-IL13 antibody (Lebrikizumab) was compared to a group of human variable region heavy chain (VH) germline amino acid sequences. A total of 5 human VH germlines were selected. Of these, one belonged to VH4 family (IGHV4-59), two belonged to VH1 family (IGHV1-46, IGHV1-69) and two belonged to VH3 family (IGHV3-15, IGHV3-23). The N-terminal Q in heavy chain was substituted with E to prevent potential pyroglutamate conversion. Human germline HJ6 was selected for the J region based on sequence similarity with the mouse sequence. The humanized VH domains were cloned into a vector encoding for human IgG1 HC constant domain.

The following nomenclature was used for the heavy chains: "HC0"-corresponds to the mouse hybridoma heavy chain. "HC0_M" corresponds to HC0_NIS to TIS in FR3 (to prevent potential glycosylation). "HC1" corresponds to humanized sequence IGHV4-59_HJ6. "HC2" corresponds to humanized sequence IGHV1-46_HJ6. "HC3" corresponds to humanized sequence IGHV1-69_HJ6. "HC4" corresponds to humanized sequence IGHV3-15_HJ6. "HC5" corresponds to humanized sequence IGHV3-23_HJ6.

Gene Synthesis and Plasmid Construction

The coding sequences for HC and LC of the antibody were generated by DNA synthesis and PCR, subsequently subcloned into pTT5-based plasmid for protein expression in mammalian cell system. The gene sequences in the expression vectors were confirmed by DNA sequencing.

Expression of Antibody Constructs

Transient expression of antibodies was performed by co-transfection of paired HC and LC constructs into CHO cells using PEI method. Briefly, CHO cells at approximately $5.5 \times 10^6$/mL in a shake flask was used as the host. Transfection was initiated by adding a mixture of 1 mg/L DNA and 7 mg/L PEI in OptiMEM™ medium (Invitrogen) to the cells followed by gentle mixing. Cells were then cultured in an incubator shaker at 120 rpm, 37° C., and 8% $CO_2$, for 9 days. Feeding with peptone and glucose was carried out 24 h later and every 2-3 days thereafter depending on the cell density and viability. The cell culture was terminated on day 9 when cell viability reduced to <80%. The conditioned medium was harvested for protein purification.

Purification of Antibody Construct

Protein purification by affinity chromatography, and ion exchange chromatography was performed using an AKTA pure instrument (GE Lifesciences). Conditional medium expressing target antibody was harvested by centrifugation at 4000 rpm, 50 min, and filtered with a 0.22 μm filter. The harvested supernatants were loaded to a column of Mabselect™ SuRe™ (GE Healthcare). After washing column with Buffer A (PBS, PH 7.4), the protein was eluted with Buffer B (1 M Glycine, pH 2.7), and immediately neutralized with 1/10 volume of Buffer D (1 M sodium citrate, pH 6.0). The affinity purified antibody was then buffer exchanged into 20 mM sodium acetate pH 5.5.

TABLE 11

Size exclusion chromatograph of anti-IL-13 constructs

| Construct ID* | Percent Monomer |
| --- | --- |
| lebrikizumab (Construct 1) | 99% |
| Construct 2 | 96% |
| Construct 3 | 95% |

TABLE 11-continued

Size exclusion chromatograph of anti-IL-13 constructs

| Construct ID* | Percent Monomer |
|---|---|
| Construct 4 | 93% |
| Construct 5 | 95% |
| Construct 6 | 97% |
| Construct 7 | 97% |
| Construct 8 | 98% |
| Construct 9 | 96% |
| Construct 10 | 99% |
| Construct 11 | 98% |
| Construct 12 | 98% |
| Construct 13 | 98% |
| Construct 14 | 98% |
| Construct 15 | 98% |
| Construct 16 | 98% |
| Construct 17 | 99% |
| Construct 18 | 98% |
| Construct 19 | 98% |
| Construct 20 | 99% |
| Construct 21 | 98% |
| Construct 22 | 98% |
| Construct 23 | 99% |
| Construct 24 | 100% |
| Construct 25 | 99% |
| Construct 26 | 97% |
| Construct 90 | 98% |
| Construct 91 | 98% |
| Construct 92 | 98% |
| Construct 93 | 98% |
| Construct 94 | 99% |
| Construct 95 | 98% |
| Construct 96 | 99% |
| Construct 97 | 97% |
| Construct 98 | 98% |
| Construct 99 | 98% |
| Construct 100 | 97% |
| Construct 101 | 99% |
| Construct 102 | 98% |
| Construct 103 | 100% |
| Construct 104 | 100% |
| Construct 105 | 100% |
| Construct 106 | 99% |
| Construct 107 | 100% |
| Construct 108 | 99% |
| Construct 109 | 99% |
| Construct 110 | 99% |
| Construct 111 | 100% |
| Construct 112 | 98% |
| Construct 113 | 98% |
| Construct 114 | 98% |
| Construct 115 | 97% |
| Construct 116 | 98% |
| Construct 117 | 98% |
| Construct 118 | 97% |
| Construct 119 | 98% |
| Construct 120 | 97% |
| Construct 121 | 96% |
| Construct 122 | 98% |
| Construct 123 | 95% |
| Construct 124 | 98% |
| Construct 125 | 98% |
| Construct 126 | 97% |
| Construct 127 | 98% |

*See construct sequences in Tables 2-8.

SEC-HPLC Analysis of Antibody Construct

Analytical SEC-HPLC was performed using Shimadzu LC-10 HPLC instrument (Shimadzu Corp.). 20 µl sample on 1 mg/mL was loaded to a Superdex® 200 Increase 5/150GL column (GE Lifesciences). The mobile phase was 2*PBS with a flow rate of 0.3 mL/min, 15 min.

Measuring Antibody-IL13 Binding Kinetics Using Surface Plasmon Resonance

A Biacore 8K SPR system (GE HealthCare) equipped with Series S Sensor Chip Protein G (Cytiva, Cat. 29179315) was used to determine the binding kinetic rate and affinity constants at 25° C. and in a running buffer of HBS-EP+ (10 mM HEPES pH 7.4, 150 mM NaCl, 3 mM EDTA, 0.05% Surfactant P20). Following a stabilization period in running buffer, the anti-IL13 mAb constructs (diluted to 1 µg/mL were captured onto flow cell 2 (active) for 60 sec at a flow rate of 10 uL/min. Recombinant Human IL-13 Protein, His Tag (Acro Cat. IL3-H52H4) was prepared at concentrations of 0, 0.39, 0.78, 1.56, 3.13, 6.25, 12.5 and 0 nM and injected over flow cell 1 (reference) and flow cell 2 (active) for 180 sec at a flow rate of 30 µL/min. Recombinant Cynomolgus IL-13 Protein, His Tag (SINO BIOLOGICAL, Cat. 11057-C07H) was prepared at concentrations of 0, 0.39, 0.78, 1.56, 3.13, 6.25, 12.5, 25 and 0 nM and injected over flow cell 1 (reference) and flow cell 2 (active) for 180 sec at a flow rate of 30 µL/min. Samples were injected in a multi-cycle manner over freshly captured mAb, by regenerating the capture surfaces with injection of glycine pH 1.5 for 30 sec at a flow rate of 30 µL/min. The data was processed and analyzed with Biacore Insight Evaluation Software Version 2.0.15.12933 (GE Healthcare) as follows. Responses from flow cell 1 (reference) were subtracted from the responses from flow cell 2 (active). The responses from the two buffer blank injections were then subtracted from the reference subtracted data (2-1) to yield double-referenced data, which were fit to an 1:1 binding model to determine the apparent association (ka) and dissociation rate constants (kd). Their ratio provided the apparent equilibrium dissociation constant or affinity constant (KD=kd/ka).

Determination of Antibody Affinity to Fc Receptors and C1q

Binding affinity ($K_D$) of antibodies to Fc receptors and C1q were determined through surface plasmon resonance (SPR) using a Biacore 8K. Briefly, an SPR chip functionalized with an anti-kappa light-chain antibody was used to capture purified antibodies normalized to 5 mg/mL, at a flow rate of 10 uL/min for 90 seconds or 120 seconds. A paired channel with only buffer was used as reference. Subsequently, varying concentrations of recombinant human CD32a (167H), CD32a (167R), CD32b, CD16a (176V), CD16a (176F), FcRn, CD64, and C1q were injected over the surface with captured purified antibody as well as the reference channel. Regeneration of the chip between different concentrations of different antigens were performed with 10 mM Glycine HCl, pH 1.5 and antibody was again captured. Association and dissociation rate constants were subsequently determined through fitting to a 1:1 Langmuir binding model or steady-state analysis model, whichever applicable, using the Biacore Insight Evaluation Software from which a $K_D$ value was derived.

Assessing Blockade by Cell-Line-Based Assays

Multiple assays were used to assess blockade of the full signalling complex of IL-13/IL13Rα1/IL-4Rα and prevention of downstream signalling. Briefly, HEK293 previously transduced to stably express both hIL-13Rα and hIL-4Rα were cultured and harvested. Cells were seeded at 200,000 cells in 100 uL per well. Cells were washed and the supernatant was discarded. A 100 uL mixture of biotinylated hIL-13 and purified antibody (1:1 by volume) that had been previously made and incubated for 1 hour was added to resuspend the cells, resulting in a final concentration of 0.05 ug/mL of hIL-13 and 0-100 nM of purified antibody. The cells were stained in this mixture at 4° C. for 1 hour. Cells were then washed and stained with 100 uL of Alexa Fluor 488-conjugated streptavidin at a 1:1000 dilution to detect binding of biotinylated hIL-13 on the cell surface. Cells were incubated at 4° C. for 1 hour, protected from light. Cells were then washed and the median fluorescence intensity (MFI) of cells in each well were recorded by FACS using a BD FACSCanto II. Subsequent data were analyzed using GraphPad Prism. $IC_{50}$ values were determined as the concentration of antibody required to inhibit 50% of the maximum MFI of biotinylated hIL-13 surface detected with incubation of 0.05 ug/mL of hIL-13 alone.

Cell-line-based assays included: inhibition of phosphorylation of STAT6 in HT-29 cells, inhibition of release of TARC in A549 cells, and inhibition of proliferation of TF-1 cells. Primary human lymphocyte-based assays included: inhibition of phosphorylation of STAT6 and inhibition of CD23 expression.

Inhibition of Phosphorylation of STAT6 in HT-29 Cells

Inhibition of STAT6 phosphorylation in HT-29 cells was used to evaluate the functional activity of antibodies to block IL-13-induced biological activity. Briefly, HT-29 cells were starved in RMPI 1640+0.1% FBS overnight. Cells were collected and seeded at 50,000 cells per well in 100 µL. Concurrently, a 100 µL mixture of hIL-13 and purified antibody (1:1 by volume) was added to the same well, resulting in a final concentration of 10 ng/ml of hIL-13 and 0-50 nM of purified antibody. Cells were incubated at 37° C. for 1 hour and subsequently fixed, permeabilized, and stained with a PE-conjugated anti-pSTAT6 antibody. The MFI of cells in each well were recorded by FACS using a BD FACSCanto II and subsequent data were analyzed using GraphPad Prism. IC50 values were determined as the concentration of antibody required to inhibit 50% of the maximum MFI of pSTAT6 detected with incubation of 10 ng/ml of hIL-13 alone. Results are summarized below.

Inhibition of Release of TARC in A549 Cells

Inhibition of TARC secretion by A549 cells was used to evaluate the functional activity of antibodies to block IL-13-induced biological activity. Briefly, A549 cells were seeded at 20,000 cells in 100 µL of DMEM+10% FBS and cultured overnight at 37° C. The next day, the cell culture media was discarded and cells were gently washed with fresh media. A 150 µL mixture of hIL-13, purified antibody, and hTNFα (1:1:1 by volume) were added to the wells, resulting in a final concentration of 20 ng/mL hIL-13, 0-100 nM purified antibody, and 200 ng/ml. Cells were incubated in this mixture at 37° C. for 20-24 hour. Following incubation, culture supernatant was collected and the amount of TARC present was analyzed using a commercial TARC ELISA kit (R&D Systems), analyzed according to manufacturer's instructions. The determined concentrations of TARC in each well were analyzed using GraphPad Prism. IC50 values were determined as the concentration of antibody required to inhibit 50% of the maximum TARC concentration detected with incubation of only 20 ng/ml of hIL-13 and 200 ng/ml hTNFα. Results are summarized below.

Inhibition of Proliferation of TF-1 Cells

The proliferation or inhibition thereof of TF-1 cells was used to evaluate the functional activity of antibodies to block IL-13-induced biological activity. Briefly, TF-1 cells were harvested and starved in RPMI1640+10% FBS without additional cytokine for 4 hours. During this time, a mixture of hIL-13 and purified antibody (1:1 by volume) was prepared 50 µL was added per well. Following starvation, TF-1 cells were again harvested and seeded at 15,000 cells in 50 µL per well, resulting in a final concentration of 4 ng/ml of hIL-13 and 0-5 nM purified antibody. Cells were subsequently incubated at 37° C. for 72 hours and proliferation of cells was quantified using CellTiter-Glo (Promega) according to manufacturer's instructions. Luminescence was recorded by SpectraMax M5 Multimode Plate Reader and data was analyzed using GraphPad Prism. IC50 values were determined as the concentration of antibody required to result in 50% of the maximum luminescence detected when TF-1 cells are incubated and cultured with 4 ng/ml of hIL-13 alone. Results are summarized below.

Inhibition of STAT6 Phosphorylation and CD23 Expression in Primary Human Lymphocytes To confirm the antagonistic activity of antibodies herein in primary cells, human peripheral blood mononuclear cells (PBMCs) obtained from healthy donors were used to evaluate the ability of antibodies herein to inhibit IL-13-induced phosphorylation of STAT6 and upregulation of CD23 expression.

Frozen human PBMCs from a previously-identified IL-13 responsive donors were thawed and revived. To determine the in vitro potency of antibodies herein in inhibiting STAT6 phosphorylation, total PBMCs were stimulated with 10 ng/ml of IL-13 and purified antibody (1:1 by volume). These cells were allowed to incubate for 15 minutes at 37° C. Phosphorylation of STAT6 was subsequently analysed by flow cytometry using a commercial anti-phosphoSTAT6 antibody, staining assessed within the specific immune population gated by lineage-specific markers CD14 and CD19. In a separate set of PBMCs, cells were allowed to incubate for 24 hours at 37° C. CD23 expression was subsequently analyzed by flow cytometry using an anti-CD23 antibody and its intensity of staining assessed within the specific immune population gated by lineage-specific markers CD14 and CD19.

Median fluorescence intensity (MFI) data from either pSTAT6 or CD23 staining was analyzed using GraphPad Prism. $IC_{50}$ values were determined as the concentration of antibody required to result in 50% of the maximum MFI detected for each marker when primary human PBMCs are incubated and cultured with 10 ng/ml of hIL-13 alone.

Protein Thermal Stability Test by Differential Scanning Fluorimetry (DSF)

SYPRO® Orange (Thermo Fisher #S6651) was supplied at 5000× concentration in 100% DMSO and diluted to 40× in the appropriate formulation buffer. The antibodies were mixed with the dye, and nine microliters of this mixture was loaded into a UNi (Unchained Labs, Cat No. 201-1010) and run with the "$T_m$ using SYPRO" application on UNCLE (Unchained Labs). Samples were subjected to a thermal ramp from 25-95° C., with a ramp rate of 0.5° C./minute and excitation at 473 nm. Full spectra were collected from 250-720 nm and UNCLE software was used to measure the area under the curve between 510-680 nm to calculate the inflection points ($T_m$) of the transition curves.

HIC-HPLC Analysis of Antibody Construct

Analytical HIC-HPLC was performed using Thermo Ulti-Mate™ 3000 instrument. A 20 µl sample at 1 mg/mL was loaded to a Thermo Scientific™ MAbPac™ HIC-Butyl HPLC column (5 µm, 4.6 mm×100 mm; Cat No. 088558). The mobile phase A was 1.5 M Ammonium sulfate+50 mM PB buffer+5% (v/v) isopropyl alcohol, pH 6.95 and the mobile phase B was 50 mM PB buffer+20% (v/v) isopropyl alcohol, pH 6.95. The gradient was 0% to 100% mobile phase B over 20 min, and flow rate was 0.5 mL/min.

Inhibition of CCL26 and CCL2 Secretion and NTRK1 Expression

Inhibition of CCL26 and CCL2 secretion and NTRK1 expression by HaCaT cells was used to evaluate the functional activity of antibodies to block IL-13-induced biological activity. HaCaT cells were seeded at 20,000 cells in 100 uL of DMEM+10% FBS and cultured overnight at 37° C. The next day, a 150 uL mixture of hIL-13 and purified antibody were added to the wells, resulting in a final concentration of 50 ng/ml of IL-13 with 0-206.5 nM purified antibody. Cells were then further incubated at 37° C. for 48 hours. Following incubation, culture supernatant was collected and levels of secreted CCL26 and CCL2 were measured using a commercial Luminex-based immunoassay kit (R&D Systems) and analyzed according to manufacturer's instructions. Determined concentrations of CCL26 and CCL2 in each well were analyzed using GraphPad Prism. $IC_{50}$ values were determined as the concentration of antibody required to inhibit 50% of the maximum concentration detected with incubation of 50 ng/ml of IL-13 alone.

Cells remaining in the assay plates were lysed and mRNA extracted for analysis of NTRK1 gene expression using a commercial Quantigene kit (ThermoFisher). Levels of NTRK1 mRNA were determined according to the manufacturer's protocol and analyzed in GraphPad Prism. NTRK1 gene expression was quantified as a ratio of NTRK1 mRNA levels relative to the housekeeping gene, PPIB, and $IC_{50}$ values calculated as the concentration of antibody required to inhibit 50% of the maximum gene expression detected using 50 ng/ml of hIL-13 alone.

Example 1: Engineered Anti-IL-13 Antibodies Exhibit Improved Affinity and Potency of Blockade of IL-13

Results
Determination of Antibody Affinity to IL-13

Using the methods described above, the affinity of Construct 133 (see construct sequence in Tables 2-8) to IL-13 and the binding kinetics thereof were assessed using surface plasmon resonance (SPR) as compared to dupilumab, lebrikizumab, and a variant of lebrikizumab with one or more amino acid substitutions in the heavy chain constant region (Construct 2 (Lebrikizumab—HC; Lebrikizumab—LC; hIgG1-LAGA YTE; Human kappa LC); see construct sequence in Tables 2-8), and tralokinumab.

As measured by SPR, Construct 133 had an affinity of 77 pM compared to 131 pM and 116 pM for lebrikizumab and tralokinumab, respectively.

The affinity of variants of lebrikizumab with one or more amino acid substitutions in the heavy chain constant region (Constructs 128-131), variants of Constructs 15 or 98 with one or more amino acid substitutions in the heavy chain constant region (Constructs 133-136 or 137-140, respectively), and variants with one or more amino acid substitutions in the heavy chain constant region (Constructs 132 and 141-144) to human and cynomolgus monkey IL-13 and the binding kinetics thereof were also assessed using SPR.

It was observed that all antibodies bound to human IL-13 with low picomolar affinity comparable to the variants of lebrikizumab. Additionally, all antibodies tested were cross-reactive to cynomolgus monkey IL-13 with sub-nanomolar affinities (Table 12).

TABLE 12

Antibody Affinity to IL-13

| Construct ID* | SPR Hu IL-13 $K_D$ (pM) | SPR Cyno IL-13 $K_D$ (pM) | ELISA Hu IL-13 $K_D$ (pM) |
|---|---|---|---|
| Lebrikizumab | 131 | 309 | N.T. |
| Tralokinumab | 116 | 1480 | N.T. |
| Construct 128 | 91.5 | 298 | 67 |
| Construct 129 | 239 | 882 | 36 |
| Construct 130 | 112 | 227 | 27 |
| Construct 131 | 75.6 | 123 | 19 |
| Construct 132 | 135 | 331 | N.T. |
| Construct 133 | 77.7 | 208 | 19 |
| Construct 134 | 105 | 330 | 50 |
| Construct 135 | 130 | 588 | N.T. |
| Construct 136 | 69.8 | 161 | 18 |
| Construct 137 | 42.1 | 246 | 26 |
| Construct 138 | 108 | 348 | N.T. |
| Construct 139 | 114 | 705 | N.T. |
| Construct 140 | 47.5 | 252 | 20 |
| Construct 141 | 107 | 329 | 25 |
| Construct 142 | 108 | 326 | 54 |
| Construct 143 | 119 | 685 | N.T. |
| Construct 144 | 26.3 | 228 | 14 |

*See construct sequences in Tables 2-8.
N.T.—Not Tested

Antibody Affinity to Fc Receptors and C1q

All antibody hIgG1-LALA YTE variants compared to lebrikizumab showed near or complete ablation of binding to all Fc gamma receptors, significantly decreased binding to C1q, and significantly increased binding to FcRn at pH 5.8 (Table 13).

TABLE 13

Antibody Affinity to Fc Receptors and C1q

| Construct ID* | D32a (167H) $K_D$ (mM) | D32a (167R) $K_D$ (mM) | D32b $K_D$ (mM) | D16a (176V) $K_D$ (mM) | D16a (176F) $K_D$ (mM) | D64 $K_D$ (nM) | C1q (Signal Relative to Rituximab) | cRn, pH 7.4 $K_D$ (mM) | cRn, pH 5.8 $K_D$ (mM) |
|---|---|---|---|---|---|---|---|---|---|
| Lebrikizumab | 5.27 | 2.38 | 2.93 | n.d. | n.d. | 1.12 | 39.6% | n.d. | 1.06 |
| Construct 133 | n.d. | n.d. | n.d. | n.d. | n.d. | n.d. | 15.9% | n.d. | 0.15 |
| Construct 134 | n.d. | 8.14 | 8.62 | n.d. | n.d. | 2.80 | 25.3% | n.d. | 0.16 |
| Construct 135 | 4.54 | 2.40 | 2.17 | n.d. | n.d. | 0.86 | 30.8% | n.d. | 0.10 |
| Construct 136 | n.d. | n.d. | n.d. | 4.67 | n.d. | n.d. | 25.4% | n.d. | 0.09 |

*See construct sequences in Tables 2-8.
n.d.—not detectable

Blockade

A. Inhibition of IL-13 Binding to hIL-13Rα/hIL-4Rα. Overexpressing Cells

Figure 2:
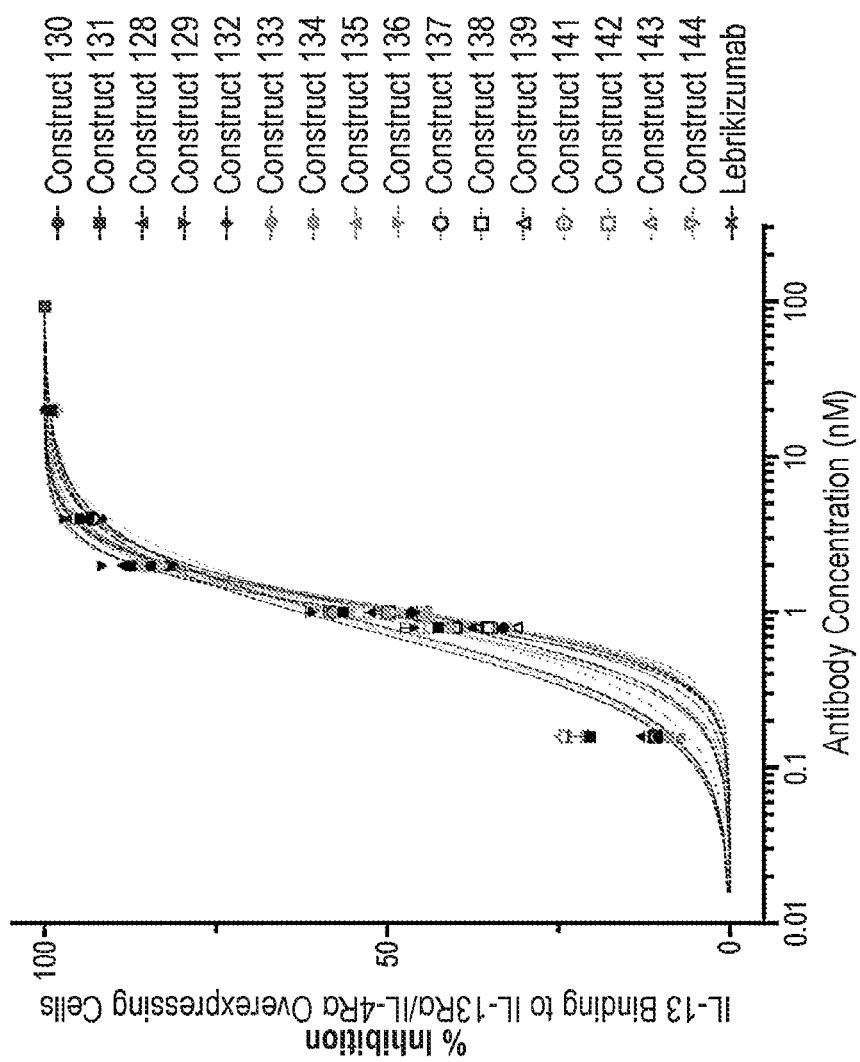
FIG. 2 is a graph depicting the percentage of inhibition of IL-13 binding to IL13Rα1/IL-4Rα overexpressing HEK293 cells that have been incubated with the indicated engineered anti-IL-13 antibodies, as determined by FACs.

IL-13 binding to cells overexpressing hIL-13Rα/hIL-4Rα was used to evaluate the functional blockade of antibodies against this binding interaction. The results of the functional blockade of antibodies described herein in blocking IL-13 binding to cells overexpressing hIL-13Rα/hIL-4Rα are provided in Table 14 and FIG. 2. In the cell-line-based assays, Construct 133 exhibited an $IC_{50}$ of 0.89 nM and inhibited IL-13 binding on an IL-13Rα1/IL-4Rα overexpression cell line, as compared to an $IC_{50}$ 1.11 nM for lebrikizumab.

TABLE 14

Blockade of IL-13 Binding to hIL-13Rα/hIL-4Rα Overexpressing Cells

| Construct ID* | Blockade of IL-13 Binding $IC_{50}$ (nM) |
|---|---|
| Lebrikizumab | 1.11 |
| Construct 128 | 0.95 |
| Construct 129 | 0.71 |
| Construct 130 | 1.05 |
| Construct 131 | 0.79 |
| Construct 132 | 0.99 |
| Construct 133 | 0.89 |
| Construct 134 | 1.08 |
| Construct 135 | 1.03 |
| Construct 136 | 1.02 |
| Construct 137 | 0.89 |
| Construct 138 | 1.01 |
| Construct 139 | 1.09 |
| Construct 141 | 0.81 |
| Construct 142 | 0.77 |
| Construct 143 | 0.74 |
| Construct 144 | 0.94 |

*See construct sequences in Tables 2-8.

B. Inhibition of IL-13-Induced Phosphorylation of STAT6 in HT-29 Cells

Inhibition of STAT6 phosphorylation in HT-29 cells was used to evaluate the functional activity of antibodies to block IL-13-induced biological activity. An $IC_{50}$ of 0.28 nM of Construct 133 was observed for inhibiting phosphorylation of STAT6 in HT-29 cells, as compared to 0.16 nM for dupilumab, 0.23 nM for lebrikizumab, and 0.41 nM for tralokinumab, respectively.

Figure 3:
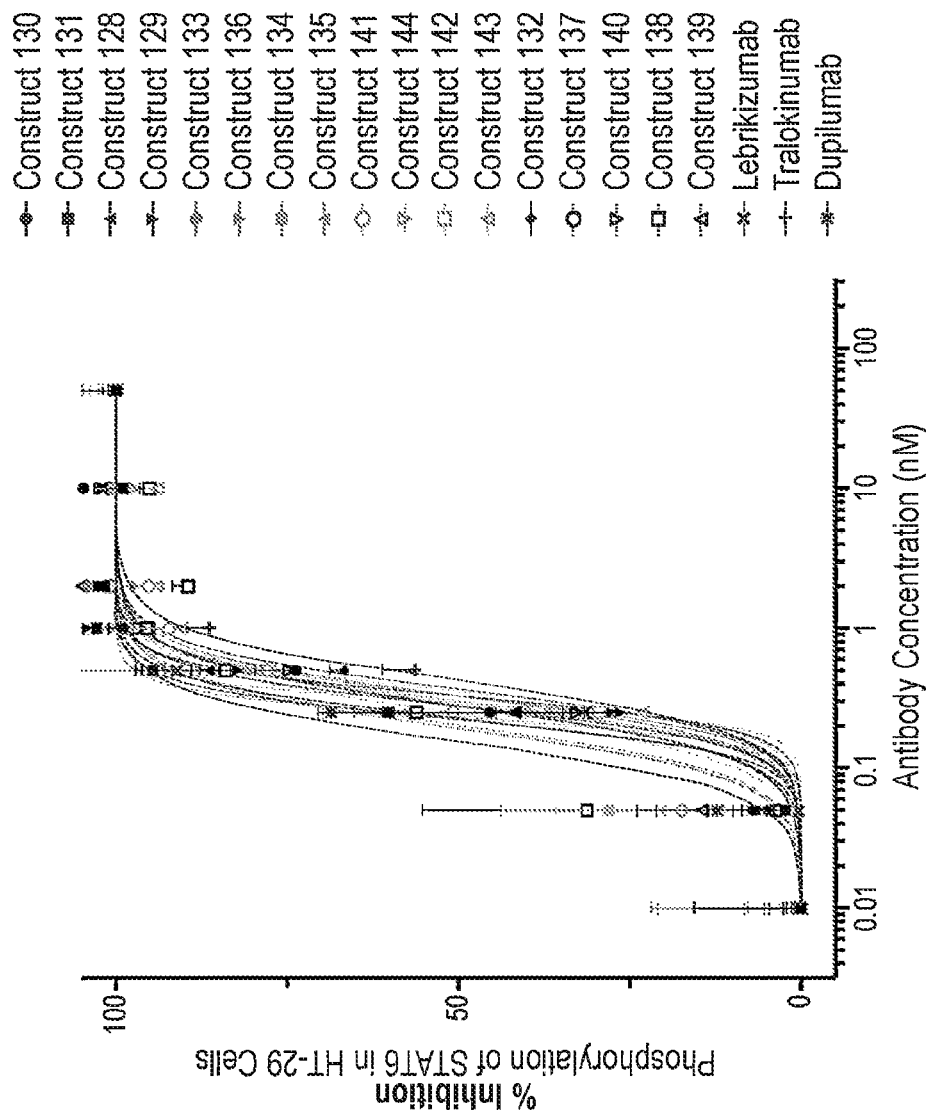
FIG. 3 is a graph depicting the percentage of inhibition of IL-13-induced phosphorylation of STAT6 in HT-29 cells that have been incubated with the indicated engineered anti-IL-13 antibodies, as determined by FACs.

Variants of lebrikizumab with one or more amino acid substitutions in the heavy chain constant region (Constructs 128-131), variants of Constructs 15 or 98 with one or more amino acid substitutions in the heavy chain constant region (Constructs 133-136 or 137-140, respectively), and variants with one or more amino acid substitutions in the heavy chain constant region (Constructs 132 and 141-144) were also tested in the same assay (Table 15 and FIG. 3).

TABLE 15

Inhibition of IL-13-Induced Phosphorylation of STAT6 in HT-29 Cells

| Construct ID* | pSTAT6 Inhibition $IC_{50}$ (nM) |
|---|---|
| Lebrikizumab | 0.23 |
| Tralokinumab | 0.41 |
| Dupilumab | 0.16 |
| Construct 128 | 0.28 |
| Construct 129 | 0.33 |
| Construct 130 | 0.28 |
| Construct 131 | 0.22 |
| Construct 132 | 0.37 |

TABLE 15-continued

Inhibition of IL-13-Induced Phosphorylation of STAT6 in HT-29 Cells

| Construct ID* | pSTAT6 Inhibition $IC_{50}$ (nM) |
|---|---|
| Construct 133 | 0.28 |
| Construct 134 | 0.20 |
| Construct 135 | 0.23 |
| Construct 136 | 0.30 |
| Construct 137 | 0.33 |
| Construct 138 | 0.19 |
| Construct 139 | 0.28 |
| Construct 140 | 0.33 |
| Construct 141 | 0.25 |
| Construct 142 | 0.29 |
| Construct 143 | 0.36 |
| Construct 144 | 0.30 |

*See construct sequences in Tables 2-8.

C. Inhibition of IL-13 TARC Secretion by Engineered Anti-IL13 Antibody Variants

Figure 4:
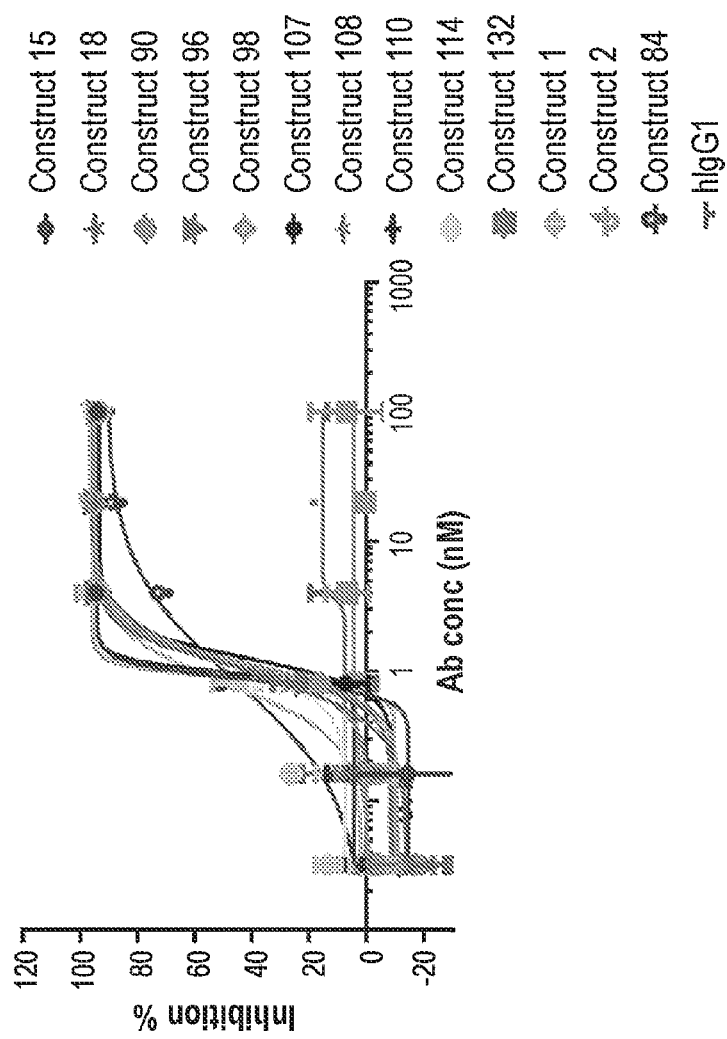
FIG. 4 is a graph depicting the percentage of inhibition of IL-13-induced release of thymus-and activation-regulated chemokine (TARC/CCL17) in the supernatant of A549 cell cultures that have been incubated with the indicated engineered anti-IL-13 antibodies, as determined by enzyme-linked immunoassay (ELISA).

Human A549 cells express IL4Rα/IL13Rα1 receptor, which responds to binding to human IL-13 by inducing pSTAT6 phosphorylation, thereby triggering expression of downstream genes involved in TH2 type allergic response. Thymus and Activation Regulated Chemokine (TARC), also known as CCL17, is one such gene product that is secreted by multiple cell types and plays a role in attracting effector immune cells such as eosinophils that are involved in inflammation. A549 cells were contacted with engineered anti-IL-13 antibodies and TARC assays were performed (FIG. 4). Anti-IL-13 antibodies inhibited secretion of TARC as measured by ELISA. The TARC secretion $IC_{50}$ profiles (Table 16) were similar to lebrikizumab, thus confirming there was a preservation of potency of the anti-IL13 antibodies for IL-13 sequestrant activity in cell-based assays.

TABLE 16

TARC secretion

| Construct ID* | TARC Release IC50 (nM) |
|---|---|
| Lebrikizumab | 0.9 |
| Construct 2 | 0.9 |
| Construct 15 | 0.9 |
| Construct 19 | 1.1 |
| Construct 19 | 1.0 |
| Construct 96 | 1.0 |
| Construct 98 | 0.9 |
| Construct 107 | 1.3 |
| Construct 108 | 1.0 |
| Construct 110 | 1.0 |
| Construct 114 | 1.1 |
| Dupilumab control | 0.8 |
| Control (Irrelevant IgG1 LAGA YTE) | No Inhibition |

*See construct sequences in Tables 2-8.

Figure 5:
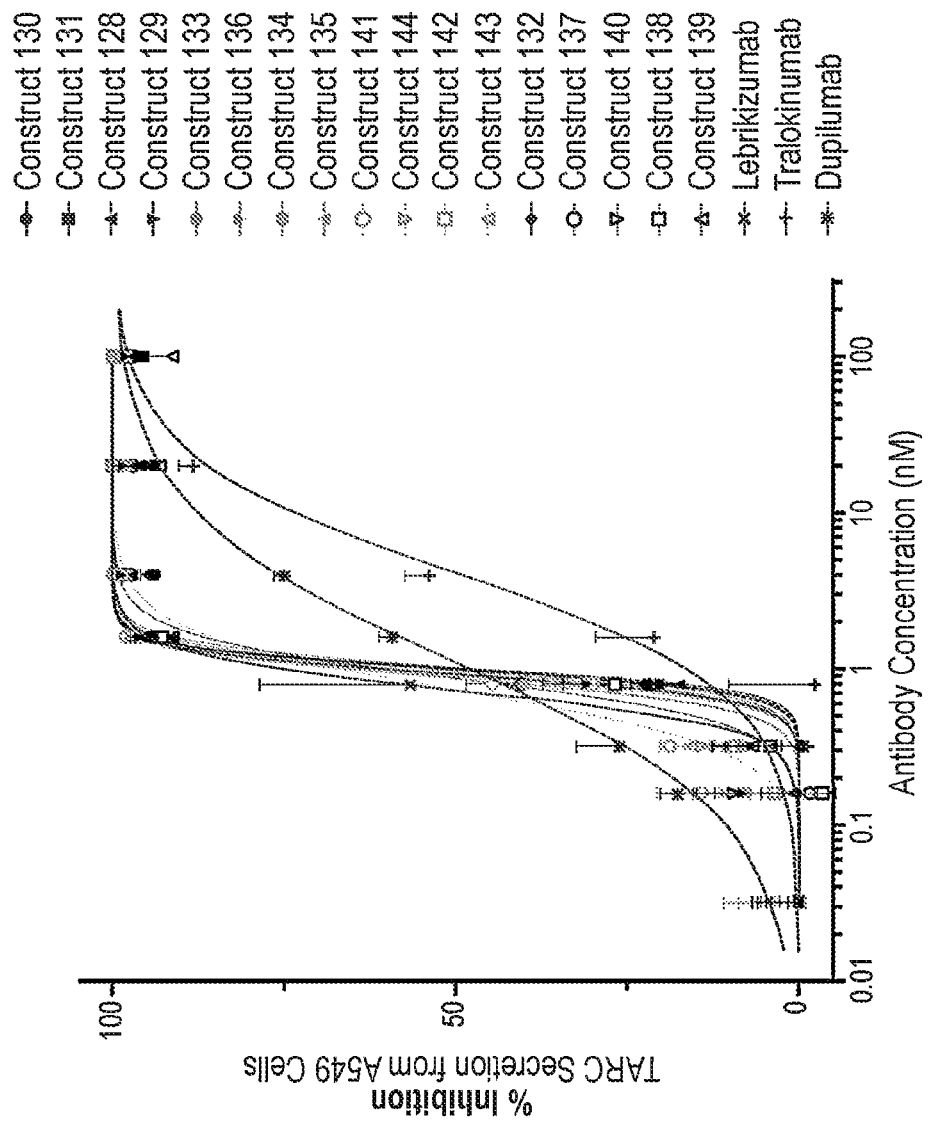
FIG. 5 is a graph depicting the percentage of inhibition of IL-13-induced release of TARC in the supernatant of A549 cell cultures that have been incubated with the indicated engineered anti-IL-13 antibodies, as determined by ELISA.

Variants of lebrikizumab with one or more amino acid substitutions in the heavy chain constant region (Constructs 128-131), variants of Constructs 15 or 98 with one or more amino acid substitutions in the heavy chain constant region (Constructs 133-136 or 137-140, respectively), and variants with one or more amino acid substitutions in the heavy chain constant region (Constructs 132 and 141-144) were tested in the same assay (Table 17 and FIG. 5). An $IC_{50}$ of 0.86 nM by Construct 133 for inhibiting release of TARC in A549 cells was observed, as compared to 1.11 nM for dupilumab, 0.74 nM for lebrikizumab, and 4.14 nM for tralokinumab, respectively.

TABLE 17

Inhibition of IL-13-Induced Release of TARC in A549 Cells

| Construct ID* | TARC Inhibition $IC_{50}$ (nM) |
|---|---|
| Lebrikizumab | 0.74 |
| Tralokinumab | 4.14 |
| Dupilumab | 1.11 |
| Construct 128 | 1.01 |
| Construct 129 | 0.92 |
| Construct 130 | 1.00 |
| Construct 131 | 0.99 |
| Construct 132 | 0.87 |
| Construct 133 | 0.86 |
| Construct 134 | 0.99 |
| Construct 135 | 0.91 |
| Construct 136 | 0.89 |
| Construct 137 | 0.87 |
| Construct 138 | 0.97 |
| Construct 139 | 1.02 |
| Construct 140 | 0.94 |
| Construct 141 | 0.73 |
| Construct 142 | 0.92 |
| Construct 143 | 0.92 |
| Construct 144 | 0.91 |

*See construct sequences in Tables 2-8.

D. Inhibition of IL-13-Induced Proliferation of TF-1 Cells

An $IC_{50}$ of 0.16 nM by Construct 133 for inhibiting proliferation of IL-13-induced TF-1 cells was observed, as compared to 0.19 nM for dupilumab, 0.20 nM lebrikizumab, and 0.59 nM for tralokinumab, respectively.

Figure 6:
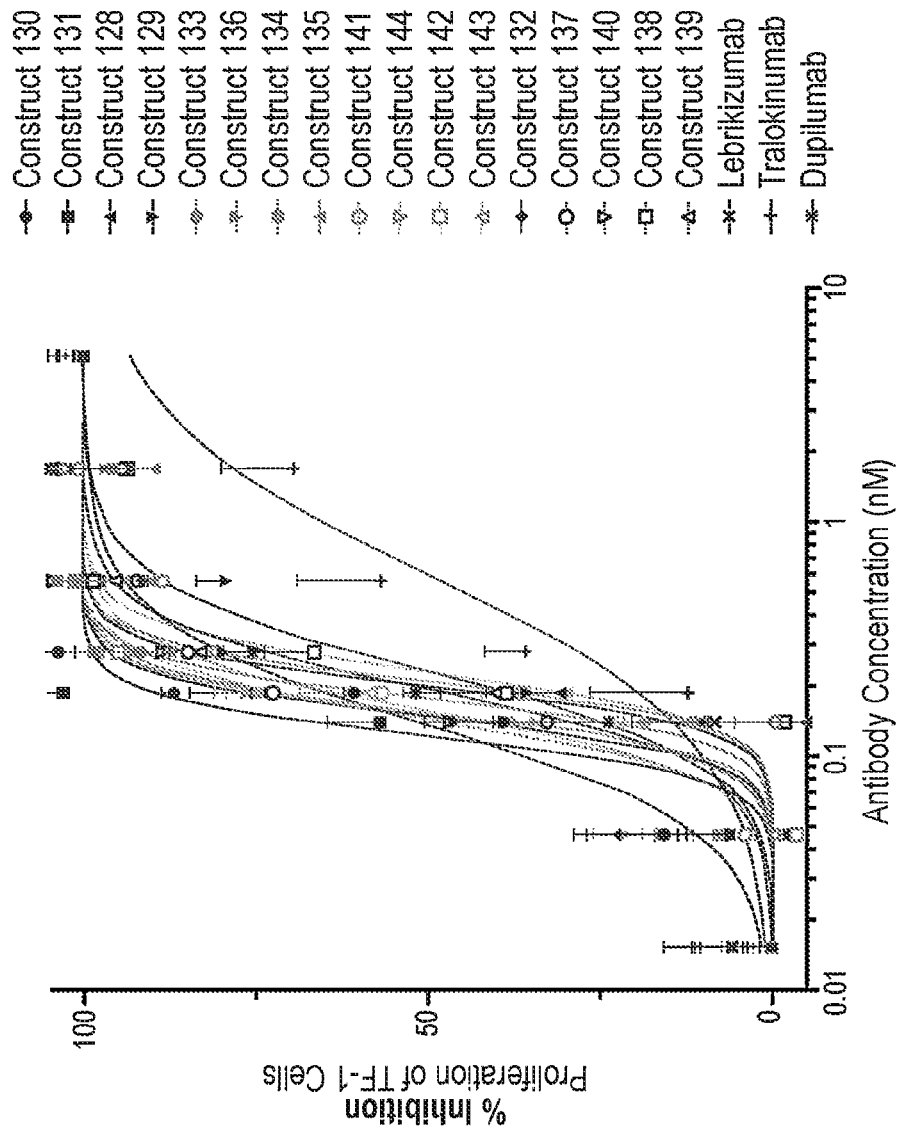
FIG. 6 is a graph depicting the percentage of inhibition of IL-13-induced proliferation of TF-1 cells that have been incubated with the indicated engineered anti-IL-13 antibodies, as quantified by a CellTiter-Glo assay.

Variants of lebrikizumab with one or more acid substitutions in the heavy chain constant region (Constructs 128-131), variants of Constructs 15 or 98 with one or more amino acid substitutions in the heavy chain constant region (Constructs 133-136 or 137-140, respectively), and variants with one or more amino acid substitutions in the heavy chain constant region (Constructs 132 and 141-144) were also tested in the same assay (Table 18 and FIG. 6).

TABLE 18

Inhibition of IL-13-Induced Proliferation of TF-1 Cells

| Construct ID* | TF-1 Proliferation Inhibition $IC_{50}$ (nM) |
|---|---|
| Lebrikizumab | 0.20 |
| Tralokinumab | 0.59 |
| Dupilumab | 0.19 |
| Construct 128 | 0.20 |
| Construct 129 | 0.21 |
| Construct 130 | 0.15 |
| Construct 131 | 0.13 |
| Construct 132 | 0.13 |
| Construct 133 | 0.15 |
| Construct 134 | 0.18 |
| Construct 135 | 0.21 |
| Construct 136 | 0.15 |
| Construct 137 | 0.16 |
| Construct 138 | 0.23 |
| Construct 139 | 0.20 |
| Construct 140 | 0.14 |
| Construct 141 | 0.19 |
| Construct 142 | 0.20 |
| Construct 143 | 0.17 |
| Construct 144 | 0.17 |

*See construct sequences in Tables 2-8.

E. Inhibition of IL-13-Induced Phosphorylation of STAT6 and CD23 Expression in Primary Human Lymphocytes In primary human lymphocytes, Construct 133 potently blocked IL-13 activity in a dose-dependent manner as exhibited by an $IC_{50}$ of 0.44 nM inhibiting phosphorylation of STAT6 compared to 0.38 nM for lebrikizumab and an $IC_{50}$ 0.85 nM in inhibiting CD23 expression compared to 0.81 nM for lebrikizumab. The results demonstrated the strong antagonistic activity that Construct 133 possessed against IL-13-mediated signalling in primary human cells.

Figure 7:
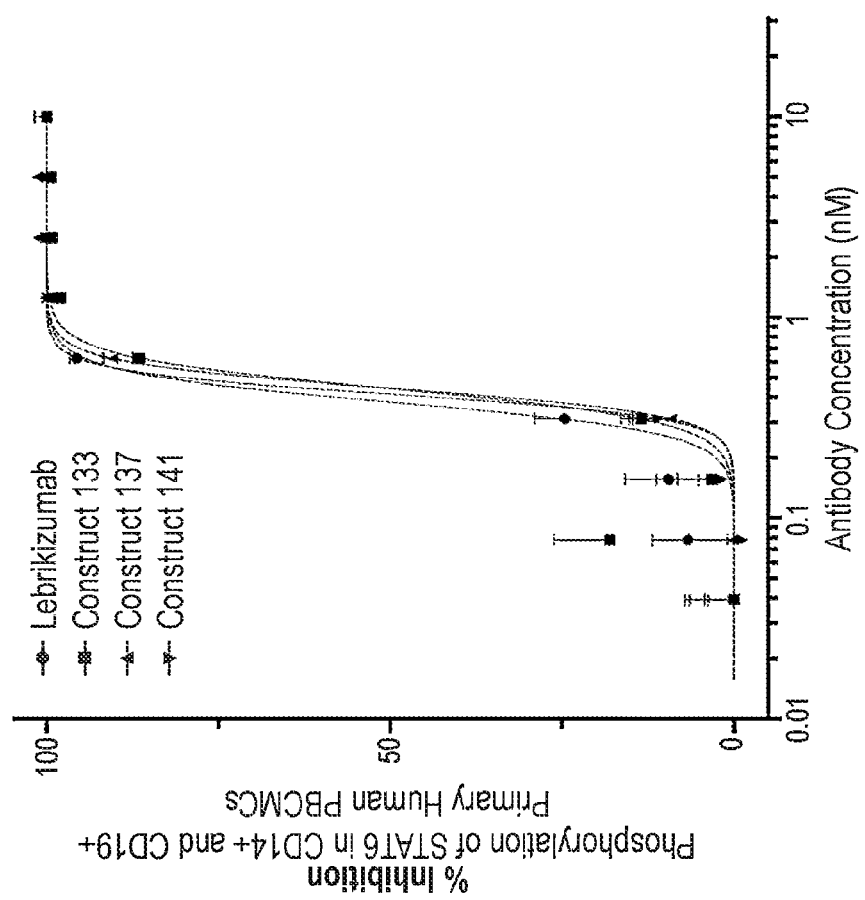
FIG. 7 is a graph depicting the percentage of inhibition of IL-13-induced phosphorylation of STAT6 in human peripheral blood mononuclear cells (PBMCs) cells that have been incubated with the indicated engineered anti-IL-13 antibodies, as determined by FACs.
Figure 8:
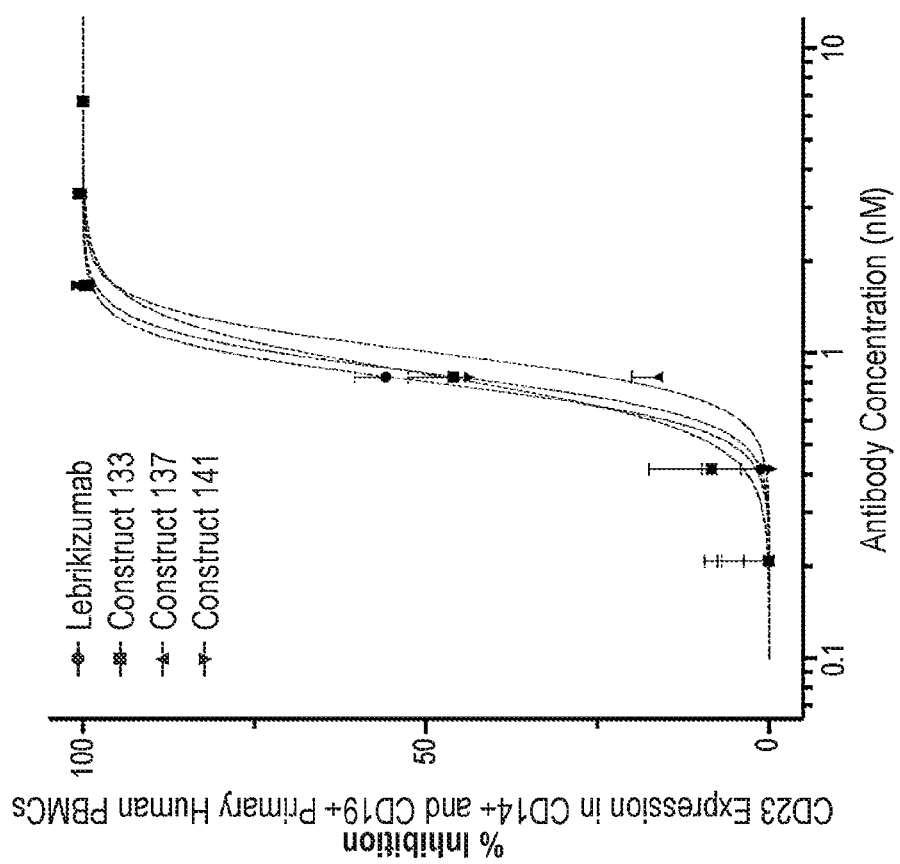
FIG. 8 is a graph depicting the percentage of inhibition of IL-13-induced CD23 expression in human peripheral blood mononuclear cells (PBMCs) cells that have been incubated with the indicated engineered anti-IL-13 antibodies, as determined by FACs.

A variant of Construct 98 with one or more amino acid substitutions in the heavy chain constant region (Construct 137), and a variant with one or more amino acid substitutions in the heavy chain constant region (Construct 141) were also tested in the same assay (Table 19, FIG. 7, and FIG. 8).

TABLE 19

Inhibition of IL-13-Induced Phosphorylation of STAT6 and CD23 in Human PBMCs

| Construct ID* | pSTAT6 Inhibition $IC_{50}$ (nM) | CD23 Expression Inhibition $IC_{50}$ (nM) |
|---|---|---|
| Lebrikizumab | 0.38 | 0.81 |
| Construct 133 | 0.44 | 0.85 |
| Construct 137 | 0.44 | 1.01 |
| Construct 141 | 0.41 | 0.86 |

Example 2: Expression of Engineered Anti-IL-13 Antibodies is Improved Over Lebrikizumab Transient expression of antibodies was performed by co-transfection of paired HC and LC constructs into CHO cells using the PEI method as described above. The relative expression of the engineered antibody constructs from the CHO cell lysates compared to lebrikizumab were then determined (Table 20) in a small-scale expression screening experiment.

TABLE 20

Expression of engineered anti-IL-13 antibodies

| Construct* | Fold Improvement in Transient CHO Expression Over lebrikizumab |
|---|---|
| Lebrikizumab | 1.0 |
| Construct 2 | 1.4 |
| Construct 3 | 8.0 |
| Construct 4 | 6.4 |
| Construct 5 | 4.3 |
| Construct 6 | 5.4 |
| Construct 7 | 7.2 |
| Construct 8 | 3.7 |
| Construct 9 | 4.3 |
| Construct 10 | 2.1 |
| Construct 11 | 2.6 |
| Construct 12 | 3.5 |
| Construct 13 | 5.2 |
| Construct 14 | 3.1 |
| Construct 15 | 5.9 |
| Construct 16 | 9.1 |
| Construct 17 | 8.4 |
| Construct 18 | 6.4 |
| Construct 19 | 6.8 |
| Construct 20 | 4.7 |
| Construct 21 | 3.9 |
| Construct 22 | 4.5 |
| Construct 23 | 2.9 |
| Construct 24 | 0.2 |
| Construct 25 | 13.2 |
| Construct 26 | 9.4 |

TABLE 20-continued

Expression of engineered anti-IL-13 antibodies

| Construct* | Fold Improvement in Transient CHO Expression Over lebrikizumab |
|---|---|
| Construct 90 | 9.9 |
| Construct 91 | 9.7 |
| Construct 92 | 11.5 |
| Construct 93 | 8.9 |
| Construct 94 | 5.6 |
| Construct 95 | 3.3 |
| Construct 96 | 6.8 |
| Construct 97 | 5.2 |
| Construct 98 | 6.8 |
| Construct 99 | 3.5 |
| Construct 100 | 8.1 |
| Construct 101 | 12.2 |
| Construct 102 | 4.1 |
| Construct 103 | 6.2 |
| Construct 104 | 6.4 |
| Construct 105 | 3.5 |
| Construct 106 | 3.9 |
| Construct 107 | 8.5 |
| Construct 108 | 6.2 |
| Construct 109 | 6.0 |
| Construct 110 | 9.7 |
| Construct 111 | 12.4 |
| Construct 112 | 12.9 |
| Construct 113 | 0.2 |
| Construct 114 | 4.4 |
| Construct 115 | 9.1 |
| Construct 116 | 7.8 |
| Construct 117 | 5.8 |
| Construct 118 | 11.8 |
| Construct 119 | 9.1 |
| Construct 120 | 7.2 |
| Construct 121 | 5.8 |
| Construct 122 | 7.8 |
| Construct 123 | 8.9 |
| Construct 124 | 9.5 |
| Construct 125 | 5.8 |
| Construct 126 | 6.2 |
| Construct 127 | 0.9 |

*See construct sequences in Tables 2-8.

Example 3: Thermostability of Engineered Anti-IL-13 Antibodies

Differential Scanning Fluorometry (DSF) was utilized to measure melting temperatures (Tm2) of lebrikizumab and the IL-13 antibodies described in Table 21. While the majority of variants exhibited a non-inferior Tm2 profile to lebrikizumab, there were a handful of variants that exhibited a significantly higher melting temperature, such as Construct 5 and Construct 15 (Table 21). Additionally, nearly all variants exhibited higher aggregation temperature, Tagg, compared to lebrikizumab. Tagg is a measure of the propensity of the mAb for forming higher molecules weight aggregates, and higher values are more desirable. Thus, the majority of the engineered variants had a more desirable aggregation temperature.

TABLE 21

Thermostability of engineered anti-IL-13 antibodies

| Construct ID* | Tm2 (° C.) | Tagg 473 (° C.) |
|---|---|---|
| Lebrikizumab | 71.8 | 68.5 |
| Construct 2 | 72.2 | 71.2 |
| Construct 3 | 73.3 | 72.1 |
| Construct 4 | 73.4 | 72.1 |
| Construct 5 | 75.9 | 76.1 |
| Construct 6 | 72.4 | 72.8 |
| Construct 7 | 72.3 | 72.8 |
| Construct 8 | 72.1 | 72.6 |
| Construct 9 | 69.1 | 72.3 |
| Construct 15 | 77.4 | 77.1 |
| Construct 16 | 72.4 | 73.0 |
| Construct 17 | 72.5 | 72.9 |
| Construct 18 | 73.1 | 73.1 |
| Construct 19 | 71.8 | 72.8 |
| Construct 20 | 71.1 | 72.0 |
| Construct 95 | 72.8 | 76.2 |
| Construct 96 | 70.8 | 71.2 |
| Construct 98 | 70.8 | 72.0 |
| Construct 104 | 68.6 | 74.1 |
| Construct 106 | 71.1 | 75.2 |
| Construct 107 | 71.2 | 74.1 |
| Construct 108 | 72.5 | 73.8 |
| Construct 110 | 71.4 | 74.0 |
| Construct 114 | 70.9 | 73.8 |

*See construct sequences in Tables 2-8.

Example 4: Engineered Anti-IL-13 Antibodies Exhibit Reduced Hydrophobicity

Hydrophobic interaction chromatography (HIC) was performed to measure the propensity of the engineered anti-IL-13 antibodies for interaction with hydrophobic surfaces (Table 22). Shorter retention times indicate less degree of hydrophobicity. All of the novel IL-13 antibodies tested showed shorter retention times (RT) compared to lebrikizumab. Thus, all of the engineered anti-13 antibodies tested exhibited reduced hydrophobicity compared to lebrikizumab.

TABLE 22

Hydrophobicity of engineered anti-IL-13 antibodies

| Construct ID* | HIC RT (min) |
|---|---|
| Lebrikizumab | 15.2 |
| Construct 2 | 15.3 |
| Construct 15 | 13.9 |
| Construct 19 | 14.1 |
| Construct 95 | 13.3 |
| Construct 96 | 14 |
| Construct 98 | 13.7 |
| Construct 104 | 14.1 |
| Construct 106 | 13.3 |
| Construct 107 | 13.3 |
| Construct 108 | 14.1 |
| Construct 110 | 14.4 |
| Construct 114 | 13.4 |

*See construct sequences in Tables 2-8.

Example 6: An Engineered Anti-IL13 Antibody Variant and Lebrikizumab have the Same Epitope on IL-13

Epitope binning describes a technique that characterizes whether two antibodies specific to the same target (in this case, IL-13) can each bind the target at the same time. mAb pairs are binned together if they block each other's ability to bind to the target antigen. mAb pairs that bin together typically bind to the same or overlapping epitopes on the antigen.

To characterize the binding of Construct 133, which comprises SEQ ID NOs: 3, 39, 439, and 469, vs. lebrikizumab, lebrikizumab was immobilized onto a sensor chip surface capable of measuring mAb-antigen interactions. IL-13 was first injected into the flow channel, where binding of IL-13 to lebrikizumab generated a response. Construct 133 was subsequently injected into the flow channel and the interaction response was recorded. In these studies, no response was observed after Construct 133 injection (see results in Table 23). This indicated that Construct 133 and lebrikizumab binned together and provided evidence to support that the two mAbs likely bind to a similar or the same epitope on IL-13.

TABLE 23

Antibody Binding

| Competitor Antibody or Construct ID* | Immobilized Lebrikizumab |
|---|---|
| Lebrikizumab | + |
| Tralokinumab | − |
| Cendakimab | − |
| Construct 133 | + |

+ indicates antibodies that bin with lebrikizumab.
− indicates antibodies that do not bin with lebrikizumab.
*See construct sequence 133 in Tables 2-8.

In a similar study, tralokunumab-ldrm (Adbry™) was found to have a binning response, suggesting that it has a different epitope on IL-13 than lebrikizumab.

To further characterize the epitopes of Construct 133 and lebrikizumab, hydrogen-deuterium exchange mass-spectrometry (HDX-MS) and cross-linking mass-spectrometry (XL-MS) were performed, as known in the art. Briefly, HDX-MS was performed using either IL-13 alone at a concentration of 20 uM or a mixed solution of IL-13 and purified antibody, with a final concentration of 20 uM and 40 uM, respectively. Incubation times of 15 s, 60 s, 180 s, 600 s, 1800 s, and 7200 s were performed before the exchange reaction was quenched and the protein mixture subject to proteolysis followed by LC-MS using a Waters Q-ToF Xevo G2-XS. Deuterium incorporation was determined for both IL-13 and the mixture, and peptide regions where deuterium incorporation was inhibited were considered likely to be involved in the binding to the purified antibody. Briefly, XL-MS was performed using a mixed solution of IL-13 and purified antibody, with a final concentration of 14.7 uM and 0.7 uM, respectively. 20 uL of this mixture was mixed with 2 uL of DSS (2 mg/mL stock in DMF) and the final solution was allowed to incubate for 180 minutes at room temperature. After this incubation, samples were subject to proteolysis using trypsin, chymotrypsin, ASP-N, elastase and thermolysin and analyzed using LC-MS using a Q-Exactive MS. Peptides were referenced against peptides identified from a previous peptide mapping experiment of IL-13 alone. IL-13 peptide regions that showed cross-linking to corresponding peptides from the antibody variable region were considered likely to be involved in the binding to the purified antibody. Both methods provided complementary data indicating specific amino acid regions where Construct 133 and lebrikizumab are likely to bind. This provided further evidence to support that the two mAbs likely bind to a highly overlapping epitope on IL-13 (FIG. 1).

These studies provide evidence that Construct 133 binds the same region on IL-13 as lebrikizumab and therefore they are more likely to have the same biological effect than if Construct 133 recognized a different region.

Example 7: An Engineered Anti-IL-13 Antibody Variant Demonstrated Significantly Extended Half-Life in NHPs and Pharmacokinetic Analysis of Anti-IL-13 Antibodies Extended Half-Life of an Anti-IL-13 Antibody Variant in NHPs To demonstrate the potential of engineered anti-IL13 antibody variants to improve dosing over current and anticipated standard of care mAbs in Alzheimer's disease (AD), among other diseases, Construct 133, which comprises SEQ ID NOs: 3, 39, 439, and 469, was studied in female non-human primates (NHPs) following a single bolus dose of 3 mg/kg, given either IV or SQ. Blood samples were collected serially starting with a sample pre-dose and subsequently at 0.167, 1, 4, 8, 24, 48, 96, 168, 336, 504, 674, 840, 1334, 1680, and 2160 hours post-dose. PK parameters of maximum observed serum concentration ($C_{max}$), time to maximum observed serum concentration ($T_{max}$), area under the serum concentration versus time curve from time 0 extrapolated to infinity ($AUC_{0-inf}$), clearance (CL), volume of distribution at steady-state ($V_{ss}$), half-life ($T_{1/2}$) and absolute subcutaneous bioavailability (F) were calculated. Data was analyzed to show mean serum concentration with standard deviation over time and a regression fit was performed.

Figure 9:
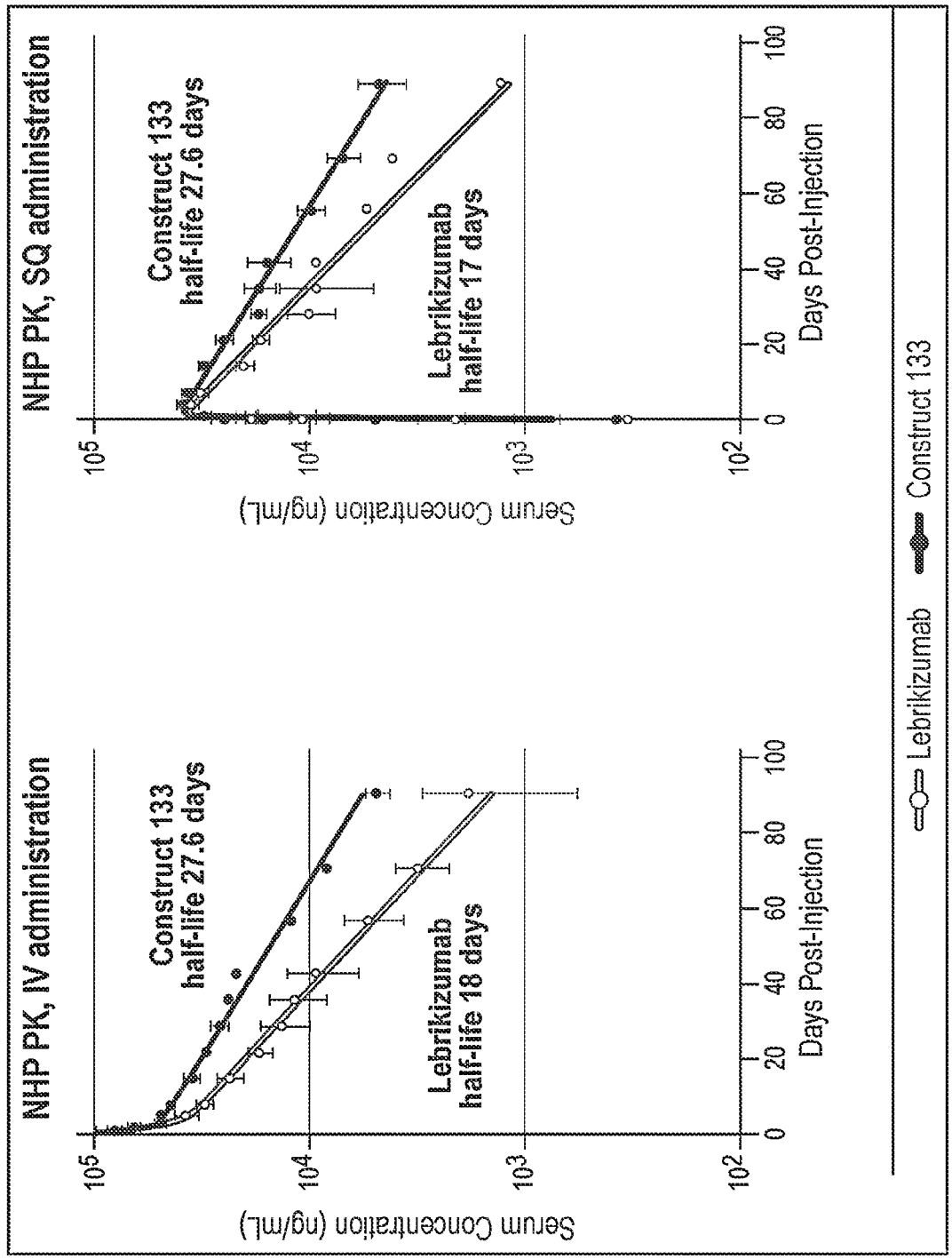
FIG. 9 is a graph depicting the serum concentration (ng/mL) of Construct 133 and lebrikizumab over time (days post injection) in non-human primates (NHPs). The half-life of Construct 15 was 27.6 days, as compared to 17 to 18 days for lebrikizumab.

In head-to-head studies of Construct 133 versus lebrikizumab in NHPs, both IV and SQ formulations of Construct 133 showed a significantly longer half-life than lebrikizumab. In these studies, the average half-life of Construct 133 was 27.6 days, as compared to 18 days for lebrikizumab, as shown in FIG. 9. Further, Construct 133 exhibited an average clearance rate of 1.45 (mL day$^{-1}$ kg$^{-1}$) in NHPs. The steady-state volume of distribution was observed to be 55.65 (mL kg$^{-1}$). Construct 133 was well-absorbed, with subcutaneous bioavailability determined to be 81.22%. Lebrikizumab exhibited an average clearance rate of 2.93 (mL day$^{-1}$ kg$^{-1}$) in NHPs. The steady-state volume of distribution was observed to be 52.10 (mL kg$^{-1}$). Lebrikizumab was well-absorbed, with subcutaneous bioavailability determined to be 75.70%. Without being bound by theory, because Construct 133 was engineered to have a YTE amino-acid substitution in the Fc region, the half-life of the IgG may have been prolonged by increasing binding to neonatal Fc receptor (FcRn) under acidic pH conditions. FcRn-bound IgG is recycled via lysosomal salvage, resulting in the IgG returning to the circulation. Construct 133's prolonged half-life may enable less frequent dosing compared to currently available treatments, which could reduce injection burden and increase compliance for patients living with atopic dermatitis and other IL-13-driven diseases.

Figure 10:
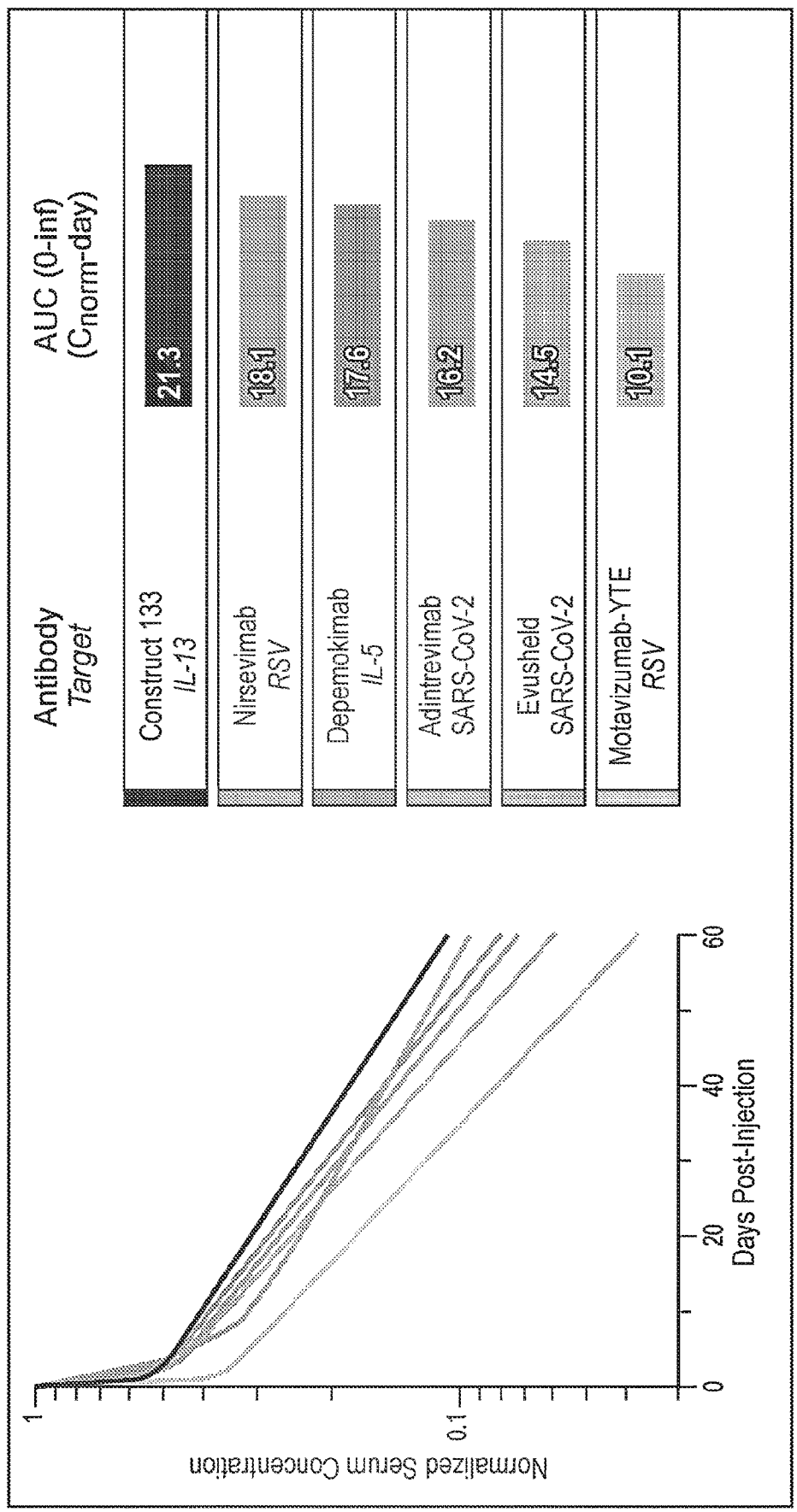
FIG. 10 is a graph depicting normalized $AUC_{0-\infty}$ ($C_{norm*day}$), or area under the curve (AUC) from dosing to infinity, among antibodies with the YTE substitution.

In a non-head-to-head comparison against third-party NHP data, Construct 133 demonstrated the highest normalized $AUC_{0-\infty}$ ($C_{norm*day}$), or area under the curve (AUC) from dosing to infinity, among antibodies with the YTE substitution, as shown in FIG. 10. Thus, the PK profile of Construct 133 appears to provide the greatest sustained concentrations, or levels of drug in the blood stream, relative to other antibodies with the YTE substitution.

The half-life extension for mAbs with YTE amino acid substitutions is dependent on the type of target (e.g., receptor vs. soluble). Therefore, the translation of NHP half-life data to human half-life data for mAbs with soluble targets was studied, and it was found that human half-life is approximately three to four times longer than NHP half-life (mean: 3.5x, median 3.1x; data not shown).

It is expected, based on this NHP half-life data, that the antibodies disclosed herein (e.g., Construct 133) will have a human half-life of approximately 80 to 110 days based on comparable mAbs with YTE amino acid substitution.

Further, based on PK modeling, with a 33-day human half-life (which, to Applicant's knowledge, would be lower than the lowest half-life for a mAb with the YTE amino acid substitutions and a soluble target reported to date), it is believed that the antibodies disclosed herein can be dosed effectively with an every two month maintenance dosing schedule. With a 50-day half-life, it is believed that the antibodies disclosed herein can be dosed effectively with an every three month maintenance dosing schedule.

To understand the maintenance dosing schedule that the antibodies disclosed herein may be able to achieve, known PK parameters for lebrikizumab were used. These PK parameters provided an understanding of how lebrikizumab was distributed throughout the body and cleared. Based on these known parameters, a two-compartment PK model with first-order absorption was built, which is standard for mAbs, to predict concentration or drug levels, over time of both lebrikizumab and the antibodies disclosed herein. Key parameters included 0.156 L/day for clearance (CL), 4.10 L for central volume (Vc), 0.239 day-1 for absorption rate (ka) and 85.6% for bioavailability.

It is believed that efficacy in inflammatory conditions, such as AD, is driven by $C_{trough}$, or the minimal concentration of the mAb. Therefore, based on the model described above, the target $C_{trough}$ of the antibodies disclosed herein was set to be equal to lebrikizumab's $C_{trough}$ in maintenance with every one month dosing, which was 31.3 mg/L. Given the overlapping epitopes of lebrikizumab and certain antibodies disclosed herein, and similarity in potency across multiple in vitro assays, the necessary exposures for potential clinical activity of the antibodies disclosed herein can be predicted. By modeling $K_{elimination}$, the elimination rate constant or the fraction of drug eliminated in a given time, and half-life to maintain concentrations of the disclosed antibodies above 31.3 mg/L, at least a 33-day half-life is would be required to dose the disclosed antibodies every two months in maintenance and at least a 50-day half-life would be required to dose the disclosed antibodies every three months in maintenance assuming a dose of 300 mg.

Thus, with a 33-day human half-life, it is believed that the antibodies disclosed herein can be dosed effectively with an every two month maintenance dosing schedule. With a 50-day half-life, it is believed that the antibodies disclosed herein can be dosed effectively with an every three month maintenance dosing schedule.

Pharmacokinetic Analysis of Anti-IL-13 Antibodies

In further experiments, multiple in vivo pharmacokinetic (PK) studies were performed where lebrikizumab, additional variants of Construct 15 or Construct 98 with one or more amino acid substitutions in the heavy chain constant region (Constructs 133-137 or 137 and 140, respectively), and/or additional variants with one or more amino acid substitutions in the heavy chain constant region (Constructs 141 and 144) were also tested.

Studies were performed using cynomolgus monkey (*Macaca fascicularis*), where any matching or subcutaneous (SQ)/intravenous (IV) cohorts were either all female, ranging from 1.5 kg to 2.0 kg in weight, or all males, ranging from 2.9 kg to 3.3 kg in weight. Animals were administered test agents by IV bolus and/or SQ injection on Day 0 at a dose of 3 mg/kg for each antibody and serum samples were taken regularly throughout the study.

Figure 11:
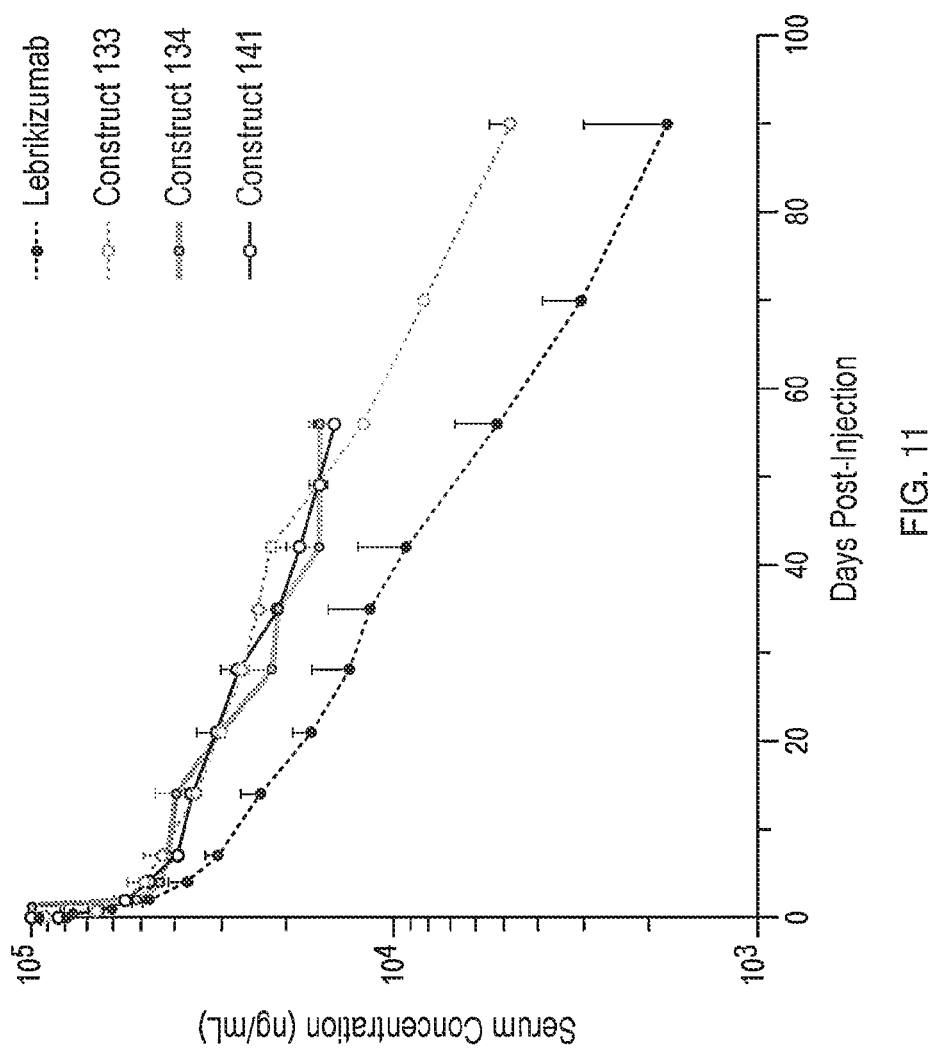
FIG. 11 is a graph depicting the serum concentration (ng/ml) of the indicated engineered anti-IL-13 antibodies administered intravenously (IV) in NHPs.
Figure 12:
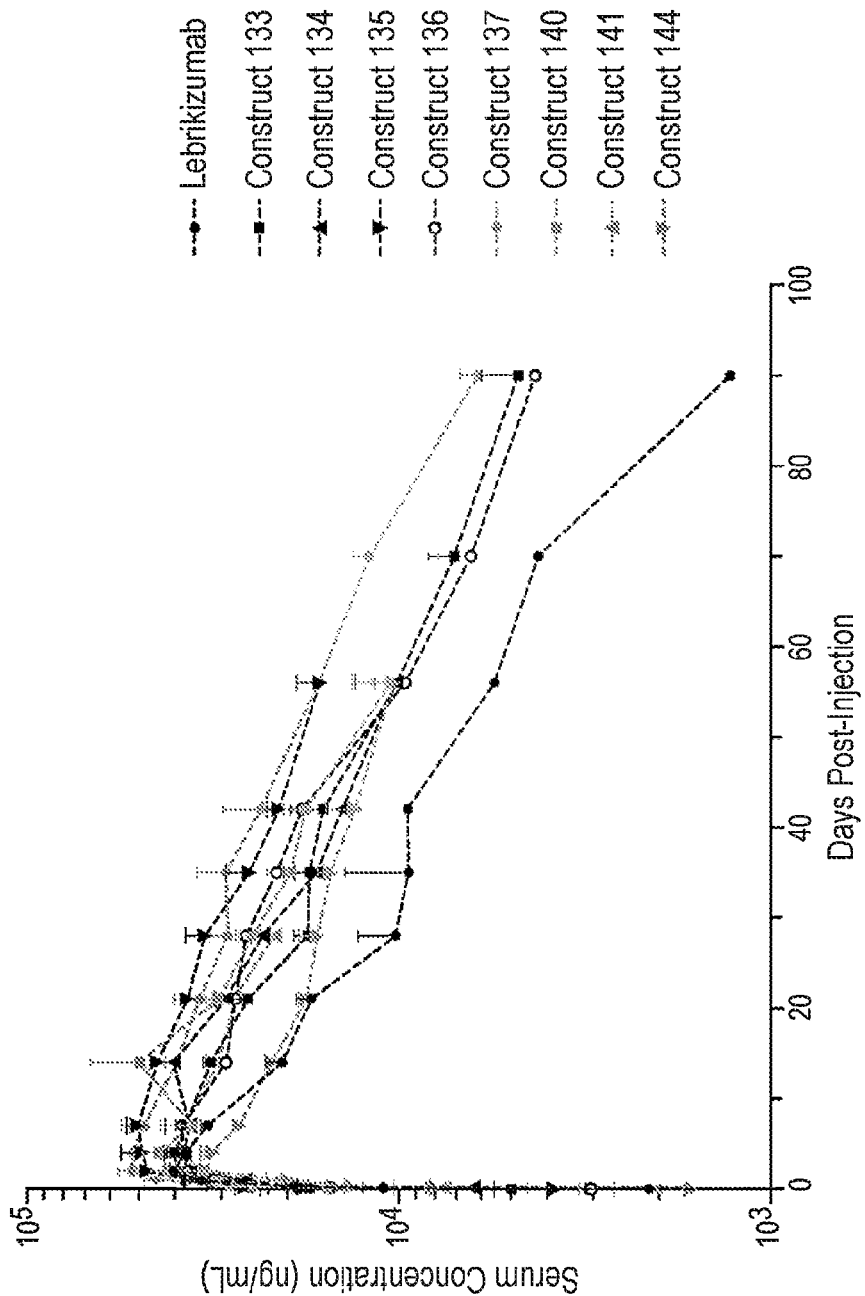
FIG. 12 is a graph depicting the serum concentration (ng/mL) of the indicated engineered anti-IL-13 antibodies administered subcutaneously (SQ) in NHPs.

PK parameters were determined from cynomolgus serum samples up to day 56 (1334 hours), with a subset of cohorts up to day 90 (2160 hours), with average PK curves are shown in FIG. 11 for IV administration and FIG. 12 for SQ administration. The PK analysis demonstrated that Constructs 133, 134, 135, 136, 137, 140, 141, and 144 each had improved half-life and reduction in serum clearance rates compared to those of lebrikizumab as reported in Table 24. In cases where bioavailability (F) could be determined, Constructs 133, 134, and 141 were shown to possess equivalent bioavailability to that of lebrikizumab (Table 25).

TABLE 24

Half-life and Serum Clearance Rates

| Construct ID[#] and Administration Group | Animal | $AUC_{inf}$ (ng · hours · $mL^{-1}$) | Half-Life (Days) | CL* (mL · $day^{-1}$ · $kg^{-1}$) | $V_{ss}$* (mL · $kg^{-1}$) |
|---|---|---|---|---|---|
| Lebrikizumab - IV | 1501 | 17447678.05 | 11.02 | 4.13 | 51.38 |
|  | 1502 | 28812691.42 | 18.86 | 2.50 | 55.87 |
|  | 1501 | 33491428.36 | 24.35 | 2.15 | 70.54 |
| Lebrikizumab - SQ | 2501 | 28290795.91 | 18.82 | 1.93 | 52.83 |
|  | 2502 | 14531783.14 | 11.33 | 3.75 | 42.26 |
|  | 2503 | 17545785.64 | 10.42 | 3.11 | 39.72 |
| Construct 133 - IV | 6501 | 54367740.94 | 30.25 | 1.32 | 53.97 |
|  | 6502 | 49429927.46 | 28.27 | 1.46 | 56.14 |
|  | 6503 | 47738132.48 | 26.22 | 1.51 | 52.07 |
| Construct 133 - SQ | 7501 | 50202816.21 | 30.85 | 1.16 | 53.73 |
|  | 7502 | 31546038.62 | 22.44 | 1.85 | 60.32 |
|  | 7503 | 41329262.82 | 27.65 | 1.41 | 57.68 |
| Construct 134 - IV | 3501 | 52254317.47 | 21.38 | 1.38 | 47.07 |
|  | 3502 | 33366131.55 | 17.24 | 2.16 | 54.75 |
|  | 3503 | 77329739.21 | 41.87 | 0.93 | 46.90 |
| Construct 134 - SQ | 4501 | 54533364.13 | 50.94 | 0.96 | 65.60 |
|  | 4502 | 36701086.34 | 20.48 | 1.43 | 42.05 |
|  | 4503 | 27442862.48 | 14.49 | 1.91 | 38.48 |
| Construct 135 - SQ | 5501 | 50614453.99 | 29.68 | 1.42 | 57.79 |
|  | 5502 | 75200216.97 | 40.07 | 0.96 | 55.48 |
|  | 5503 | 61123113.94 | 27.93 | 1.18 | 48.56 |
| Construct 136 - SQ | 8501 | 47846929.29 | 27.86 | 1.50 | 56.97 |
|  | 8502 | 32127535.46 | 21.51 | 2.24 | 66.76 |
|  | 8503 | 44101872.29 | 30.83 | 1.63 | 68.10 |
| Construct 137 - SQ | 9501 | 46216823.54 | 16.57 | 1.56 | 52.59 |
|  | 9502 | 32421239.31 | 25.86 | 2.22 | 68.74 |
|  | 9503 | 44629524.73 | 34.27 | 1.61 | 70.01 |
| Construct 140 - SQ | 10501 | 51739935.51 | 27.32 | 1.39 | 49.24 |
|  | 10502 | 41305658.5 | 21.82 | 1.74 | 53.20 |
|  | 10503 | 47527303.18 | 32.84 | 1.51 | 72.48 |
| Construct 141 - IV | 4089 | 45698126.79 | 27.2 | 1.58 | 60.29 |
|  | 2095 | 62600360.39 | 31.99 | 1.15 | 55.01 |
|  | 3027 | 53748965.77 | 33.88 | 1.34 | 63.50 |
| Construct 141 - SQ | 1131 | 56004213.41 | 45.72 | 0.97 | 66.44 |
|  | 1083 | 38648918.97 | 31.47 | 1.41 | 64.56 |
|  | 1127 | 27810354.27 | 21.22 | 1.96 | 63.03 |
| Construct 144 - SQ | 11501 | 28455075.58 | 21.78 | 2.53 | 85.42 |
|  | 11502 | 22141956.08 | 18.99 | 3.25 | 81.00 |
|  | 11503 | 45675112.33 | 43.35 | 1.58 | 103.64 |

*These values are adjusted for bioavailability in cohorts Lebrikizumab, Construct 133, Construct 134, and Construct 141.
[#]See construct sequences in Tables 2-8.

TABLE 25

Construct Bioavailability

| Construct ID* | Bioavailability (%) |
|---|---|
| Lebrikizumab | 75.70% |
| Construct 133 | 81.22% |
| Construct 134 | 72.83% |
| Construct 141 | 75.57% |

*See construct sequences in Tables 2-8.

Figure 13:
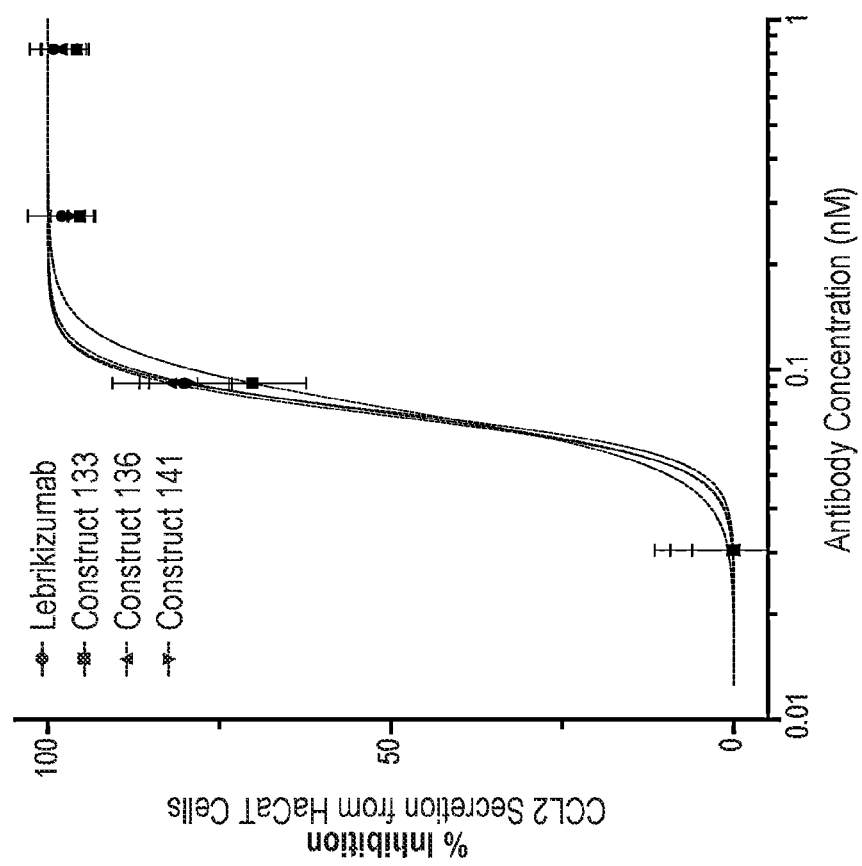
FIG. 13 is a graph depicting the percentage of inhibition of IL-13-induced CCL2 secretion in HaCaT cells that have been incubated with the indicated engineered anti-IL-13 antibodies, as determined by Luminex.
Figure 14:
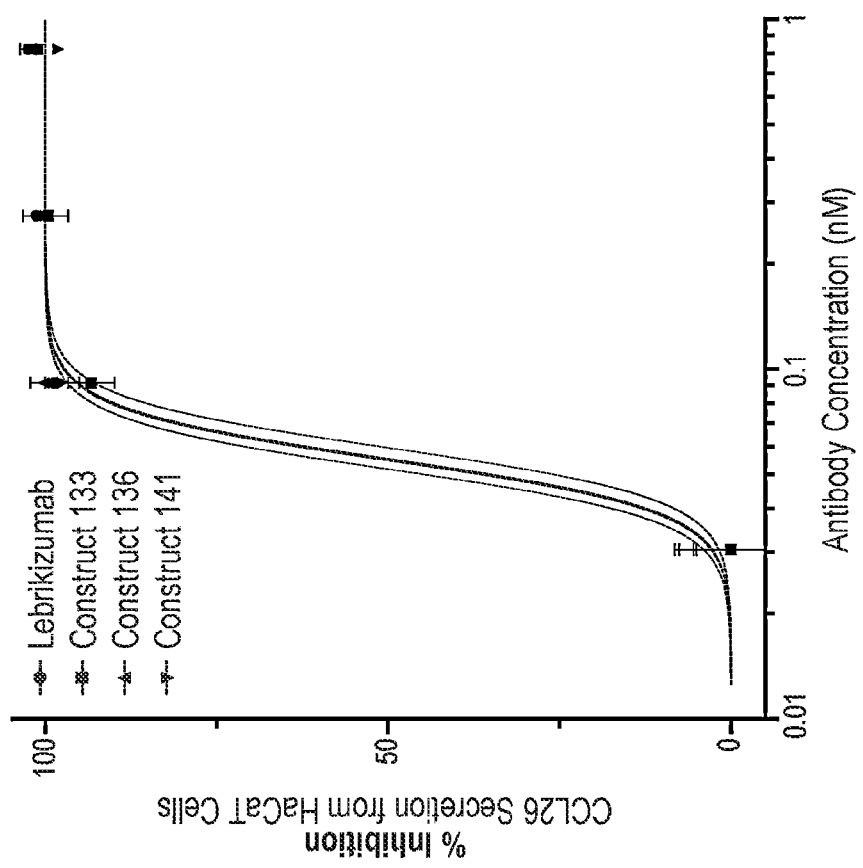
FIG. 14 is a graph depicting the percentage of inhibition of CCL26 secretion in HaCaT cells that have been incubated with the indicated engineered anti-IL-13 antibodies, as determined by Luminex.
Figure 15:
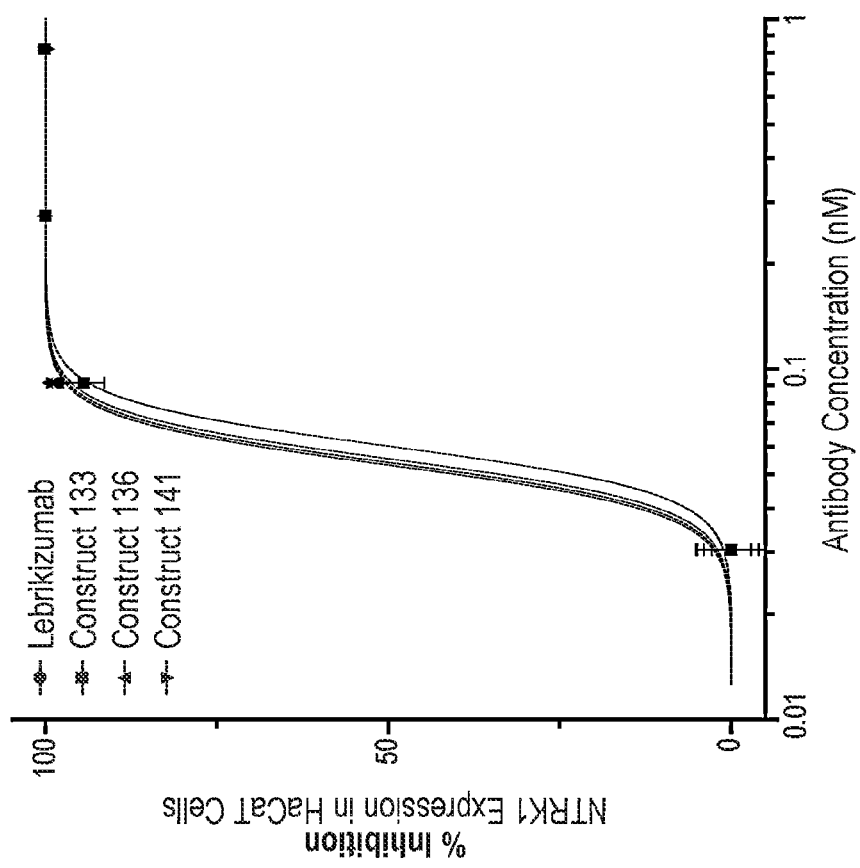
FIG. 15 is a graph depicting the percentage of inhibition of NTRK1 gene expression in HaCaT cells that have been incubated with the indicated engineered anti-IL-13 antibodies, as determined by QuantiGene assay.

Example 8. Inhibition of IL-13 Induced Secretion of CCL2 and CCL26 and Expression of NTRK1 in HaCaT Cells Inhibition of CCL26 (eotaxin-3) and CCL2 (MCP-1) secretion (FIG. 13 and FIG. 14, respectively) and NTRK1 expression (FIG. 15) by HaCaT cells was used to evaluate the functional activity of antibodies to block IL-13-induced biological activity. HaCaT cells were seeded at 20,000 cells in 100 uL of DMEM+10% FBS and cultured overnight at 37° C. The next day, a 150 uL mixture of hIL-13 and purified antibody were added to the wells, resulting in a final concentration of 50 ng/ml of IL-13 with 0-206.5 nM purified antibody. Cells were then further incubated at 37° C. for 48 hours. Following incubation, culture supernatant was collected and levels of secreted CCL26 and CCL2 were measured using a commercial Luminex-based immunoassay kit (R&D Systems) and analyzed according to manufacturer's instructions. Determined concentrations of CCL26 and CCL2 in each well were analyzed using GraphPad Prism. $IC_{50}$ values were determined as the concentration of antibody required to inhibit 50% of the maximum concentration detected with incubation of 50 ng/ml of IL-13 alone.

Cells remaining in the assay plates were lysed and mRNA extracted for analysis of NTRK1 gene expression using a commercial Quantigene kit (ThermoFisher). Levels of NTRK1 mRNA were determined according to the manufacturer's protocol and analyzed in GraphPad Prism. NTRK1 gene expression was quantified as a ratio of NTRK1 mRNA levels relative to the housekeeping gene, PPIB, and $IC_{50}$ values calculated as the concentration of antibody required to inhibit 50% of the maximum gene expression detected using 50 ng/ml of hIL-13 alone. Results are summarized in Table 26.

TABLE 26

CCL26 and CCL2 secretion and NTRK1 expression

| Construct ID* | CCL2 Secretion $IC_{50}$ (nM) | CCL26 Secretion $IC_{50}$ (nM) | NTRK1 Expression $IC_{50}$ (nM) |
|---|---|---|---|
| Lebrikizumab | 0.076 | 0.055 | 0.056 |
| Construct 133 | 0.077 | 0.060 | 0.062 |
| Construct 136 | 0.074 | 0.052 | 0.053 |
| Construct 141 | 0.075 | 0.055 | 0.054 |

*See construct sequences in Tables 2-8.

Example 9. Monomer Purity after Affinity Capture from Stable Pools

The monomer purity from one-step affinity capture is a determinant for the final yield and unit cost of an antibody under cGMP production. To characterize this, briefly, CHO stable pools were generated separately for each antibody in a workstream that led to master cell bank selection for cGMP production. The affinity capture step was performed using a Mabselect SuRe column. Novel IgG1 variants (e.g., Constructs 132, 133, 136, 137, 140, 141, and 144) remained a clear solution with <15% aggregate after the one-step purification. Novel IgG4 variants (Constructs 134, 135, 138, 139, 142, and 143) had an opalescent appearance with some precipitation and an aggregation sensitivity (>68% aggregate) when using an elution buffer of 50 mM sodium citrate, 150 mM sodium chloride at pH 3.0. The novel IgG4 variants had lower aggregate levels when eluted with either 50 mM acetic acid, pH 2.8 or with 100 mM sodium acetate, 800 mM arginine at pH 3.5. At the higher pH of 3.5, the arginine was needed to retain a suitable recovery.

Results are summarized in Table 27. Novel IgG1 and IgG4 variants demonstrate greater monomer purity directly out of affinity capture with optimized elution conditions when compared to lebrikizumab variants (Constructs 128-131).

TABLE 27

Anti-IL-13 Antibody Monomer Purity

| Construct ID* | One-Step Monomer Purity (%) |
|---|---|
| Construct 128 | 87.7 |
| Construct 129 | 90.5 |
| Construct 130 | 81.6 |
| Construct 131 | 82.9 |
| Construct 132 | 94.7 |
| Construct 133 | 90.9 |
| Construct 134 | 91.7 |
| Construct 135 | 91.4 |
| Construct 136 | 90.3 |
| Construct 137 | 92.7 |
| Construct 138 | 94.0 |
| Construct 139 | 92.0 |
| Construct 140 | 89.7 |
| Construct 141 | 94.1 |
| Construct 142 | 90.1 |
| Construct 143 | 91.5 |
| Construct 144 | 92.4 |

*See construct sequences in Tables 2-8.

Example 10. Accelerated Stability

As demonstrated by this example, novel variants in an IgG1 construct had a lower propensity to aggregate and were more resistant to changes in the basic species under various stress conditions, as shown in Table 28. The proportion of basic species was determined through capillary isoelectric focusing (ciEF), performed as known in the art. The variants related to lebrikizumab (Constructs 128-131) and IgG4 variants (Constructs 134, 135, 142, and 143); as described in Examples 1-7) were more susceptible to aggregation and changes in the basic species compared to the novel IgG1 variants (e.g., Constructs 132, 133, 136, 137, 140, 141, and 144).

TABLE 28

Anti-IL-13 Antibody Stability Change

| Construct ID* | 40° C. Stability-Change in Monomer Purity | 40° C. Stability-Change Basic Species | pH 3.5 Stability - Change Monomer Purity | pH 3.5 Stability - Change Basic Species |
|---|---|---|---|---|
| Construct 128 | −10.0% | +26.5% | −10.0% | +6.3% |
| Construct 129 | −3.2% | +8.2% | −12.7% | +5.7% |
| Construct 130 | −2.2% | −13.8% | −1.1% | +1.5% |
| Construct 131 | −2.1% | −11.2% | −1.6% | +0.6% |
| Construct 132 | −0.8% | +2.4% | −0.7% | +1.2% |
| Construct 133 | −2.1% | +0.9% | −1.3% | +0.9% |
| Construct 134 | −1.4% | +10.3% | −19.5% | +13.3% |
| Construct 135 | −1.8% | +2.1% | −15.7% | +8.0% |
| Construct 136 | −0.9% | +1.5% | −1.4% | +0.4% |
| Construct 137 | −1.5% | +2.4% | −1.3% | +1.6% |
| Construct 140 | −3.6% | +1.5% | −1.4% | +0.8% |
| Construct 141 | −2.5% | +0.0% | −0.5% | +0.5% |
| Construct 142 | −4.0% | +7.1% | −8.9% | +6.5% |
| Construct 143 | −4.3% | +5.1% | −11.1% | +5.1% |
| Construct 144 | −3.0% | +2.0% | −0.1% | +1.2% |

*See construct sequences in Tables 2-8.
Assessment of clones for changes in monomer purity and basic species were evaluated at day 0 and day 14 for 40° C. stability and at day 0 and day 2 for pH 3.5 stability.
N.T.—Not Tested.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

Informal sequence listing

| Description | Sequence | SEQ ID NO |
|---|---|---|
| Heavy Chain Variable domain HC0 | QVQLQESGPGLVAPSQSLSITCTVSGFSLNAYSVNWVRQP PGKGLEWLGMIWGDGKIVYNSALKSRLNISKDSSKSQVFL KMSSLQSDDTARYYCAGDGYYPYAMDNWGHGTSVTVSS | SEQ ID NO: 1 |
| Heavy Chain Variable domain HC0_M | QVQLQESGPGLVAPSQSLSITCTVSGFSLNAYSVNWVRQP PGKGLEWLGMIWGDGKIVYNSALKSRLTISKDSSKSQVFL KMSSLQSDDTARYYCAGDGYYPYAMDNWGHGTSVTVSS | SEQ ID NO: 2 |
| Heavy Chain Variable domain HC1 | EVQLQESGPGLVKPSETLSLTCTVSGFSLNAYSVNWIRQPP GKGLEWLGMIWGDGKIVYNSALKSRLTISKDSSKNQVSLK LSSVTAADTAVYYCAGDGYYPYAMDNWGQGTTVTVSS | SEQ ID NO: 3 |
| Heavy Chain Variable domain HC2 | EVQLVQSGAEVKKPGASVKVSCKASGFSLNAYSVNWVR QAPGQGLEWLGMIWGDGKIVYNSALKSRLTITKDSSTSTV YMELSSLRSEDTAVYYCAGDGYYPYAMDNWGQGTTVTV SS | SEQ ID NO: 4 |
| Heavy Chain Variable domain HC3 | EVQLVQSGAEVKKPGSSVKVSCKASGFSLNAYSVNWVRQ APGQGLEWLGMIWGDGKIVYNSALKSRLTITKDSSTSTVY MELSSLRSEDTAVYYCAGDGYYPYAMDNWGQGTTVTVS S | SEQ ID NO: 5 |
| Heavy Chain Variable domain HC4 | EVQLVESGGGLVKPGGSLRLSCAASGFSLNAYSVNWVRQ APGKGLEWLGMIWGDGKIVYNSALKSRLTISKDSSKNTVY LQMNSLKTEDTAVYYCAGDGYYPYAMDNWGQGTTVTV SS | SEQ ID NO: 6 |
| Heavy Chain Variable domain HC5 | EVQLLESGGGLVQPGGSLRLSCAASGFSLNAYSVNWVRQ APGKGLEWLGMIWGDGKIVYNSALKSRLTISKDSSKNTVY LQMNSLRAEDTAVYYCAGDGYYPYAMDNWGQGTTVTV SS | SEQ ID NO: 7 |

| Description | Sequence | SEQ ID NO |
|---|---|---|
| Heavy Chain Variable domain HC6 | EVQLQESGPGLVKPSETLSLTCTVSGGSLNAYSVNWVRQP PGKGLEWLGMIWGDGKIVYNSALKSRLTISLDTSKSQVFL KMSSLTAADTAVYYCARDGYYPYAMDNWGQGTTVTVSS | SEQ ID NO: 8 |
| Heavy Chain Variable domain HC7 | QVQLQESGPGLVKPSETLSLTCTVSGGSLNAYSWNWVRQ PPGKGLEWLGYIYGDGKTNYNPALKSRLTISLDTSKSQVF LKMSSLTAADTAVYYCARDGYYYYAMDVWGQGTTVTV SS | SEQ ID NO: 9 |
| Heavy Chain Variable domain HC5m1 | EVQLLESGGGLVQPGGSLRLSCAASGYSLNAYSVNWVRQ APGKGLEWLGMIWGDGKIVYNSALKSRLTISKDSSKNTVY LQMNSLRAEDTAVYYCAGDGYYPYAMDNWGQGTTVTV SS | SEQ ID NO: 10 |
| Heavy Chain Variable domain HC5m2 | EVQLLESGGGLVQPGGSLRLSCAASGFSLRAYSVNWVRQ APGKGLEWLGMIWGDGKIVYNSALKSRLTISKDSSKNTVY LQMNSLRAEDTAVYYCAGDGYYPYAMDNWGQGTTVTV SS | SEQ ID NO: 11 |
| Heavy Chain Variable domain HC5m3 | EVQLLESGGGLVQPGGSLRLSCAASGFSLHAYSVNWVRQ APGKGLEWLGMIWGDGKIVYNSALKSRLTISKDSSKNTVY LQMNSLRAEDTAVYYCAGDGYYPYAMDNWGQGTTVTV SS | SEQ ID NO: 12 |
| Heavy Chain Variable domain HC5m4 | EVQLLESGGGLVQPGGSLRLSCAASGFSLDAYSVNWVRQ APGKGLEWLGMIWGDGKIVYNSALKSRLTISKDSSKNTVY LQMNSLRAEDTAVYYCAGDGYYPYAMDNWGQGTTVTV SS | SEQ ID NO: 13 |
| Heavy Chain Variable domain HC5m5 | EVQLLESGGGLVQPGGSLRLSCAASGFSLYAYSVNWVRQ APGKGLEWLGMIWGDGKIVYNSALKSRLTISKDSSKNTVY LQMNSLRAEDTAVYYCAGDGYYPYAMDNWGQGTTVTV SS | SEQ ID NO: 14 |
| Heavy Chain Variable domain HC5m6 | EVQLLESGGGLVQPGGSLRLSCAASGFSLSAYSVNWVRQ APGKGLEWLGMIWGDGKIVYNSALKSRLTISKDSSKNTVY LQMNSLRAEDTAVYYCAGDGYYPYAMDNWGQGTTVTV SS | SEQ ID NO: 15 |
| Heavy Chain Variable domain HC5m7 | EVQLLESGGGLVQPGGSLRLSCAASGFSLNRYSVNWVRQ APGKGLEWLGMIWGDGKIVYNSALKSRLTISKDSSKNTVY LQMNSLRAEDTAVYYCAGDGYYPYAMDNWGQGTTVTV SS | SEQ ID NO: 16 |
| Heavy Chain Variable domain HC5m8 | EVQLLESGGGLVQPGGSLRLSCAASGFSLNKYSVNWVRQ APGKGLEWLGMIWGDGKIVYNSALKSRLTISKDSSKNTVY LQMNSLRAEDTAVYYCAGDGYYPYAMDNWGQGTTVTV SS | SEQ ID NO: 17 |
| Heavy Chain Variable domain HC5m9 | EVQLLESGGGLVQPGGSLRLSCAASGFSLNHYSVNWVRQ APGKGLEWLGMIWGDGKIVYNSALKSRLTISKDSSKNTVY LQMNSLRAEDTAVYYCAGDGYYPYAMDNWGQGTTVTV SS | SEQ ID NO: 18 |
| Heavy Chain Variable domain HC5m10 | EVQLLESGGGLVQPGGSLRLSCAASGFSLNQYSVNWVRQ APGKGLEWLGMIWGDGKIVYNSALKSRLTISKDSSKNTVY LQMNSLRAEDTAVYYCAGDGYYPYAMDNWGQGTTVTV SS | SEQ ID NO: 19 |
| Heavy Chain | EVQLLESGGGLVQPGGSLRLSCAASGFSLNEYSVNWVRQ APGKGLEWLGMIWGDGKIVYNSALKSRLTISKDSSKNTVY | SEQ ID NO: 20 |

| Description | Sequence | SEQ ID NO |
|---|---|---|
| Variable domain HC5m11 | LQMNSLRAEDTAVYYCAGDGYYPYAMDNWGQGTTVTVSS | |
| Heavy Chain Variable domain HC5m12 | EVQLLESGGGLVQPGGSLRLSCAASGFSLNSYSVNWVRQAPGKGLEWLGMIWGDGKIVYNSALKSRLTISKDSSKNTVYLQMNSLRAEDTAVYYCAGDGYYPYAMDNWGQGTTVTVSS | SEQ ID NO: 21 |
| Heavy Chain Variable domain HC5m13 | EVQLLESGGGLVQPGGSLRLSCAASGFSLNYYSVNWVRQAPGKGLEWLGMIWGDGKIVYNSALKSRLTISKDSSKNTVYLQMNSLRAEDTAVYYCAGDGYYPYAMDNWGQGTTVTVSS | SEQ ID NO: 22 |
| Heavy Chain Variable domain HC5m14 | EVQLLESGGGLVQPGGSLRLSCAASGFSLNAESVNWVRQAPGKGLEWLGMIWGDGKIVYNSALKSRLTISKDSSKNTVYLQMNSLRAEDTAVYYCAGDGYYPYAMDNWGQGTTVTVSS | SEQ ID NO: 23 |
| Heavy Chain Variable domain HC5m15 | EVQLLESGGGLVQPGGSLRLSCAASGFSLNAYSVNWVRQAPGKGLEWLGMIWSDGKIVYNSALKSRLTISKDSSKNTVYLQMNSLRAEDTAVYYCAGDGYYPYAMDNWGQGTTVTVSS | SEQ ID NO: 24 |
| Heavy Chain Variable domain HC5m16 | EVQLLESGGGLVQPGGSLRLSCAASGFSLNAYSVNWVRQAPGKGLEWLGMIWADGKIVYNSALKSRLTISKDSSKNTVYLQMNSLRAEDTAVYYCAGDGYYPYAMDNWGQGTTVTVSS | SEQ ID NO: 25 |
| Heavy Chain Variable domain HC5m17 | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGHGYYPYAMDNWGQGTTVTVSS | SEQ ID NO: 26 |
| Heavy Chain Variable domain HC5m18 | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDLYYPYAMDNWGQGTTVTVSS | SEQ ID NO: 27 |
| Heavy Chain Variable domain HC5m19 | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDKYYPYAMDNWGQGTTVTVSS | SEQ ID NO: 28 |
| Heavy Chain Variable domain HC5m20 | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDGYYGYAMDNWGQGTTVTVSS | SEQ ID NO: 29 |
| Heavy Chain Variable domain HC5m21 | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDGYYAYAMDNWGQGTTVTVSS | SEQ ID NO: 30 |
| Heavy Chain Variable domain HC5m22 | EVQLLESGGGLVQPGGSLRLSCAASGFSLNAYSVNWVRQAPGKGLEWLGMIWGDGKIVYNSALKSRLTISKDSSKNTVYLQMNSLRAEDTAVYYCAGDGYYSYAMDNWGQGTTVTVSS | SEQ ID NO: 31 |

-continued

| Description | Sequence | SEQ ID NO |
|---|---|---|
| Heavy Chain Variable domain HC5m23 | EVQLLESGGGLVQPGGSLRLSCAASGFSLNAYSVNWVRQ APGKGLEWLGMIWGDGKIVYNSALKSRLTISKDSSKNTVY LQMNSLRAEDTAVYYCAGDGYYTYAMDNWGQGTTVTV SS | SEQ ID NO: 32 |
| Light Chain Variable domain LC0 | NIVLTQSPASLAVSLGQRATISCRASKSVDSYGNSFMHWY QQKPGQPPKLLIYLASNLESGVPARFSGSGSRTDFTLTIDPV EADDAASYYCQQNNEDPRTFGGGTKLEIK | SEQ ID NO: 33 |
| Light Chain Variable domain LC1 | DIQLTQSPSSLSASVGDRVTITCRASKSVDSYGNSFMHWY QQKPGKAPKLLIYLASNLESGVPSRFSGSGSRTDFTLTISSL QPEDFATYYCQQNNEDPRTFGGGTKVEIK | SEQ ID NO: 34 |
| Light Chain Variable domain LC2 | DIQLTQSPSSLSASVGDRVTITCRASKSVDSYGNSFMHWY QQKPGKAPKLLIYLASNLESGVPSRFSGSGSRTDFTLTISSL QPEDFATYYCQQNNEDPRTFGGGTKVEIK | SEQ ID NO: 35 |
| Light Chain Variable domain LC3 | EIVLTQSPATLSVSPGERATLSCRASKSVDSYGNSFMHWY QQKPGQAPRLLIYLASNLESGIPARFSGSGSRTEFTLTISSL QSEDFAVYYCQQNNEDPRTFGGGTKVEIK | SEQ ID NO: 36 |
| Light Chain Variable domain LC4 | DIVLTQSPLSLPVTPGEPASISCRASKSVDSYGNSFMHWYL QKPGQSPQLLIYLASNLESGVPDRFSGSGSRTDFTLKISRVE AEDVGVYYCQQNNEDPRTFGGGTKVEIK | SEQ ID NO: 37 |
| Light Chain Variable domain LC5 | DIVLTQSPDSLAVSLGERATINCRASKSVDSYGNSFMHWY QQKPGQPPKLLIYLASNLESGVPDRFSGSGSTDFTLTISSL QAEDVAVYYCQQNNEDPRTFGGGTKVEIK | SEQ ID NO: 38 |
| Light Chain Variable domain LC6 | DIQLTQSPSSLSASVGDRVTITCRASKSVDSYGNSFMHWY QQKPGKAPKLLIYLASNLESGVPSRFSGSGSTDFTLTISSL QPEDFATYYCQQNNEDPRTFGGGTKVEIK | SEQ ID NO: 39 |
| Light Chain Variable domain LC7 | EIVLTQSPATLSVSPGERATLSCRASKSVDSYGNSFMHWY QQKPGQAPRLLIYLASNLESGIPARFSGSGSTEFTLTISSL QSEDFAVYYCQQNNEDPRTFGGGTKVEIK | SEQ ID NO: 40 |
| Light Chain Variable domain LC8 | DIVLTQSPLSLPVTPGEPASISCRASKSVDSYGNSFMHWYL QKPGQSPQLLIYLASNLESGVPDRFSGSGSTDFTLKISRVE AEDVGVYYCQQNNEDPRTFGGGTKVEIK | SEQ ID NO: 41 |
| Light Chain Variable domain LC9 | DIVLTQSPASLAVSPGERATISCRASKSVDSYGNSFMHWY QQKPGQPPKLLIYLASNLESGVPDRFSGSGSTDFTLTISRV EADDVAVYYCQQNNEDPRTFGGGTKLEIK | SEQ ID NO: 42 |
| Light Chain Variable domain LC10 | DIVLTQSPASLAVSPGERATISCRASQSVDSNGNNFLHWY QQKPGQPPKLLIYLASNRESGVPDRFSGSGSTDFTLTISR VEADDVAVYYCQQNNHTPRTFGGGTKLEIK | SEQ ID NO: 43 |
| Light Chain Variable domain LC6_m1 | DIQLTQSPSSLSASVGDRVTITCRASKSVDSYGNSRMHWY QQKPGKAPKLLIYLASNLESGVPSRFSGSGSTDFTLTISSL QPEDFATYYCQQNNEDPRTFGGGTKVEIK | SEQ ID NO: 44 |
| Light Chain Variable domain LC6_m2 | DIQLTQSPSSLSASVGDRVTITCRASKSVDSYGNSSMHWY QQKPGKAPKLLIYLASNLESGVPSRFSGSGSTDFTLTISSL QPEDFATYYCQQNNEDPRTFGGGTKVEIK | SEQ ID NO: 45 |
| Light Chain Variable domain LC6_m3 | DIQLTQSPSSLSASVGDRVTITCRASKSVDSYGNSFMHWY QQKPGKAPKLLIRLASNLESGVPSRFSGSGSTDFTLTISSL QPEDFATYYCQQNNEDPRTFGGGTKVEIK | SEQ ID NO: 46 |

| Informal sequence listing | | |
|---|---|---|
| Description | Sequence | SEQ ID NO |
| Light Chain Variable domain LC6_m4 | DIQLTQSPSSLSASVGDRVTITCRASKSVDSYGNSFMHWY QQKPGKAPKLLIFLASNLESGVPSRFSGSGSGTDFTLTISSL QPEDFATYYCQQNNEDPRTFGGGTKVEIK | SEQ ID NO: 47 |
| Light Chain Variable domain LC6_m5 | DIQLTQSPSSLSASVGDRVTITCRASKSVDSYGNSFMHWY QQKPGKAPKLLIYLASHLESGVPSRFSGSGSGTDFTLTISSL QPEDFATYYCQQNNEDPRTFGGGTKVEIK | SEQ ID NO: 48 |
| Light Chain Variable domain LC6_m6 | DIQLTQSPSSLSASVGDRVTITCRASKSVDSYGNSFMHWY QQKPGKAPKLLIYLASDLESGVPSRFSGSGSGTDFTLTISSL QPEDFATYYCQQNNEDPRTFGGGTKVEIK | SEQ ID NO: 49 |
| Light Chain Variable domain LC6_m7 | DIQLTQSPSSLSASVGDRVTITCRASKSVDSYGNSFMHWY QQKPGKAPKLLIYLASQLESGVPSRFSGSGSGTDFTLTISSL QPEDFATYYCQQNNEDPRTFGGGTKVEIK | SEQ ID NO: 50 |
| Light Chain Variable domain LC6_m8 | DIQLTQSPSSLSASVGDRVTITCRASKSVDSYGNSFMHWY QQKPGKAPKLLIYLASELESGVPSRFSGSGSGTDFTLTISSL QPEDFATYYCQQNNEDPRTFGGGTKVEIK | SEQ ID NO: 51 |
| Light Chain Variable domain LC6_m9 | DIQLTQSPSSLSASVGDRVTITCRASKSVDSYGNSFMHWY QQKPGKAPKLLIYLASNLESGVPSRFSGSGSGTDFTLTISSL QPEDFATYYCQQNHEDPRTFGGGTKVEIK | SEQ ID NO: 52 |
| Light Chain Variable domain LC6_m10 | DIQLTQSPSSLSASVGDRVTITCRASKSVDSYGNSFMHWY QQKPGKAPKLLIYLASNLESGVPSRFSGSGSGTDFTLTISSL QPEDFATYYCQQNYEDPRTFGGGTKVEIK | SEQ ID NO: 53 |
| Light Chain Variable domain LC6_11 | DIQLTQSPSSLSASVGDRVTITCRASKSVDSYGNSFMHWY QQKPGKAPKLLIYLASNLESGVPSRFSGSGSGTDFTLTISSL QPEDFATYYCQQNSEDPRTFGGGTKVEIK | SEQ ID NO: 54 |
| Light Chain Variable domain LC6_m12 | DIQLTQSPSSLSASVGDRVTITCRASKSVDSYGNSFMHWY QQKPGKAPKLLIYLASNLESGVPSRFSGSGSGTDFTLTISSL QPEDFATYYCQQNNRDPRTFGGGTKVEIK | SEQ ID NO: 55 |
| Light Chain Variable domain LC6_m13 | DIQLTQSPSSLSASVGDRVTITCRASKSVDSYGNSFMHWY QQKPGKAPKLLIYLASNLESGVPSRFSGSGSGTDFTLTISSL QPEDFATYYCQQNNDDPRTFGGGTKVEIK | SEQ ID NO: 56 |
| Light Chain Variable domain LC6_m14 | DIQLTQSPSSLSASVGDRVTITCRASKSVDSYGNSFMHWY QQKPGKAPKLLIYLASNLESGVPSRFSGSGSGTDFTLTISSL QPEDFATYYCQQNNQDPRTFGGGTKVEIK | SEQ ID NO: 57 |
| Parental Kabat HCDR1 | AYSVN | SEQ ID NO: 58 |
| HC5_m7 Kabat HCDR1 | RYSVN | SEQ ID NO: 59 |
| HC5_m8 Kabat HCDR1 | KYSVN | SEQ ID NO: 60 |
| HC5_m9 Kabat HCDR1 | HYSVN | SEQ ID NO: 61 |

-continued

Informal sequence listing

| Description | Sequence | SEQ ID NO |
|---|---|---|
| HC5_m10 Kabat HCDR1 | QYSVN | SEQ ID NO: 62 |
| HC5_m11 Kabat HCDR1 | EYSVN | SEQ ID NO: 63 |
| HC5_m12 Kabat HCDR1 | SYSVN | SEQ ID NO: 64 |
| HC5_m13 Kabat HCDR1 | YYSVN | SEQ ID NO: 65 |
| HC5_m14 Kabat HCDR1 | AESVN | SEQ ID NO: 66 |
| Lebrikizumab Chothia HCDR1 | GFSLSAY | SEQ ID NO: 67 |
| Parental Chothia HCDR1 | GFSLNAY | SEQ ID NO: 68 |
| HC6 Chothia HCDR1 | GGSLNAY | SEQ ID NO: 69 |
| HC7 Chothia HCDR1 | GGSLNAY | SEQ ID NO: 70 |
| HC5_m1 Chothia HCDR1 | GYSLNAY | SEQ ID NO: 71 |
| HC5_m2 Chothia HCDR1 | GFSLRAY | SEQ ID NO: 72 |
| HC5_m3 Chothia HCDR1 | GFSLHAY | SEQ ID NO: 73 |
| HC5_m4 Chothia HCDR1 | GFSLDAY | SEQ ID NO: 74 |
| HC5_m5 Chothia HCDR1 | GFSLYAY | SEQ ID NO: 75 |
| HC5_m7 Chothia HCDR1 | GFSLNRY | SEQ ID NO: 76 |
| HC5_m8 Chothia HCDR1 | GFSLNKY | SEQ ID NO: 77 |
| HC5_m9 Chothia HCDR1 | GFSLNHY | SEQ ID NO: 78 |
| HC5_m10 Chothia HCDR1 | GFSLNQY | SEQ ID NO: 79 |

Informal sequence listing

| Description | Sequence | SEQ ID NO |
|---|---|---|
| HC5_m11 Chothia HCDR1 | GFSLNEY | SEQ ID NO: 80 |
| HC5_m12 Chothia HCDR1 | GFSLNSY | SEQ ID NO: 81 |
| HC5_m13 Chothia HCDR1 | GFSLNYY | SEQ ID NO: 82 |
| HC5_m14 Chothia HCDR1 | GFSLNAE | SEQ ID NO: 83 |
| Lebrikizumab IMGT HCDR1 | GFSLSAYS | SEQ ID NO: 84 |
| Parental IMGT HCDR1 | GFSLNAYS | SEQ ID NO: 85 |
| HC6 IMGT HCDR1 | GGSLNAYS | SEQ ID NO: 86 |
| HC5_m1 IMGT HCDR1 | GYSLNAYS | SEQ ID NO: 87 |
| HC5_m2 IMGT HCDR1 | GFSLRAYS | SEQ ID NO: 88 |
| HC5_m3 IMGT HCDR1 | GFSLHAYS | SEQ ID NO: 89 |
| HC5_m4 IMGT HCDR1 | GFSLDAYS | SEQ ID NO: 90 |
| HC5_m5 IMGT HCDR1 | GFSLYAYS | SEQ ID NO: 91 |
| HC5_m6 IMGT HCDR1 | GFSLSAYS | SEQ ID NO: 92 |
| HC5_m7 IMGT HCDR1 | GFSLNRYS | SEQ ID NO: 93 |
| HC5_m8 IMGT HCDR1 | GFSLNKYS | SEQ ID NO: 94 |
| HC5_m9 IMGT HCDR1 | GFSLNHYS | SEQ ID NO: 95 |
| HC5_m10 IMGT HCDR1 | GFSLNQYS | SEQ ID NO: 96 |
| HC5_m11 IMGT HCDR1 | GFSLNEYS | SEQ ID NO: 97 |

-continued

Informal sequence listing

| Description | Sequence | SEQ ID NO |
|---|---|---|
| HC5_m13 IMGT HCDR1 | GFSLNYYS | SEQ ID NO: 98 |
| HC5_m14 IMGT HCDR1 | GFSLNAES | SEQ ID NO: 99 |
| Parental Kabat HCDR2 | MIWGDGKIVYNSALKS | SEQ ID NO: 100 |
| HC7 Kabat HCDR2 | YIYGDGKTNYNPALKS | SEQ ID NO: 101 |
| HC5_m15 Kabat HCDR2 | MIWSDGKIVYNSALKS | SEQ ID NO: 102 |
| HC5_m16 Kabat HCDR2 | MIWADGKIVYNSALKS | SEQ ID NO: 103 |
| Parental Chothia HCDR2 | WGDGK | SEQ ID NO: 104 |
| HC7 Chothia HCDR2 | YGDGK | SEQ ID NO: 105 |
| HC5_m15 Chothia HCDR2 | WSDGK | SEQ ID NO: 106 |
| HC5_m16 Chothia HCDR2 | WADGK | SEQ ID NO: 107 |
| Parental IMGT HCDR2 | IWGDGKI | SEQ ID NO: 108 |
| HC7 IMGT HCDR2 | IYGDGKT | SEQ ID NO: 109 |
| HC5_m15 IMGT HCDR2 | IWSDGKI | SEQ ID NO: 110 |
| HC5_m16 IMGT HCDR2 | IWADGKI | SEQ ID NO: 111 |
| Parental Kabat and Chothia HCDR3 | DGYYPYAMDN | SEQ ID NO: 112 |
| HC7 Kabat and Chothia HCDR3 | DGYYYYAMDV | SEQ ID NO: 113 |
| HC5_m17 Kabat and Chothia HCDR3 | HGYYPYAMDN | SEQ ID NO: 114 |

Informal sequence listing

| Description | Sequence | SEQ ID NO |
|---|---|---|
| HC5_m18 Kabat and Chothia HCDR3 | DLYYPYAMDN | SEQ ID NO: 115 |
| HC5_m19 Kabat and Chothia HCDR3 | DKYYPYAMDN | SEQ ID NO: 116 |
| HC5_m20 Kabat and Chothia HCDR3 | DGYYGYAMDN | SEQ ID NO: 117 |
| HC5_m21 Kabat and Chothia HCDR3 | DGYYAYAMDN | SEQ ID NO: 118 |
| HC5_m22 Kabat and Chothia HCDR3 | DGYYSYAMDN | SEQ ID NO: 119 |
| HC5_m23 Kabat and Chothia HCDR3 | DGYYTYAMDN | SEQ ID NO: 120 |
| HC5_m12 IMGT HCDR1 | GNSLNSYS | SEQ ID NO: 121 |
| | | SEQ ID NO: 122 |
| | | SEQ ID NO: 123 |
| | | SEQ ID NO: 124 |
| | | SEQ ID NO: 125 |
| | | SEQ ID NO: 126 |
| | | SEQ ID NO: 127 |
| | | SEQ ID NO: 128 |
| | | SEQ ID NO: 129 |
| Parental IMGT HCDR3 | AGDGYYPYAMDN | SEQ ID NO: 130 |
| HC6 IMGT HCDR3 | ARDGYYPYAMDN | SEQ ID NO: 131 |
| HC7 IMGT HCDR3 | ARDGYYYYAMDV | SEQ ID NO: 132 |
| HC5_m17 IMGT HCDR3 | AGHGYYPYAMDN | SEQ ID NO: 133 |

| Informal sequence listing | | |
|---|---|---|
| Description | Sequence | SEQ ID NO |
| HC5_m18 IMGT HCDR3 | AGDLYYPYAMDN | SEQ ID NO: 134 |
| HC5_m19 IMGT HCDR3 | AGDKYYPYAMDN | SEQ ID NO: 135 |
| HC5_m20 IMGT HCDR3 | AGDGYYGYAMDN | SEQ ID NO: 136 |
| HC5_m21 IMGT HCDR3 | AGDGYYAYAMDN | SEQ ID NO: 137 |
| HC5_m22 IMGT HCDR3 | AGDGYYSYAMDN | SEQ ID NO: 138 |
| HC5_m23 IMGT HCDR3 | AGDGYYTYAMDN | SEQ ID NO: 139 |
| HC1_m6 IMGT HCDR3 | AGDGYYPYAMDN | SEQ ID NO: 140 |
| Parental Kabat and Chothia LCDR1 | RASKSVDSYGNSFMH | SEQ ID NO: 141 |
| LC10 Kabat and Chothia LCDR1 | RASQSVDSNGNNFLH | SEQ ID NO: 142 |
| LC6_m1 Kabat and Chothia LCDR1 | RASKSVDSYGNSRMH | SEQ ID NO: 143 |
| LC6_m2 Kabat and Chothia LCDR1 | RASKSVDSYGNSSMH | SEQ ID NO: 144 |
|  |  | SEQ ID NO: 145 |
|  |  | SEQ ID NO: 146 |
|  |  | SEQ ID NO: 147 |
|  |  | SEQ ID NO: 148 |
| Parental IMGT LCDR1 | KSVDSYGNSF | SEQ ID NO: 149 |
| LC10 IMGT LCDR1 | QSVDSNGNNF | SEQ ID NO: 150 |
| LC6_m1 IMGT LCDR1 | KSVDSYGNSR | SEQ ID NO: 151 |

-continued

| Informal sequence listing | | |
|---|---|---|
| Description | Sequence | SEQ ID NO |
| LC6_m2 IMGT LCDR1 | KSVDSYGNSS | SEQ ID NO: 152 |
| Parental Kabat and Chothia LCDR2 | LASNLES | SEQ ID NO: 153 |
| LC6_m5 Kabat and Chothia LCDR2 | LASHLES | SEQ ID NO: 154 |
| LC6_m6 Kabat and Chothia LCDR2 | LASDLES | SEQ ID NO: 155 |
| LC6_m7 Kabat and Chothia LCDR2 | LASQLES | SEQ ID NO: 156 |
| LC6_m8 Kabat and Chothia LCDR2 | LASELES | SEQ ID NO: 157 |
| LC10 Kabat and Chothia LCDR2 | LASNRES | SEQ ID NO: 158 |
| | | SEQ ID NO: 159 |
| | | SEQ ID NO: 160 |
| | | SEQ ID NO: 161 |
| | | SEQ ID NO: 162 |
| | | SEQ ID NO: 163 |
| | | SEQ ID NO: 164 |
| Parental Kabat, Chothia and IMGT LCDR3 | QQNNEDPRT | SEQ ID NO: 165 |
| LC10 Kabat, Chothia and IMGT LCDR3 | QQNNHTPRT | SEQ ID NO: 166 |
| LC6_m9 Kabat, Chothia and IMGT LCDR3 | QQNHEDPRT | SEQ ID NO: 167 |

-continued

| Informal sequence listing | | |
|---|---|---|
| Description | Sequence | SEQ ID NO |
| LC6_m10 Kabat, Chothia and IMGT LCDR3 | QQNYEDPRT | SEQ ID NO: 168 |
| LC6_m11 Kabat, Chothia and IMGT LCDR3 | QQNSEDPRT | SEQ ID NO: 169 |
| LC6_m12 Kabat, Chothia and IMGT LCDR3 | QQNNRDPRT | SEQ ID NO: 170 |
| LC6_m13 Kabat, Chothia and IMGT LCDR3 | QQNNDDPRT | SEQ ID NO: 171 |
| LC6_m14 Kabat, Chothia and IMGT LCDR3 | QQNNQDPRT | SEQ ID NO: 172 |
| | | SEQ ID NO: 173 |
| | | SEQ ID NO: 174 |
| | | SEQ ID NO: 175 |
| | | SEQ ID NO: 176 |
| | | SEQ ID NO: 177 |
| | | SEQ ID NO: 178 |
| | | SEQ ID NO: 179 |
| | | SEQ ID NO: 180 |
| | | SEQ ID NO: 181 |
| | | SEQ ID NO: 182 |
| | | SEQ ID NO: 183 |
| | | SEQ ID NO: 184 |
| | | SEQ ID NO: 185 |
| | | SEQ ID NO: 186 |
| | | SEQ ID NO: 187 |

Informal sequence listing

| Description | Sequence | SEQ ID NO |
|---|---|---|
| | | SEQ ID NO: 188 |
| HC Framework Region 1 HC0 Kabat | QVQLQESGPGLVAPSQSLSITCTVSGFSLN | SEQ ID NO: 198 |
| HC Framework Region 1 HC0_M Kabat | QVQLQESGPGLVAPSQSLSITCTVSGFSLN | SEQ ID NO: 198 |
| HC Framework Region 1 HC1 Kabat | EVQLQESGPGLVKPSETLSLTCTVSGFSLN | SEQ ID NO: 200 |
| HC Framework Region 1 HC2 Kabat | EVQLVQSGAEVKKPGASVKVSCKASGFSLN | SEQ ID NO: 201 |
| HC Framework Region 1 HC3 Kabat | EVQLVQSGAEVKKPGSSVKVSCKASGFSLN | SEQ ID NO: 202 |
| HC Framework Region 1 HC4 Kabat | EVQLVESGGGLVKPGGSLRLSCAASGFSLN | SEQ ID NO: 203 |
| HC Framework Region 1 HC5 Kabat | EVQLLESGGGLVQPGGSLRLSCAASGFSLN | SEQ ID NO: 204 |
| HC Framework Region 1 HC6 Kabat | EVQLQESGPGLVKPSETLSLTCTVSGGSLN | SEQ ID NO: 205 |
| HC Framework Region 1 HC7 Kabat | QVQLQESGPGLVKPSETLSLTCTVSGGSLN | SEQ ID NO: 206 |
| HC Framework Region 1 HC5_m1 Kabat | EVQLLESGGGLVQPGGSLRLSCAASGYSLN | SEQ ID NO: 207 |
| HC Framework Region 1 HC5_m2 Kabat | EVQLLESGGGLVQPGGSLRLSCAASGFSLR | SEQ ID NO: 208 |
| HC Framework Region 1 HC5_m3 Kabat | EVQLLESGGGLVQPGGSLRLSCAASGFSLH | SEQ ID NO: 209 |
| HC Framework Region 1 HC5_m4 Kabat | EVQLLESGGGLVQPGGSLRLSCAASGFSLD | SEQ ID NO: 210 |

-continued

| Description | Sequence | SEQ ID NO |
|---|---|---|
| HC Framework Region 1 HC5_m5 Kabat | EVQLLESGGGLVQPGGSLRLSCAASGFSLY | SEQ ID NO: 211 |
| HC Framework Region 1 HC5_m6 Kabat | EVQLLESGGGLVQPGGSLRLSCAASGFSLS | SEQ ID NO: 212 |
| HC Framework Region 1 HC5_m7 Kabat | EVQLLESGGGLVQPGGSLRLSCAASGFSLN | SEQ ID NO: 204 |
| HC Framework Region 1 HC5_m8 Kabat | EVQLLESGGGLVQPGGSLRLSCAASGFSLN | SEQ ID NO: 204 |
| HC Framework Region 1 HC5_m9 Kabat | EVQLLESGGGLVQPGGSLRLSCAASGFSLN | SEQ ID NO: 204 |
| HC Framework Region 1 HC5_m10 Kabat | EVQLLESGGGLVQPGGSLRLSCAASGFSLN | SEQ ID NO: 204 |
| HC Framework Region 1 HC5_m11 Kabat | EVQLLESGGGLVQPGGSLRLSCAASGFSLN | SEQ ID NO: 204 |
| HC Framework Region 1 HC5_m12 Kabat | EVQLLESGGGLVQPGGSLRLSCAASGFSLN | SEQ ID NO: 204 |
| HC Framework Region 1 HC5_m13 Kabat | EVQLLESGGGLVQPGGSLRLSCAASGFSLN | SEQ ID NO: 204 |
| HC Framework Region 1 HC5_m14 Kabat | EVQLLESGGGLVQPGGSLRLSCAASGFSLN | SEQ ID NO: 204 |
| HC Framework Region 1 HC5_m15 Kabat | EVQLLESGGGLVQPGGSLRLSCAASGFSLN | SEQ ID NO: 204 |
| HC Framework Region 1 HC5_m16 Kabat | EVQLLESGGGLVQPGGSLRLSCAASGFSLN | SEQ ID NO: 204 |

Informal sequence listing

| Description | Sequence | SEQ ID NO |
|---|---|---|
| HC Framework Region 1 HC5_m17 Kabat | EVQLLESGGGLVQPGGSLRLSCAASGFSLN | SEQ ID NO: 204 |
| HC Framework Region 1 HC5_m18 Kabat | EVQLLESGGGLVQPGGSLRLSCAASGFSLN | SEQ ID NO: 204 |
| HC Framework Region 1 HC5_m19 Kabat | EVQLLESGGGLVQPGGSLRLSCAASGFSLN | SEQ ID NO: 204 |
| HC Framework Region 1 HC5_m20 Kabat | EVQLLESGGGLVQPGGSLRLSCAASGFSLN | SEQ ID NO: 204 |
| HC Framework Region 1 HC5_m21 Kabat | EVQLLESGGGLVQPGGSLRLSCAASGFSLN | SEQ ID NO: 204 |
| HC Framework Region 1 HC5_m22 Kabat | EVQLLESGGGLVQPGGSLRLSCAASGFSLN | SEQ ID NO: 204 |
| HC Framework Region 1 HC5_m24 Kabat | EVQLLESGGGLVQPGGSLRLSCAASGFSLN | SEQ ID NO: 204 |
| LC Framework Region 1LC0 Kabat | NIVLTQSPASLAVSLGQRATISC | SEQ ID NO: 230 |
| LC Framework Region 1 LC1 Kabat | DIQLTQSPSSLSASVGDRVTITC | SEQ ID NO: 231 |
| LC Framework Region 1 LC2 Kabat | DIQLTQSPSSLSASVGDRVTITC | SEQ ID NO: 231 |
| LC Framework Region 1 LC3 Kabat | EIVLTQSPATLSVSPGERATLSC | SEQ ID NO: 233 |
| LC Framework Region 1 LC4 Kabat | DIVLTQSPLSLPVTPGEPASISC | SEQ ID NO: 234 |
| LC Framework Region 1 LC5 Kabat | DIVLTQSPDSLAVSLGERATINC | SEQ ID NO: 235 |

| Informal sequence listing | | |
|---|---|---|
| Description | Sequence | SEQ ID NO |
| LC Framework Region 1 LC6 Kabat | DIQLTQSPSSLSASVGDRVTITC | SEQ ID NO: 231 |
| LC Framework Region 1 LC7 Kabat | EIVLTQSPATLSVSPGERATLSC | SEQ ID NO: 233 |
| LC Framework Region 1 LC8 Kabat | DIVLTQSPLSLPVTPGEPASISC | SEQ ID NO: 234 |
| LC Framework Region 1 LC9 Kabat | DIVLTQSPASLAVSPGERATISC | SEQ ID NO: 239 |
| LC Framework Region 1 LC10 Kabat | DIVLTQSPASLAVSPGERATISC | SEQ ID NO: 239 |
| LC Framework Region 1 LC6_m1 Kabat | DIQLTQSPSSLSASVGDRVTITC | SEQ ID NO: 231 |
| LC Framework Region 1 LC6_m2 Kabat | DIQLTQSPSSLSASVGDRVTITC | SEQ ID NO: 231 |
| LC Framework Region 1 LC6_m3 Kabat | DIQLTQSPSSLSASVGDRVTITC | SEQ ID NO: 231 |
| LC Framework Region 1 LC6_m4 Kabat | DIQLTQSPSSLSASVGDRVTITC | SEQ ID NO: 231 |
| LC Framework Region 1 LC6_m5 Kabat | DIQLTQSPSSLSASVGDRVTITC | SEQ ID NO: 231 |
| LC Framework Region 1 LC6_m6 Kabat | DIQLTQSPSSLSASVGDRVTITC | SEQ ID NO: 231 |
| LC Framework Region 1 LC6_m7 Kabat | DIQLTQSPSSLSASVGDRVTITC | SEQ ID NO: 231 |
| LC Framework Region 1 LC6_m8 Kabat | DIQLTQSPSSLSASVGDRVTITC | SEQ ID NO: 231 |

| Informal sequence listing | | |
|---|---|---|
| Description | Sequence | SEQ ID NO |
| LC Framework Region 1 LC6_m9 Kabat | DIQLTQSPSSLSASVGDRVTITC | SEQ ID NO: 231 |
| LC Framework Region 1 LC6_m10 Kabat | DIQLTQSPSSLSASVGDRVTITC | SEQ ID NO: 231 |
| LC Framework Region 1 LC6_m11 Kabat | DIQLTQSPSSLSASVGDRVTITC | SEQ ID NO: 231 |
| LC Framework Region 1 LC6_m12 Kabat | DIQLTQSPSSLSASVGDRVTITC | SEQ ID NO: 231 |
| LC Framework Region 1 LC6_m13 Kabat | DIQLTQSPSSLSASVGDRVTITC | SEQ ID NO: 231 |
| LC Framework Region 1 LC6_m14 Kabat | DIQLTQSPSSLSASVGDRVTITC | SEQ ID NO: 231 |
| Lebrikizumab-HC | WIRQPPGKALEWLA | SEQ ID NO: 255 |
| HC Framework Region 2 HC0 | WVRQPPGKGLEWLG | SEQ ID NO: 256 |
| HC Framework Region 2 HC0_M Kabat | WVRQPPGKGLEWLG | SEQ ID NO: 256 |
| HC Framework Region 2 HC1 Kabat | WIRQPPGKGLEWLG | SEQ ID NO: 258 |
| HC Framework Region 2 HC2 Kabat | WVRQAPGQGLEWLG | SEQ ID NO: 259 |
| HC Framework Region 2 HC3 Kabat | WVRQAPGQGLEWLG | SEQ ID NO: 259 |
| HC Framework Region 2 HC4 Kabat | WVRQAPGKGLEWLG | SEQ ID NO: 262 |
| HC Framework Region 2 HC5 Kabat | WVRQAPGKGLEWLG | SEQ ID NO: 262 |

-continued

| Description | Sequence | SEQ ID NO |
|---|---|---|
| HC Framework Region 2 HC6 Kabat | WVRQPPGKGLEWLG | SEQ ID NO: 263 |
| HC Framework Region 2 HC7 Kabat | WVRQPPGKGLEWLG | SEQ ID NO: 263 |
| HC Framework Region 2 HC5_m1 Kabat | WVRQAPGKGLEWLG | SEQ ID NO: 262 |
| HC Framework Region 2 HC5_m2 Kabat | WVRQAPGKGLEWLG | SEQ ID NO: 262 |
| HC Framework Region 2 HC5_m3 Kabat | WVRQAPGKGLEWLG | SEQ ID NO: 262 |
| HC Framework Region 2 HC5_m4 Kabat | WVRQAPGKGLEWLG | SEQ ID NO: 262 |
| HC Framework Region 2 HC5_m5 Kabat | WVRQAPGKGLEWLG | SEQ ID NO: 262 |
| HC Framework Region 2 HC5_m6 Kabat | WVRQAPGKGLEWLG | SEQ ID NO: 262 |
| HC Framework Region 2 HC5_m7 Kabat | WVRQAPGKGLEWLG | SEQ ID NO: 262 |
| HC Framework Region 2 HC5_m8 Kabat | WVRQAPGKGLEWLG | SEQ ID NO: 262 |
| HC Framework Region 2 HC5_m9 Kabat | WVRQAPGKGLEWLG | SEQ ID NO: 262 |
| HC Framework Region 2 HC5_m10 Kabat | WVRQAPGKGLEWLG | SEQ ID NO: 262 |

-continued

| Description | Sequence | SEQ ID NO |
|---|---|---|
| HC Framework Region 2 HC5_m11 Kabat | WVRQAPGKGLEWLG | SEQ ID NO: 262 |
| HC Framework Region 2 HC5_m12 Kabat | WVRQAPGKGLEWLG | SEQ ID NO: 262 |
| HC Framework Region 2 HC5_m13 Kabat | WVRQAPGKGLEWLG | SEQ ID NO: 262 |
| HC Framework Region 2 HC5_m14 Kabat | WVRQAPGKGLEWLG | SEQ ID NO: 262 |
| HC Framework Region 2 HC5_m15 Kabat | WVRQAPGKGLEWLG | SEQ ID NO: 262 |
| HC Framework Region 2 HC5_m16 Kabat | WVRQAPGKGLEWLG | SEQ ID NO: 262 |
| HC Framework Region 2 HC5_m17 Kabat | WVRQAPGKGLEWLG | SEQ ID NO: 262 |
| HC Framework Region 2 HC5_m18 Kabat H | WVRQAPGKGLEWLG | SEQ ID NO: 262 |
| HC Framework Region 2 HC5_m19 Kabat | WVRQAPGKGLEWLG | SEQ ID NO: 262 |
| HC Framework Region 2 HC5_m20 Kabat | WVRQAPGKGLEWLG | SEQ ID NO: 262 |
| HC Framework Region 2 HC5_m21 Kabat | WVRQAPGKGLEWLG | SEQ ID NO: 262 |
| HC Framework Region 2 HC5_m22 Kabat | WVRQAPGKGLEWLG | SEQ ID NO: 262 |

| Informal sequence listing | | |
|---|---|---|
| Description | Sequence | SEQ ID NO |
| HC Framework Region 2 HC5_m24 Kabat | WVRQAPGKGLEWLG | SEQ ID NO: 262 |
| Lebrikizumab-LC | WYQQKPGQPPKLLIY | SEQ ID NO: 286 |
| LC Framework Region 2 LC0 Kabat | WYQQKPGQPPKLLIY | SEQ ID NO: 286 |
| LC Framework Region 2 LC1 Kabat | WYQQKPGKAPKLLIY | SEQ ID NO: 288 |
| LC Framework Region 2 LC2 Kabat | WYQQKPGKAPKLLIY | SEQ ID NO: 288 |
| LC Framework Region 2 LC3 Kabat | WYQQKPGQAPRLLIY | SEQ ID NO: 290 |
| LC Framework Region 2 LC4 Kabat | WYLQKPGQSPQLLIY | SEQ ID NO: 291 |
| LC Framework Region 2 LC5 Kabat | WYQQKPGQPPKLLIY | SEQ ID NO: 286 |
| LC Framework Region 2 LC6 Kabat | WYQQKPGKAPKLLIY | SEQ ID NO: 288 |
| LC Framework Region 2 LC7 Kabat | WYQQKPGQAPRLLIY | SEQ ID NO: 290 |
| LC Framework Region 2 LC8 Kabat | WYLQKPGQSPQLLIY | SEQ ID NO: 291 |
| LC Framework Region 2 LC9 Kabat | WYQQKPGQPPKLLIY | SEQ ID NO: 292 |
| LC Framework Region 2 LC10 Kabat | WYQQKPGQPPKLLIY | SEQ ID NO: 286 |
| LC Framework Region 2 LC6_m1 Kabat | WYQQKPGKAPKLLIY | SEQ ID NO: 288 |

-continued

| Informal sequence listing | | |
|---|---|---|
| Description | Sequence | SEQ ID NO |
| LC Framework Region 2 LC6_m2 Kabat | WYQQKPGKAPKLLIY | SEQ ID NO: 288 |
| LC Framework Region 2 LC6_m3 Kabat | WYQQKPGKAPKLLIR | SEQ ID NO: 300 |
| LC Framework Region 2 LC6_m4 Kabat | WYQQKPGKAPKLLIF | SEQ ID NO: 301 |
| LC Framework Region 2 LC6_m5 Kabat | WYQQKPGKAPKLLIY | SEQ ID NO: 288 |
| LC Framework Region 2 LC6_m6 Kabat | WYQQKPGKAPKLLIY | SEQ ID NO: 288 |
| LC Framework Region 2 LC6_m7 Kabat | WYQQKPGKAPKLLIY | SEQ ID NO: 288 |
| LC Framework Region 2 LC6_m8 Kabat | WYQQKPGKAPKLLIY | SEQ ID NO: 288 |
| LC Framework Region 2 LC6_m9 Kabat | WYQQKPGKAPKLLIY | SEQ ID NO: 288 |
| LC Framework Region 2 LC6_m10 Kabat | WYQQKPGKAPKLLIY | SEQ ID NO: 288 |
| LC Framework Region 2 LC6_m11 Kabat | WYQQKPGKAPKLLIY | SEQ ID NO: 288 |
| LC Framework Region 2 LC6_m12 Kabat | WYQQKPGKAPKLLIY | SEQ ID NO: 288 |
| LC Framework Region 2 LC6_m13 Kabat | WYQQKPGKAPKLLIY | SEQ ID NO: 288 |

| Informal sequence listing | | |
|---|---|---|
| Description | Sequence | SEQ ID NO |
| LC Framework Region 2 LC6_m14 Kabat | WYQQKPGKAPKLLIY | SEQ ID NO: 288 |
| Lebrikizumab-HC | RLTISKDTSKNQVVLTMTNMDPVDTATYYCAG | SEQ ID NO: 311 |
| HC Framework Region 3 HC0 Kabat | RLNISKDSSKSQVFLKMSSLQSDDTARYYCAG | SEQ ID NO: 312 |
| HC Framework Region 3 HC0_M Kabat | RLTISKDSSKSQVFLKMSSLQSDDTARYYCAG | SEQ ID NO: 313 |
| HC Framework Region 3 HC1 Kabat | RLTISKDSSKNQVSLKLSSVTAADTAVYYCAG | SEQ ID NO: 314 |
| HC Framework Region 3 HC2 Kabat | RLTITKDSSTSTVYMELSSLRSEDTAVYYCAG | SEQ ID NO: 315 |
| HC Framework Region 3 HC3 Kabat | RLTITKDSSTSTVYMELSSLRSEDTAVYYCAG | SEQ ID NO: 315 |
| HC Framework Region 3 HC4 Kabat | RLTISKDSSKNTVYLQMNSLKTEDTAVYYCAG | SEQ ID NO: 317 |
| HC Framework Region 3 HC5 Kabat | RLTISKDSSKNTVYLQMNSLRAEDTAVYYCAG | SEQ ID NO: 318 |
| HC Framework Region 3 HC6 Kabat | RLTISLDTSKSQVFLKMSSLTAADTAVYYCAR | SEQ ID NO: 319 |
| HC Framework Region 3 HC7 Kabat | RLTISLDTSKSQVFLKMSSLTAADTAVYYCAR | SEQ ID NO: 317 |
| HC Framework Region 3 HC5_m1 Kabat | RLTISKDSSKNTVYLQMNSLRAEDTAVYYCAG | SEQ ID NO: 318 |
| HC Framework Region 3 HC5_m2 Kabat | RLTISKDSSKNTVYLQMNSLRAEDTAVYYCAG | SEQ ID NO: 318 |
| HC Framework Region 3 HC5_m3 Kabat | RLTISKDSSKNTVYLQMNSLRAEDTAVYYCAG | SEQ ID NO: 318 |

-continued

| Description | Sequence | SEQ ID NO |
|---|---|---|
| HC Framework Region 3 HC5_m4 Kabat | RLTISKDSSKNTVYLQMNSLRAEDTAVYYCAG | SEQ ID NO: 318 |
| HC Framework Region 3 HC5_m5 Kabat | RLTISKDSSKNTVYLQMNSLRAEDTAVYYCAG | SEQ ID NO: 318 |
| HC Framework Region 3 HC5_m6 Kabat | RLTISKDSSKNTVYLQMNSLRAEDTAVYYCAG | SEQ ID NO: 318 |
| HC Framework Region 3 HC5_m7 Kabat | RLTISKDSSKNTVYLQMNSLRAEDTAVYYCAG | SEQ ID NO: 318 |
| HC Framework Region 3 HC5_m8 Kabat | RLTISKDSSKNTVYLQMNSLRAEDTAVYYCAG | SEQ ID NO: 318 |
| HC Framework Region 3 HC5_m9 Kabat | RLTISKDSSKNTVYLQMNSLRAEDTAVYYCAG | SEQ ID NO: 318 |
| HC Framework Region 3 HC5_m10 Kabat | RLTISKDSSKNTVYLQMNSLRAEDTAVYYCAG | SEQ ID NO: 318 |
| HC Framework Region 3 HC5_m11 Kabat | RLTISKDSSKNTVYLQMNSLRAEDTAVYYCAG | SEQ ID NO: 318 |
| HC Framework Region 3 HC5_m12 Kabat | RLTISKDSSKNTVYLQMNSLRAEDTAVYYCAG | SEQ ID NO: 318 |
| HC Framework Region 3 HC5_m13 Kabat | RLTISKDSSKNTVYLQMNSLRAEDTAVYYCAG | SEQ ID NO: 318 |
| HC Framework Region 3 HC5_m14 Kabat | RLTISKDSSKNTVYLQMNSLRAEDTAVYYCAG | SEQ ID NO: 318 |
| HC Framework Region 3 HC5_m15 Kabat | RLTISKDSSKNTVYLQMNSLRAEDTAVYYCAG | SEQ ID NO: 318 |

Informal sequence listing

| Description | Sequence | SEQ ID NO |
|---|---|---|
| HC Framework Region 3 HC5_m16 Kabat | RLTISKDSSKNTVYLQMNSLRAEDTAVYYCAG | SEQ ID NO: 318 |
| HC Framework Region 3 HC5_m17 Kabat | RLTISKDSSKNTVYLQMNSLRAEDTAVYYCAG | SEQ ID NO: 318 |
| HC Framework Region 3 HC5_m18 Kabat | RLTISKDSSKNTVYLQMNSLRAEDTAVYYCAG | SEQ ID NO: 318 |
| HC Framework Region 3 HC5_m19 Kabat | RLTISKDSSKNTVYLQMNSLRAEDTAVYYCAG | SEQ ID NO: 318 |
| HC Framework Region 3 HC5_m20 Kabat | RLTISKDSSKNTVYLQMNSLRAEDTAVYYCAG | SEQ ID NO: 318 |
| HC Framework Region 3 HC5_m21 Kabat | RLTISKDSSKNTVYLQMNSLRAEDTAVYYCAG | SEQ ID NO: 318 |
| HC Framework Region 3 HC5_m22 Kabat | RLTISKDSSKNTVYLQMNSLRAEDTAVYYCAG | SEQ ID NO: 318 |
| HC Framework Region 3 HC5_m24 Kabat | RLTISKDSSKNTVYLQMNSLRAEDTAVYYCAG | SEQ ID NO: 318 |
| Lebrikizumab-LC | GVPDRFSGSGSGTDFTLTISSLQAEDVAVYYC | SEQ ID NO: 343 |
| LC Framework Region 3 LC0 Kabat | GVPARFSGSGSRTDFTLTIDPVEADDAASYYC | SEQ ID NO: 344 |
| LC Framework Region 3 LC1 Kabat | GVPSRFSGSGSRTDFTLTISSLQPEDFATYYC | SEQ ID NO: 345 |
| LC Framework Region 3 LC2 Kabat | GVPSRFSGSGSRTDFTLTISSLQPEDFATYYC | SEQ ID NO: 345 |
| LC Framework Region 3 LC3 Kabat | GIPARFSGSGSRTEFTLTISSLQSEDFAVYYC | SEQ ID NO: 347 |

Informal sequence listing

| Description | Sequence | SEQ ID NO |
|---|---|---|
| LC Framework Region 3 LC4 Kabat | GVPDRFSGSGSRTDFTLKISRVEAEDVGVYYC | SEQ ID NO: 348 |
| LC Framework Region 3 LC6 Kabat | GVPDRFSGSGSGTDFTLTISSLQAEDVAVYYC | SEQ ID NO: 349 |
| LC Framework Region 3 LC7 Kabat | GIPARFSGSGSGTEFTLTISSLQSEDFAVYYC | SEQ ID NO: 351 |
| LC Framework Region 3 LC8 Kabat | GVPDRFSGSGSGTDFTLKISRVEAEDVGVYYC | SEQ ID NO: 352 |
| LC Framework Region 3 LC9 Kabat | GVPDRFSGSGSGTDFTLTISRVEADDVAVYYC | SEQ ID NO: 353 |
| LC Framework Region 3 LC10 Kabat | GVPDRFSGSGSGTDFTLTISRVEADDVAVYYC | SEQ ID NO: 353 |
| LC Framework Region 3 LC6_m1 Kabat | GVPSRFSGSGSGTDFTLTISSLQPEDFATYYC | SEQ ID NO: 349 |
| LC Framework Region 3 LC6_m2 Kabat | GVPSRFSGSGSGTDFTLTISSLQPEDFATYYC | SEQ ID NO: 349 |
| LC Framework Region 3 LC6_m3 Kabat | GVPSRFSGSGSGTDFTLTISSLQPEDFATYYC | SEQ ID NO: 349 |
| LC Framework Region 3 LC6_m4 Kabat | GVPSRFSGSGSGTDFTLTISSLQPEDFATYYC | SEQ ID NO: 349 |
| LC Framework Region 3 LC6_m5 Kabat | GVPSRFSGSGSGTDFTLTISSLQPEDFATYYC | SEQ ID NO: 349 |
| LC Framework Region 3 LC6_m6 Kabat | GVPSRFSGSGSGTDFTLTISSLQPEDFATYYC | SEQ ID NO: 349 |
| LC Framework Region 3 LC6_m7 Kabat | GVPSRFSGSGSGTDFTLTISSLQPEDFATYYC | SEQ ID NO: 349 |

-continued

Informal sequence listing

| Description | Sequence | SEQ ID NO |
|---|---|---|
| LC Framework Region 3 LC6_m8 Kabat | GVPSRFSGSGSGTDFTLTISSLQPEDFATYYC | SEQ ID NO: 349 |
| LC Framework Region 3 LC6_m9 Kabat | GVPSRFSGSGSGTDFTLTISSLQPEDFATYYC | SEQ ID NO: 349 |
| LC Framework Region 3 LC6_m10 Kabat | GVPSRFSGSGSGTDFTLTISSLQPEDFATYYC | SEQ ID NO: 349 |
| LC Framework Region 3 LC6_m11 Kabat | GVPSRFSGSGSGTDFTLTISSLQPEDFATYYC | SEQ ID NO: 349 |
| LC Framework Region 3 LC6_m12 Kabat | GVPSRFSGSGSGTDFTLTISSLQPEDFATYYC | SEQ ID NO: 349 |
| LC Framework Region 3 LC6_m13 Kabat | GVPSRFSGSGSGTDFTLTISSLQPEDFATYYC | SEQ ID NO: 349 |
| LC Framework Region 3 LC6_m14 Kabat | GVPSRFSGSGSGTDFTLTISSLQPEDFATYYC | SEQ ID NO: 349 |
| Lebrikizumab-HC | WGQGSLVTVSS | SEQ ID NO: 368 |
| HC Framework Region 4 HC0 | WGHGTSVTVSS | SEQ ID NO: 369 |
| HC Framework Region 4 HC0_M Kabat | WGHGTSVTVSS | SEQ ID NO: 369 |
| HC Framework Region 4 HC1 Kabat | WGQGTTVTVSS | SEQ ID NO: 371 |
| HC Framework Region 4 HC2 Kabat | WGQGTTVTVSS | SEQ ID NO: 371 |
| HC Framework Region 4 HC3 Kabat | WGQGTTVTVSS | SEQ ID NO: 371 |

Informal sequence listing

| Description | Sequence | SEQ ID NO |
|---|---|---|
| HC Framework Region 4 HC4 Kabat | WGQGTTVTVSS | SEQ ID NO: 371 |
| HC Framework Region 4 HC5 Kabat | WGQGTTVTVSS | SEQ ID NO: 371 |
| HC Framework Region 4 HC6 Kabat | WGQGTTVTVSS | SEQ ID NO: 371 |
| HC Framework Region 4 HC7 Kabat | WGQGTTVTVSS | SEQ ID NO: 371 |
| HC Framework Region 4 HC5_m1 Kabat | WGQGTTVTVSS | SEQ ID NO: 371 |
| HC Framework Region 4 HC5_m2 Kabat | WGQGTTVTVSS | SEQ ID NO: 371 |
| HC Framework Region 4 HC5_m3 Kabat | WGQGTTVTVSS | SEQ ID NO: 371 |
| HC Framework Region 4 HC5_m4 Kabat | WGQGTTVTVSS | SEQ ID NO: 371 |
| HC Framework Region 4 HC5_m5 Kabat | WGQGTTVTVSS | SEQ ID NO: 371 |
| HC Framework Region 4 HC5_m6 Kabat | WGQGTTVTVSS | SEQ ID NO: 371 |
| HC Framework Region 4 HC5_m7 Kabat | WGQGTTVTVSS | SEQ ID NO: 371 |
| HC Framework Region 4 HC5_m8 Kabat | WGQGTTVTVSS | SEQ ID NO: 371 |
| HC Framework Region 4 HC5_m9 Kabat | WGQGTTVTVSS | SEQ ID NO: 371 |

-continued

| Description | Sequence | SEQ ID NO |
|---|---|---|
| HC Framework Region 4 HC5_m10 Kabat | WGQGTTVTVSS | SEQ ID NO: 371 |
| HC Framework Region 4 HC5_m11 Kabat | WGQGTTVTVSS | SEQ ID NO: 371 |
| HC Framework Region 4 HC5_m12 Kabat | WGQGTTVTVSS | SEQ ID NO: 371 |
| HC Framework Region 4 HC5_m13 Kabat | WGQGTTVTVSS | SEQ ID NO: 371 |
| HC Framework Region 4 HC5_m14 Kabat | WGQGTTVTVSS | SEQ ID NO: 371 |
| HC Framework Region 4 HC5_m15 Kabat | WGQGTTVTVSS | SEQ ID NO: 371 |
| HC Framework Region 4 HC5_m16 Kabat | WGQGTTVTVSS | SEQ ID NO: 371 |
| HC Framework Region 4 HC5_m17 Kabat | WGQGTTVTVSS | SEQ ID NO: 371 |
| HC Framework Region 4 HC5_m18 Kabat | WGQGTTVTVSS | SEQ ID NO: 371 |
| HC Framework Region 4 HC5_m19 Kabat | WGQGTTVTVSS | SEQ ID NO: 371 |
| HC Framework Region 4 HC5_m20 Kabat | WGQGTTVTVSS | SEQ ID NO: 371 |
| HC Framework Region 4 HC5_m21 Kabat | WGQGTTVTVSS | SEQ ID NO: 371 |

-continued

| Description | Sequence | SEQ ID NO |
|---|---|---|
| HC Framework Region 4 HC5_m22 Kabat | WGQGTTVTVSS | SEQ ID NO: 371 |
| HC Framework Region 4 HC5_m24 Kabat | WGQGTTVTVSS | SEQ ID NO: 371 |
| Lebrikizumab-LC | FGGGTKVEIK | SEQ ID NO: 400 |
| LC Framework Region 4 LC0 Kabat | FGGGTKLEIK | SEQ ID NO: 401 |
| LC Framework Region 4 LC1 Kabat | FGGGTKVEIK | SEQ ID NO: 400 |
| LC Framework Region 4 LC2 Kabat | FGGGTKVEIK | SEQ ID NO: 400 |
| LC Framework Region 4 LC3 Kabat | FGGGTKVEIK | SEQ ID NO: 400 |
| LC Framework Region 4 LC4 Kabat | FGGGTKVEIK | SEQ ID NO: 400 |
| LC Framework Region 4 LC5 Kabat | FGGGTKVEIK | SEQ ID NO: 400 |
| LC Framework Region 4 LC6 Kabat | FGGGTKVEIK | SEQ ID NO: 400 |
| LC Framework Region 4 LC7 Kabat | FGGGTKVEIK | SEQ ID NO: 400 |
| LC Framework Region 4 LC8 Kabat | FGGGTKVEIK | SEQ ID NO: 400 |
| LC Framework Region 4 LC9 Kabat | FGGGTKLEIK | SEQ ID NO: 401 |
| LC Framework Region 4 LC10 Kabat | FGGGTKLEIK | SEQ ID NO: 401 |

| Informal sequence listing | | |
|---|---|---|
| Description | Sequence | SEQ ID NO |
| LC Framework Region 4 LC6_m1 Kabat | FGGGTKVEIK | SEQ ID NO: 400 |
| LC Framework Region 4 LC6_m2 Kabat | FGGGTKVEIK | SEQ ID NO: 400 |
| LC Framework Region 4 LC6_m3 Kabat | FGGGTKVEIK | SEQ ID NO: 400 |
| LC Framework Region 4 LC6_m4 Kabat | FGGGTKVEIK | SEQ ID NO: 400 |
| LC Framework Region 4 LC6_m5 Kabat | FGGGTKVEIK | SEQ ID NO: 400 |
| LC Framework Region 4 LC6_m6 Kabat | FGGGTKVEIK | SEQ ID NO: 400 |
| LC Framework Region 4 LC6_m7 Kabat | FGGGTKVEIK | SEQ ID NO: 400 |
| LC Framework Region 4 LC6_m8 Kabat | FGGGTKVEIK | SEQ ID NO: 400 |
| LC Framework Region 4 LC6_m9 Kabat | FGGGTKVEIK | SEQ ID NO: 400 |
| LC Framework Region 4 LC6_m10 Kabat | FGGGTKVEIK | SEQ ID NO: 400 |
| LC Framework Region 4 LC6_m11 Kabat | FGGGTKVEIK | SEQ ID NO: 400 |
| LC Framework Region 4 LC6_m12 Kabat | FGGGTKVEIK | SEQ ID NO: 400 |

| Description | Sequence | SEQ ID NO |
|---|---|---|
| LC Framework Region 4 LC6_m13 Kabat | FGGGTKVEIK | SEQ ID NO: 400 |
| LC Framework Region 4 LC6_m14 Kabat | FGGGTKVEIK | SEQ ID NO: 400 |
| Heavy Chain hIgG1 | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLMISRTPEVTCVVVDVSHEDPEVK FNWYVDGVEVHNAKTKPREEQYNSTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSC SVMHEALHNHYTQKSLSLSPG | SEQ ID NO: 425 |
| Heavy Chain hIgG4 | ASTKGPSVFPLAPCSRSTSESTAALGCLVKDYFPEP VTVSWNSGALTSGVHTFPAVLQSSGLYSLSSVVTVPSSSL GTKTYTCNVDHKPSNTKVDKRVESKYGPPCPSCPAPEFLG GPSVFLFPPKPKDTLMISRTPEVTCVVVDVSQEDPEVQFN WYVDGVEVHNAKTKPREEQFNSTYRVVSVLTVLHQDWL NGKEYKCKVSNKGLPSSIEKTISKAKGQPREPQVYTLPPSQ EEMTKNQVSLTCLVKGFYPSDIAVEWESNGQPENNYKTTP PVLDSDGSFFLYSRLTVDKSRWQEGNVFSCSVMHEALHN HYTQKSLSLSLGK | SEQ ID NO: 426 |
| Heavy Chain IgG4-SP | ASTKGPSVFPLAPCSRSTSESTAALGCLVKDYFPEP VTVSWNSGALTSGVHTFPAVLQSSGLYSLSSVVTVPSSSL GTKTYTCNVDHKPSNTKVDKRVESKYGPPCPPCPAPEFLG GPSVFLFPPKPKDTLMISRTPEVTCVVVDVSQEDPEVQFN WYVDGVEVHNAKTKPREEQFNSTYRVVSVLTVLHQDWL NGKEYKCKVSNKGLPSSIEKTISKAKGQPREPQVYTLPPSQ EEMTKNQVSLTCLVKGFYPSDIAVEWESNGQPENNYKTTP PVLDSDGSFFLYSRLTVDKSRWQEGNVFSCSVMHEALHN HYTQKSLSLSLGK | SEQ ID NO: 427 |
| Heavy Chain IgG4-SPLE | ASTKGPSVFPLAPCSRSTSESTAALGCLVKDYFPEP VTVSWNSGALTSGVHTFPAVLQSSGLYSLSSVVTVPSSSL GTKTYTCNVDHKPSNTKVDKRVESKYGPPCPPCPAPEELG GPSVFLFPPKPKDTLMISRTPEVTCVVVDVSQEDPEVQFN WYVDGVEVHNAKTKPREEQFNSTYRVVSVLTVLHQDWL NGKEYKCKVSNKGLPSSIEKTISKAKGQPREPQVYTLPPSQ EEMTKNQVSLTCLVKGFYPSDIAVEWESNGQPENNYKTTP PVLDSDGSFFLYSRLTVDKSRWQEGNVFSCSVMHEALHN HYTQKSLSLSLGK | SEQ ID NO: 428 |
| Heavy Chain IgG2 | ASTKGPSVFPLAPCSRSTSESTAALGCLVKDYFPEP VTVSWNSGALTSGVHTFPAVLQSSGLYSLSSVVTVPSSNF GTQTYTCNVDHKPSNTKVDKTVERKCCVECPPCPAPPVA GPSVFLFPPKPKDTLMISRTPEVTCVVVDVSHEDPEVQFN WYVDGVEVHNAKTKPREEQFNSTFRVVSVLTVVHQDWL NGKEYKCKVSNKGLPAPIEKTISKTKGQPREPQVYTLPPSR EEMTKNQVSLTCLVKGFYPSDIA VEWESNGQPENNYKTTPPMLDSDGSFFLYSKLTVDKSRW QQGNVFSCSVMHEALHNHYTQKSLSLSP | SEQ ID NO: 429 |
| Heavy Chain hIgG1-N297A | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLMISRTPEVTCVVVDVSHEDPEVK FNWYVDGVEVHNAKTKPREEQYASTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSC SVMHEALHNHYTQKSLSLSPG | SEQ ID NO: 430 |

-continued

Informal sequence listing

| Description | Sequence | SEQ ID NO |
|---|---|---|
| Heavy Chain hIgG1-D265A | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLMISRTPEVTCVVVAVSHEDPEVK FNWYVDGVEVHNAKTKPREEQYNSTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSC SVMHEALHNHYTQKSLSLSPG | SEQ ID NO: 431 |
| Heavy Chain hIgG1-LALA | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE AAGGPSVFLFPPKPKDTLMISRTPEVTCVVVDVSHEDPEV KFNWYVDGVEVHNAKTKPREEQYNSTYRVVSVLTVLHQ DWLNGKEYKCKVSNKALPAPIEKTISKAKGQPREPQVYTL PPSRDELTKNQVSLTCLVKGFYPSDIAVEWESNGQPENNY KTTPPVLDSDGSFFLYSKLTVDKSRWQQGNVFSC SVMHEALHNHYTQKSLSLSPG | SEQ ID NO: 432 |
| Heavy Chain hIgG1-LAGA | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LAGAPSVFLFPPKPKDTLMISRTPEVTCVVVDVSHEDPEVK FNWYVDGVEVHNAKTKPREEQYNSTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSC SVMHEALHNHYTQKSLSLSPG | SEQ ID NO: 433 |
| Heavy Chain hIgG1-LALAGA | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE AAGAPSVFLFPPKPKDTLMISRTPEVTCVVVDVSHEDPEV KFNWYVDGVEVHNAKTKPREEQYNSTYRVVSVLTVLHQ DWLNGKEYKCKVSNKALPAPIEKTISKAKGQPREPQVYTL PPSRDELTKNQVSLTCLVKGFYPSDIAVEWESNGQPENNY KTTPPVLDSDGSFFLYSKLTVDKSRWQQGNVFSC SVMHEALHNHYTQKSLSLSPG | SEQ ID NO: 434 |
| Heavy Chain hIgG1-LALAPG | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE AAGGPSVFLFPPKPKDTLMISRTPEVTCVVVDVSHEDPEV KFNWYVDGVEVHNAKTKPREEQYNSTYRVVSVLTVLHQ DWLNGKEYKCKVSNKALGAPIEKTISKAKGQPREPQVYTL PPSRDELTKNQVSLTCLVKGFYPSDIAVEWESNGQPENNY KTTPPVLDSDGSFFLYSKLTVDKSRWQQGNVFSC SVMHEALHNHYTQKSLSLSPG | SEQ ID NO: 435 |
| Heavy Chain hIgG1-YTE | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLYITREPEVTCVVVDVSHEDPEVK FNWYVDGVEVHNAKTKPREEQYNSTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSC SVMHEALHNHYTQKSLSLSPG | SEQ ID NO: 436 |
| Heavy Chain hIgG1-N297A/YTE | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLYITREPEVTCVVVDVSHEDPEVK FNWYVDGVEVHNAKTKPREEQYASTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSC SVMHEALHNHYTQKSLSLSPG | SEQ ID NO: 437 |
| Heavy Chain hIgG1-D265A/YTE | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLYITREPEVTCVVVAVSHEDPEVK | SEQ ID NO: 438 |

| Description | Sequence | SEQ ID NO |
|---|---|---|
| | FNWYVDGVEVHNAKTKPREEQYNSTYRVVSVLTVLHQD<br>WLNGKEYKCKVSNKALPAPIEKTISKAKGQPREPQVYTLP<br>PSRDELTKNQVSLTCLVKGFYPSDIAVEWESNGQPENNYK<br>TTPPVLDSDGSFFLYSKLTVDKSRWQQGNVFSC<br>SVMHEALHNHYTQKSLSLSPG | |
| Heavy Chain hIgG1-LALA/YTE | ASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKKVEPKSCDKTHTCPPCPAPE<br>AAGGPSVFLFPPKPKDTLYITREPEVTCVVVDVSHEDPEVK<br>FNWYVDGVEVHNAKTKPREEQYNSTYRVVSVLTVLHQD<br>WLNGKEYKCKVSNKALPAPIEKTISKAKGQPREPQVYTLP<br>PSRDELTKNQVSLTCLVKGFYPSDIAVEWESNGQPENNYK<br>TTPPVLDSDGSFFLYSKLTVDKSRWQQGNVFSC<br>SVMHEALHNHYTQKSLSLSPG | SEQ ID NO: 439 |
| Heavy Chain hIgG1-LAGA/YTE | ASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKKVEPKSCDKTHTCPPCPAPE<br>LAGAPSVFLFPPKPKDTLYITREPEVTCVVVDVSHEDPEVK<br>FNWYVDGVEVHNAKTKPREEQYNSTYRVVSVLTVLHQD<br>WLNGKEYKCKVSNKALPAPIEKTISKAKGQPREPQVYTLP<br>PSRDELTKNQVSLTCLVKGFYPSDIAVEWESNGQPENNYK<br>TTPPVLDSDGSFFLYSKLTVDKSRWQQGNVFSC<br>SVMHEALHNHYTQKSLSLSPG | SEQ ID NO: 440 |
| Heavy Chain hIgG1-LALAGA/YTE | ASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKKVEPKSCDKTHTCPPCPAPE<br>AAGAPSVFLFPPKPKDTLYITREPEVTCVVVDVSHEDPEVK<br>FNWYVDGVEVHNAKTKPREEQYNSTYRVVSVLTVLHQD<br>WLNGKEYKCKVSNKALPAPIEKTISKAKGQPREPQVYTLP<br>PSRDELTKNQVSLTCLVKGFYPSDIAVEWESNGQPENNYK<br>TTPPVLDSDGSFFLYSKLTVDKSRWQQGNVFSC<br>SVMHEALHNHYTQKSLSLSPG | SEQ ID NO: 441 |
| Heavy Chain hIgG1-LALAPG/YTE | ASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKKVEPKSCDKTHTCPPCPAPE<br>AAGGPSVFLFPPKPKDTLYITREPEVTCVVVDVSHEDPEVK<br>FNWYVDGVEVHNAKTKPREEQYNSTYRVVSVLTVLHQD<br>WLNGKEYKCKVSNKALGAPIEKTISKAKGQPREPQVYTLP<br>PSRDELTKNQVSLTCLVKGFYPSDIAVEWESNGQPENNYK<br>TTPPVLDSDGSFFLYSKLTVDKSRWQQGNVFSC<br>SVMHEALHNHYTQKSLSLSPG | SEQ ID NO: 442 |
| Heavy Chain hIgG1-LS | ASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKKVEPKSCDKTHTCPPCPAPE<br>LLGGPSVFLFPPKPKDTLMISRTPEVTCVVVDVSHEDPEVK<br>FNWYVDGVEVHNAKTKPREEQYNSTYRVVSVLTVLHQD<br>WLNGKEYKCKVSNKALPAPIEKTISKAKGQPREPQVYTLP<br>PSRDELTKNQVSLTCLVKGFYPSDIAVEWESNGQPENNYK<br>TTPPVLDSDGSFFLYSKLTVDKSRWQQGNVFSC<br>SVLHEALHSHYTQKSLSLSPG | SEQ ID NO: 443 |
| Heavy Chain hIgG1-N297A/LS | ASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKKVEPKSCDKTHTCPPCPAPE<br>LLGGPSVFLFPPKPKDTLMISRTPEVTCVVVDVSHEDPEVK<br>FNWYVDGVEVHNAKTKPREEQYASTYRVVSVLTVLHQD<br>WLNGKEYKCKVSNKALPAPIEKTISKAKGQPREPQVYTLP<br>PSRDELTKNQVSLTCLVKGFYPSDIAVEWESNGQPENNYK<br>TTPPVLDSDGSFFLYSKLTVDKSRWQQGNVFSC<br>SVLHEALHSHYTQKSLSLSPG | SEQ ID NO: 444 |

-continued

Informal sequence listing

| Description | Sequence | SEQ ID NO |
|---|---|---|
| Heavy Chain hIgG1-D265A/LS | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLMISRTPEVTCVVVAVSHEDPEVK FNWYVDGVEVHNAKTKPREEQYNSTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSC SVLHEALHSHYTQKSLSLSPG | SEQ ID NO: 445 |
| Heavy Chain hIgG1-LALA/LS | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE AAGGPSVFLFPPKPKDTLMISRTPEVTCVVVDVSHEDPEV KFNWYVDGVEVHNAKTKPREEQYNSTYRVVSVLTVLHQ DWLNGKEYKCKVSNKALPAPIEKTISKAKGQPREPQVYTL PPSRDELTKNQVSLTCLVKGFYPSDIAVEWESNGQPENNY KTTPPVLDSDGSFFLYSKLTVDKSRWQQGNVFSC SVLHEALHSHYTQKSLSLSPG | SEQ ID NO: 446 |
| Heavy Chain hIgG1-LAGA/LS | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LAGAPSVFLFPPKPKDTLMISRTPEVTCVVVDVSHEDPEVK FNWYVDGVEVHNAKTKPREEQYNSTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSC SVLHEALHSHYTQKSLSLSPG | SEQ ID NO: 447 |
| Heavy Chain hIgG1-LALAGA/LS | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE AAGAPSVFLFPPKPKDTLMISRTPEVTCVVVDVSHEDPEV KFNWYVDGVEVHNAKTKPREEQYNSTYRVVSVLTVLHQ DWLNGKEYKCKVSNKALPAPIEKTISKAKGQPREPQVYTL PPSRDELTKNQVSLTCLVKGFYPSDIAVEWESNGQPENNY KTTPPVLDSDGSFFLYSKLTVDKSRWQQGNVFSC SVLHEALHSHYTQKSLSLSPG | SEQ ID NO: 448 |
| Heavy Chain hIgG1-LALAPG/LS | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE AAGGPSVFLFPPKPKDTLMISRTPEVTCVVVDVSHEDPEV KFNWYVDGVEVHNAKTKPREEQYNSTYRVVSVLTVLHQ DWLNGKEYKCKVSNKALGAPIEKTISKAKGQPREPQVYTL PPSRDELTKNQVSLTCLVKGFYPSDIAVEWESNGQPENNY KTTPPVLDSDGSFFLYSKLTVDKSRWQQGNVFSC SVLHEALHSHYTQKSLSLSPG | SEQ ID NO: 449 |
| Heavy Chain hIgG1-DHS | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLMISRTPEVTCVVVDVSHEDPEVK FNWYVDGVEVHNAKTKPREEQYNSTYRVVSVLTVDHHD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSC SVMHEALHSHYTQKSLSLSPG | SEQ ID NO: 450 |
| Heavy Chain hIgG1-N297A/DHS | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLMISRTPEVTCVVVDVSHEDPEVK FNWYVDGVEVHNAKTKPREEQYASTYRVVSVLTVDHHD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSC SVMHEALHSHYTQKSLSLSPG | SEQ ID NO: 451 |
| Heavy Chain hIgG1-D265A/DHS | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLMISRTPEVTCVVVAVSHEDPEVK | SEQ ID NO: 452 |

| Description | Sequence | SEQ ID NO |
|---|---|---|
| | FNWYVDGVEVHNAKTKPREEQYNSTYRVVSVLTVDHHD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSC SVMHEALHSHYTQKSLSLSPG | |
| Heavy Chain hIgG1-LALA/DHS | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE AAGGPSVFLFPPKPKDTLMISRTPEVTCVVVDVSHEDPEV KFNWYVDGVEVHNAKTKPREEQYNSTYRVVSVLTVDHH DWLNGKEYKCKVSNKALPAPIEKTISKAKGQPREPQVYTL PPSRDELTKNQVSLTCLVKGFYPSDIAVEWESNGQPENNY KTTPPVLDSDGSFFLYSKLTVDKSRWQQGNVFSC SVMHEALHSHYTQKSLSLSP | SEQ ID NO: 453 |
| Heavy Chain hIgG1-LAGA/DHS | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LAGAPSVFLFPPKPKDTLMISRTPEVTCVVVDVSHEDPEVK FNWYVDGVEVHNAKTKPREEQYNSTYRVVSVLTVDHHD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSC SVMHEALHSHYTQKSLSLSPG | SEQ ID NO: 454 |
| Heavy Chain hIgG1-LALAGA/DHS | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE AAGAPSVFLFPPKPKDTLMISRTPEVTCVVVDVSHEDPEV KFNWYVDGVEVHNAKTKPREEQYNSTYRVVSVLTVDHH DWLNGKEYKCKVSNKALPAPIEKTISKAKGQPREPQVYTL PPSRDELTKNQVSLTCLVKGFYPSDIAVEWESNGQPENNY KTTPPVLDSDGSFFLYSKLTVDKSRWQQGNVFSC SVMHEALHSHYTQKSLSLSPG | SEQ ID NO: 455 |
| Heavy Chain hIgG1-LALAPG/DHS | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE AAGGPSVFLFPPKPKDTLMISRTPEVTCVVVDVSHEDPEV KFNWYVDGVEVHNAKTKPREEQYNSTYRVVSVLTVDHH DWLNGKEYKCKVSNKALGAPIEKTISKAKGQPREPQVYTL PPSRDELTKNQVSLTCLVKGFYPSDIAVEWESNGQPENNY KTTPPVLDSDGSFFLYSKLTVDKSRWQQGNVFSC SVMHEALHSHYTQKSLSLSPG | SEQ ID NO: 456 |
| Heavy Chain IgG4-YTE | ASTKGPSVFPLAPCSRSTSESTAALGCLVKDYFPEP VTVSWNSGALTSGVHTFPAVLQSSGLYSLSSVVTVPSSSL GTKTYTCNVDHKPSNTKVDKRVESKYGPPCPSCPAPEFLG GPSVFLFPPKPKDTLYITREPEVTCVVVDVSQEDPEVQFN WYVDGVEVHNAKTKPREEQFNSTYRVVSVLTVLHQDWL NGKEYKCKVSNKGLPSSIEKTISKAKGQPREPQVYTLPPSQ EEMTKNQVSLTCLVKGFYPSDIAVEWESNGQPENNYKTTP PVLDSDGSFFLYSRLTVDKSRWQEGNVFSCSVMHEALHN HYTQKSLSLSLGK | SEQ ID NO: 457 |
| Heavy Chain IgG4-SP/YTE | ASTKGPSVFPLAPCSRSTSESTAALGCLVKDYFPEP VTVSWNSGALTSGVHTFPAVLQSSGLYSLSSVVTVPSSSL GTKTYTCNVDHKPSNTKVDKRVESKYGPPCPPCPAPEFLG GPSVFLFPPKPKDTLYITREPEVTCVVVDVSQEDPEVQFN WYVDGVEVHNAKTKPREEQFNSTYRVVSVLTVLHQDWL NGKEYKCKVSNKGLPSSIEKTISKAKGQPREPQVYTLPPSQ EEMTKNQVSLTCLVKGFYPSDIAVEWESNGQPENNYKTTP PVLDSDGSFFLYSRLTVDKSRWQEGNVFSCSVMHEALHN HYTQKSLSLSLGK | SEQ ID NO: 458 |

Informal sequence listing

| Description | Sequence | SEQ ID NO |
|---|---|---|
| Heavy Chain IgG4-SPLE/YTE | ASTKGPSVFPLAPCSRSTSESTAALGCLVKDYFPEP<br>VTVSWNSGALTSGVHTFPAVLQSSGLYSLSSVVTVPSSSL<br>GTKTYTCNVDHKPSNTKVDKRVESKYGPPCPPCPAPEELG<br>GPSVFLFPPKPKDTLYITREPEVTCVVVDVSQEDPEVQFN<br>WYVDGVEVHNAKTKPREEQFNSTYRVVSVLTVLHQDWL<br>NGKEYKCKVSNKGLPSSIEKTISKAKGQPREPQVYTLPPSQ<br>EEMTKNQVSLTCLVKGFYPSDIAVEWESNGQPENNYKTTP<br>PVLDSDGSFFLYSRLTVDKSRWQEGNVFSCSVMHEALHN<br>HYTQKSLSLSLGK | SEQ ID NO: 459 |
| Heavy Chain IgG4-LS | ASTKGPSVFPLAPCSRSTSESTAALGCLVKDYFPEP<br>VTVSWNSGALTSGVHTFPAVLQSSGLYSLSSVVTVPSSSL<br>GTKTYTCNVDHKPSNTKVDKRVESKYGPPCPSCPAPEFLG<br>GPSVFLFPPKPKDTLMISRTPEVTCVVVDVSQEDPEVQFN<br>WYVDGVEVHNAKTKPREEQFNSTYRVVSVLTVLHQDWL<br>NGKEYKCKVSNKGLPSSIEKTISKAKGQPREPQVYTLPPSQ<br>EEMTKNQVSLTCLVKGFYPSDIAVEWESNGQPENNYKTTP<br>PVLDSDGSFFLYSRLTVDKSRWQEGNVFSCSVLHEALHSY<br>TQKSLSLSLGK | SEQ ID NO: 460 |
| Heavy Chain IgG4-SP/LS | ASTKGPSVFPLAPCSRSTSESTAALGCLVKDYFPEP<br>VTVSWNSGALTSGVHTFPAVLQSSGLYSLSSVVTVPSSSL<br>GTKTYTCNVDHKPSNTKVDKRVESKYGPPCPPCPAPEFLG<br>GPSVFLFPPKPKDTLMISRTPEVTCVVVDVSQEDPEVQFN<br>WYVDGVEVHNAKTKPREEQFNSTYRVVSVLTVLHQDWL<br>NGKEYKCKVSNKGLPSSIEKTISKAKGQPREPQVYTLPPSQ<br>EEMTKNQVSLTCLVKGFYPSDIAVEWESNGQPENNYKTTP<br>PVLDSDGSFFLYSRLTVDKSRWQEGNVFSCSVLHEALHSH<br>YTQKSLSLSLGK | SEQ ID NO: 461 |
| Heavy Chain IgG4-SPLE/LS | ASTKGPSVFPLAPCSRSTSESTAALGCLVKDYFPEP<br>VTVSWNSGALTSGVHTFPAVLQSSGLYSLSSVVTVPSSSL<br>GTKTYTCNVDHKPSNTKVDKRVESKYGPPCPPCPAPEELG<br>GPSVFLFPPKPKDTLMISRTPEVTCVVVDVSQEDPEVQFN<br>WYVDGVEVHNAKTKPREEQFNSTYRVVSVLTVLHQDWL<br>NGKEYKCKVSNKGLPSSIEKTISKAKGQPREPQVYTLPPSQ<br>EEMTKNQVSLTCLVKGFYPSDIAVEWESNGQPENNYKTTP<br>PVLDSDGSFFLYSRLTVDKSRWQEGNVFSCSVLHEALHSH<br>YTQKSLSLSLGK | SEQ ID NO: 462 |
| Heavy Chain IgG4-DHS | ASTKGPSVFPLAPCSRSTSESTAALGCLVKDYFPEP<br>VTVSWNSGALTSGVHTFPAVLQSSGLYSLSSVVTVPSSSL<br>GTKTYTCNVDHKPSNTKVDKRVESKYGPPCPSCPAPEFLG<br>GPSVFLFPPKPKDTLMISRTPEVTCVVVDVSQEDPEVQFN<br>WYVDGVEVHNAKTKPREEQFNSTYRVVSVLTVDHHDWL<br>NGKEYKCKVSNKGLPSSIEKTISKAKGQPREPQVYTLPPSQ<br>EEMTKNQVSLTCLVKGFYPSDIAVEWESNGQPENNYKTTP<br>PVLDSDGSFFLYSRLTVDKSRWQEGNVFSCSVMHEALHS<br>HYTQKSLSLSLGK | SEQ ID NO: 463 |
| Heavy Chain IgG4-SP/DHS | ASTKGPSVFPLAPCSRSTSESTAALGCLVKDYFPEP<br>VTVSWNSGALTSGVHTFPAVLQSSGLYSLSSVVTVPSSSL<br>GTKTYTCNVDHKPSNTKVDKRVESKYGPPCPPCPAPEFLG<br>GPSVFLFPPKPKDTLMISRTPEVTCVVVDVSQEDPEVQFN<br>WYVDGVEVHNAKTKPREEQFNSTYRVVSVLTVDHHDWL<br>NGKEYKCKVSNKGLPSSIEKTISKAKGQPREPQVYTLPPSQ<br>EEMTKNQVSLTCLVKGFYPSDIAVEWESNGQPENNYKTTP<br>PVLDSDGSFFLYSRLTVDKSRWQEGNVFSCSVMHEALHS<br>HYTQKSLSLSLGK | SEQ ID NO: 464 |
| Heavy Chain IgG4-SPLE/DHS | ASTKGPSVFPLAPCSRSTSESTAALGCLVKDYFPEP<br>VTVSWNSGALTSGVHTFPAVLQSSGLYSLSSVVTVPSSSL<br>GTKTYTCNVDHKPSNTKVDKRVESKYGPPCPPCPAPEELG<br>GPSVFLFPPKPKDTLMISRTPEVTCVVVDVSQEDPEVQFN<br>WYVDGVEVHNAKTKPREEQFNSTYRVVSVLTVDHHDWL<br>NGKEYKCKVSNKGLPSSIEKTISKAKGQPREPQVYTLPPSQ<br>EEMTKNQVSLTCLVKGFYPSDIAVEWESNGQPENNYKTTP<br>PVLDSDGSFFLYSRLTVDKSRWQEGNVFSCSVMHEALHS<br>HYTQKSLSLSLGK | SEQ ID NO: 465 |
| Heavy Chain IgG2-YTE | ASTKGPSVFPLAPCSRSTSESTAALGCLVKDYFPEP<br>VTVSWNSGALTSGVHTFPAVLQSSGLYSLSSVVTVPSSNF<br>GTQTYTCNVDHKPSNTKVDKTVERKCCVECPPCPAPPVA<br>GPSVFLFPPKPKDTLYITREPEVTCVVVDVSHEDPEVQFN | SEQ ID NO: 466 |

| Description | Sequence | SEQ ID NO |
|---|---|---|
| | WYVDGVEVHNAKTKPREEQFNSTFRVVSVLTVVHQDWL NGKEYKCKVSNKGLPAPIEKTISKTKGQPREPQVYTLPPSR EEMTKNQVSLTCLVKGFYPSDIA VEWESNGQPENNYKTTPPMLDSDGSFFLYSKLTVDKSRW QQGNVFSCSVLHEALHSHYTQKSLSLSP | |
| Heavy Chain IgG2-LS | ASTKGPSVFPLAPCSRSTSESTAALGCLVKDYFPEP VTVSWNSGALTSGVHTFPAVLQSSGLYSLSSVVTVPSSNF GTQTYTCNVDHKPSNTKVDKTVERKCCVECPPCPAPPVA GPSVFLFPPKPKDTLMISRTPEVTCVVVDVSHEDPEVQFN WYVDGVEVHNAKTKPREEQFNSTFRVVSVLTVVHQDWL NGKEYKCKVSNKGLPAPIEKTISKTKGQPREPQVYTLPPSR EEMTKNQVSLTCLVKGFYPSDIA VEWESNGQPENNYKTTPPMLDSDGSFFLYSKLTVDKSRW QQGNVFSCSVMHEALHNHYTQKSLSLSP | SEQ ID NO: 467 |
| Heavy Chain IgG2-DHS | ASTKGPSVFPLAPCSRSTSESTAALGCLVKDYFPEP VTVSWNSGALTSGVHTFPAVLQSSGLYSLSSVVTVPSSNF GTQTYTCNVDHKPSNTKVDKTVERKCCVECPPCPAPPVA GPSVFLFPPKPKDTLMISRTPEVTCVVVDVSHEDPEVQFN WYVDGVEVHNAKTKPREEQFNSTFRVVSVLTVVHQDWL NGKEYKCKVSNKGLPAPIEKTISKTKGQPREPQVYTLPPSR EEMTKNQVSLTCLVKGFYPSDIAVEWESNGQPENNYKTTP PMLDSDGSFFLYSKLTVDKSRWQQGNVFSCSVMHEALHS HYTQKSLSLSP | SEQ ID NO: 468 |
| Light Chain Human kappa LC | RTVAAPSVFIFPPSDEQLKSGTASVVCLLNNFYPRE AKVQWKVDNALQSGNSQESVTEQDSKDSTYSLSSTLTLS KADYEKHKVYACEVTHQGLSSPVTKSFNRGEC | SEQ ID NO: 469 |
| Lebrikizumab Heavy Chain Variable Region | QVTLRESGPALVKPTQTLTLTCTVSGFSLSAYSVNW IRQPPGKALEWLAMIWGDGKIVYNSALKSRLTISKDTSKN QVVLTMTNMDPVDTATYYCAGDGYYPYAMDNWGQSL VTVSS | SEQ ID NO: 470 |
| Lebrikizumab Light Chain Variable Region | DIVMTQSPDSLSVSLGERATINCRASKSVDSYGNSF MHWYQQKPGQPPKLLIYLASNLESGVPDRFSGSGSGTDFT LTISSLQAEDVAVYYCQQNNEDPRTFGGGTKVEIK | SEQ ID NO: 471 |
| Human IL-13 Full sequence | MHPLLNPLLLALGLMALLLTTVIALTCLGGFASPGP VPPSTALRELIEELVNITQNQKAPLCNGSMVWSINLTAGM YCAALESLINVSGCSAIEKTQRMLSGFCPHKVSAGQFSSLH VRDTKIEVAQFVKDLLLHLKKLFREGRFN | SEQ ID NO: 472 |
| Cynomolgus Monkey IL-13 Full sequence | MALLLTMVIALTCLGGFASPSPVPPSTALKELIEELV NITQNQKAPLCNGSMVWSINLTAGVYCAALESLINVSGCS AIEKTQRMLNGFCPHKVSAGQFSSLRVRDTKIEVAQFVKD LLVHLKKLFREGQFN | SEQ ID NO: 473 |
| Mouse IL-13 Full sequence | MALWVTAVLALACLGGLAAPGPVPRSVSLPLTLKE LIEELSNITQDQTPLCNGSMVWSVDLAAGGFCVALDSLTNI SNCNAIYRTQRILHGLCNRKAPTTVSSLPDTKIEVAHFITKL LSYTKQLFRHGPF | SEQ ID NO: 474 |
| Rat IL-13 Full sequence | MALWVTAVLALACLGGLATPGPVRRSTSPPVALRE LIEELSNITQDQKTSLCNSSMVWSVDLTAGGFCAALESLTN ISSCNAIHRTQRILNGLCNQKASDVASSPPDTKIEVAQFISK LLNYSKQLFRYGH | SEQ ID NO: 475 |
| Human IL-13 Leader sequence | MHPLLNPLLLALGLMALLLTTVIA | SEQ ID NO: 476 |
| Cynomolgus Monkey IL-13 Leader sequence | MALLLTMVIALTCLGGFA | SEQ ID NO: 477 |

-continued

Informal sequence listing

| Description | Sequence | SEQ ID NO |
|---|---|---|
| Mouse IL-13 Leader sequence | MALWVTAVLALACLGGLA | SEQ ID NO: 478 |
| Rat IL-13 Leader sequence | MALWVTAVLALACLGGLA | SEQ ID NO: 479 |
| Human IL-13 Main chain sequence | LTCLGGFASPGPVPPSTALRELIEELVNITQNQKAPL CNGSMVWSINLTAGMYCAALESLINVSGCSAIEKTQRMLS GFCPHKVSAGQFSSLHVRDTKIEVAQFVKDLLLHLKKLFR EGRFN | SEQ ID NO: 480 |
| Cynomolgus Monkey IL-13 Main chain sequence | SPSPVPPSTALKELIEELVNITQNQKAPLCNGSMVW SINLTAGVYCAALESLINVSGCSAIEKTQRMLNGFCPHKVS AGQFSSLRVRDTKIEVAQFVKDLLVHLKKLFREGQFN | SEQ ID NO: 481 |
| Mouse IL-13 Main chain sequence | APGPVPRSVSLPLTLKELIEELSNITQDQTPLCNGSM VWSVDLAAGGFCVALDSLTNISNCNAIYRTQRILHGLCNR KAPTTVSSLPDTKIEVAHFITKLLSYTKQLFRHGPF | SEQ ID NO: 482 |
| Rat IL-13 Main chain sequence | TPGPVRRSTSPPVALRELIEELSNITQDQKTSLCNSS MVWSVDLTAGGFCAALESLTNISSCNAIHRTQRILNGLCN QKASDVASSPPDTKIEVAQFISKLLNYSKQLFRYGH | SEQ ID NO: 483 |
| hIgG1-LA | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLMISRTPEVTCVVVDVSHEDPEVK FNWYVDGVEVHNAKTKPREEQYNSTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSCSVLHEAL HAHYTQKSLSLSPG | SEQ ID NO: 484 |
| hIgG1-N297A/LA | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLMISRTPEVTCVVVDVSHEDPEVK FNWYVDGVEVHNAKTKPREEQYASTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSCSVLHEAL HAHYTQKSLSLSPG | SEQ ID NO: 485 |
| hIgG1-D265A/LA | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLMISRTPEVTCVVVAVSHEDPEVK FNWYVDGVEVHNAKTKPREEQYNSTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSCSVLHEAL HAHYTQKSLSLSPG | SEQ ID NO: 486 |
| hIgG1-LALA/LA | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE AAGGPSVFLFPPKPKDTLMISRTPEVTCVVVDVSHEDPEV KFNWYVDGVEVHNAKTKPREEQYNSTYRVVSVLTVLHQ DWLNGKEYKCKVSNKALPAPIEKTISKAKGQPREPQVYTL PPSRDELTKNQVSLTCLVKGFYPSDIAVEWESNGQPENNY KTTPPVLDSDGSFFLYSKLTVDKSRWQQGNVFSCSVLHEA LHAHYTQKSLSLSPG | SEQ ID NO: 487 |
| hIgG1-LAGA/LA | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LAGAPSVFLFPPKPKDTLMISRTPEVTCVVVDVSHEDPEVK FNWYVDGVEVHNAKTKPREEQYNSTYRVVSVLTVLHQD | SEQ ID NO: 488 |

| Description | Sequence | SEQ ID NO |
|---|---|---|
| | WLNGKEYKCKVSNKALPAPIEKTISKAKGQPREPQVYTLP<br>PSRDELTKNQVSLTCLVKGFYPSDIAVEWESNGQPENNYK<br>TTPPVLDSDGSFFLYSKLTVDKSRWQQGNVFSCSVLHEAL<br>HAHYTQKSLSLSPG | |
| hIgG1-<br>LALAGA/LA | ASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKKVEPKSCDKTHTCPPCPAPE<br>AAGAPSVFLFPPKPKDTLMISRTPEVTCVVVDVSHEDPEV<br>KFNWYVDGVEVHNAKTKPREEQYNSTYRVVSVLTVLHQ<br>DWLNGKEYKCKVSNKALPAPIEKTISKAKGQPREPQVYTL<br>PPSRDELTKNQVSLTCLVKGFYPSDIAVEWESNGQPENNY<br>KTTPPVLDSDGSFFLYSKLTVDKSRWQQGNVFSCSVLHEA<br>LHAHYTQKSLSLSPG | SEQ ID<br>NO: 489 |
| hIgG1-<br>LALAPG/LA | ASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKKVEPKSCDKTHTCPPCPAPE<br>AAGGPSVFLFPPKPKDTLMISRTPEVTCVVVDVSHEDPEV<br>KFNWYVDGVEVHNAKTKPREEQYNSTYRVVSVLTVLHQ<br>DWLNGKEYKCKVSNKALGAPIEKTISKAKGQPREPQVYTL<br>PPSRDELTKNQVSLTCLVKGFYPSDIAVEWESNGQPENNY<br>KTTPPVLDSDGSFFLYSKLTVDKSRWQQGNVFSCSVLHEA<br>LHAHYTQKSLSLSPG | SEQ ID<br>NO: 490 |
| hIgG1-<br>N434A | ASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKKVEPKSCDKTHTCPPCPAPE<br>LLGGPSVFLFPPKPKDTLMISRTPEVTCVVVDVSHEDPEVK<br>FNWYVDGVEVHNAKTKPREEQYNSTYRVVSVLTVLHQD<br>WLNGKEYKCKVSNKALPAPIEKTISKAKGQPREPQVYTLP<br>PSRDELTKNQVSLTCLVKGFYPSDIAVEWESNGQPENNYK<br>TTPPVLDSDGSFFLYSKLTVDKSRWQQGNVFSCSVMHEAL<br>HAHYTQKSLSLSPG | SEQ ID<br>NO: 491 |
| hIgG1-<br>N297A/<br>N434A | ASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKKVEPKSCDKTHTCPPCPAPE<br>LLGGPSVFLFPPKPKDTLMISRTPEVTCVVVDVSHEDPEVK<br>FNWYVDGVEVHNAKTKPREEQYASTYRVVSVLTVLHQD<br>WLNGKEYKCKVSNKALPAPIEKTISKAKGQPREPQVYTLP<br>PSRDELTKNQVSLTCLVKGFYPSDIAVEWESNGQPENNYK<br>TTPPVLDSDGSFFLYSKLTVDKSRWQQGNVFSCSVMHEAL<br>HAHYTQKSLSLSPG | SEQ ID<br>NO: 492 |
| hIgG1-<br>D265A/<br>N434A | ASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKKVEPKSCDKTHTCPPCPAPE<br>LLGGPSVFLFPPKPKDTLMISRTPEVTCVVVAVSHEDPEVK<br>FNWYVDGVEVHNAKTKPREEQYNSTYRVVSVLTVLHQD<br>WLNGKEYKCKVSNKALPAPIEKTISKAKGQPREPQVYTLP<br>PSRDELTKNQVSLTCLVKGFYPSDIAVEWESNGQPENNYK<br>TTPPVLDSDGSFFLYSKLTVDKSRWQQGNVFSCSVMHEAL<br>HAHYTQKSLSLSPG | SEQ ID<br>NO: 493 |
| hIgG1-<br>LALA/<br>N434A | ASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKKVEPKSCDKTHTCPPCPAPE<br>AAGGPSVFLFPPKPKDTLMISRTPEVTCVVVDVSHEDPEV<br>KFNWYVDGVEVHNAKTKPREEQYNSTYRVVSVLTVLHQ<br>DWLNGKEYKCKVSNKALPAPIEKTISKAKGQPREPQVYTL<br>PPSRDELTKNQVSLTCLVKGFYPSDIAVEWESNGQPENNY<br>KTTPPVLDSDGSFFLYSKLTVDKSRWQQGNVFSCSVMHE<br>ALHAHYTQKSLSLSPG | SEQ ID<br>NO: 494 |
| hIgG1-<br>LAGA/<br>N434A | ASTKGPSVFPLAPSSKSTSGGTAALGCLVKDYFPEP<br>VTVSWNSGALTSGVHTFPAVLQSSGLYSLSSVVTVPSSSL<br>GTQTYICNVNHKPSNTKVDKKVEPKSCDKTHTCPPCPAPE<br>LAGAPSVFLFPPKPKDTLMISRTPEVTCVVVDVSHEDPEVK<br>FNWYVDGVEVHNAKTKPREEQYNSTYRVVSVLTVLHQD<br>WLNGKEYKCKVSNKALPAPIEKTISKAKGQPREPQVYTLP<br>PSRDELTKNQVSLTCLVKGFYPSDIAVEWESNGQPENNYK<br>TTPPVLDSDGSFFLYSKLTVDKSRWQQGNVFSCSVMHEAL<br>HAHYTQKSLSLSPG | SEQ ID<br>NO: 495 |

| Description | Sequence | SEQ ID NO |
|---|---|---|
| hIgG1-LALAGA/N434A | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE AAGAPSVFLFPPKPKDTLMISRTPEVTCVVVDVSHEDPEV KFNWYVDGVEVHNAKTKPREEQYNSTYRVVSVLTVLHQ DWLNGKEYKCKVSNKALPAPIEKTISKAKGQPREPQVYTL PPSRDELTKNQVSLTCLVKGFYPSDIAVEWESNGQPENNY KTTPPVLDSDGSFFLYSKLTVDKSRWQQGNVFSCSVMHE ALHAHYTQKSLSLSPG | SEQ ID NO: 496 |
| hIgG1-LALAPG/N434A | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE AAGGPSVFLFPPKPKDTLMISRTPEVTCVVVDVSHEDPEV KFNWYVDGVEVHNAKTKPREEQYNSTYRVVSVLTVLHQ DWLNGKEYKCKVSNKALGAPIEKTISKAKGQPREPQVYTL PPSRDELTKNQVSLTCLVKGFYPSDIAVEWESNGQPENNY KTTPPVLDSDGSFFLYSKLTVDKSRWQQGNVFSCSVMHE ALHAHYTQKSLSLSPG | SEQ ID NO: 497 |
| hIgG1-N434W | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLMISRTPEVTCVVVDVSHEDPEVK FNWYVDGVEVHNAKTKPREEQYNSTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSCSVMHEAL HWHYTQKSLSLSPG | SEQ ID NO: 498 |
| hIgG1-N297A/N434W | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLMISRTPEVTCVVVDVSHEDPEVK FNWYVDGVEVHNAKTKPREEQYASTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSCSVMHEAL HWHYTQKSLSLSPG | SEQ ID NO: 499 |
| hIgG1-D265A/N434W | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LLGGPSVFLFPPKPKDTLMISRTPEVTCVVVAVSHEDPEVK FNWYVDGVEVHNAKTKPREEQYNSTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSCSVMHEAL HWHYTQKSLSLSPG | SEQ ID NO: 500 |
| hIgG1-LALA/N434W | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE AAGGPSVFLFPPKPKDTLMISRTPEVTCVVVDVSHEDPEV KFNWYVDGVEVHNAKTKPREEQYNSTYRVVSVLTVLHQ DWLNGKEYKCKVSNKALPAPIEKTISKAKGQPREPQVYTL PPSRDELTKNQVSLTCLVKGFYPSDIAVEWESNGQPENNY KTTPPVLDSDGSFFLYSKLTVDKSRWQQGNVFSCSVMHE ALHWHYTQKSLSLSPG | SEQ ID NO: 501 |
| hIgG1-LAGA/N434W | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE LAGAPSVFLFPPKPKDTLMISRTPEVTCVVVDVSHEDPEVK FNWYVDGVEVHNAKTKPREEQYNSTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSCSVMHEAL HWHYTQKSLSLSPG | SEQ ID NO: 502 |
| hIgG1-LALAGA/N434W | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE | SEQ ID NO: 503 |

| Description | Sequence | SEQ ID NO |
|---|---|---|
| | AAGAPSVFLFPPKPKDTLMISRTPEVTCVVVDVSHEDPEV KFNWYVDGVEVHNAKTKPREEQYNSTYRVVSVLTVLHQ DWLNGKEYKCKVSNKALPAPIEKTISKAKGQPREPQVYTL PPSRDELTKNQVSLTCLVKGFYPSDIAVEWESNGQPENNY KTTPPVLDSDGSFFLYSKLTVDKSRWQQGNVFSCSVMHE ALHWHYTQKSLSLSPG | |
| hIgG1-LALAPG/ N434W | ASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKKVEPKSCDKTHTCPPCPAPE AAGGPSVFLFPPKPKDTLMISRTPEVTCVVVDVSHEDPEV KFNWYVDGVEVHNAKTKPREEQYNSTYRVVSVLTVLHQ DWLNGKEYKCKVSNKALGAPIEKTISKAKGQPREPQVYTL PPSRDELTKNQVSLTCLVKGFYPSDIAVEWESNGQPENNY KTTPPVLDSDGSFFLYSKLTVDKSRWQQGNVFSCSVMHE ALHWHYTQKSLSLSPG | SEQ ID NO: 504 |
| hIgG1/DQ | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRDPEVTCVVVDVSHEDPEVKFNW YVDGVEVHNAKTKPREEQYNSTYRVVSVLQVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 505 |
| hIgG1-N297A/DQ | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRDPEVTCVVVDVSHEDPEVKFNW YVDGVEVHNAKTKPREEQYASTYRVVSVLQVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 506 |
| hIgG1-D265A/DQ | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRDPEVTCVVVAVSHEDPEVKFNW YVDGVEVHNAKTKPREEQYNSTYRVVSVLQVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 507 |
| hIgG1-LALA/DQ | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRDPEVTCVVVDVSHEDPEVKFNW YVDGVEVHNAKTKPREEQYNSTYRVVSVLQVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 508 |
| hIgG1-LAGA/DQ | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELAGA PSVFLFPPKPKDTLMISRDPEVTCVVVDVSHEDPEVKFNW YVDGVEVHNAKTKPREEQYNSTYRVVSVLQVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 509 |
| hIgG1-LALAGA/DQ | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGA PSVFLFPPKPKDTLMISRDPEVTCVVVDVSHEDPEVKFNW YVDGVEVHNAKTKPREEQYNSTYRVVSVLQVLHQDWLN GKEYKCKVSNKALPAPIEKTISKAKGQPREPQVYTLPPSRD ELTKNQVSLTCLVKGFYPSDIAVEWESNGQPENNYKTTPP | SEQ ID NO: 510 |

| Description | Sequence | SEQ ID NO |
|---|---|---|
| | VLDSDGSFFLYSKLTVDKSRWQQGNVFSCSVMHEALHNH YTQKSLSLSPG | |
| hIgG1-LALAPG/DQ | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRDPEVTCVVVDVSHEDPEVKFNW YVDGVEVHNAKTKPREEQYNSTYRVVSVLQVLHQDWLN GKEYKCKVSNKALGAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPG | SEQ ID NO: 511 |
| hIgG1/DW | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRDPEVTCVVVDVSHEDPEVKFNW YVDGVEVHNAKTKPREEQYNSTYRVVSVLWVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 512 |
| hIgG1-N297A/DW | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRDPEVTCVVVDVSHEDPEVKFNW YVDGVEVHNAKTKPREEQYASTYRVVSVLWVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 513 |
| hIgG1-D265A/DW | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRDPEVTCVVVAVSHEDPEVKFNW YVDGVEVHNAKTKPREEQYNSTYRVVSVLWVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 514 |
| hIgG1-LALA/DW | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRDPEVTCVVVDVSHEDPEVKFNW YVDGVEVHNAKTKPREEQYNSTYRVVSVLWVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 515 |
| hIgG1-LAGA/DW | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELAGA PSVFLFPPKPKDTLMISRDPEVTCVVVDVSHEDPEVKFNW YVDGVEVHNAKTKPREEQYNSTYRVVSVLWVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 516 |
| hIgG1-LALAGA/DW | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGA PSVFLFPPKPKDTLMISRDPEVTCVVVDVSHEDPEVKFNW YVDGVEVHNAKTKPREEQYNSTYRVVSVLWVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 517 |

-continued

Informal sequence listing

| Description | Sequence | SEQ ID NO |
|---|---|---|
| hIgG1-LALAPG/DW | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRDPEVTCVVVDVSHEDPEVKFNW YVDGVEVHNAKTKPREEQYNSTYRVVSVLWVLHQDWLN GKEYKCKVSNKALGAPIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHN HYTQKSLSLSPG | SEQ ID NO: 518 |
| hIgG1/YD | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLYISRDPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 519 |
| hIgG1-N297A/YD | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLYISRDPEVTCVVVDVSHEDPEVKFNW YVDGVEVHNAKTKPREEQYASTYRVVSVLTVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 520 |
| hIgG1-D265A/YD | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLYISRDPEVTCVVVAVSHEDPEVKFNW YVDGVEVHNAKTKPREEQYNSTYRVVSVLTVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 521 |
| hIgG1-LALA/YD | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLYISRDPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 522 |
| hIgG1-LAGA/YD | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELAGA PSVFLFPPKPKDTLYISRDPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 523 |
| hIgG1-LALAGA/YD | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGA PSVFLFPPKPKDTLYISRDPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSRD ELTKNQVSLTCLVKGFYPSDIAVEWESNGQPENNYKTTPP VLDSDGSFFLYSKLTVDKSRWQQGNVFSCSVMHEALHNH YTQKSLSLSPG | SEQ ID NO: 524 |
| hIgG1-LALAPG/YD | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLYISRDPEVTCVVVDVSHEDPEVKFNW | SEQ ID NO: 525 |

| Description | Sequence | SEQ ID NO |
|---|---|---|
| | YVDGVEVHNAKTKPREEQYNSTYRVVSVLTVLHQDWLN<br>GKEYKCKVSNKALGAPIEKTISKAKGQPREPQVYTLPPSR<br>DELTKNQVSLTCLVKGFYPSDIAVEWESNGQPENNYKTTP<br>PVLDSDGSFFLYSKLTVDKSRWQQGNVFSCSVMHEALHN<br>HYTQKSLSLSPG | |
| hIgG1/QVV | ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKKVEPKSCDKTHTCPPCPAPELLGG<br>PSVFLFPPKPKDTLMISRTPEVTCVVVDVSHEDPEVKFNW<br>YVDGVEVHNAKTKPREEQYNSTYRVVSVLQVLHVDWLN<br>GKEYKCKVSNKALPAPIEKTISKAKGQPREPQVYTLPPSRD<br>ELTKNQVSLTCLVKGFYPSDIVVEWESNGQPENNYKTTPP<br>VLDSDGSFFLYSKLTVDKSRWQQGNVFSCSVMHEALHNH<br>YTQKSLSLSPG | SEQ ID NO: 526 |
| hIgG1-N297A/QVV | ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKKVEPKSCDKTHTCPPCPAPELLGG<br>PSVFLFPPKPKDTLMISRTPEVTCVVVDVSHEDPEVKFNW<br>YVDGVEVHNAKTKPREEQYASTYRVVSVLQVLHVDWLN<br>GKEYKCKVSNKALPAPIEKTISKAKGQPREPQVYTLPPSRD<br>ELTKNQVSLTCLVKGFYPSDIVVEWESNGQPENNYKTTPP<br>VLDSDGSFFLYSKLTVDKSRWQQGNVFSCSVMHEALHNH<br>YTQKSLSLSPG | SEQ ID NO: 527 |
| hIgG1-D265A/QVV | ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKKVEPKSCDKTHTCPPCPAPELLGG<br>PSVFLFPPKPKDTLMISRTPEVTCVVVAVSHEDPEVKFNW<br>YVDGVEVHNAKTKPREEQYNSTYRVVSVLQVLHVDWLN<br>GKEYKCKVSNKALPAPIEKTISKAKGQPREPQVYTLPPSRD<br>ELTKNQVSLTCLVKGFYPSDIVVEWESNGQPENNYKTTPP<br>VLDSDGSFFLYSKLTVDKSRWQQGNVFSCSVMHEALHNH<br>YTQKSLSLSPG | SEQ ID NO: 528 |
| hIgG1-LALA/QVV | ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKKVEPKSCDKTHTCPPCPAPEAAGG<br>PSVFLFPPKPKDTLMISRTPEVTCVVVDVSHEDPEVKFNW<br>YVDGVEVHNAKTKPREEQYNSTYRVVSVLQVLHVDWLN<br>GKEYKCKVSNKALPAPIEKTISKAKGQPREPQVYTLPPSRD<br>ELTKNQVSLTCLVKGFYPSDIVVEWESNGQPENNYKTTPP<br>VLDSDGSFFLYSKLTVDKSRWQQGNVFSCSVMHEALHNH<br>YTQKSLSLSPG | SEQ ID NO: 529 |
| hIgG1-LAGA/QVV | ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKKVEPKSCDKTHTCPPCPAPELAGA<br>PSVFLFPPKPKDTLMISRTPEVTCVVVDVSHEDPEVKFNW<br>YVDGVEVHNAKTKPREEQYNSTYRVVSVLQVLHVDWLN<br>GKEYKCKVSNKALPAPIEKTISKAKGQPREPQVYTLPPSRD<br>ELTKNQVSLTCLVKGFYPSDIVVEWESNGQPENNYKTTPP<br>VLDSDGSFFLYSKLTVDKSRWQQGNVFSCSVMHEALHNH<br>YTQKSLSLSPG | SEQ ID NO: 530 |
| hIgG1-LALAGA/QVV | ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKKVEPKSCDKTHTCPPCPAPEAAGA<br>PSVFLFPPKPKDTLMISRTPEVTCVVVDVSHEDPEVKFNW<br>YVDGVEVHNAKTKPREEQYNSTYRVVSVLQVLHVDWLN<br>GKEYKCKVSNKALPAPIEKTISKAKGQPREPQVYTLPPSRD<br>ELTKNQVSLTCLVKGFYPSDIVVEWESNGQPENNYKTTPP<br>VLDSDGSFFLYSKLTVDKSRWQQGNVFSCSVMHEALHNH<br>YTQKSLSLSPG | SEQ ID NO: 531 |

-continued

Informal sequence listing

| Description | Sequence | SEQ ID NO |
|---|---|---|
| hIgG1-LALAPG/QVV | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLQVLHVDWLN GKEYKCKVSNKALGAPIEKTISKAKGQPREPQVYTLPPSR DELTKNQVSLTCLVKGFYPSDIVVEWESNGQPENNYKTTP PVLDSDGSFFLYSKLTVDKSRWQQGNVFSCSVMHEALHN HYTQKSLSLSPG | SEQ ID NO: 532 |
| hIgG1/DDRVV | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRDPEVTCVVVDVSHEDPEVKFNW YVDGVEVDNAKTKPREEQYNSTYRVVSVLRVLHVDWLN GKEYKCKVSNKALPAPIEKTISKAKGQPREPQVYTLPPSRD ELTKNQVSLTCLVKGFYPSDIVVEWESNGQPENNYKTTPP VLDSDGSFFLYSKLTVDKSRWQQGNVFSCSVMHEALHNH YTQKSLSLSPG | SEQ ID NO: 533 |
| hIgG1-N297A/DDRVV | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRDPEVTCVVVDVSHEDPEVKFNW YVDGVEVDNAKTKPREEQYASTYRVVSVLRVLHVDWLN GKEYKCKVSNKALPAPIEKTISKAKGQPREPQVYTLPPSRD ELTKNQVSLTCLVKGFYPSDIVVEWESNGQPENNYKTTPP VLDSDGSFFLYSKLTVDKSRWQQGNVFSCSVMHEALHNH YTQKSLSLSPG | SEQ ID NO: 534 |
| hIgG1-D265A/DDRVV | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRDPEVTCVVVAVSHEDPEVKFNW YVDGVEVDNAKTKPREEQYNSTYRVVSVLRVLHVDWLN GKEYKCKVSNKALPAPIEKTISKAKGQPREPQVYTLPPSRD ELTKNQVSLTCLVKGFYPSDIVVEWESNGQPENNYKTTPP VLDSDGSFFLYSKLTVDKSRWQQGNVFSCSVMHEALHNH YTQKSLSLSPG | SEQ ID NO: 535 |
| hIgG1-LALA/DDRVV | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRDPEVTCVVVDVSHEDPEVKFNW YVDGVEVDNAKTKPREEQYNSTYRVVSVLRVLHVDWLN GKEYKCKVSNKALPAPIEKTISKAKGQPREPQVYTLPPSRD ELTKNQVSLTCLVKGFYPSDIVVEWESNGQPENNYKTTPP VLDSDGSFFLYSKLTVDKSRWQQGNVFSCSVMHEALHNH YTQKSLSLSPG | SEQ ID NO: 536 |
| hIgG1-LAGA/DDRVV | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELAGA PSVFLFPPKPKDTLMISRDPEVTCVVVDVSHEDPEVKFNW YVDGVEVDNAKTKPREEQYNSTYRVVSVLRVLHVDWLN GKEYKCKVSNKALPAPIEKTISKAKGQPREPQVYTLPPSRD ELTKNQVSLTCLVKGFYPSDIVVEWESNGQPENNYKTTPP VLDSDGSFFLYSKLTVDKSRWQQGNVFSCSVMHEALHNH YTQKSLSLSPG | SEQ ID NO: 537 |
| hIgG1-LALAGA/DDRVV | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGA PSVFLFPPKPKDTLMISRDPEVTCVVVDVSHEDPEVKFNW YVDGVEVDNAKTKPREEQYNSTYRVVSVLRVLHVDWLN GKEYKCKVSNKALPAPIEKTISKAKGQPREPQVYTLPPSRD ELTKNQVSLTCLVKGFYPSDIVVEWESNGQPENNYKTTPP VLDSDGSFFLYSKLTVDKSRWQQGNVFSCSVMHEALHNH YTQKSLSLSPG | SEQ ID NO: 538 |
| hIgG1-LALAPG/DDRVV | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRDPEVTCVVVDVSHEDPEVKFNW | SEQ ID NO: 539 |

| Informal sequence listing | | |
|---|---|---|
| Description | Sequence | SEQ ID NO |
| | YVDGVEVDNAKTKPREEQYNSTYRVVSVLRVLHVDWLN GKEYKCKVSNKALGAPIEKTISKAKGQPREPQVYTLPPSR DELTKNQVSLTCLVKGFYPSDIVVEWESNGQPENNYKTTP PVLDSDGSFFLYSKLTVDKSRWQQGNVFSCSVMHEALHN HYTQKSLSLSPG | |

The invention claimed is:

1. An isolated antibody that binds Interleukin 13 (IL-13), wherein the antibody comprises
a heavy chain variable region sequence set forth in SEQ ID NO: 3 and
a light chain variable region sequence set forth in SEQ ID NO: 39, and
wherein the antibody comprises a human IgG1 Fc region with LALA and/or YTE mutations.

2. The isolated antibody of claim 1, wherein the antibody is a humanized or chimeric antibody.

3. The isolated antibody of claim 2, wherein the antibody is a humanized antibody.

4. The isolated antibody of claim 1, wherein the antibody is a monoclonal antibody.

5. The isolated antibody of claim 1, wherein the antibody binds an IL-13 sequence set forth in SEQ ID NO: 472 or SEQ ID NO: 473.

6. The isolated antibody of claim 1, wherein the antibody binds to an IL-13 sequence set forth in SEQ ID NO: 472 or SEQ ID NO: 473 with a $K_D$ of less than or equal to about 1, 2, 3, 4, 5, 6, 7, 8, or $9 \times 10^{-9}$ M, as measured by surface plasmon resonance (SPR).

7. The isolated antibody of claim 1, wherein the antibody binds to an IL-13 sequence set forth in SEQ ID NO: 472 or SEQ ID NO: 473 with a $K_D$ of less than or equal to about $1 \times 10^{-10}$ M, as measured by SPR.

8. The isolated antibody of claim 1, wherein the antibody binds to human IL-13 with a $K_D$ of less than or equal to about $1 \times 10^{-9}$ M, as measured by SPR.

9. The isolated antibody of claim 1, wherein the antibody is formulated for subcutaneous injection.

10. The isolated antibody of claim 1, wherein the antibody is formulated for intravenous injection.

11. A composition comprising the isolated antibody of claim 1 and a pharmaceutically acceptable excipient.

12. A kit comprising:
(a) the isolated antibody that binds IL-13 of claim 1; and
(b) instructions for use.

13. The isolated antibody of claim 1, wherein the antibody comprises a human IgG1 Fc region with LALA and YTE mutations.

14. The isolated antibody of claim 1, wherein the antibody comprises a human IgG1 Fc region with YTE mutations.

15. An isolated antibody that binds IL-13, wherein the antibody comprises
a heavy chain variable region sequence set forth in SEQ ID NO: 3 and
a light chain variable region sequence set forth in SEQ ID NO: 39.

16. The isolated antibody of claim 15, wherein the antibody comprises a human IgG1 Fc region.

17. The isolated antibody of claim 15, wherein the antibody binds to an IL-13 sequence set forth in SEQ ID NO: 472 or SEQ ID NO: 473 with a $K_D$ of less than or equal to about $1 \times 10^{-10}$ M, as measured by SPR.

18. The isolated antibody of claim 17, wherein the antibody comprises a human IgG1 Fc region with LALA and YTE mutations.

19. An isolated antibody that binds IL-13, wherein the antibody comprises a heavy chain variable region sequence set forth in SEQ ID NO: 3, a light chain variable region sequence set forth in SEQ ID NO: 39, a constant heavy chain sequence set forth in SEQ ID NO: 439, and a constant light chain sequence set forth in SEQ ID NO: 469.

20. The isolated antibody of claim 19, wherein the antibody is formulated for subcutaneous injection.

21. A composition comprising the isolated antibody of claim 19 and a pharmaceutically acceptable excipient.

* * * * *